United States Patent [19]
Culpepper et al.

[11] Patent Number: 5,596,072
[45] Date of Patent: Jan. 21, 1997

[54] METHOD OF REFOLDING HUMAN IL-13

[75] Inventors: Janice Culpepper, Mountain View; Andrew McKenzie, Redwood City; Warren Dang, San Jose; Gerard Zurawski, Redwood City, all of Calif.

[73] Assignee: Schering Corporation, Kenilworth, N.J.

[21] Appl. No.: 12,543

[22] Filed: Feb. 1, 1993

Related U.S. Application Data

[63] Continuation-in-part of Ser. No. 933,416, Aug. 21, 1992, abandoned.
[51] Int. Cl.$^6$ .............................. C07K 1/00; C07K 14/54
[52] U.S. Cl. ........................ 530/351; 530/412; 530/402; 435/69.1; 424/85.2; 930/141
[58] Field of Search ........................ 435/69.1; 530/350, 530/351, 412; 424/85.2; 930/141

[56] References Cited

FOREIGN PATENT DOCUMENTS

0506574A1  3/1992  European Pat. Off. ........ C12N 15/19

OTHER PUBLICATIONS

T. Tsuji et al. Biochemistry 26:3129 1987.
A. N. J. McKenzie, et al., "Interleukin 13, a T–Cell–Derived Cytokine That Regulates Human Monocyte and B–Cell Function," *Proc. Natl. Acad. Sci, USA.*, 90:3735–3739, Apr. 1993.
Juha Punnonen, et al., "Interleukin 13 Induces Interleukin 4–Independent IgG4 and IgE Synthesis and CD23 Expression by Human B Cells," *Proc. Natl. Acad. Sci. USA.*, 90:3730–3734, Apr. 1993.
Sandra M. Zurawski, et al., "Receptors for Interleukin–13 and Interleukin–4 Are Complex and Share a Novel Component That Functions in Signal Transduction," *EMBO J.*, 12:2663–2670, Jul. 1993.
Brown et al, "A Family of Small Inducible Proteins Secreted by Leukocytes Are Members of a New Superfamily That Includes Leukocyte and Fibroblast–Derived Inflammatory Agents, Growth Factors, and Indicators of Various Activation Processes," *The Journal of Immunology*, vol. 142, No. 2, pp. 679–687, Jan. 1989.
Caput et al. "Protéine à activité de type cytokine, ADN recombinant codant pour cette protéine, cellules et micro-organismes transformés"; publication date, Sep. 30, 1992; European Patent Application No. 0 506 574 A1; (English translation of abstract attached).
Caput et al. "Protéine à activité de type cytokine, ADN recombinant codant pour cette protéine, cellules animales transformées"; publication date, Oct. 2, 1992; French Application No. FR 2 674 537–A1; (English translation of abstract attached).
Cherwinski et al., "Two Types of Mouse Helper T Cell Clone," *Journal of Experimental Medicine*, vol. 166, pp. 1229–1244, Nov. 1987.
Minty et al., "Molecular Cloning of a Novel Human Lymphokine," abstract, No. 24, 8th International Congress of Immunology, Budapest, Hungary, Aug. 23–28, 1992.
Mosmann et al., "Two Types of Murine Helper T Clone," *The Journal of Immunology*, vol. 136, No. 7, pp. 2348–2357, Apr. 1986.
van Kimmendade et al., "Expression, renaturation and purification of recombinant human interluekin 4 from *Escherichia coli*," *European Journal of Biochemistry*, vol. 173, pp. 109–114, 1988.

*Primary Examiner*—Garnette D. Draper
*Assistant Examiner*—Lorraine M. Spector
*Attorney, Agent, or Firm*—Edwin P. Ching

[57] ABSTRACT

Nucleic acids encoding human IL-13, and purified IL-13 proteins and fragments thereof. Antibodies, both polyclonal and monoclonal, are also provided. Methods of using the compositions for both diagnostic and therapeutic utilities are provided.

10 Claims, 61 Drawing Sheets

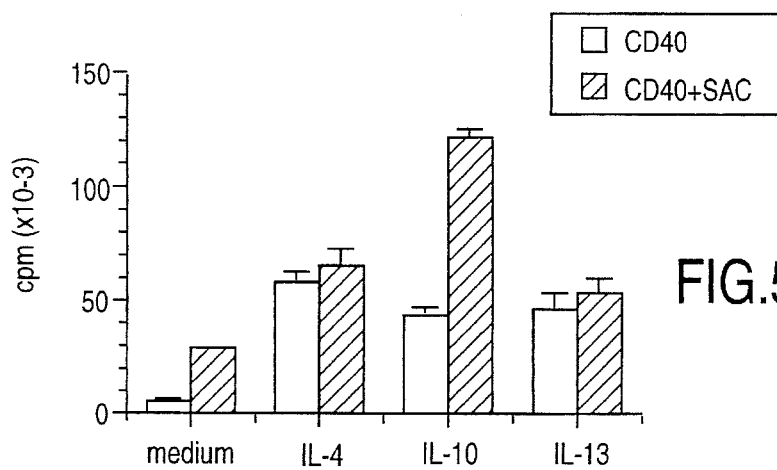
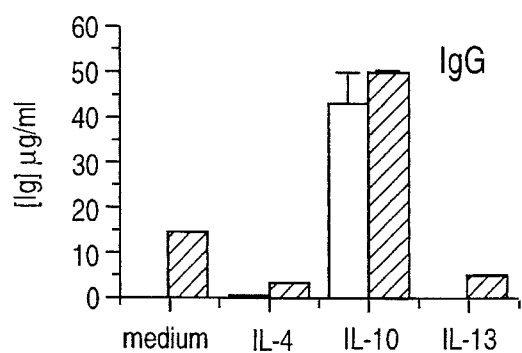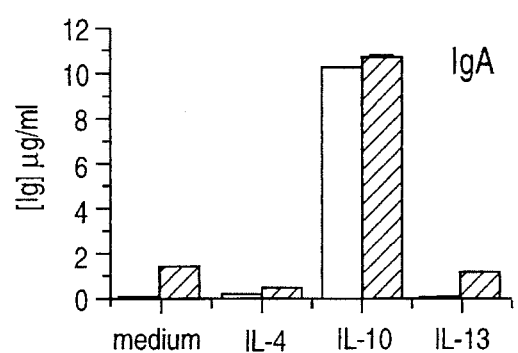
FIG.5B  FIG.5C
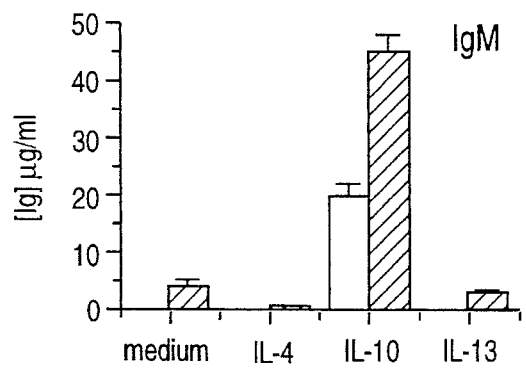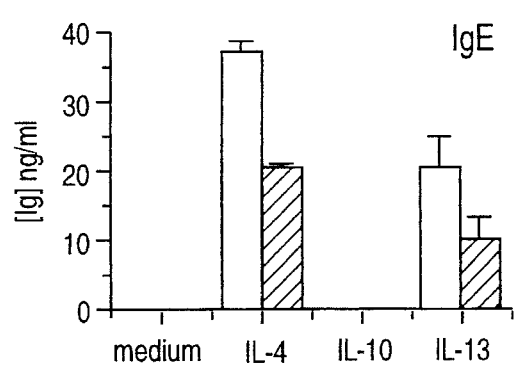
FIG.5D  FIG.5E

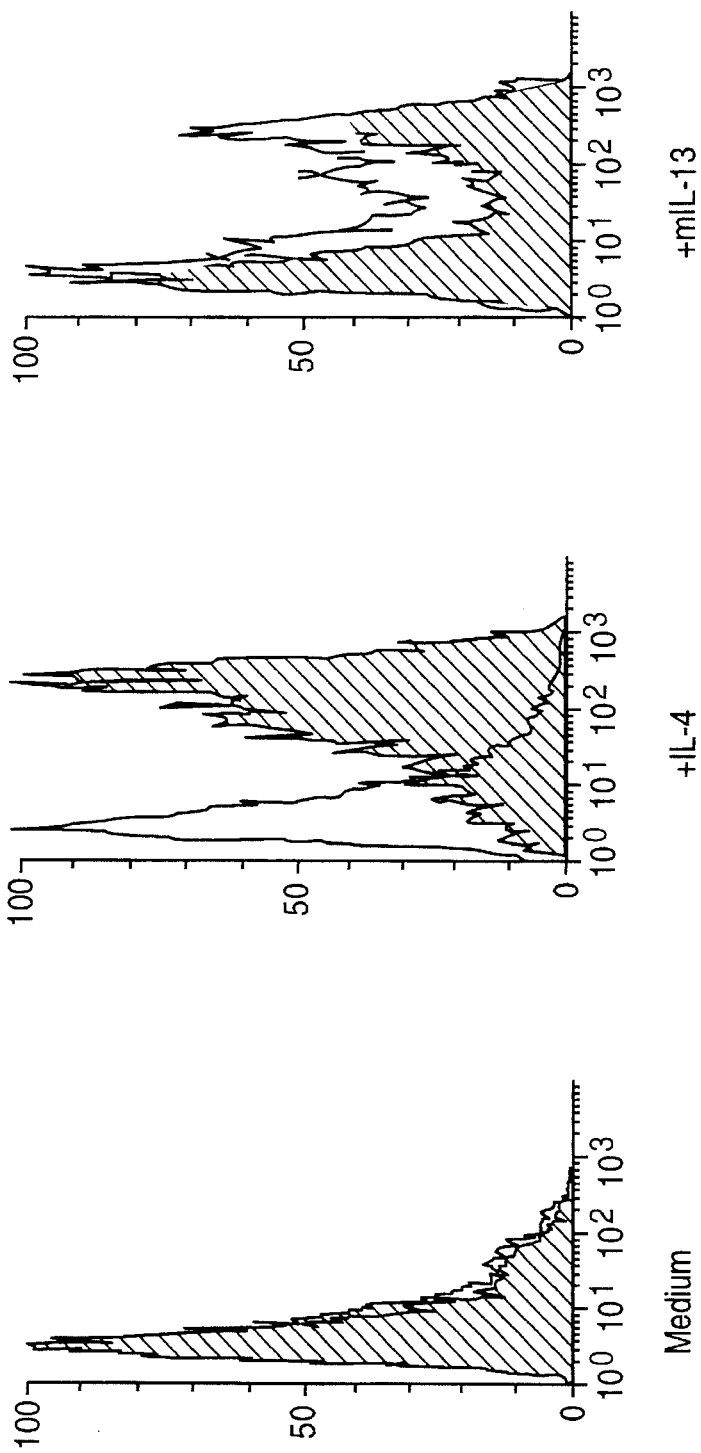

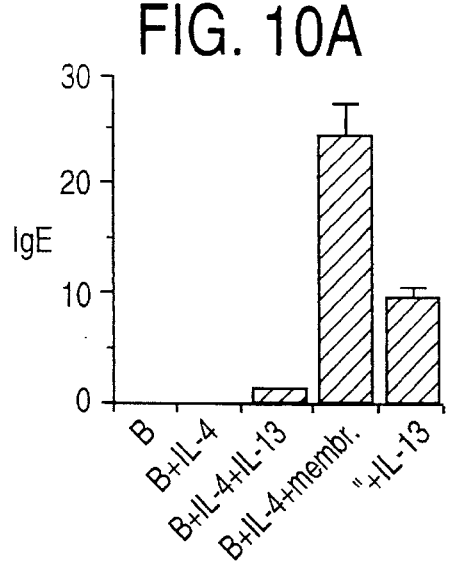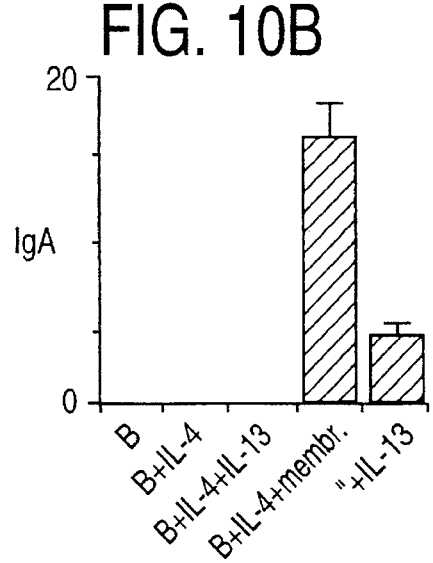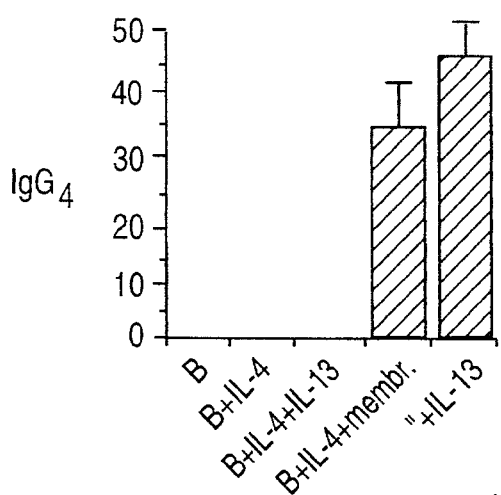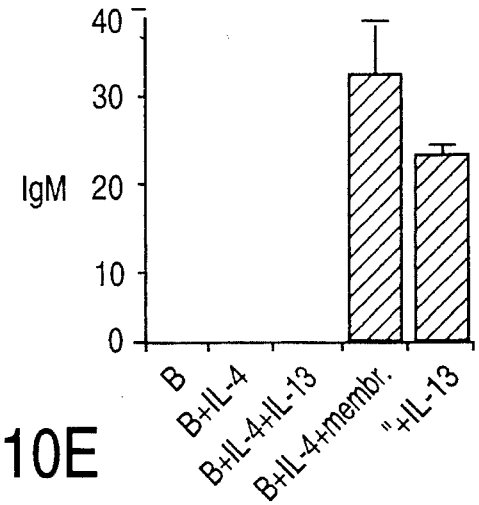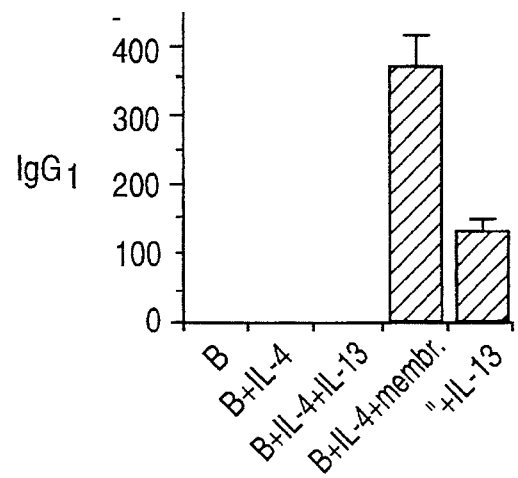

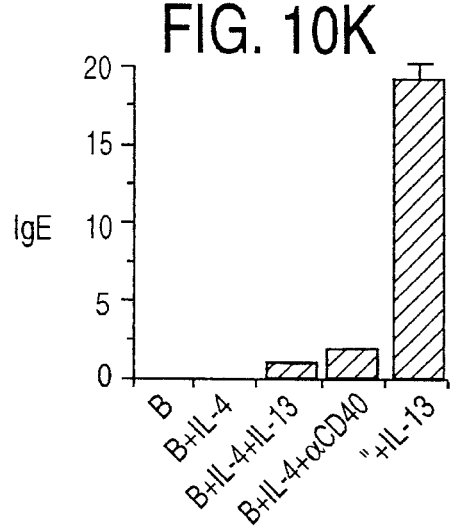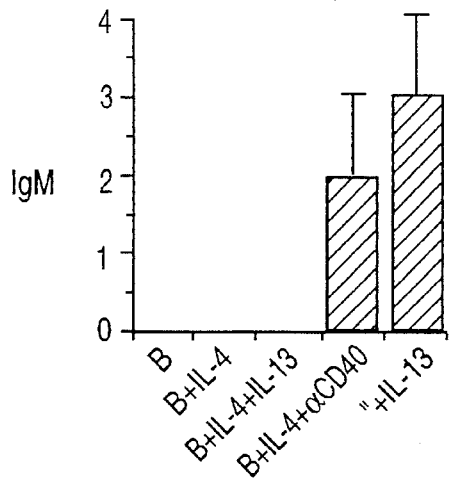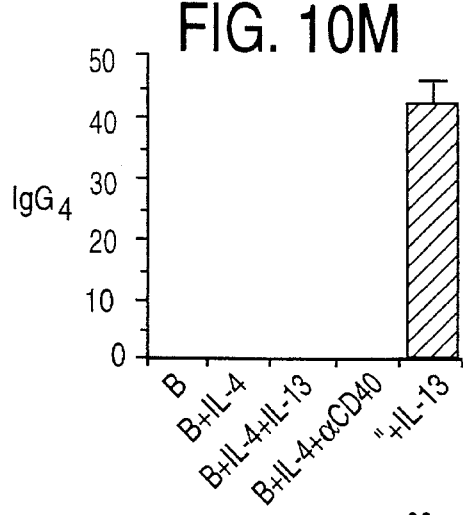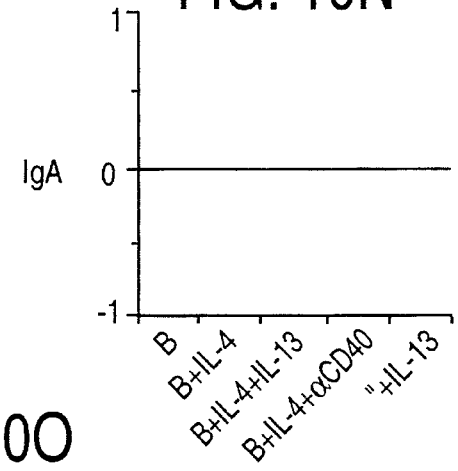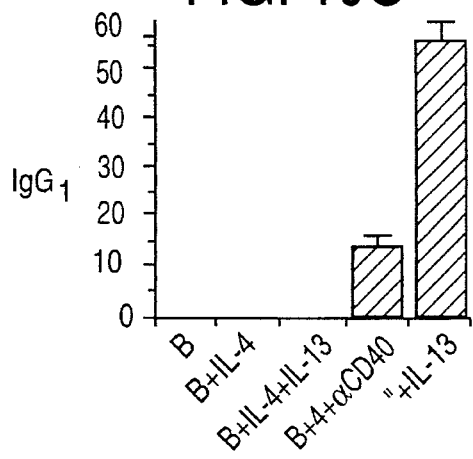

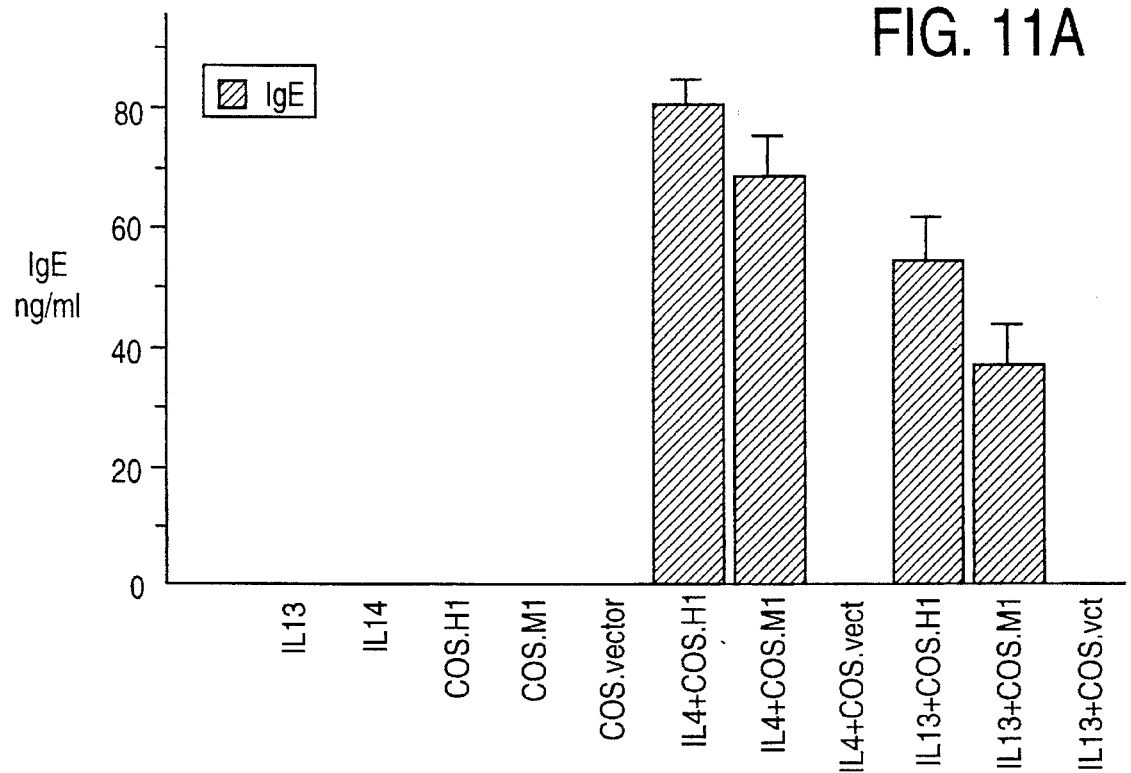
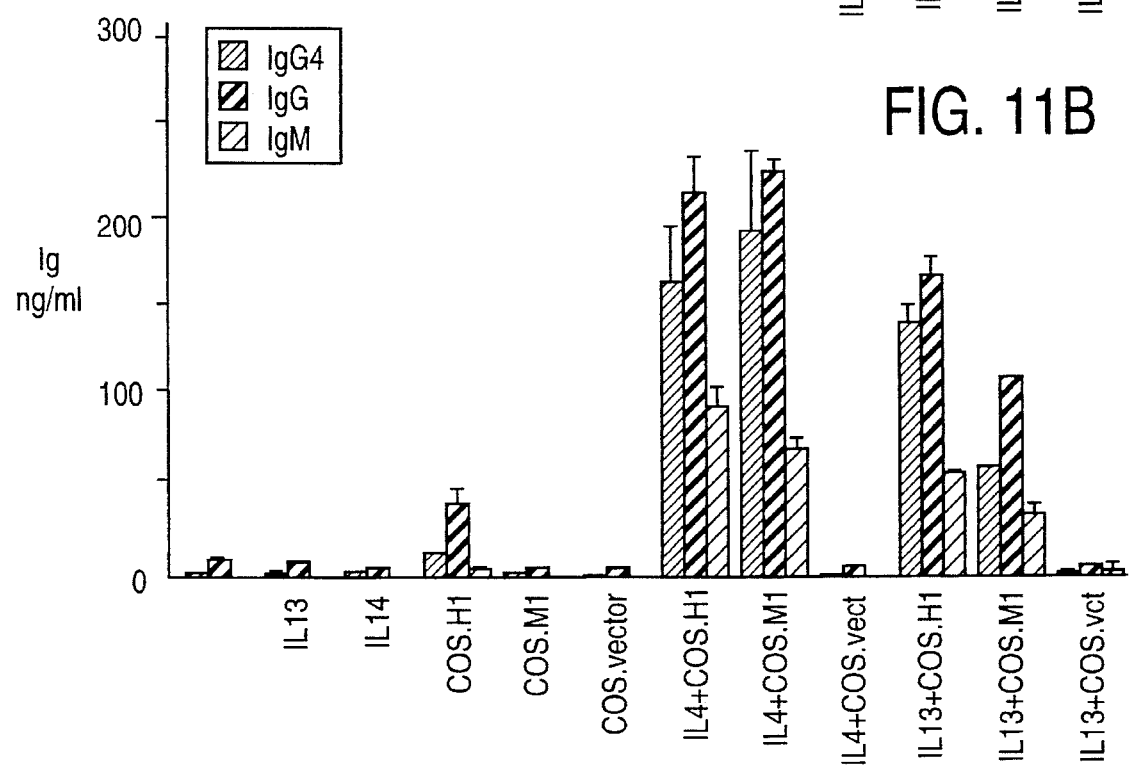

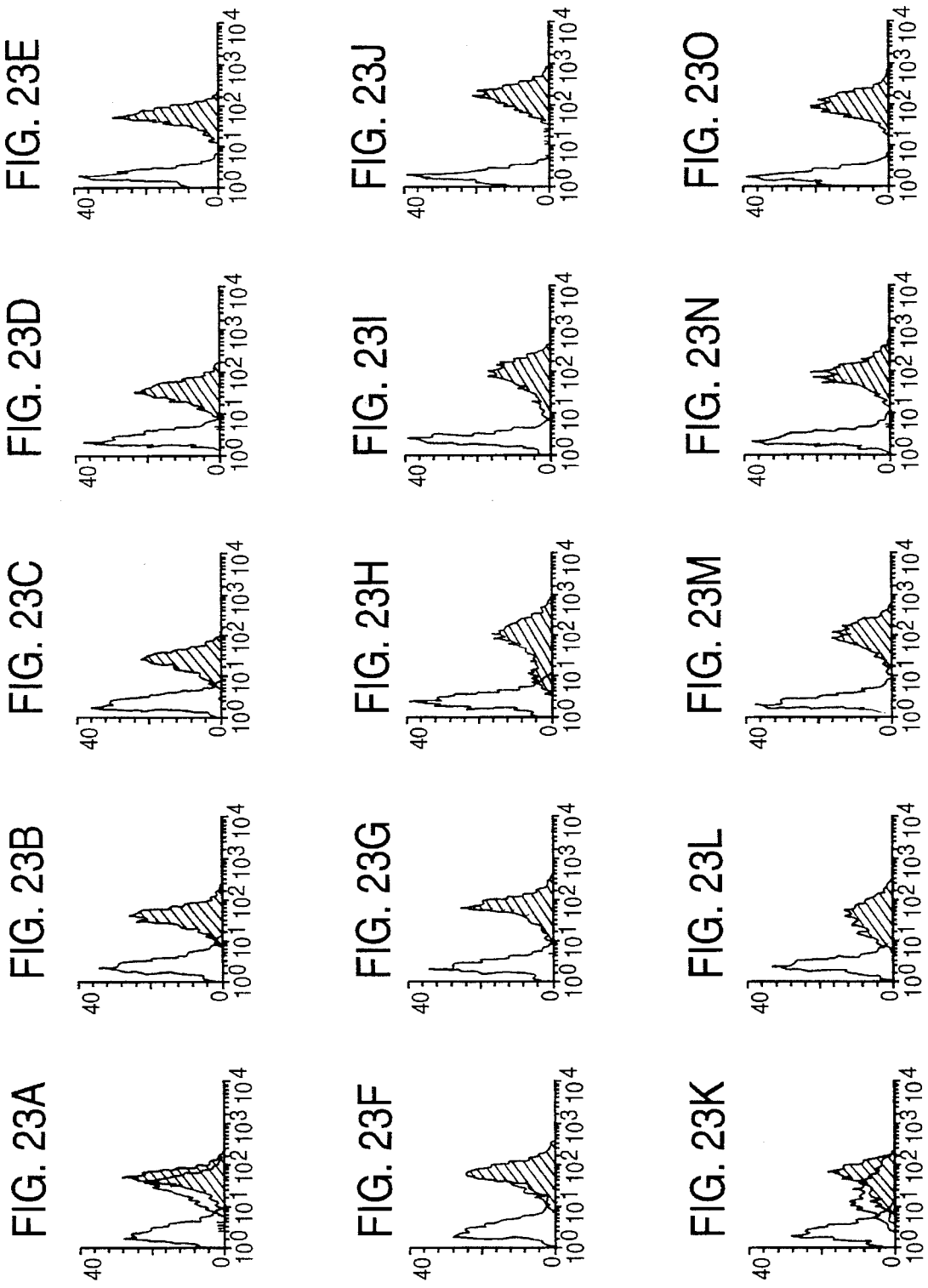

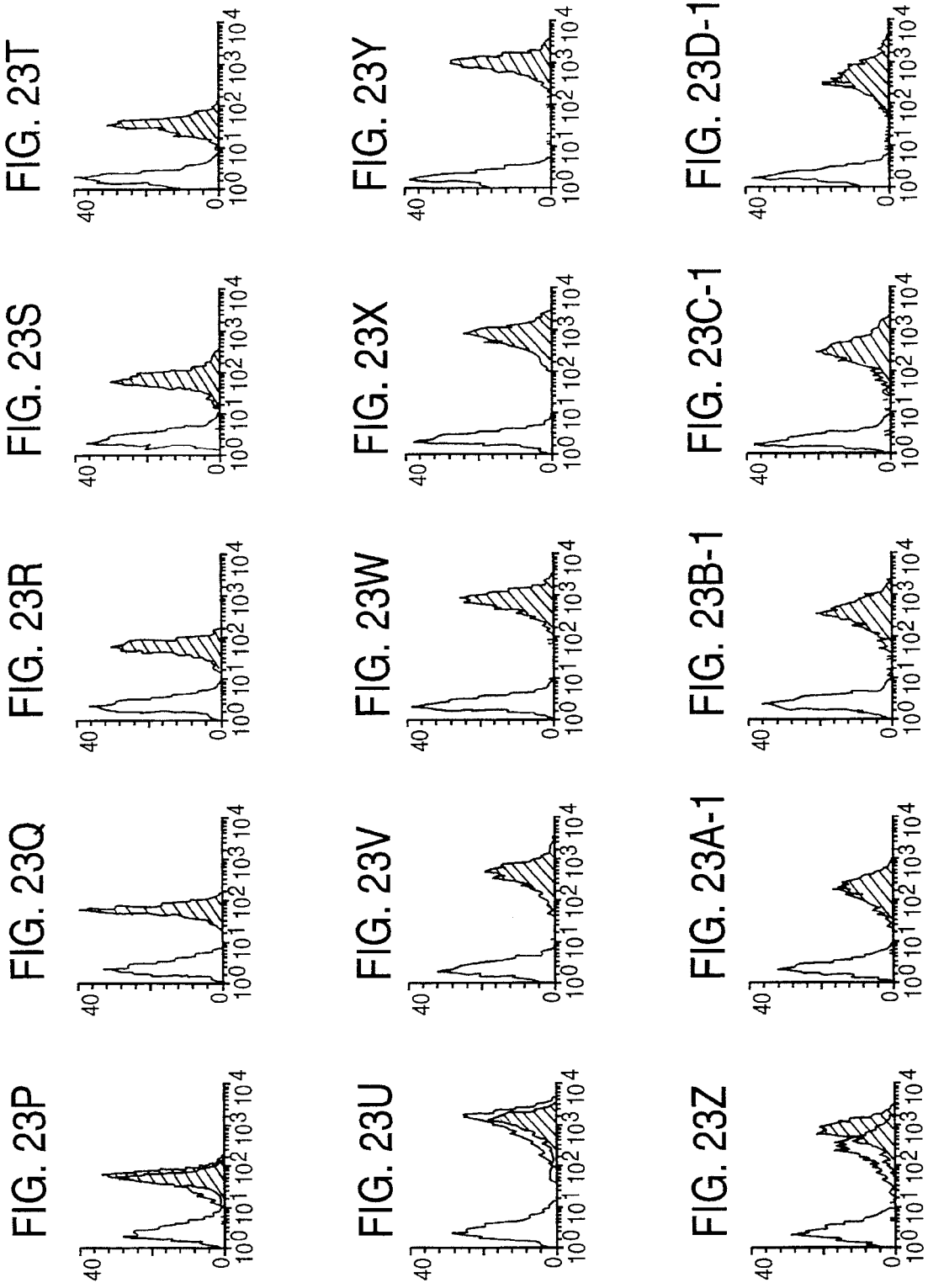

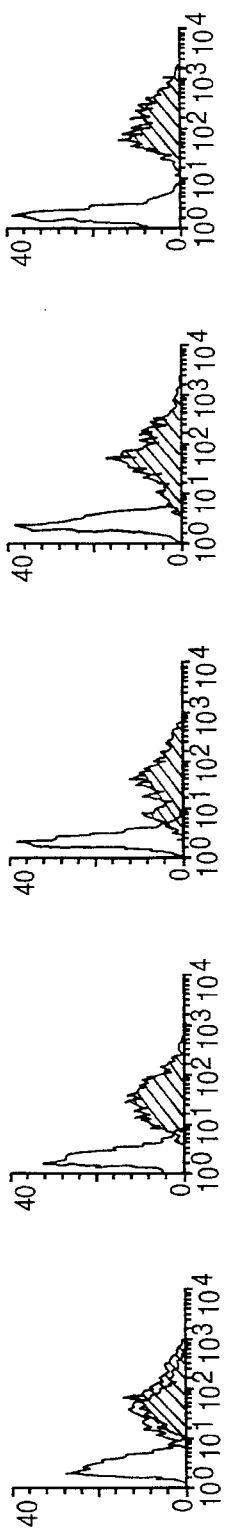
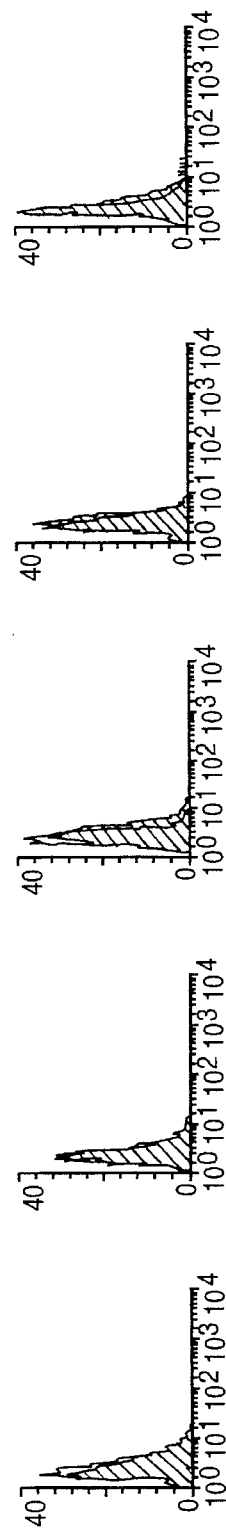
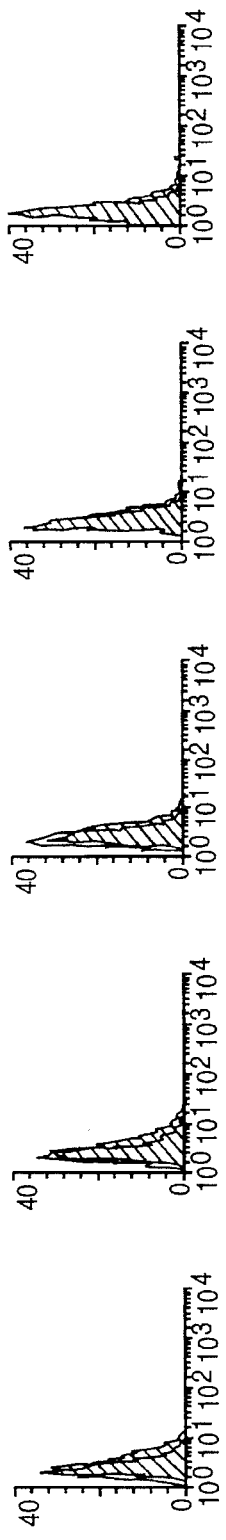

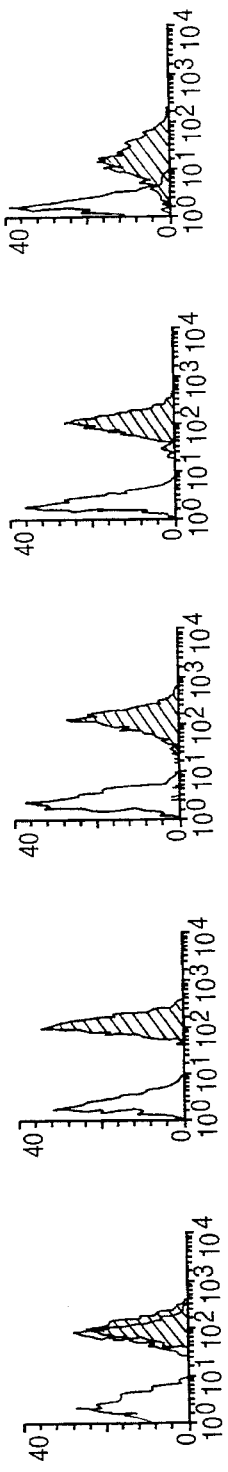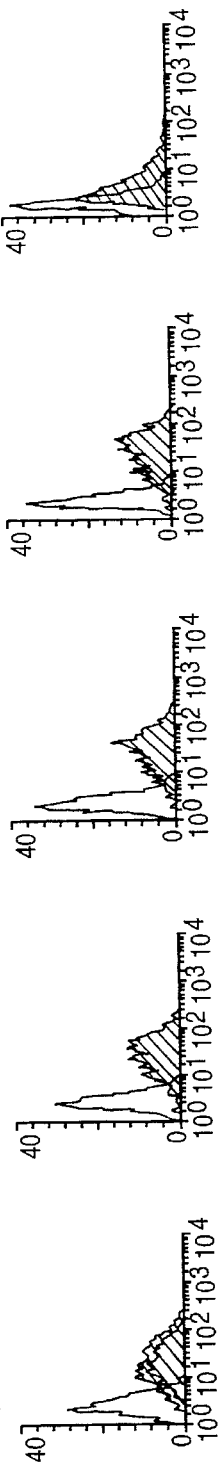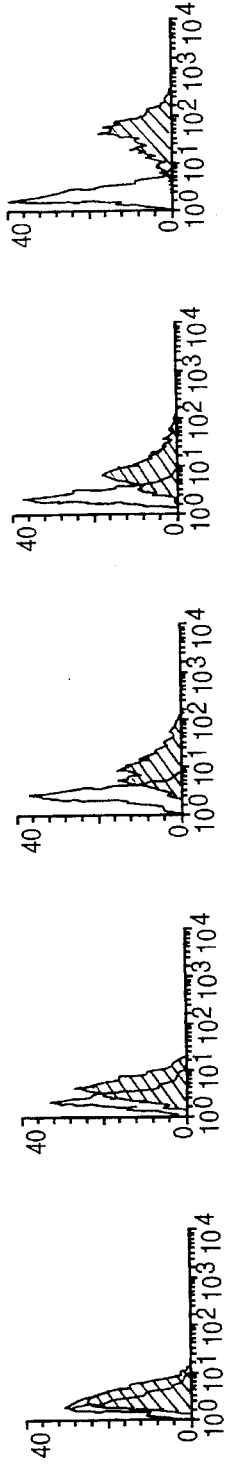

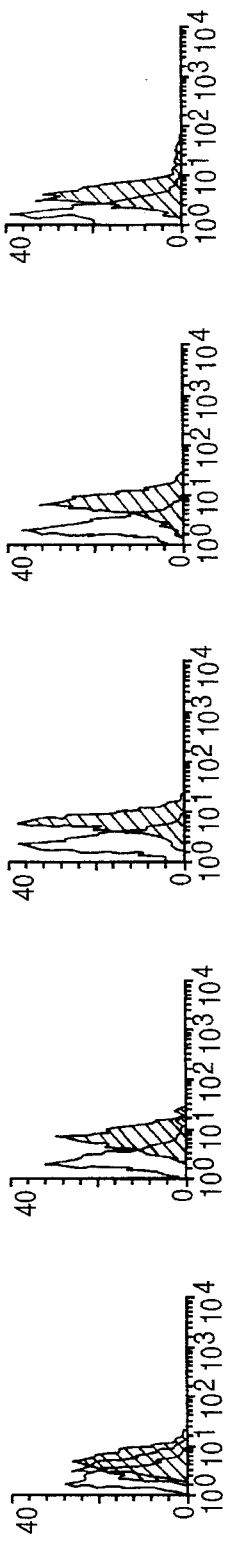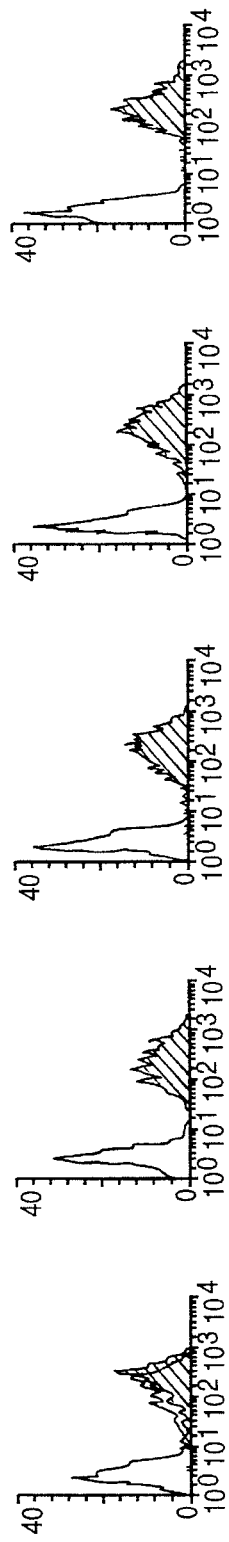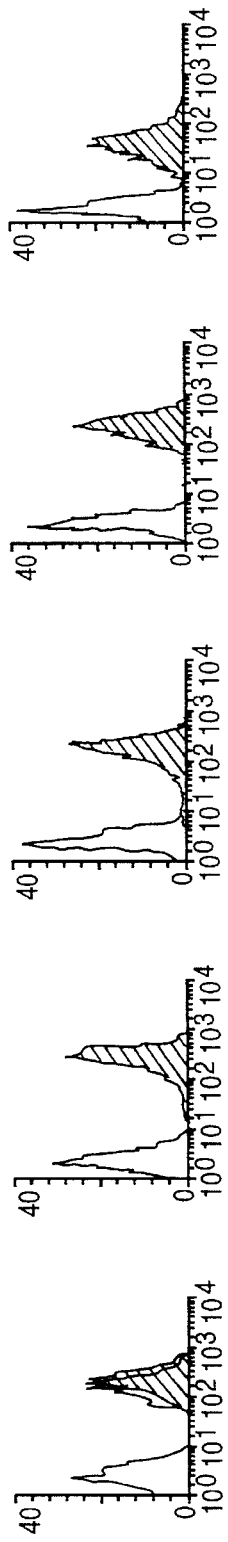

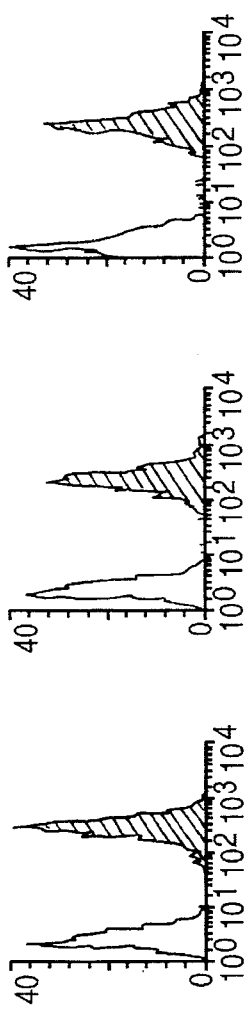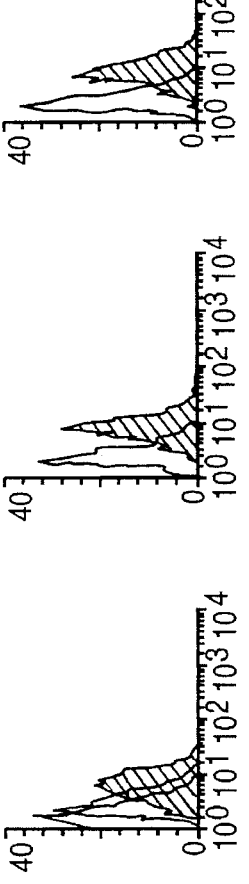
FIG. 23B-3, FIG. 23A-3, FIG. 23Z-2, FIG. 23Y-2, FIG. 23X-2, FIG. 23G-3, FIG. 23F-3, FIG. 23E-3, FIG. 23D-3, FIG. 23C-3

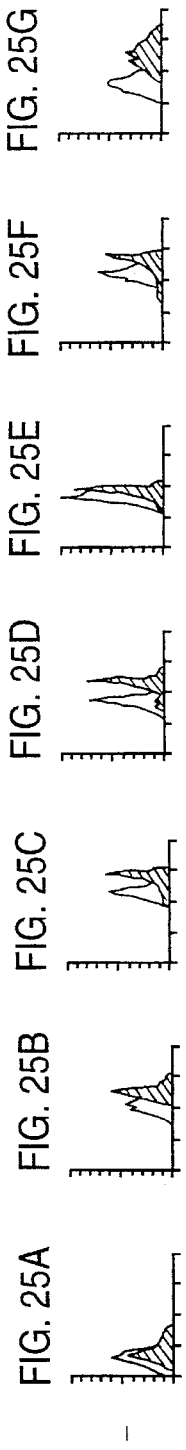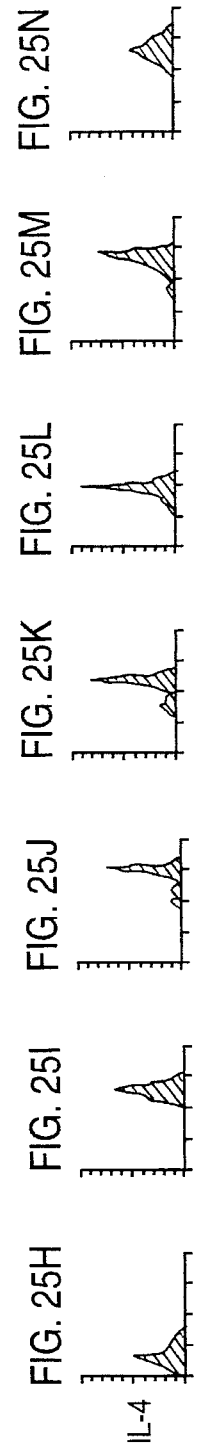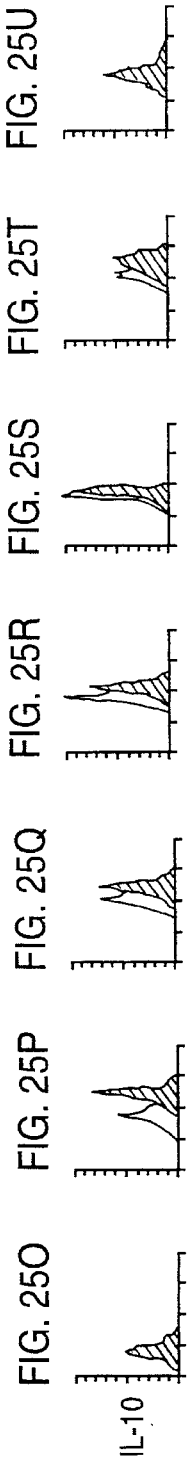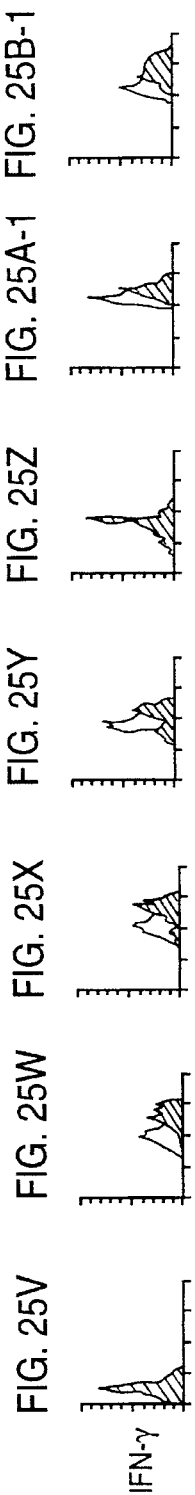

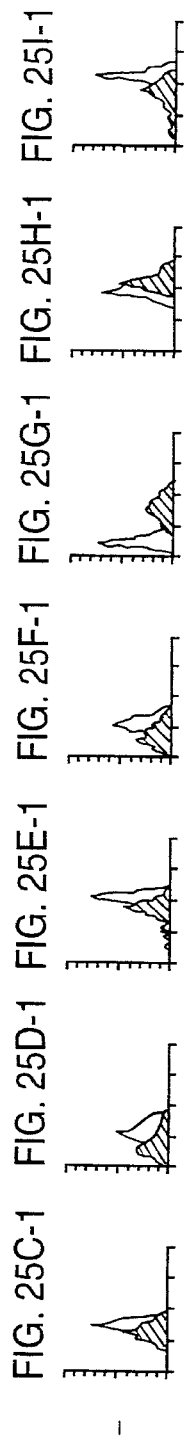
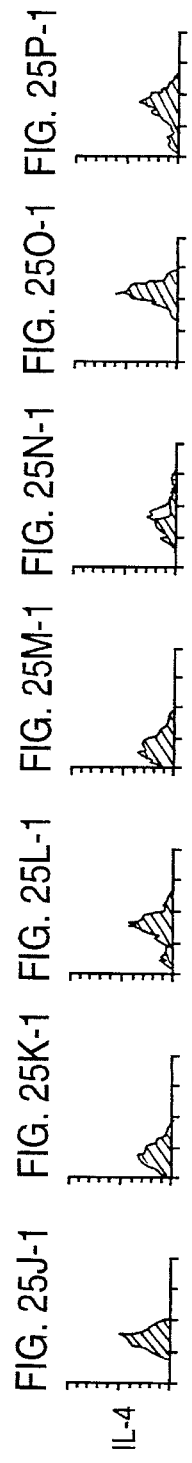
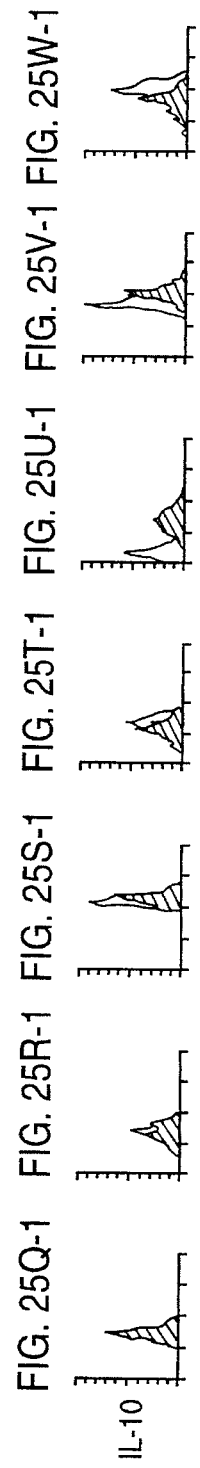
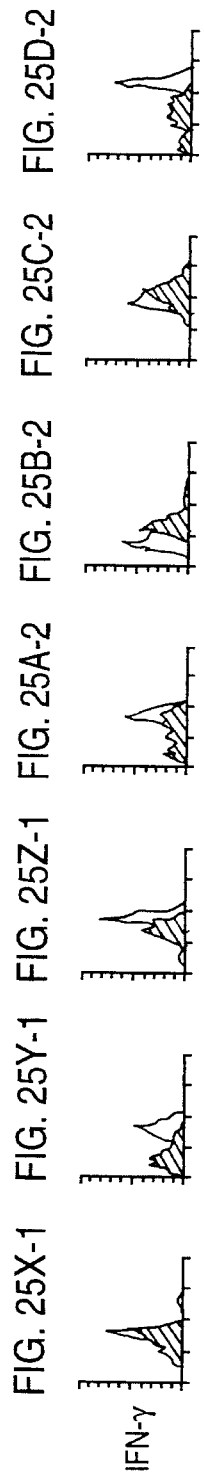

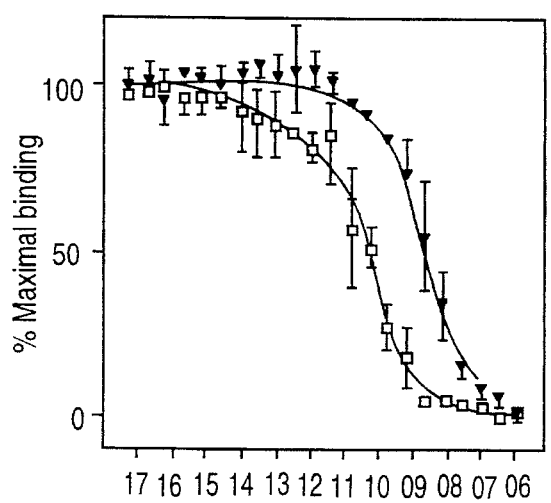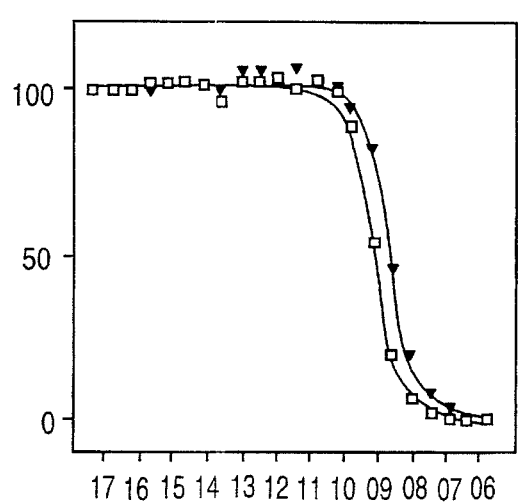

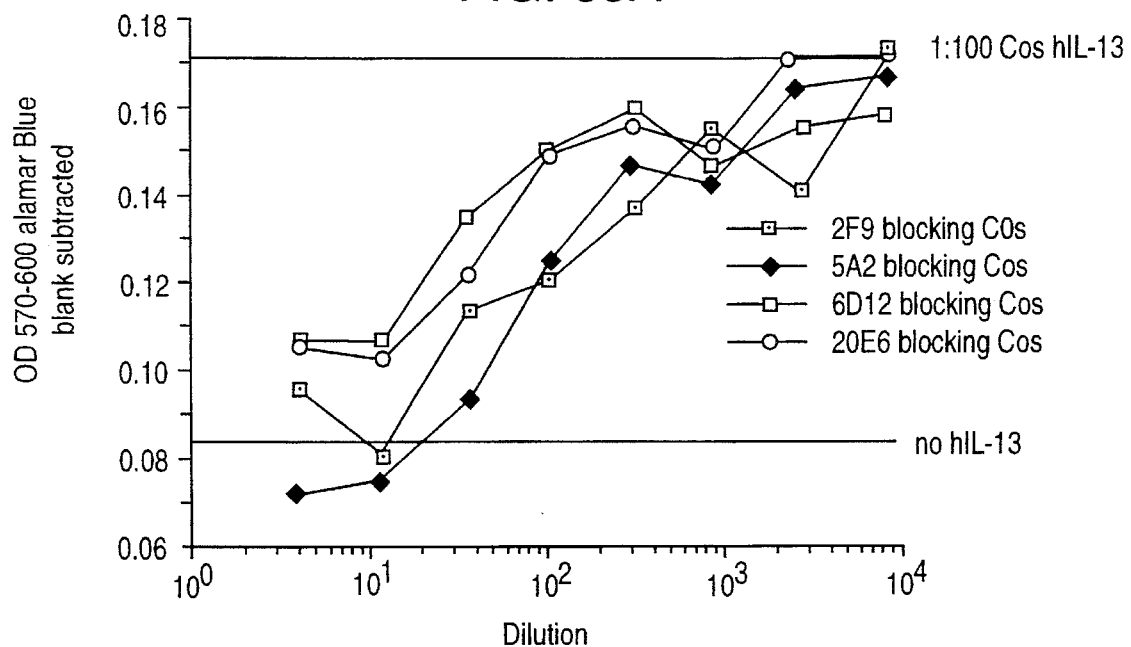
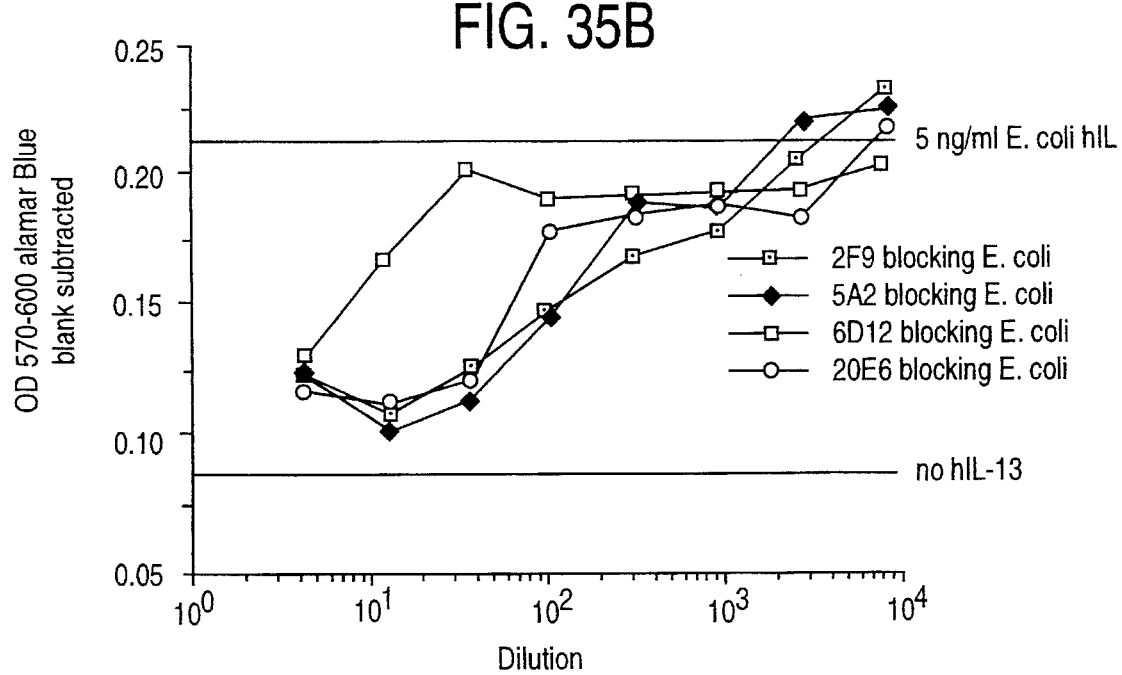

METHOD OF REFOLDING HUMAN IL-13

This application is a continuation-in-part of commonly assigned patent application U.S. Ser. No. 07/933,416, filed on Aug. 21, 1992, now abandoned, which is incorporated herein by reference.

FIELD OF THE INVENTION

The present invention relates to compositions and methods for affecting the human immune system. In particular, it provides nucleic acids, proteins, and antibodies which regulate immune system response and development. Diagnostic and therapeutic uses of these materials are also disclosed.

BACKGROUND OF THE INVENTION

Recombinant DNA technology refers generally to the technique of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, actually to control expression of the cDNA and thereby direct synthesis of the encoded product in the host.

For some time, it has been known that the mammalian immune response is based on a series of complex cellular interactions, called the "immune network." Recent research has provided new insights into the inner workings of this network. While it remains clear that much of the response does, in fact, revolve around the network-like interactions of lymphocytes, macrophages, granulocytes, and other cells, immunologists now generally hold the opinion that soluble proteins, known as lymphokines, cytokines, or monokines, play a critical role in controlling these cellular interactions. Thus, there is considerable interest in the isolation, characterization, and mechanisms of action of cell modulatory factors, an understanding of which should lead to significant advancements in the diagnosis and therapy of numerous medical abnormalities, e.g., immune system disorders.

Lymphokines apparently mediate cellular activities in a variety of ways. They have been shown to support the proliferation, growth, and differentiation of the pluripotent hematopoietic stem cells into vast numbers of progenitors comprising diverse cellular lineages making up a complex immune system. These interactions between the cellular components are necessary for a healthy immune response. These different cellular lineages often respond in a different manner when lymphokines are administered in conjunction with other agents.

Cell lineages especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and various other cells (including other T-cells) making up the immune network.

Another important cell lineage is the mast cell (which has not been positively identified in all mammalian species), which is a granule-containing connective tissue cell located proximal to capillaries throughout the body. These cells are found in especially high concentrations in the lungs, skin, and gastrointestinal and genitourinary tracts. Mast cells play a central role in allergy-related disorders, particularly anaphylaxis as follows: when selected antigens crosslink one class of immunoglobulins bound to receptors on the mast cell surface, the mast cell degranulates and releases mediators, e.g., histamine, serotonin, heparin, and prostaglandins, which cause allergic reactions, e.g., anaphylaxis.

Research to better understand and thus potentially treat therapeutically various immune disorders has been hampered by the general inability to maintain cells of the immune system in vitro. Immunologists have discovered that culturing these cells can be accomplished through the use of T-cell and other cell supernatants, which contain various growth factors, including many of the lymphokines.

The detection, isolation, and purification of these factors are extremely difficult, being frequently complicated by the complexity of the supernatants they are typically located in, the divergencies and cross-overs of activities of the various components in the mixtures, the sensitivity (or lack thereof) of the assays utilized to ascertain the factors' properties, the frequent similarity in the range of molecular weights and other characteristics of the factors, and the very low concentration of the factors in their natural setting.

As more lymphokines become available, primarily through molecular cloning, interest has heightened in finding clinical applications for them. Because of physiological similarities to hormones (e.g., soluble factors, growth mediators, action via cell receptors), potential uses of lymphokines have been analogized to the current uses of hormones, e.g. Dexter, Nature, Vol. 321, pg. 198 (1986). One hope is that the levels of lymphokines in a patient can be manipulated directly or indirectly to bring about a beneficial immune response, e.g., suppression in the case of inflammation, allergy, or tissue rejection, or stimulation or potentiation in the case of infection or malignant growth. Other potential clinical uses of lymphokines include maintaining and expanding in vitro populations of certain immune system cells of one person for eventual reintroduction into the same or another person for a beneficial effect. For example, investigations are currently underway to determine whether populations of lymphokine-activated killer T cells of a patient can be expanded outside his or her body then reinjected to bring about an enhanced antitumor response. Another potential clinical use of lymphokines, particularly colony stimulating factors, such as granulocyte-macrophage colony stimulating factor (GM-CSF), and factors which enhance their activities, is in stimulating blood cell generation, for example, in pre-or post-chemotherapy or radiation therapy against tumors, in treatment of myeloid hypoplasias, or in treatment of neutrophil deficiency syndromes, Dexter, Nature Vol. 321, pg. 198 (1986). Another area where such factors would be useful is in bone marrow transplant therapy, which is being used increasingly to treat aplastic anemia and certain leukemias. Regulation of rejection mechanisms will be useful in organ transplantation situations.

There are two properties of lymphokines that have important consequences for such clinical applications: individual lymphokines are frequently pleiotropic, and the biological effects of one lymphokine can usually be modulated by at least one other lymphokine, either by inhibition or by potentiation. Thus, in many cases, addition of a lymphokine can affect diverse physiological responses, and combination therapies will often be advantageous over administration of a single lymphokine.

Most cytokines are not constitutively produced, but are produced after activation of the producer cells. Production after activation is typically only short-lived, usually for only a few days. Typically, cytokines are effective in the picogram to nanogram per ml range.

Table 4 from Feldman (1992) "Cytokines", pp. 438–440 in Roitt et al. (eds) *The Encyclopedia of Immunology*, Academic Press, New York, lists common cytokines and their predominant activities. More detailed descriptions are available from specific chapters in the Encyclopedia directed towards each individual cytokine.

TABLE 4 common cytokines

| cytokine | properties |
| --- | --- |
| IL-1α | Activates lymphocytes, acute phase response, |
| IL-1β | strongly proinflammatory, radioprotective |
| IL-2 | Activators of T, NK, B, macrophages |
| IL-3 | Multiple actions, hemopoietic cell growth; precursors of mast cells |
| IL-4 | B cell activating factor, T cell activator, growth and stimulating factor |
| IL-5 | B cell growth and differentiation factor, regulates production of granulocytes and macrophages |
| IL-6 | B cell differentiating factor, activation of T and B cells, induces acute phase response |
| IL-7 | Pre-B and pre-T cell growth factor, T cell growth factor |
| IL-8 | Involved in migration of neutrophils and T cells |
| TNF-α | Proinflammatory cytokine, induces acute phase response, thrombosis, cachexia |
| TNF-β (lymphotoxin) | as above |

A number of small inducible proteins secreted by leukocytes were reported by Brown et al. (1989) *J. Immunol.* 142:679–687. These proteins were described as part of a family of small, secreted, and inducible mouse and human proteins which are distantly related to a family of growth and inflammatory factors. It describes a class of "P600 induction-specific cDNA clones" but no biological activity was reported. No human equivalent had been isolated until now.

From the foregoing, it is evident that the discovery and development of new lymphokines could contribute to new therapies for a wide range of degenerative or abnormal conditions which directly or indirectly involve the immune system and/or hematopoietic cells. In particular, the discovery and development of lymphokines which enhance or potentiate the beneficial activities of known lymphokines would be highly advantageous. The present invention provides new interleukin compositions and related compounds, and methods for their use.

SUMMARY OF THE INVENTION

The present invention is directed to human interleukin-13 (IL-13) and its biological activities. It includes nucleic acids coding for polypeptides themselves and methods for their production and use. The nucleic acids of the invention are characterized by their homology to cloned complementary DNA (cDNA) sequences enclosed herein, and/or by functional assays for IL-13 activity applied to the polypeptides, which are typically encoded by these nucleic acids. Methods for modulating or intervening in the control of an immune response are provided.

The invention is based, in part, on the discovery and cloning of human cDNAs which are capable of expressing proteins having IL-13 activity. cDNA clones include human cDNA inserts of plasmid vectors pB21.2Bf and paI0.66, which contain partial and full length sequences, respectively. Equivalent vectors may be constructed by using polymerase chain reaction (PCR) techniques and the sequences of the inserts.

The present invention provides an isolated nucleic acid comprising a segment homologous to a sequence of human IL-13 disclosed in Table 1. Typically, the segment is at least about 50 nucleotides, and will often encode a protein exhibiting a biological activity characteristic of a human IL-13, e.g., an amino acid sequence of Table 1. In other embodiments, the segment is at least 80% homologous to the coding sequence disclosed in Table 1. In other embodiments, the nucleic acid will further encode a second protein. The invention also encompasses a vector or a cell containing the nucleic acid.

Alternatively, the nucleic acid can be a recombinant nucleic acid with a segment homologous to a sequence of human IL-13 disclosed in Table 1. Usually, this will encode a human IL-13 or may encode a fusion protein. The invention also embraces vectors, e.g., expression vectors, and cells containing the nucleic acid.

In alternative embodiments, the invention provides an isolated human IL-13 protein or peptide. In some embodiments, the protein has a full length sequence disclosed in Table 1, or will be a mutein thereof, and may include an altered post-translational modification pattern, e.g., glycosylation variants. Other embodiments include a fusion protein comprising a peptide of human IL-13, and cells containing such.

In another embodiment, the invention provides a method of refolding a guanidine denatured mouse P600 or human IL-13 protein comprising solubilizing said protein in 6M guanidine at a concentration of about 2.5 mg/ml; diluting the guanidine to about 60 mM over a period of hours in the presence of both reduced and oxidized glutathione; and incubating the diluted guanidine solution for at least about 12 hrs.

The invention also provides an antibody which specifically binds to human IL-13, e.g., a mouse, a monoclonal, or a chimeric antibody. It also provides a method of supporting monocyte or B cell profileration in a sample, or sustaining viability of said cell, by contacting the sample with an effective amount of human IL-13, alone or in combination with another cytokine, e.g., IL-4 or IL-10. In some embodiments, methods are provided for detecting human IL-13 in a sample by contacting the sample with a binding composition which recognizes human IL-13 or a nucleic acid which hybridizes to a nucleic acid encoding a human IL-13. The binding composition can be a monoclonal antibody, and the sample can be a blood sample.

In other embodiments, the invention provides methods of modulating the growth of a hemopoietic B cell or T cell by contacting the cell with an effective amount of an IL-13 and IL-4 combination or antagonists thereto, including an IL-4 antagonist. The hemopoietic cell growth can be accompanied by cell differentiation to antibody producing cells.

The invention further provides methods of modulating proliferation of a myeloid precursor cell by contacting the cell with an effective amount of a human IL-13, mouse P600, or agonists or antagonists thereof. Often the modulating proliferation is accompanied by cell differentiation.

Methods of modulating the immune response to an infection or allergen are provided, e.g., by administering an effective amount of a human IL-13, mouse P600, or agonists or antagonists thereof, including an IL-4 antagonist. And the invention provides methods of sustaining cell viability of a myeloid precursor cell by contacting the cell with an effective amount of a human IL-13, a mouse P600, or an agonist or antagonist thereof, including an IL-4 antagonist, and combinations with additional cytokines, including IL-4 and IL-10.

BRIEF DESCRIPTION OF THE DRAWINGS

FIG. 2A shows dose dependence with murine P600. $^3$H-TdR uptake was measured at day 3. FIG. 2B shows time kinetics with 30 ng/ml mP600, 50 U/ml IL-4, 100 ng/ml hIL-10. $^3$H-TdR uptake was measured at day 3 and 4.

FIG. 3A shows dose dependence with murine P600. FIG. 3B shows dose dependence with human IL-13. $^3$H-TdR uptake was measured at day 6. FIG. 3C shows time kinetics with 30 ng/ml hIL-13, 50 U/ml IL-4, 100 ng/ml IL-10. $^3$H-TdR uptake was measured at day 6, 9, and 12. FIG. 3D shows cell counts for each.

FIG. 4A: With 50 U/ml IL-4. FIG. 4B: With 100 ng/ml IL-10. ($^3$H)TdR uptake was measured at day 6. FIG. 4C: Time course.

FIGS. 5A–5E show IL-13 induces anti-CD40 activated B lymphocytes to secrete IgE. $5\times10^4$ purified B cells were cultured on $2.5\times10^3$ irradiated CDw32 L cells with 0.5 µg/ml mAb89 with or without increasing concentrations of mIL-13 with or without 50 U/ml IL-4. FIG. 5A shows ($^3$H)TdR uptake; FIG. 5B shows IgG production; FIG. 5C shows IgA production; FIG. 5D shows IgM production; and FIG. 5E shows IgE production. IgE levels (ng/ml) were determined after a culture period of 10 days. They are expressed as mean±SD values of quadruplicate determinations.

FIGS. 6A–6D show IL-13 induces CD23 and transferring receptors on a subpopulation of B cells. $5\times10^4$ purified B cells were cultured on $2.5\times10^5$ irradiated CDw32 L cells with 0.5 µg/ml mAB89 with or without 50 U/ml of IL-4 or hIL-13. After six days, cells were harvested and stained with FITC labeled anti-CD23 mAb25 (FIGS. 6A–6C) or FITC labeled anti-transferrin receptor (FIG. 6D) and samples were analyzed with a FACSan. Horizontal axes illustrate log of fluorescence and vertical axes indicate relative cell numbers.

FIG. 8A: B cell profileration, ($^3$H)TdR uptake was measured at day 6. FIG. 8B: IgE secretion. IgE levels were determined by ELISA in day 12 supernatants. Cultures were performed in triplicates and means±SD, of one representative experiment out of three for FIG. 8A and one representative experiment of two for FIG. 8B, are presented.

FIGS. 10A–10O illustrate the effect of human IL-13 on differentiation of B cells as determined by evaluating surface Ig. FIGS. 10A–10E show the results of culturing activated human B cells with human IL-13, IL-4 and stimulatory activated B21 T cells. FIGS. 10K–10O show results of similar experiments where the B cells were stimulated with anti-CD40 antibodies.

FIGS. 11A–11B show induction of Ig synthesis by IL-13 or IL-4 and COS cells expressing CD40L.

FIG. 13A: Northern analysis of 10 µg of mRNA isolated from the CD4$^+$ T-cell clone B21 activated with 1 µg/ml PHA for 4 h. Poly A$^+$ RNA was isolated as described for A10 mRNA in Materials and Methods. FIG. 13B: PCR analysis. lane 1, H$_2$O; lane 2, B21 CD4$^+$ T-cell clone; lane 3, HI CD4$^+$ T-cell clone; lane 4, B21 activated for 4 h with 1 µg/ml PHA; lane 5, H2 CD4$^+$ T-cell clone; lane 6, A10 CD8$^+$ T-cell clone; lane 7, S40 CD8$^+$ T-cell clone; lane 8, S11 CD8$^+$ T-cell clone; lane 9, solo γδ T-cell clone; lane 10; purified NK cells; lane 11, purified CD20$^+$ B cells; lane 12, JY B cells; lane 13, heart; lane 14, brain; lane 15, small intestine; lane 16, kidney; lane 17, fetal liver; lane 18, fetal bone marrow; lane 19, fetal thymus. PCR products were electrophoresed through 1.2% agarose and visualized under UV by staining with ethdium bromide. PCR products were the expected sizes, 730 bp and 500 bp for CD40L and HPRT respectively, and were confirmed as CD40L and HPRT cDNA's by Southern analysis using probes specific for these genes.

FIGS. 14A–14D show induction of CD40L mRNA. The CD4$^+$ T-cell clone B21 was activated for the times indicated with: (FIG. 14A) Calcium ionophore A23187 (500 ng/ml)+PMA (1 ng/ml); (FIG. 14B) anti-CD3 mAb (1 µg/ml); (FIG. 14C) anti-CD3 mAb (1 µg/ml)+PMA; or (FIG. 14D) PHA (0.2 µg/ml)+PMA (0.1 mM). RNA was isolated and subjected to Northern analysis.

FIGS. 16C and 16D show the effects of neutralizing anti-IL-4 mAb ($\alpha$IL-4, 10 μg/ml) on IL-13- (FIG. 16C) and IL-4- (FIG. 16D) induced IgE synthesis, respectively. FIG. 16D also shows IgE synthesis induced by combination of IL-4 and IL-13 (500 U/ml). The data represent mean±SEM of IgE levels of 12 replicates in three experiments (16A–16B). In FIGS. 16C–16D one representative experiment out of three is shown.

FIG. 19A is with CD19+, sIGM+ B cells; and FIG. 19B is with CD19+, CD10+, sIGM- pre-B cells.

FIG. 21A shows cells after 10 days in medium supplemented with IL-10. FIG. 21B shows cells after 5 days in medium supplemented with both IL-10 and mouse P600. Similar results are obtained using human IL-13.

FIGS. 22A through 22Y-1 illustrate the effect of human IL-13 on cell differentiation, as determined by FACS analysis. Adherent human PBMC's were grown for 5 days. During this time, the cells detach from the plates. The detached cells, treated with the indicated factor, are analyzed by FACS analysis for various markers. Note that the mean and dispersion of labeling of various markers are affected by growth in the presence of the mouse P600. The results of FACS analysis for: CD11a, CD11b, CD11c, and CD54 are shown in FIGS. 22A–22C, 22D–22F, 22G–22I, and 22J–22L, respectively; Class I MHC marker W6/32, Class II MHC markers Q5/13, PdV5.2, and L-3 in FIGS. 22M–22O, 22P–22R, 22S–22U, and 22Y–22X, respectively; CD58, CD32, CD16, and CD23, in FIGS. 22Y through 22A-1, 22B-1 through 22D-1, 22E-1 through 22G-1, and 22H-1 through 22J-1, respectively; IL-2R$\alpha$ (CD25) CD44, CD14, and CD18 in FIGS. 22K-1 through 22M-1, 22N-1 through 22P-1, 22Q-1 through 22S-1, and 22T-1 through 22V-1, respectively; and B7 in FIGS. 22W-1 through 22Y-1. In each series, the first panel corresponds to growth in normal medium, the second panel corresponds to growth with IL-10 added, and the third panel corresponds to growth with mouse P600 added.

FIGS. 23-A through 23G-3 show the differences in activity of different sources of mouse P600 and human IL-13.

COS7 produced mouse P600 and human IL-13 and *E. coli* produced mouse P600 are shown. FIGS. 23A–23Y shows analysis of CD11a, CD11b, CD11c, CD54, and MHC class I markers in FIGS. 23A–23E, 23F–23J, 23K–23O, 23P–23T, and 23U–23Y, respectively; FIGS. 23Z through 23X-1 show analysis of MHC class II markers Q5/15, PdV5.2, and L-3, and CD7 and CD32 in FIGS. 23-Z through 23D-1, 23F-1 through 23I-1, 23N-1 through 23S-1, and 23T-1 through 23X-1, respectively; FIGS. 23Y-1 through 23W-2 show analysis of CD 16, CD25(IL-2Rn), CD44, and CD14 markers in FIGS. 23Y-1 through 23C-2, 23D-2 through 23H-2, 23I-2 through 23M-2, 23N-2 through 23R-2, and 23S-2 through 23W-2, respectively; and FIGS. 23X-2 through 23G-3 show analysis of CD18 and B7 markers in FIGS. 23X-2 through 23B-3 and FIGS. 23C-2 through and 23G-2, respectively. The first panel in each group corresponds, on the far left to cells without fluorescent markers, to normal cells, and to COS supernatants from mock transfected cells. The second panel of each group corresponds to growth with IL-6 added. The third panel of each group corresponds to growth with mouse P600 derived from transfected COS cell supernatants. The fourth panel of each group corresponds to growth with human IL-13 derived from supernatants of transfected COS cells. The fifth panel of each group corresponds to growth in the presence of *E. coli* produced mouse P600.

FIGS. 25A through 25D-2 show the effect of cytokines on the expression of cell surface antigens by monocytes. Human monocytes were cultured in medium, IL-4 (400 U/ml), IL-10 (200 U/ml) or IFN-$\gamma$ (100 U/ml) in the (light) absence or the (hatched) presence of IL-13 (50 ng/ml) for 120 hrs and the expression of cell surface antigens was determined by indirect immunofluorescence. In FIGS. 25A through 25B-1, panels in columns 1, 2, 3, 4, and 5 are control, CD11b, CD11c, CD18, CD29, VLA-5, and HLA-DR/DP, respectively. In FIGS. 25C-1 through 25D-1, panels in columns 1, 2, 3, 4, and 5 are B7, CD16, CD32, CD64, CD23, CD13, and CD14, respectively. Panels in rows are treated as indicated.

(FIG. 28A) 1.6×10$^6$ TF-1 cells per point. (FIG. 28B) 1.0×10$^6$ Ba/F3 hIL-4R-S cells per point. Abscissa in −log [M] protein.

(FIG. 29A) Th0 CD4$^+$ B21 T cells. (FIG. 29B) PHA-activated PBMNC. Abscissa in −log [M] protein.

FIGS. 30A–30B show that hIL-4.Y124D is specifically defective in binding to high affinity IL-4R on TF-1 cells. Various amounts of non-labeled hIL-4 (open square) and hIL-4.Y124D (solid triangle) were incubated for 2 h at 4° C. with 10$^{-10}$M I$^{125}$-hIL-4 and cells. I$^{125}$-hIL-4 bound to cells was then determined. Error bars are standard deviations (n=2). Other experiments, including some that use hIL-4-Y124D as the labeled ligand, gave analogous results. (FIG. 30A) 1.26×10$^6$ (TF-1 cells per point. 10$^{-6}$M hGM-CSF did not compete for binding of I$^{125}$-hIL-4. (FIG. 30B) 1.8×10$^6$ Ba/F3 hIL-4R-S cells per point. 10$^{-6}$M mIL-3 did not compete for binding of I$^{125}$-hIL-4. Analysis with the Ligand computer program of the combined data for binding to Ba/F3 hIL-4R-S cells estimated K$_d$=1.6×10$^{-10}$M (%CV or standard error divided by the value=15%) for hIL-4 and K$_d$=6.2×10$^{-10}$M (%CF=15%) for hIL-4.Y124D. Abscissa in −log [M] protein.

FIGS. 35A–35B show blocking activity of various monoclonal antibodies of IL-13 effect on TF-1 cells. Two different sources of IL-13 are tested, from COS supernatants (FIG. 35A) and *E. coli* (FIG. 35B).

FIG. 36 is JES10 Ab on 1:15 dilution of COS h1L-13. FIGS. 37A–37B are various JES10 sups. on 0.5 μg/ml *E. coli* IL-13.

DETAILED DESCRIPTION OF THE PREFERRED EMBODIMENTS

Outline

Figure 1:
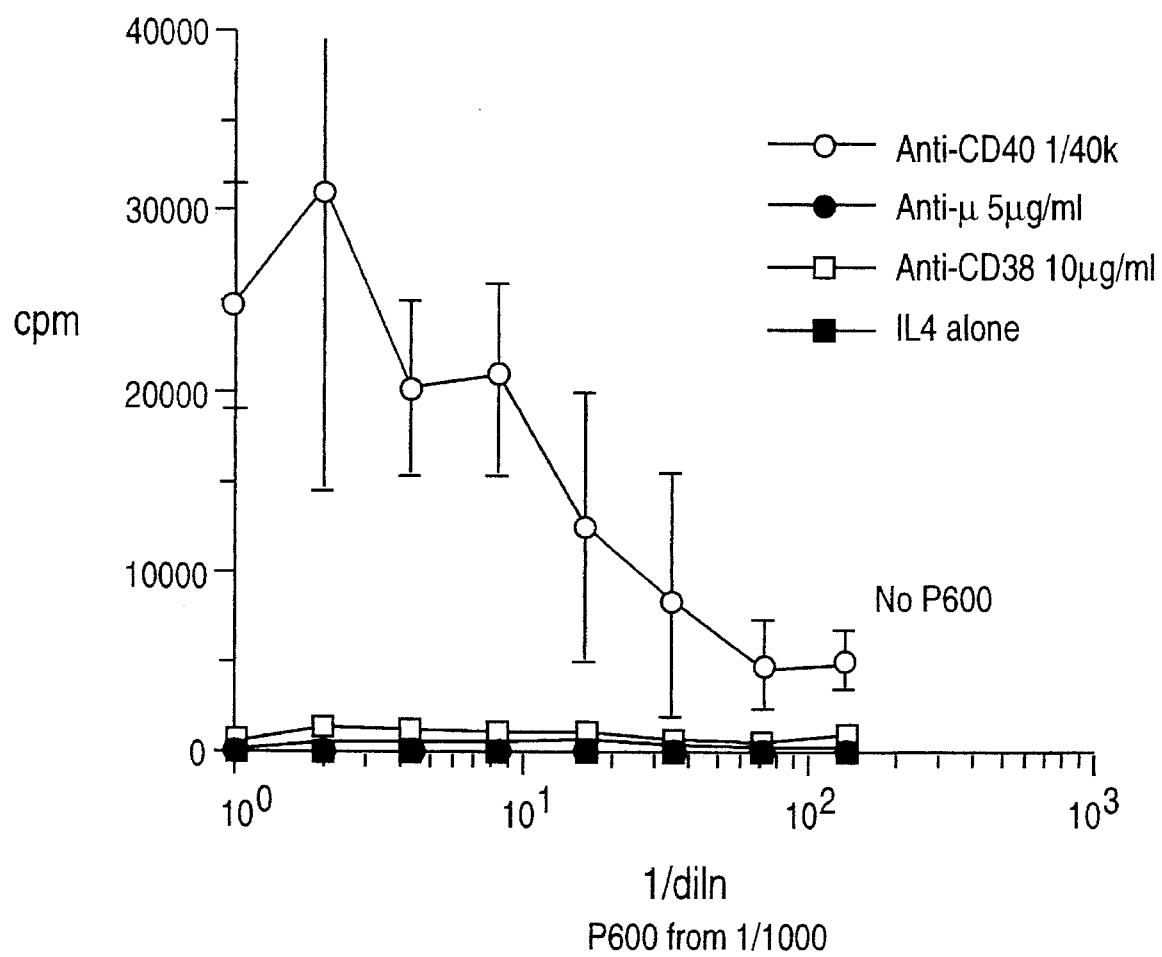
FIG. 1 illustrates the ability of mouse P600 made from *E. coli* to stimulate or costimulate profileration of large in vivo activated mouse B cells.

I. General
II. Activities
  A. B cells
    1. cofactor/factor proliferation; cell viability
    2. sustained survival of B cells; selectivity
    3. modification of Ig surface, markers
    4. effects on CD40
    5. IgE switching
  B. PBMC and macrophages
    1. induction of morphological change
    2. modification of cell surface markers
    3. nitric oxide synthesis
    4. IL-β; IL-6
    5. ADCC
  C. IL-4 antagonist; interactions
  D. overview of biological activities
III. Nucleic acids
  A. encoding fragments, sequence, probes
  B. mutations, chimeras, fusions
  C. making nucleic acids
  D. vectors, cells comprising
IV. Proteins, Peptides
  A. fragments, sequence, immunogens, antigens
  B. muteins
  C. agonists/antagonists, functional equivalents
  D. making proteins
V. Methods to make nucleic acids, proteins
VI. Antibodies
  A. polyclonals
  B. monoclonal, Kd
  C. anti-idiotypic antibodies
  D. hybridoma cell lines
VII. Uses of IL-13 compositions, nucleic acids
  A. ELISA
  B. assay mRNA encoding
  C. qualitative/quantitative
  D. kits
VIII. Therapeutic compositions, methods
  A. combination compositions
  B. unit dose
  C. administration I. General The present invention provides the amino acid sequence and DNA sequence of human interleukin molecules having particular defined properties, both structural and biological, designated herein as human interleukin-13 (IL-13). This molecule was obtained using a mouse gene encoding a related mouse protein designated P600.

Some of the standard methods are described or referenced, e.g., in Maniatis et al. (1982) *Molecular Cloning, A Laboratory Manual,* Cold Spring Harbor Laboratory, Cold Spring Harbor Press; Sambrook et al. (1989) *Molecular Cloning: A Laboratory Manual,* (2d ed.), vols 1–3, CSH Press, N.Y.; Ausubel et al., *Biology,* Greene Publishing Associates, Brooklyn, N.Y.; or Ausubel et al. (1987 and periodic supplements) *Current Protocols in Molecular Biology*, Greene/Wiley, New York; all of which are each incorporated herein by reference.

Isolation of the human gene presented obstacles which prevented others from succeeding. Earlier attempts to isolate the human homologue of the mouse P600 protein using oligonucleotide probes and primers ended in failure. Difficulties in using such methods often arise from the inability to select primers of sufficient length which provide a sufficient signal to noise ratio to allow isolation of correct clones. Moreover, many mouse cell lines fail to produce detectable levels of mRNA for the mouse gene, even using highly sensitive polymerase chain reaction (PCR) techniques. Because the homology of the mouse and human genes is relatively low, about 60%, relatively long probes are needed to provide sufficiently high homology to assure a discernible positive signal by hybridization. But before isolation of the human gene, it was impossible to know the degree of homology or to predict which regions of the target gene exhibit high homology from which the probe should be selected. In fact, multiple attempts using various probes, alone or in combination, to isolate the gene from various libraries ended in failure. The library from which an intermediate clone of less than full length was isolated failed to provide the correct clone when screened with oligonucleotide or genomic DNA probes. In fact, clones isolated using the genomic mouse sequence as a probe turned out to be false positives, i.e., they did not encode the human equivalent as evaluated by sequencing. At least one other research group also failed to isolate the gene using a similar approach.

Applicants devised a different approach which successfully led to isolating a human homologue to the mouse P600 gene. Instead of using oligonucleotide probes of relatively short length, a probe corresponding to nearly the full length coding region of the mouse gene was used. Moreover, the cell type used to make the cDNA library was quite important. As indicated above, expression of the mouse gene varied dramatically in different cell types. The human B21 cells used to produce the cDNA library which provided the positive clone described herein turn out to be a cell type which expresses the human gene at a relatively high level.

However, this fact was not apparent when the earlier screening was performed. In addition, the positive signal arising from the hybridization was difficult to distinguish from background. The hybridization and wash conditions used in the screening were quite important, and slightly more harsh wash conditions could have easily eliminated any positive signal. See, e.g., Wetmur and Davidson (1968) *J. Molecular Biology* 31:349–370, which is incorporated herein by reference.

The initially isolated clone, designated pB21.Bf2, was less than full length. Isolating a full length clone required use of yet another cDNA library. Thus, the isolation of the full length human clone, designated pA10.66 required investment of significant time and resources. After knowing the regions of high homology between the mouse and human genes, isolation using oligonucleotide probes of relatively short length would now be relatively straightforward.

The procedure used to isolate the human IL-13 is broadly set forth below. A cDNA library, constructed in a pCD vector, was prepared from RNA isolated from human B21 cells. These cells are human T cells which, it is now understood, exhibit many of the same markers as the cells providing the mouse clone. Several modifications and unusual techniques were utilized to overcome problems associated with isolating a cDNA clone when probing the library with oligonucleotides. In particular, instead of using oligonucleotide probes of relatively short length, a near full length double stranded probe of about 400 nucleotides was selected. Although previous attempts using a B21 derived cDNA library had failed, the near full length double stranded probe provided faint positive signals. Although several experienced molecular biologists were highly skeptical that the faint signals were real, continued pursuit of those signals led to ultimate success.

The initial human isolate showed homology to the mouse gene, but lacked part of the amino terminal coding portion. Thus, this intermediate isolate was less than a full length clone. Attempts to isolate a full length clone from the B21 derived library failed. However, upon selection of another cDNA library, the near full length human probe allowed isolation of the full length human clone.

A complete nucleotide and corresponding amino acid sequence of the pA10.66 clone is shown in Table 1. This sequence corresponds to SEQ ID NO: 1. Table 1 discloses both the nucleotide sequence of the sequence encoding IL-13, and its deduced amino acid sequence. Table 2 compares the gene sequence of Table 1 to a published gene sequence of the mouse P600 protein. Table 3 compares the amino acid sequences of the human IL-13 and the published mouse P600 sequence.

TABLE 1

Nucleotide and amino acid sequence of huIL-13. SEQ ID NO: 1 and 2.

```
            10          20          30          40     >   50              59
TTCGGCATCC GCTCCTCAAT CCTCTCCTGT TGGCACTGGG CCTC ATG GCG CTT TTG TTG
                                                  MET Ala Leu Leu Leu 68              77              86              95          104             113
ACC ACG GTC ATT GCT CTC ACT TGC CTT GGC GGC TTT GCC TCC CCA GGC CCT GTG
Thr Thr Val Ile Ala Leu Thr Cys Leu Gly Gly Phe Ala Ser Pro Gly Pro Val 122             131             140             149         158             167
CCT CCC TCT ACA GCC CTC AGG GAG CTC ATT GAG GAG CTG GTC AAC ATC ACC CAG
Pro Pro Ser Thr Ala Leu Arg Glu Leu Ile Glu Glu Leu Val Asn Ile Thr Gln 176             185             194             203         212             221
AAC CAG AAG GCT CCG CTC TGC AAT GGC AGC ATG GTA TGG AGC ATC AAC CTG ACA
Asn Gln Lys Ala Pro Leu Cys Asn Gly Ser MET Val Trp Ser Ile Asn Leu Thr 230             239             248             257         266             276
GCT GGC ATG TAC TGT GCA GCC CTG GAA TCC CTG ATC AAC GTG TCA GGC TGC AGT
Ala Gly MET Tyr Cys Ala Ala Leu Glu Ser Leu Ile Asn Val Ser Gly Cys Ser
```

TABLE 1-continued

Nucleotide and amino acid sequence of huIL-13. SEQ ID NO: 1 and 2.

```
      284             293             302             311             320             329
GCC ATC GAG AAG ACC CAG AGG ATG CTG AGC GGA TTC TGC CCG CAC AAG GTC TCA
Ala Ile Glu Lys Thr Gln Arg MET Leu Ser Gly Phe Cys Pro His Lys Val Ser 338             347             358         365             374             383
GCT GGG CAG TTT TCC AGC TTG CAT GTC CGA GAC ACC AAA ATC GAG GTG GCC CAG
Ala Gly Gln Phe Ser Ser Leu His Val Arg Asp Thr Lys Ile Glu Val Ala Gln 392             401         410             419             428             437
TTT GTA AAG GAC CTG CTC TTA CAT TTA AAG AAA CTT TTT CGC GAG GGA CGG TTC
Phe Val Lys Asp Leu Leu Leu His Leu Lys Lys Leu Phe Arg Glu Gly Arg Phe

>             453             463             473             483             493             503
AAC TGA  AACTTCGAAA GCATCATTAT TTGCAGAGAC AGGACCTGAC TATTGAAGTT GCAGATTCAT
Asn .

613             523             533             543             553             563             673
TTTTCTTTCT GATGTCAAAA ATGTCTTGGG TAGGCGGGAA GGAGGGTTAG GGAGGGGTAA AATTCCTTAG 583             593             603             613             623             633             643
CTTAGACCTC AGCCTGTGCT GCCCGTCTTC AGCCTAGCCG ACCTCAGCCT TCCCCTTGCC CAGGGCTCAG 653             663             673             683             693             703             713
CCTGGTGGGC CTCCTCTGTC CAGGGCCCTG AGCTCGGTGG ACCCAGGGAT GACATGTCCC TACACCCCTC 723             733             743             753             763             773             783
CCCTGCCCTA GAGCACACTG TAGCATTACA GTGGGTGCCC CCCTTGCCAG ACATGTGGTG GGACAGGGAC 793             803             813             823             833             843             853
CCACTTCACA CACAGGCAAC TGAGGCAGAC AGCAGCTCAG GCACACTTCT TCTTGGTCTT ATTTATTATT 863             873             883             893             903             913             923
GTGTGTTATT TAAATGAGTG TGTTTGTCAC CGTTGGGGAT TGGGGAAGAC TGTGGCTGCT GGCACTTGGA 933             943             953             963             973             983             993
GCCAAGGGTT CAGAGACTCA GGGCCCCAGC ACTAAAGCAG TGGACCCAG GAGTCCCTGG TAATAAGTAC 1003            1013            1023            1033            1043            1053            1063
TGTGTACAGA ATTCTGCTAC CTCACTGGGG TCCTGGGGCC TCGGAGCCTC ATCCGAGGCA GGGTCAGGAG 1073            1083            1093            1103            1113            1123            1133
AGGGGCAGAA CAGCCGCTCC TGTCTGCCAG CCAGCAGCCA GCTCTCAGCC AACGAGTAAT TTATTGTTTT 1143            1153            1163            1173            1183            1193            1203
TCCTCGTATT TAAATATTAA ATATGTTAGC AAAGAGTTAA TATATAGAAG GTACCTTGA ACACTGGGGG 1213            1223            1233            1243            1253            1253            1273
AGGGGACATT GAACAAGTTG TTTCATTGAC TATCAAACTG AAGCCAGAAA TAAAGTTGGT GACAGATAAA

1283
AAAAAAAAAA AAAAAAA
```

TABLE 2

Comparison of human and mouse IL-13 nucleic acid sequences. SEQ ID NO: 1 and 3.
Sequence alignment of human and mouse:

```
    Human
                                      |                              22
                                      TTCGGCATCCGCTCCTCAATCC
    Mouse
    |                                                              57
    GACAAGCCAGCAGCCTAGGCCAGCCCACAGTTCTACAGCTCCCTGGT 23 TCTCCTGTTGGCACTGGGCCTCATGGCGCTTTTGTTGACCACGGTCATTG              72
    | | | |     | | | |  | | | | | |   | | | | | | | | | | |    |   | | | |  |
 58 TCTCTCACTGGCTCTGGGCTTCATGGCGCTCTGGGTGACTGCAGTCCTGG             107

73 CTCTCACTTGCCTTGGCGGCTTTGCCTCCCCAGGCC............CT             110
    | | | |   | | | | | | | | | | | |   | |     | | | |  | | | | | | | | |  |                            | |
108 CTCTTGCTTGCCTTGGTGGTCTCGCCGCCCCAGGGCCGGTGCCAAGATCT             157

111 GTGCCTCCCTCTACAGCCCTCAGGGAGCTCATTGAGGAGCTGGTCAACAT             160
    | | |   | | |    | |          | | | |  |  | | | | | | |   | | | | | | | | | | | |     | | | | | |
158 GTGTCTCTCCCTCTGACCCTTAAGGAGCTT ATTGAGGAGCTGAGCAACAT             207
```

TABLE 2-continued

Comparison of human and mouse IL-13 nucleic acid sequences. SEQ ID NO: 1 and 3.
Sequence alignment of human and mouse:

```
161 CACCCAGAACCAGAAGGCTCCGCTCTGCAATGGCAGCATGGTATGGAGCA        210
    ||| ||  |||||||    |||| || ||||| ||||||||||||||||||
208 CACACAAGACCAGA...CTCCCCTGTGCAACGGCAGCATGGTATGGAGTG        254

211 TCAACCTGACAGCTGGCATGTACTGTGCAGCCCTGGAATCCCTGATCAAC        260
    |  ||||| |  ||||||  || ||||||  |||||||||| |||| ||||
255 TGGACCTGGCCGCTGGCGGGTTCTGTGTAGCCCTGGATTCCCTGACCAAC        304

261 GTGTCAGGCTGCAGTGCCATCGAGAAGACCCAGAGGATGCTGAGCGGATT        310
    | ||    |||| |||||||| | |||||||||||||| ||  ||  |
305 ATCTCCAATTGCAATGCCATCTACAGGACCCAGAGGATATTGCATGGCCT        354

311 CTGCCCGCACAAGGTCTCAGCTGGGCAGTTTTCCAGCTTGCATGTCCGAG        360
    |||      | |||||| |  ||      | | ||||||     |||  |
355 CTGTAACCGCAAGGCCCCCACT...ACGGTCTCCAGC......CTCCCCG        395

361 ACACCAAAATCGAGGTGGCCCAGTTTGTAAAGGACCTGCTCTTACATTTA        410
    |  |||||||||||| ||| ||||| |||  |  ||||||| |  |   |
396 ATACCAAAATCGAAGTAGCCCACTTTATAACAAAACTGCTCAGCTACACA        445

411 AAGAAACTTTTTCGCGAGGGACGGTTCAACTGAAACTTCGAAAGCATCAT        460
    ||| |||| |||||| ||||| |||  ||| | |||
446 AAGCAACTGTTTCGCCACGGCCCCTTCTAATGA................        478

461 TATTTGCAGAGACAGGACCTGACTATTGAAGTTGCAGATTCATTTTTTCTT        510
    |  ||||||           |||| ||  || || ||  ||||||||| |||
479 .....GGAGAGACCATCCCTGGGCATCTCAGCTGTGGACTCATTTTTCCTT        523

511 TCTGATGTCAAAAATGTCTTGGG.TAGGCGGGAAGGAGGGTTAGGGAGG.        558
    ||| |  ||| |   | || ||| ||||  || ||||||||||  |||||
524 TCTCACATCAGACTTTGCTGGGGAGAGGCAGGGAGGAGGGTTGAGGAGGA        573

559 GGTAAAATTCCTTAGCTTAGACCTCAGCCTGTGCTGCCCGTCTTCAGCCT        608
    |   |  ||| |||  ||||| |  ||||||||||| |||| ||    ||
574 AGGGAGATGCCTCAGCTTTGGCCTCAGCCTGCACTGCCTGCCTAGTGCTC        623

609 AGCCGACCTCAGCCTTCCCCTTGCCCAGGGCTCAGCCTGGTGGGCCTCCT        658
    ||                        ||  ||||||||||
624 AG.........................GGTCTCAGCCTGG..........        638

659 CTGTCCAGGGCCCTGAGCTCGGTGGACCCAGGGATGACATGTCCCTACAC        708
         ||   |||  |||  |      |||| |       ||||  |
639 .....CAACACCCCCACCCC.....ACCC........CCACCCCCGCCGC        670

709 CCCTCCCCTGCCCTAGAGCACACTGTAGCATTACAGTGGGTGCCCCCCTT        758
    |||  |||  |||||  || |  ||||   |||| ||  |||    | |
671 CCCATCCCATCCCTACAGAAAACTGCAGCAAGACCGTGAGTCCAGCC...        717

759 GCCAGACATGTGTGGGACAGGGACCCACTTCACACACAGGCAACTGAGG        808
    |||||                   ||  | |||||||  |||||||||||
718 ........TGTGG..........CCTGGTCCACACA.GGGCAACTGAGG        747

809 CAGACAGCAGCTCAGGCACACTTCTTCTTGGTCTTATTTATTA...TTGT        855
    ||| ||||||||    ||||| ||||||||| |||||||||||    ||||
748 CAGGCAGCAGCTTGAGCACATTTCTTCTTGATCTTATTTATTATGGTTGT        797

856 GTGTTATTTAAATGAGTGTGTTTGT.CACCGTTGGGGATTGGGGAAGACT        904
    ||||||||||||||||||| ||  || |||   |||||| ||
798 GTGTTATTTAAATGAGTCTGTCAGTATCCCGGTGGGGACATGG.......        840

905 GTGGCTGCTGGCACTTGGAGCCAAGGGTTCAGAGACTCAGGGCCCCAGCA        954
                  |||  ||| | |           ||  |||| ||||||
841 ..............TTTGCTGCCTATG.......CCCTGGGGGCTCCAGCA        870

955 CTAAAGCAGTGGACCCCAGGAGTCCCTGGTAATAAGTACTGTGTACAGAA        1004
    |  ||||||||   | | || |||||||| ||| | |||||| |||| ||
871 TTGAAGCAGTGG.GCTCTGGGGTCCCTGGCAAT.ATTACTGTATACATAA        918

1005 TTCTGCTACCTCACTGGGGTCCTGGGGCCTCGGAGCCTCATCCGAGGCAG        1054
     |||||||||||||        |||  |||||  |||  |||||||||||
919  CTCTGCTACCTCA........CTGTAGCCTCCAGGTCTCACCCCAGGCAG        960
```

TABLE 2-continued

Comparison of human and mouse IL-13 nucleic acid sequences. SEQ ID NO: 1 and 3.
Sequence alignment of human and mouse:

```
1055  G.... GTCAGGAGAGGGCCAGAACAGCCGCTCCTGTGCCA. GCCAGCA      1099
      |     |||  ||  ||  ||||  ||   |  |||||||||||| | |||||
 961  GAGATGGGAGGGGA. GGCCAGAGCA. ACACTCCTGTGCCACGGCAGCA     1008

1100  GCCAGCTCTCAGCCAACGAGTAATTTATTGTTTT. TCCTCGTATTTAAA.    1147
      |||||  ||||||||   |  |||  ||||||||||  |  ||   ||||||||
1009  ACCAGCCCTCAGCCATGAAATAACTTATTGTTTTGTTCTTATATTTAAAG    1058

1148  TATTAAATATGTTAGCAAAGAGT... TAATATATAGAAGGGT. ACCTTGA   1193
      ||||||||  ||||||||||||||    ||||||||  ||||   |   |||
1059  TATTAAATAGCTTAGCAAAGAGTTAATAATATATGGAAGAATGGCCTGTT    1108

1194  ACACT..... :.............. GGGGGAGGG.......... GACAT  1212
      |||||                       |||||||||           | ||
1109  ACACTCAAGGTGATGTGTAGTGAATGGGGGAGGGTGGTGGGTTTGTCAC     1158

1213  TGAACAAGTTGTTTCATTGACTATCAAACT. GAAGCCAGAAATAAAGTTG    1261
      ||||||  |  |||||||||||||  ||||||||||  ||  |||||||||||
1159  TGAACAAACT. TTTCATTGACTGTCAAACTAGAAACCGGAAATAAAGATG    1207

1262  GTACAGATAAAAAA                                        1276
      ||||||||||||||
1208  GTGACAGATAAAAAA                                       1222
```

TABLE 3

Comparison of human and mouse IL-13 amino acid sequences.
The mouse is in lower case (SEQ ID NO: 4) and the HUMAN is in
upper case (SEQ ID NO: 2). The A10 clone includes the Gln at
position 98, which is absent in certain other clones. The matching
amino acids are indicated by an *.

```
met  ala  leu  trp  val  thr  ala  val  leu  ala  leu  ala  cys  leu  gly
 *    *    *         *         *    *         *              *    *    *
MET  ALA  LEU  LEU  LEU  THR  THR  VAL  ILE  ALA  LEU  THR  CYS  LEU  GLY
gly  leu  ala  ala  pro  gly  pro  val  pro  arg  ser  val  ser  leu  ser
 *         *         *    *    *    *    *
GLY  PHE  ALA  SER  PRO  GLY  PRO  VAL  PRO                    PRO  SER
leu  thr  leu  lys  glu  leu  ile  glu  glu  leu  ser  asn  ile  thr  gln
           *         *    *    *         *         *         *    *    *
THR  ALA  LEU  ARG  GLU  LEU  ILE  GLU  GLU  LEU  VAL  ASN  ILE  THR  GLN
asp  gln  thr       pro  leu  cys  asn  gly  ser  met  val  trp  ser  ile
           *              *         *         *         *    *         *
ASN  GLN  LYS  ALA  PRO  LEU  CYS  ASN  GLY  SER  MET  VAL  TRP  SER  ILE
asp  leu  ala  ala  gly  gly  phe  cys  val  ala  leu  asp  ser  leu  thr
      *              *    *         *              *         *    *
ASN  LEU  THR  ALA  GLY  MET  TYR  CYS  ALA  ALA  LEU  GLU  SER  LEU  ILE
asn  ile  ser  asn  cys  asn  ala  ile  tyr  arg  thr  gln  arg  ile  leu
 *         *         *         *    *              *         *         *
ASN  VAL  SER  GLY  CYS  SER  ALA  ILE  GLU  LYS  THR  GLN  ARG  MET  LEU
his  gly  leu  cys  asn  arg  lys  ala  pro  thr  thr       val  ser  ser
                *         *                   *    *              *    *
SER  GLY  PHE  CYS  PRO  HIS  LYS  VAL  SER  ALA  GLY  GLN  PHE  SER  SER
leu  pro       arg  thr  lys  ile  glu  val  ala  his  phe  ile  thr
 *              *    *    *    *         *         *         *
LEU  HIS  VAL  ARG  ASP  THR  LYS  ILE  GLU  VAL  ALA  GLN  PHE  VAL  LYS
lys  leu  leu  ser  tyr  thr  lys  gln  leu  phe  arg  his
                *              *         *    *    *
ASP  LEU  LEU  LEU  HIS  LEU  LYS  LYS  LEU  PHE  ARG  GLU
gly  pro  phe
 *         *
GLY  ARG  PHE  ASN
```

As used herein, the term IL-13 shall be used to describe a protein comprising a protein or peptide segment having the amino acid sequence shown in Table 1, or a fragment thereof. It also refers to a polypeptide which functionally affects cells or subcellular components in a manner similar to the IL-13 allele whose sequence is provided. It also encompasses allelic and other variants of the protein described. Typically, it will bind to its corresponding biological receptor with high affinity, e.g., at least about 100 nM, usually better than about 30 nM, preferably better than about 10 nM, and more preferably at better than about 3 nM. The term shall also be used herein to refer to related naturally occurring forms, e.g., alleles and metabolic variants of the human protein.

This invention also encompasses proteins or peptides having substantial amino acid sequence homology with the amino acid sequence in Table 1, but excluding any protein or peptide which exhibits substantially the same or lesser amino acid sequence homology than does the corresponding P600 protein found in the mouse.

A polypeptide "fragment", or "segment", is a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids. Sequences of segments of different proteins can be compared to one another over appropriate length stretches.

Amino acid sequence homology, or sequence identity, is determined by optimizing residue matches, if necessary, by introducing gaps as required. See, e.g., Needleham, et al., (1970) *J. Mol. Biol.* 48:443–453; Sankoff et al., (1983) chapter one in *Time Warps, String Edits, and Macromolecules: The Theory and Practice of Sequence Comparsion*, Addison-Wesley, Reading, Mass.; and software packages from IntelliGenetics, Mountain View, Calif.; and the University of Wisconsin Genetics Computer Group, Madison, Wis.; each of which is incorporated herein by reference. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are intended to include natural allelic and interspecies variations in each respective receptor sequence. Typical homologous proteins or peptides will have from 50–100% homology (if gaps can be introduced), to 60–100% homology (if conservative substitutions are included) with an amino acid sequence segment of Table 1. Homology measures will be at least about 50%, generally at least 58%, more generally at least 63%, often at least 69%, more often at least 75%, typically at least 81%, more typically at least 86%, usually at least 90%, more usually at least 93%, preferably at least 95%, and more preferably at least 97%, and in particularly preferred embodiments, at least 98% or more. The degree of homology will vary with the length of the compared segments. Homologous proteins or peptides, such as the allelic variants, will share most biological activities with the embodiment described in Table 1. As used herein, the term "biological activity" is used to describe, without limitation, inducing characteristic cell stimulation, Ig production, cellular differentiation, or cell viability functions, or more structural properties as receptor binding and cross-reactivity with antibodies raised against the same or an allelic variant of the described human IL-13.

The terms ligand, agonist, antagonist, and analog include molecules that modulate the characteristic cellular responses to IL-13 or IL-13-like proteins, as well as molecules possessing the more standard structural binding competition features of ligand-receptor interactions, e.g., where the receptor is a natural receptor or an antibody. The cellular responses likely are mediated through binding of IL-13 to cellular receptors. Also, a ligand is a molecule which serves either as a natural ligand to which said receptor, or an analog thereof, binds, or a molecule which is a functional analog of the natural ligand. The functional analog may be a ligand with structural modifications, or may be a wholly unrelated molecule which has a molecular shape which interacts with the appropriate ligand binding determinants. The ligands may serve as agonists or antagonists, see, e.g., Goodman et al. (eds) (1990) *Goodman & Gilman's: The Pharmacological Bases of Therapeutics*, Pergamon Press, New York.

II. Activities

The human IL-13 protein has a number of different biological activities. The human IL-13 is homologous to the mouse P600 protein, but has structural differences. For example, the human IL-13 gene coding sequence has only about 50% homology with the nucleotide coding sequence of mouse P600. At the amino acid level, there is about 66% identity.

The mouse P600 molecule has rather minimally defined biological activities. In particular, it has the ability to stimulate undifferentiated mouse bone marrow cells to undergo early stages of differentiation. The mouse P600 protein appears to activate both mouse cells and human cells in this assay.

The present disclosure also describes new activities which have been discovered using the mouse P600 molecule. The difference in structure between the human IL-13 and the homologous mouse P600 protein introduce some uncertainty about whether the two proteins will have identical functional properties. However, the handful of identified activities appear to be shared between the homologues. It is likely that many of the activities of mouse P600 on mouse cells or human cells will also apply to the human IL-13. In fact, the cross species activities indicate that many structural features are not critical in the function of the molecules.

In particular, the human IL-13 exhibits a number of identified activities when provided to human cells. The Examples section below describes procedures used to study the effects of human IL-13 on cell viability, morphology, proliferation, and differentiation. In particular, human IL-13 affects B cells, PBMC, and macrophages. On B cells, the cytokine affects proliferation, alone or in combination with other cytokines; sustains cell viability: affects survivability; causes modification of Ig surface markers, has effects specifically on CD40; and affects IgE switching. On PBHC or macrophages, it induces morphological changes, causes changes of cell surface markers, affects nitric oxide production, affects IL-I1$\alpha$ and IL-6 expression, and affects antigen dependent cell-mediated cytotoxicity (ADCC). Importantly, the similarity between IL-4 and IL-13 leads to antagonists of IL-13 whose structures are based upon similar antagonists of IL-4.

A. B cells 1. cofactor/factor proliferation; cell viability

FIG. 1 illustrates the ability of mouse P600 made from *E. coli* to stimulate or costimulate proliferation of large in vivo activated mouse B cells. The data indicate that the combination of IL-4, anti-soluble CD40, and mouse P600 induces proliferation of these cells. However, since the large in vivo activated mouse B cells may contain some monocytes and other cells, other cells may be induced to secrete various growth factors which support the proliferation observed. Thus, the mouse P600 stimulates the B cells, either directly or indirectly, alone or in combination with other factors. Human IL-13 should exhibit similar biological activity.

2. sustained survival of B cells; selectivity

FIGS. 2 through 9 illustrate this activity.

3. modification of Ig surface markers

Figure 10F:
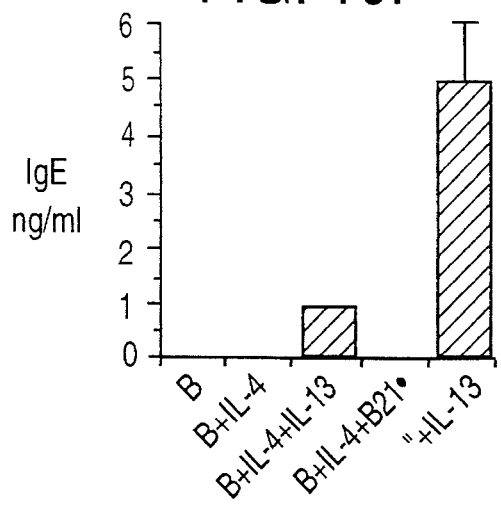
FIGS. 10F–10J show results of similar experiments where membranes isolated from the B21 activated T cells were substituted for the intact cells.
Figure 10G:
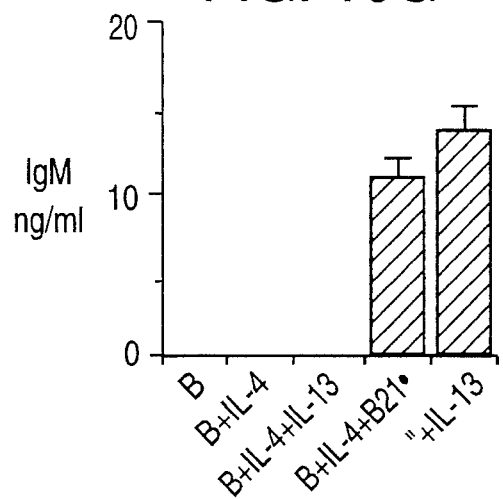
Figure 10H:
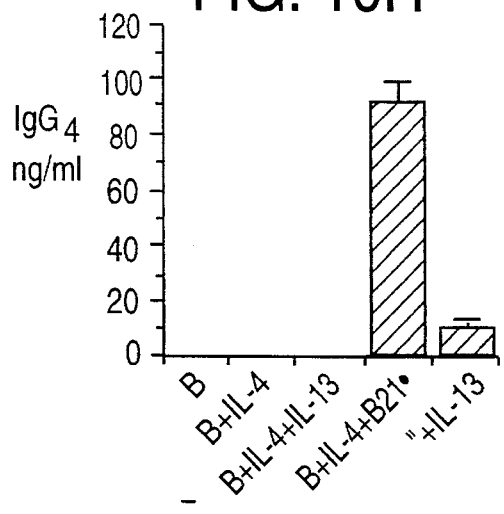
Figure 10I:
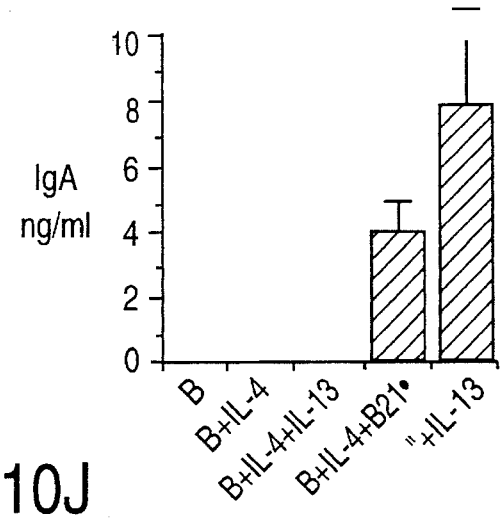
Figure 10J:
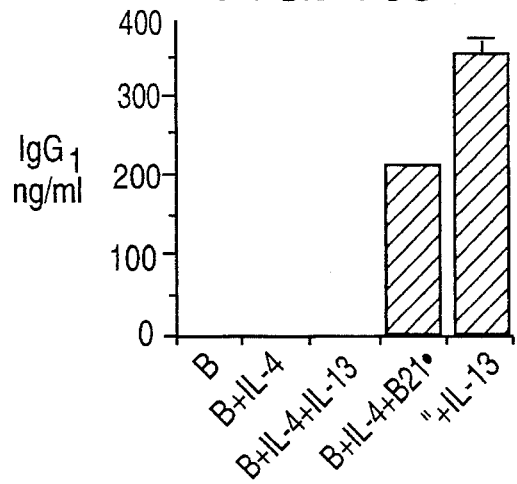
Figure 12A:
FIGS. 12A–12D show aggregation of human B cells induced by CD40L transfectants. JY cells ($2\times10^5$) were co-cultured for 5 h in 1 ml with $10^4$ COS-7 cells transfected with pJFE14 vector (FIG. 12A) or transfected with pJFE-14-hCD40L and expressing human CD40L (FIG. 12B). Similarly, CD20$^+$(>98%) B cells (5,000) were co-cultured for 24 h with 500 COS-7 cells either not expressing (FIG. 12C) or expressing (FIG. 12D) the human CD40L.
Figure 12B:
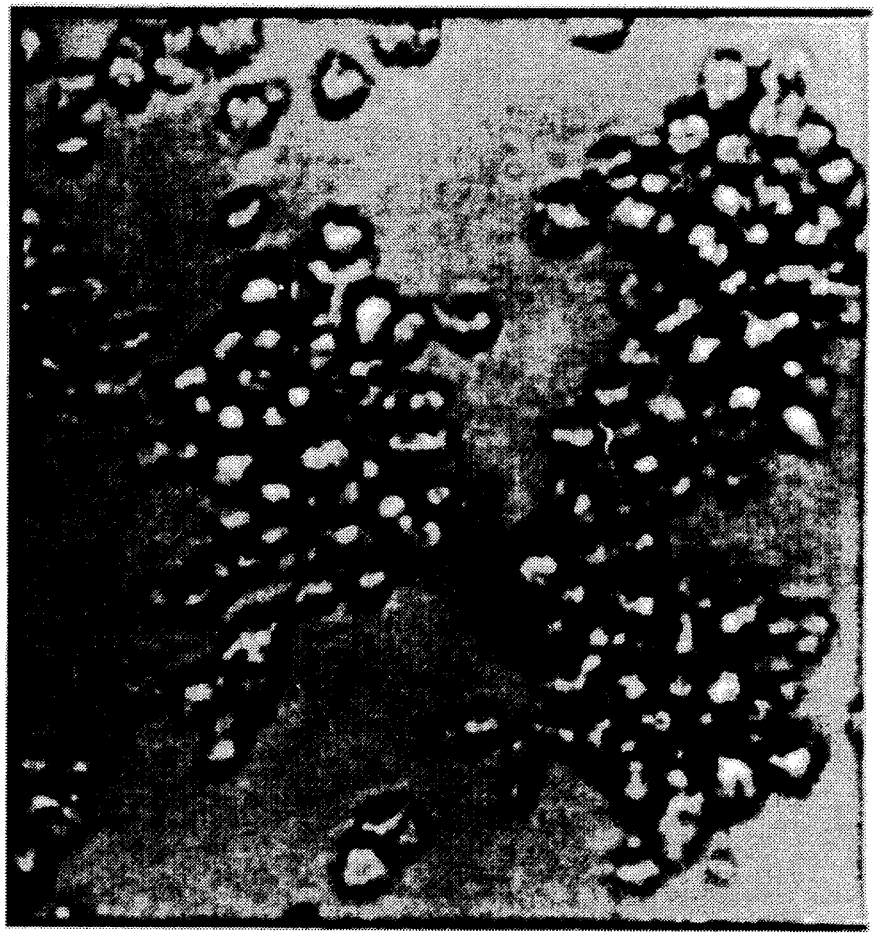
Figure 12C:
Figure 12D:

B cells activated by B21 antigen presenting cells (APC), their membranes, or anti-CD40 appear to exhibit modified Ig expression patterns after exposure to mouse P600 or human IL-13. FIGS. 10A through 10O shows data on measurements of the levels of expression of various surface Ig molecules when human IL-13 is co-administered to B cells with an inducing agent, e.g., activated B21 T cells, membranes from activated B21 T cells, or anti-CD40 antibodies. The changes in Ig production are suggestive of accelerated differentiation of either IgE class switching, or IgA switching. Both possibilities are consistent with a differentiation effect caused by mouse P600 or human IL-13.

FIGS. 11A through 11B illustrate induction of Ig synthesis by IL-13, see description below.

4. effects on CD40

FIGS. 12A through 12D and 14A through 14D illustrate this activity.

5. IgE switching

FIGS. 15A through 20A and 20A through 20B illustrate this activity. See also Table B1 and FIGS. 5A through 5E.

B. PBMC and macrophages 1. induction of morphological change

Figure 21A:
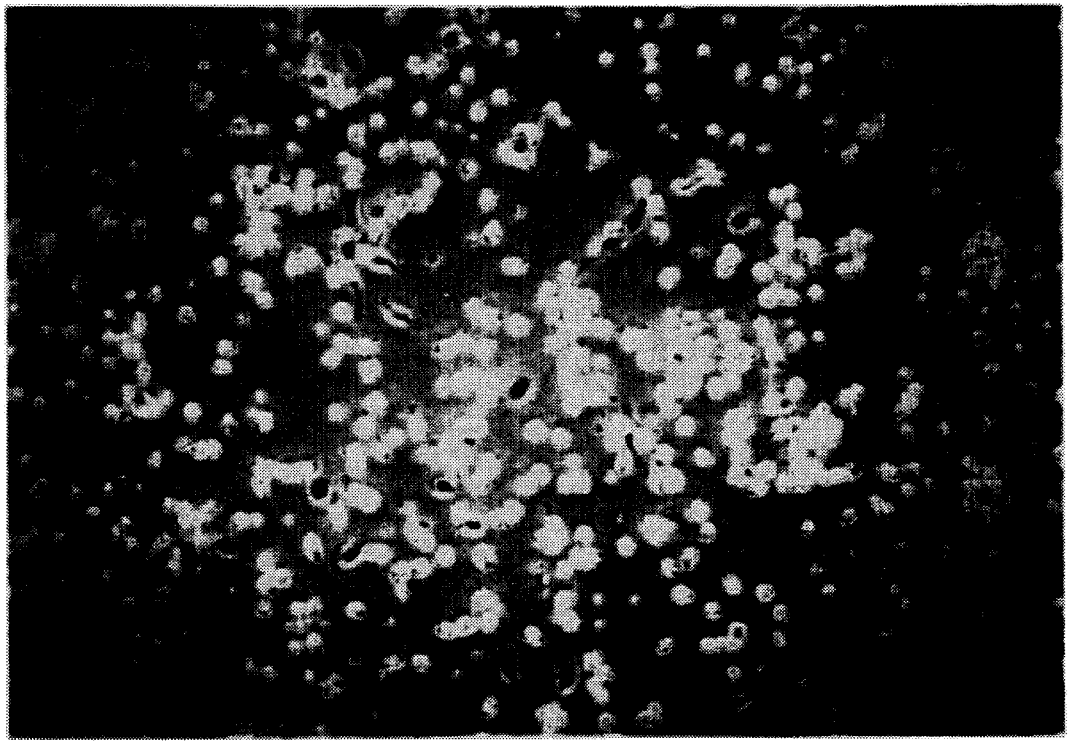
FIGS. 21A–21B illustrate the morphological changes in adherent cells upon treatment with mouse P600 (IL-13).
Figure 21B:
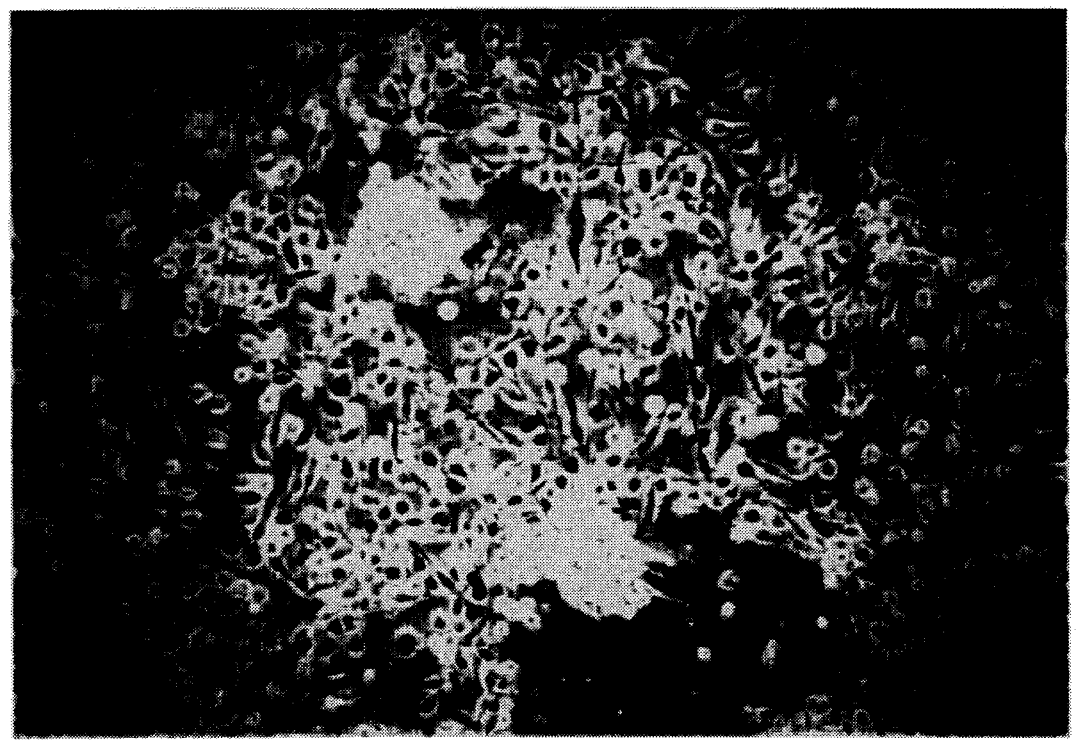

The mouse P600 also induces morphological changes in adherent human peripheral blood mononuclear cells. FIGS. 21A–21B show untreated adherent cells and treated cells. The treated cells exhibit significantly different morphology and clusters of small cells. The generic cells have rounded up, and there is evidence of clonal proliferation, observations which are consistent with induction of cell proliferation.

2. modification of cell surface markers

Figure 22A:
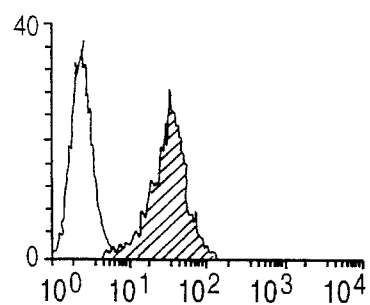
Figure 22B:
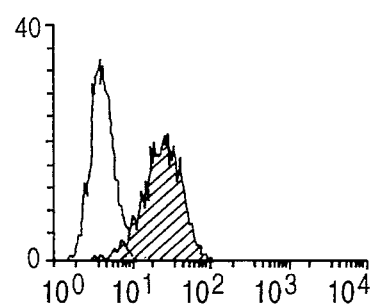
Figure 22C:
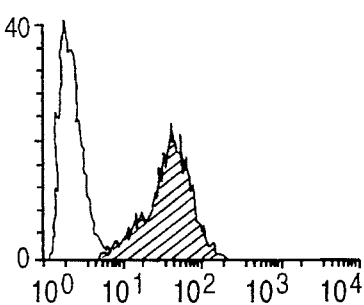
Figure 22D:
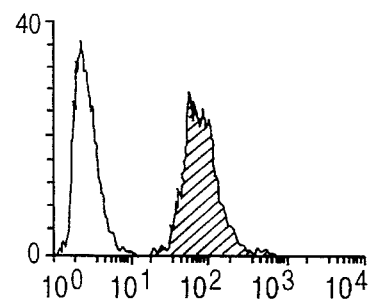
Figure 22E:
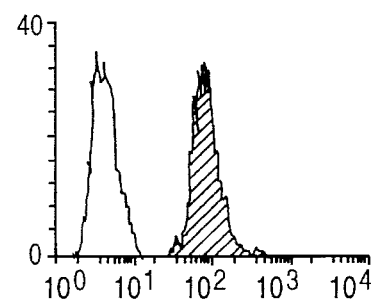
Figure 22F:
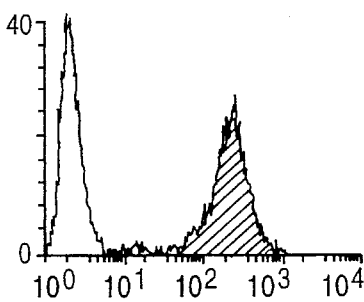
Figure 22G:
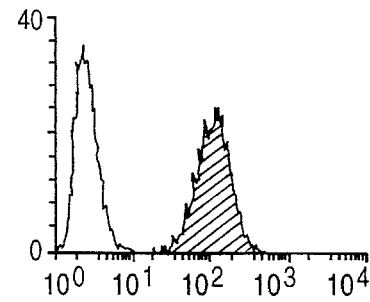
Figure 22H:
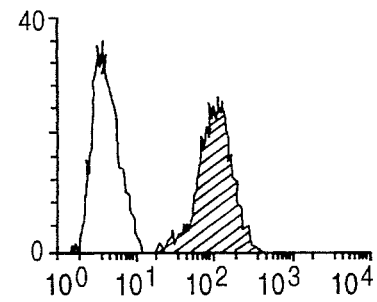
Figure 22I:
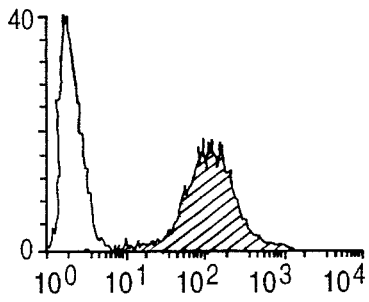
Figure 22J:
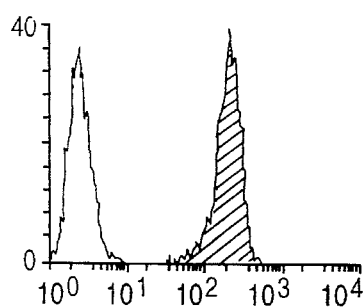
Figure 22K:
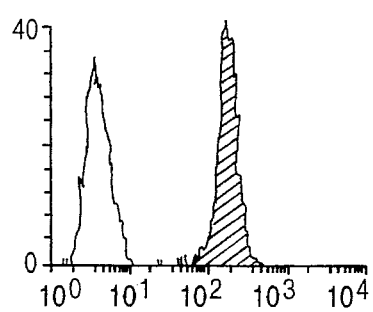
Figure 22L:
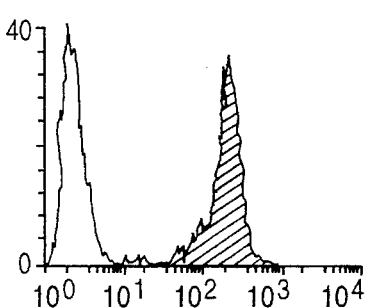
Figure 22M:
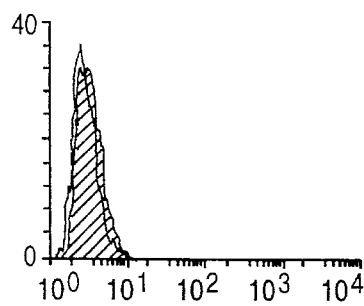
Figure 22N:
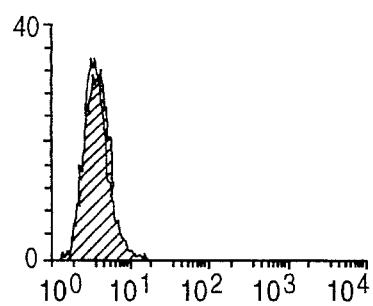
Figure 22O:
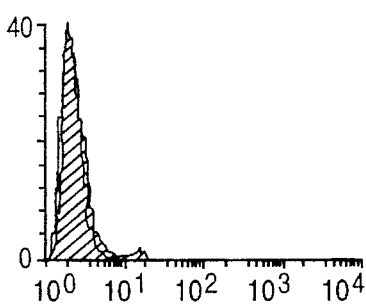
Figure 22P:
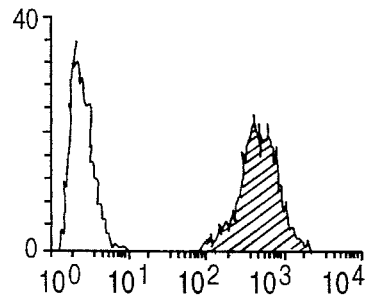
Figure 22Q:
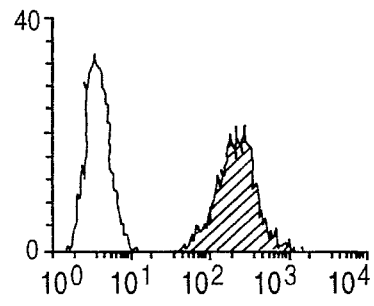
Figure 22R:
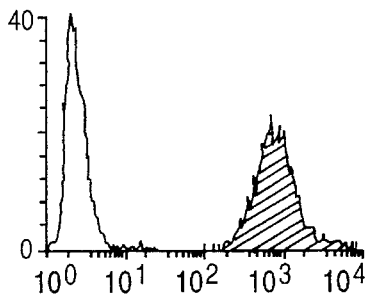
Figure 22S:
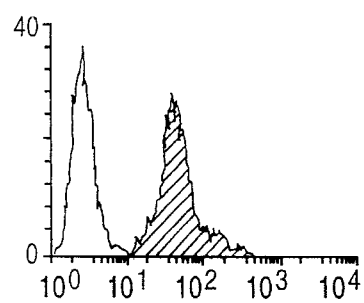
Figure 22T:
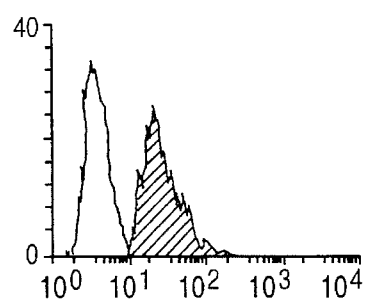
Figure 22U:
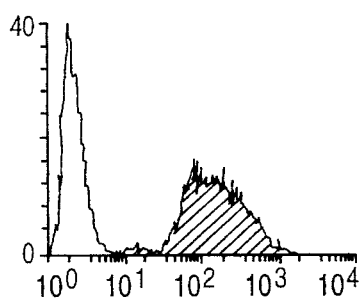
Figure 22V:
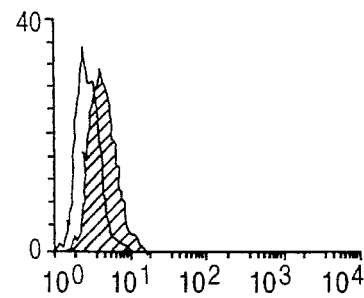
Figure 22W:
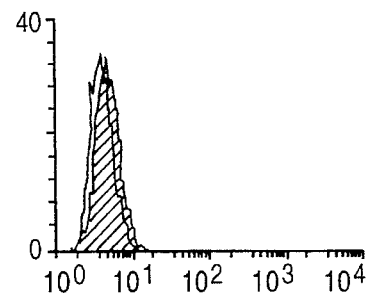
Figure 22X:
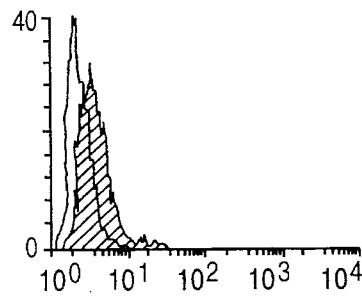
Figure 22Y:
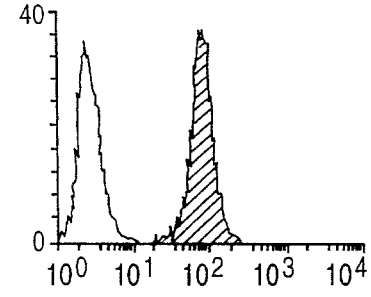
Figure 22Z:
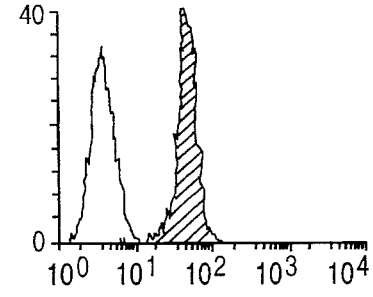
Figures 1, 22A:
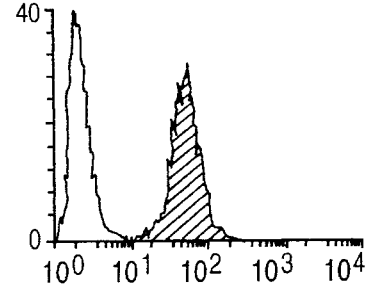
Figures 1, 22B:
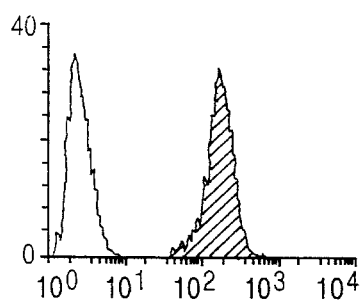
Figures 1, 22C:
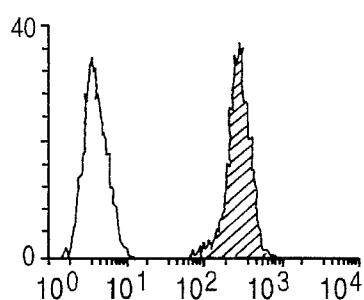
Figures 1, 22D:
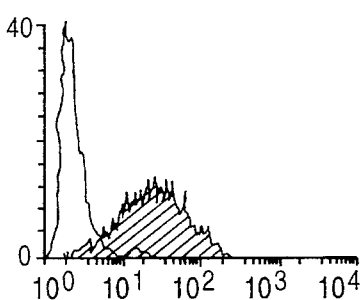
Figures 1, 22E:
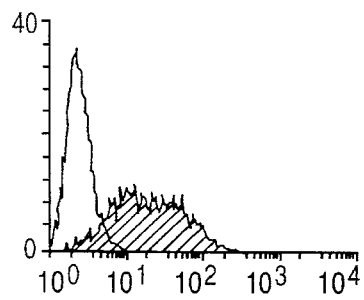
Figures 1, 22F:
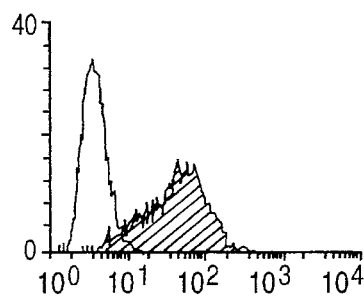
Figures 1, 22G:
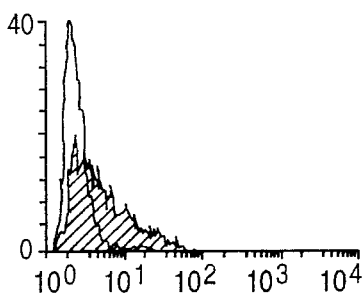
Figures 1, 22H:
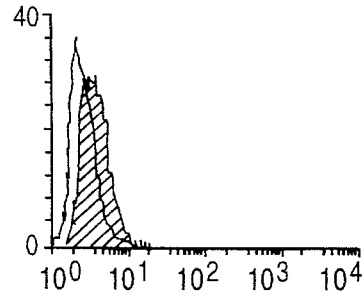
Figures 1, 22I:
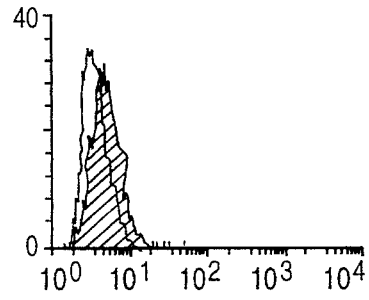
Figures 1, 22J:
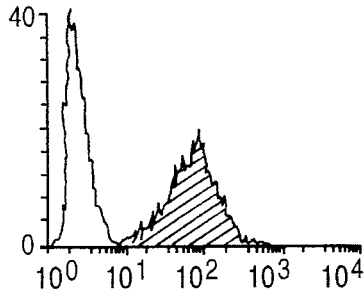
Figures 1, 22K:
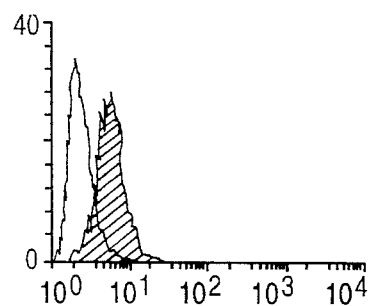
Figures 1, 22L:
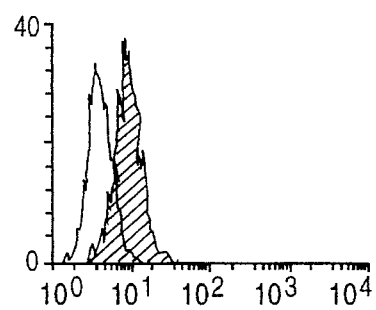
Figures 1, 22M:
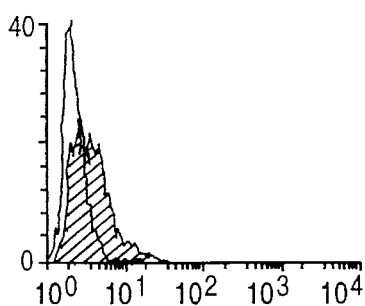
Figures 1, 22N:
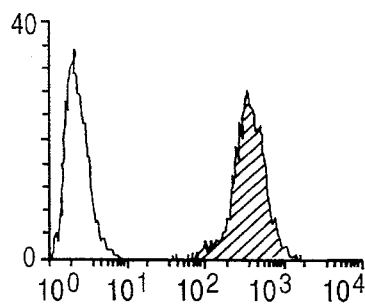
Figures 1, 22O:
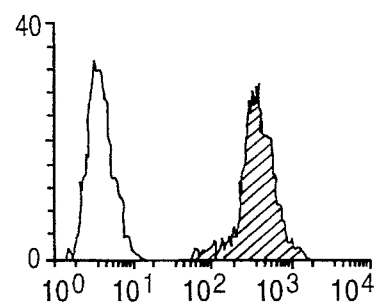
Figures 1, 22P:
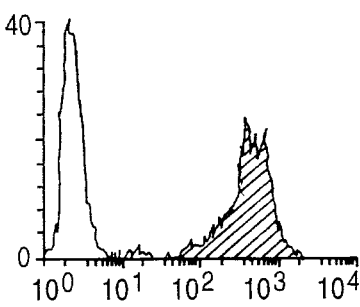
Figures 1, 22Q:
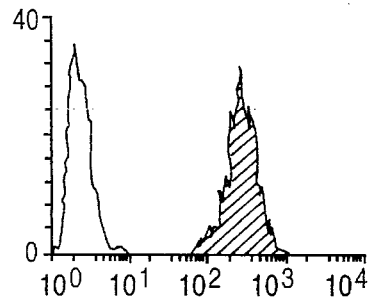
Figures 1, 22R:
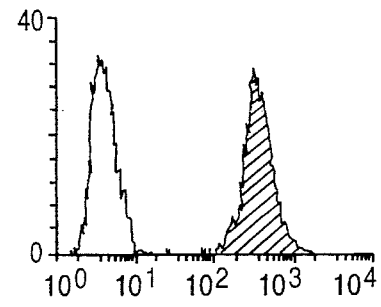
Figures 1, 22S:
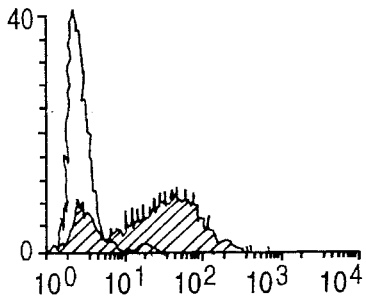
Figures 1, 22T:
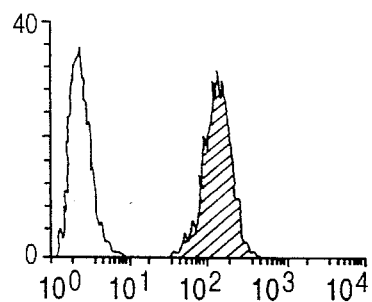
Figures 1, 22U:
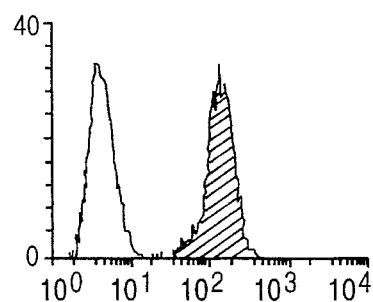
Figures 1, 22V:
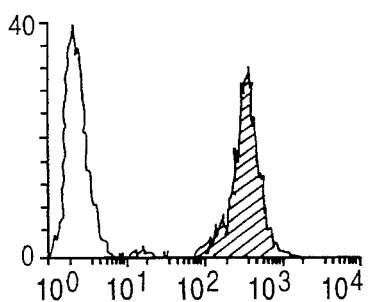
Figures 1, 22W:
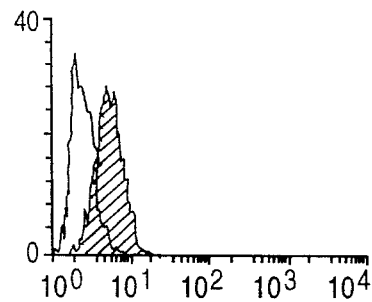
Figures 1, 22X:
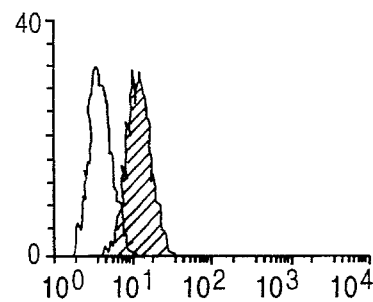
Figures 1, 22Y:
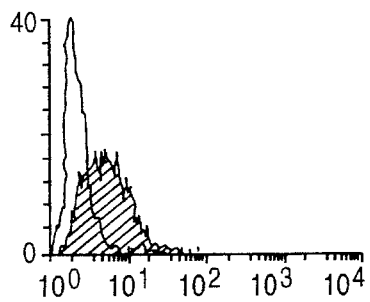

Mouse P600 induces significant changes in the cell surface markers of adherent cells from peripheral blood. These adherent cells are mostly monocytes, e.g., macrophage precursors, but also include more differentiated cell types, dendritic cells, and some B cells. FIGS. 22A through 22Y-1 show, at five days, the changes in surface markers induced by mouse P600. Human IL-13 has similar effects, as indicated by FIGS. 23A through 23G-3.

Many of the cell surface makers on these adherent cells are up regulated or down regulated, or their dispersion in expression level changes. In particular, FIGS. 22A through 22Y-1 shows that the following markers tend to increase on a per cell basis: CD11b, CD11c, class II MHC (measured by Q5/13 or Pc1v5.2), CD 23, and CD18. In contrast, per cell expression of the following is decreased: CD32, CD16, IL-2Rα, and CD14. The homogeneity of per cell expression is changed for CD32, CD14, and B7. There is no change for CD11α, CD54, class II MHC (measured by DQ), and CD58. Although the presented data show no change for CD44 and class I MHC, other experiments indicated increase in expression levels.

These changes in expression level are detectable also at 10 days, and in certain cases exhibit a more dramatic shift, whereas others may show a lesser shift. Depending on subsets of cells, some features may have been lost by ten days.

The data in FIGS. 23A through 23G shows that in spite of the sequence divergence of the mouse P600 and the human IL-13, the two molecules seem to cause similar changes in the adherent human cells. It is likely that activities found for one of the molecules will be found also by the other. In addition, the molecules appear to exhibit cross-species activities, e.g., the mouse P600 is active on human cells, and the human IL-13 is active on mouse cells.

3. nitric oxide synthesis

Figure 24A:
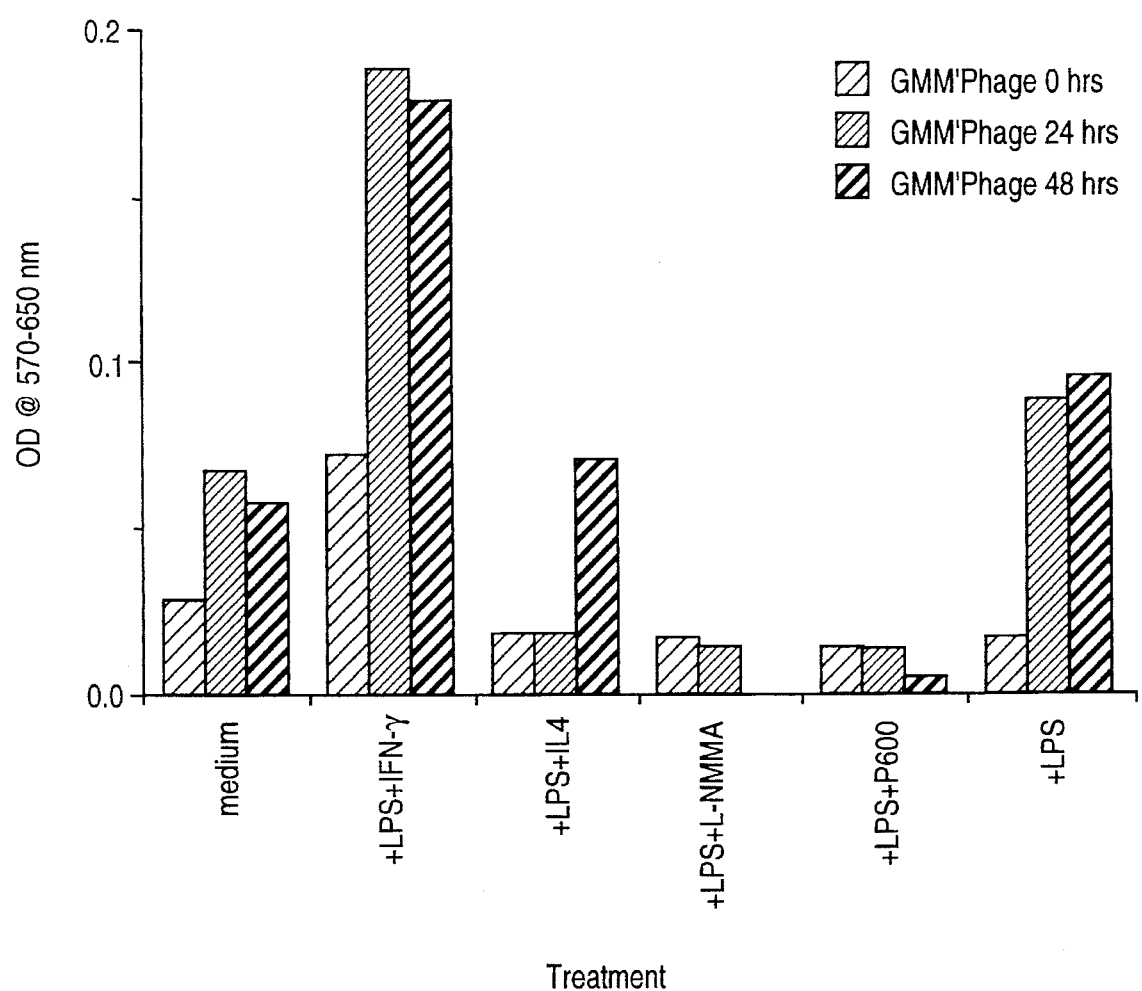
FIGS. 24A–24C show that IL-13 inhibits production of nitric oxide by macrophages stimulated with LPS. Macrophages are activated to produce NO by stimulation with LPS at 3 μg/ml in the appropriate Figs., either with or without prior stimulation with cytokines, as indicated. The macrophages were incubated for 16 h with the cytokines (if used) 16 h prior to treatment with LPS. Supernatants were taken at the indicated times relative to LPS addition, i.e., 0 h is the time of addition of LPS. Supernatants were assayed for NO production by the standard Griess assay for nitrites.
Figure 24B:
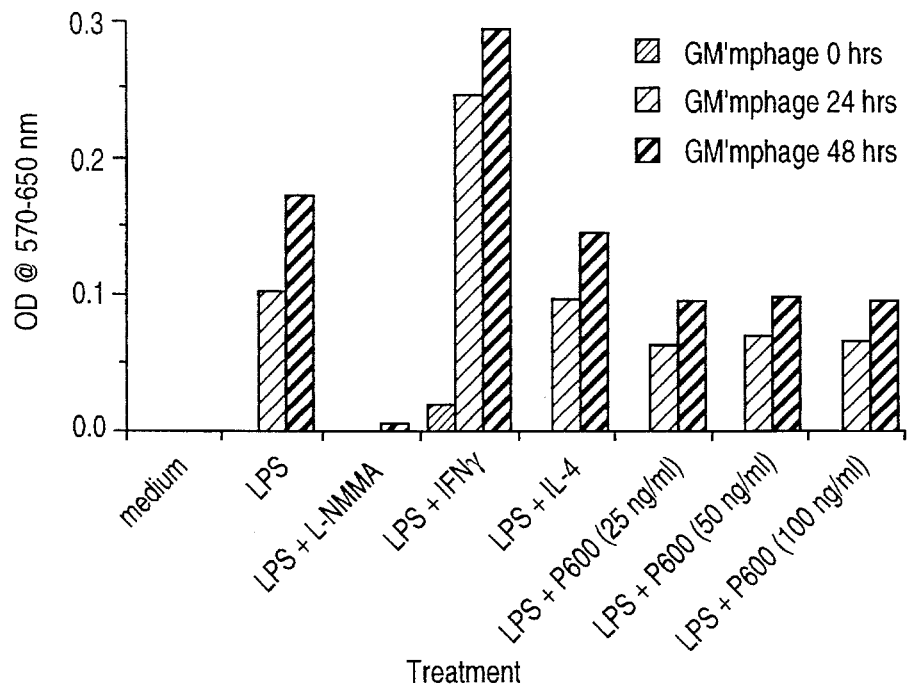
Figure 24C:
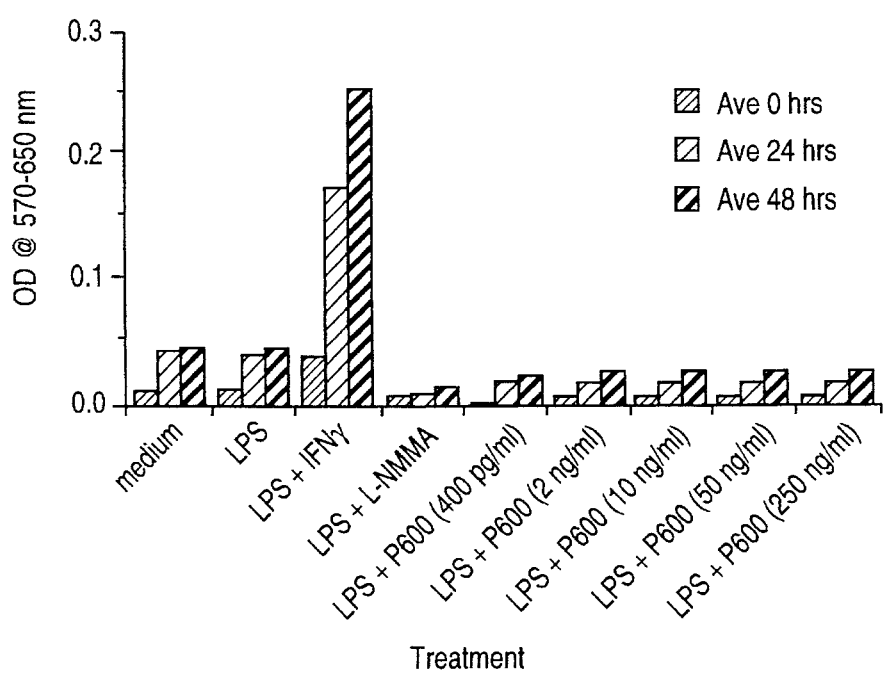

FIGS. 24A–24C, illustrate this activity.

4. effect on IL-1α; IL6-; IL-10; and TNF-α production Table 4 illustrates these activities.

TABLE 4

IL-13 effect on IL-1α; IL-6; IL-10 and (TNF-α production by LPS activated human monocytes.

|  | IL-1α (ng/ml) | IL-6 (ng/ml) | IL-10 (ng/ml) | TNF-α (ng/ml) |
|---|---|---|---|---|
| medium | 0 | 0 | 0 | 0 |
| LPS | 8.1 | 54.4 | 35.4 | 2.2 |
| LPS + IL-4 | 1.7 | 33.1 | 30 | .7 |
| LPS + IL-13 | 2 | 35.4 | 22 | .5 |
| LPS + IL-10 | 0 | 8.6 | nd | 0 |
| LPS + αIL-10 mAb | 12 | 101 | nd | 10.6 |
| LPS + αIL-10 mAb + IL-4 | 3.7 | 59.5 | ND | 1.2 |
| LPS + αIL-10 mAb + IL-4 | 5.4 | 79.5 | nd | 1.5 |

These results indicate that IL-4 and IL-13 inhibit the production of IL-1α, IL-6, IL-10, and TNF-α by LPS activated human monocytes. IL-10 also inhibits the production of IL-1α, IL-6, and TNF-α by LPS activated human monocytes. IL-10 is produced by human monocytes and inhibits IL-1α, IL-6, and TNF-α in an autoregulatory fashion. Addition of IL-10 neutralizing mAb 19F1 shows that endogenously produced IL-10 also inhibits the production of IL-1α, IL-6, and TNF-α. The inhibitory effects of IL-4 and IL-13 on cytokine production by LPS activated human monocytes are independent of IL-10 since IL-4 and IL-13 inhibit the production of IL-1α, IL-6, and TNF-α in the presence of neutralizing anti-IL-10 mAb 19F1.

5. Antigen dependent cell-mediated cytotoxicity

FIGS. 25A–25D-1 through 26 illustrate this activity.

C. IL-4 antagonist; interactions

FIGS. 27A through 27D through 33A and 33B illustrate the action of an IL-4 antagonist on the action of IL-13.

D. biological relevance

The mouse P600 protein can sustain or promote the proliferation of large in vivo activated B cells. As such, the factor appears to be either a stimulatory or costimulatory factor useful in promoting activated B cell growth. The human IL-13 is therefore expected to be a useful factor in circumstances where activated B cell growth is desired. These include genetic, developmental, or acquired immune system deficiencies, e.g., congenital aglobulinemias, immature infants, or chemotherapy patients. In vitro experiments would be performed to determine what effects IL-13 possesses. In particular, dose response relationships for various immunological assays will be tested with the compositions of this invention. See, e.g., Coligan et al., (1991) *Current Protocols in Immunology*, Greene/Wiley, New York, which is incorporated by reference for activity screens.

Regarding the proliferative response, mouse P600 induces changes in morphology of the monocyte cells. The monocyte cells consist primarily of macrophage precursors, and similar results should apply to monocyte equivalents found in organs or tissues other than the peripheral blood, e.g., the aveolar, intraperitoneal, or spleen/lymph macrophage precursors. The IL-13 or antagonist, e.g., antibody or IL-4 antagonist, would be indicated for conditions where regulation of localized or systemic immune responses is desired and appropriate. The effects on class II MHC are especially relevant in these contexts.

Besides a growth factor/cofactor activity, the human IL-13 also affects differentiation of various cells of the immune system. For instance, in activated B cells, it accelerates or promotes the differentiation of Ig producing cells. It induces the B cells to produce Ig molecules characteristic of later or faster differentiation. As such, the human IL-13 and mouse P600 appear to be a differentiation factor for B cells.

Thus, Ig production should be regulatable by IL-13, alone or in combination with other factors. Agonists and antagonists, when provided in appropriate amounts and schedules, will be useful in treating or controlling abnormal B cell conditions, or to accelerate or decelerate B cell differentiation when appropriate.

Peripheral blood monocytes are also sensitive to the presence of both human IL-13 and mouse P600. These cells, consisting primarily of macrophage precursors and more differentiated cell types, exhibit both a proliferative response and a differentiation response.

In one context, IL-4 is appropriate in antitumor situations, e.g., to stimulate an endogenous response to counter the tumor, IL-13 should also be a useful therapeutic. In a different context of proliferative disorder, after radiotherapy or chemotherapy, where the immune function is typically compromised, IL-13 would be useful to restore function by promoting recovery and differentiation of the remaining immune function. See, e.g., Moller (ed) (1992) "Fc Receptors" in *Immunological Reviews* 125: 1–98. Similar problems exist in transplantation contexts, as well as in other genetic or developmental immunodeficiencies, e.g., in newborn infants. See, e.g., Baker et al. (1992) *N. E. J. Med.* 327:213–219.

In fact, the role of IL-13 in promoting restoration of immune function under these circumstances is supported by the cell marker changes observed. With respect to cell marker differentiation, the general trend is that the class II MHC markers are affected. Also, CD23 is affected. The effects on class II MHC markers indicate that systemic responsiveness to infections can be modulated with IL-13 or mouse P600, or agonists or antagonists thereof. The observed decreases in CD32 and CD16 indicated a lowered receptor for IgG Fc, which would be correlated with a lessened response to infections. If so, an IL-13 antagonist, or mouse P600 antagonist, would be useful in stimulating an immunoglobulin response. This antagonistic activity could lead to increased Fcγ receptor expression and functional increase in opsonization and clearance of infective particles.

Antagonists to IL-13, e.g., antibodies or IL-4 antagonist, would be indicated for modulating B cell growth and proliferation, perhaps regulating excessive humoral responses. Various autoimmune conditions or hyperimmunoglobulinemias should respond to treatment with appropriate amounts of antagonists administered over defined schedules. IL-4 antagonist will be a preferred antagonist for IL-13 effects.

The CD23 marker, which is a low affinity Fcg receptor, affects IgE expression, the mediator of allergic response. However, soluble CD23 up regulates IgE. Thus, modulating Fcε receptor via IL-13 would modulate the functional allergic response. See, e.g., Aubry et al. (1992) *Nature* 358:505–507, which is incorporated herein by reference. This is one of the more striking activities of the IL-13.

Likewise, IL-13 mediates changes in CD11 marker expression, which are associated with cell adhesion, e.g., cell-cell contacts, Thus, increasing CD11 should facilitate cellular interaction and the functional results therefrom. See also Springer et al. (1988) *Leukocyte Adhesion Molecules,* Springer-Verlag, New York, which is incorporated herein by reference.

III. Nucleic Acids

This invention contemplates use of isolated nucleic acid or fragments which encode this or a closely related protein, or fragments thereof, to encode a biologically active corresponding polypeptide. In addition, this invention covers isolated or recombinant DNA which encodes a biologically active protein or polypeptide having characteristic IL-13 activity. Typically, the nucleic acid is capable of hybridizing, under appropriate conditions, with a nucleic acid sequence segment shown in Table 1. Said biologically active protein or polypeptide can be a full length protein, or fragment, and will typically have a segment of amino acid sequence highly homologous to one shown in Table 1. Further, this invention covers the use of isolated or recombinant nucleic acid, or fragments thereof, which encode proteins having fragments which are homologous to the disclosed IL-13 protein. The isolated nucleic acids can have the respective regulatory sequences in the 5' and 3' flanks, e.g., promoters, enhancers, poly-A addition signals, and others from the natural gene.

An "isolated" nucleic acid is a nucleic acid, e.g., an RNA, DNA, or a mixed polymer, which is substantially pure, e.g., separated from other components which naturally accompany a native sequence, such as ribosomes, polymerases, and flanking genomic sequences from the originating species. The term embraces a nucleic acid sequence which has been removed from its naturally occurring environment, and includes recombinant or cloned DNA isolates, which are thereby distinguishable from naturally occurring compositions, and chemically synthesized analogs or analogs biologically synthesized by heterologous systems. A substantially pure molecule includes isolated forms of the molecule, either completely or substantially pure.

An isolated nucleic acid will generally be a homogeneous composition of molecules, but will, in some embodiments, contain heterogeneity, preferably minor. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence. Typically this intervention involves in vitro manipulation, although under certain circumstances it may involve more classical animal breeding techniques. Alternatively, it can be a nucleic acid made by generating a sequence comprising fusion of two fragments which are not naturally contiguous to each other, but is meant to exclude products of nature, e.g., naturally occurring mutants as found in their natural state. Thus, for example, products made by transforming cells with any unnaturally occurring vector is encompassed, as are nucleic acids comprising sequence derived using any synthetic oligonucleotide process. Such a process is often done to replace a codon with a redundant codon encoding the same or a conservative amino acid, while typically introducing or removing a restriction enzyme sequence recognition site. Alternatively, the process is performed to join together nucleic acid segments of desired functions to generate a single genetic entity comprising a desired combination of functions not found in the commonly available natural forms, e.g., encoding a fusion protein. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode similar polypeptides to fragments of the interleukins, and fusions of sequences from various different interleukin or related molecules, e.g., growth factors.

A "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides. Typically, fragments of different genetic sequences can be compared to one another over appropriate length stretches.

A nucleic acid which codes for an IL-13 will be particularly useful to identify genes, mRNA, and cDNA species which code for itself or closely related proteins, as well as DNAs which code for allelic or other genetic variants, e.g., from different individuals. Preferred probes for such screens are those regions of the interleukin which are conserved between different allelic variants, and will preferably be full length or nearly so. In other situations, allele specific sequences will be more useful.

This invention further covers recombinant nucleic acid molecules and fragments having a nucleic acid sequence identical to or highly homologous to the isolated DNA set forth herein. In particular, the sequences will often be operably linked to DNA segments which control transcription, translation, and DNA replication. These additional segments typically assist in expression of the desired nucleic acid segment.

Homologous nucleic acid sequences, when compared to one another or Table 1 sequences, exhibit significant similarity. The standards for homology in nucleic acids are either measures for homology generally used in the art by sequence comparison or based upon hybridization conditions. Comparative hybridization conditions are described in greater detail below.

Substantial homology in the nucleic acid sequence comparison context means either that the segments, or their complementary strands, when compared, are identical when optimally aligned, with appropriate nucleotide insertions or deletions, in at least about 60% of the nucleotides, generally at least 66%, ordinarily at least 71%, often at least 76%, more often at least 80%, usually at least 84%, more usually at least 88%, typically at least 91%, more typically at least about 93%, preferably at least about 95%, more preferably at least about 96 to 98% or more, and in particular embodiments, as high at about 99% or more of the nucleotides. Alternatively, substantial homology exists when the segments will hybridize under selective hybridization conditions, to a strand or its complement, typically using a sequence derived from Table 1. Typically, selective hybridization will occur when there is at least about 55% homology over a stretch of at least about 14 nucleotides, more typically at least about 65%, preferably at least about 75%, and more preferably at least about 90%. See, Kanehisa (1984) *Nuc. Acids Res.* 12:203–213, which is incorporated herein by reference. The length of homology comparison, as described, may be over longer stretches, and in certain embodiments will be over a stretch of at least about 17 nucleotides, generally at least about 20 nucleotides, ordinarily at least about 24 nucleotides, usually at least about 28 nucleotides, typically at least about 32 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters typically controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is much more important than the measure of any single parameter. See, e.g., Wetmur and Davidson (1968) *J. Mol. Biol.* 31:349–370, which is hereby incorporated herein by reference.

The isolated DNA can be readily modified by nucleotide substitutions, nucleotide deletions, nucleotide insertions, and inversions of nucleotide stretches. These modifications result in novel DNA sequences which encode this protein, its derivatives, or proteins having IL-13 activity. These modified sequences can be used to produce mutant proteins (muteins) or to enhance the expression of variant species. Enhanced expression may involve gene amplification, increased transcription, increased translation, and other mechanisms. Such mutant IL-13 derivatives include predetermined or site-specific mutations of the protein or its fragments. "Mutant IL-13" as used herein encompasses a polypeptide otherwise falling within the homology definition of the human IL-13 as set forth above, but having an amino acid sequence which differs from that of human IL-13 as found in nature, whether by way of deletion, substitution, or insertion. In particular, "site specific mutant IL-13" encompasses a protein having substantial homology with a protein of Table 1, and typically shares most of the biological activities of the form disclosed herein.

Although site specific mutation sites are predetermined, mutants need not be site specific. Human IL-13 mutagenesis can be achieved by making amino acid insertions or deletions in the gene, coupled with expression. Substitutions, deletions, insertions, or any combinations may be generated to arrive at a final construct. Insertions include amino- or carboxy- terminal fusions. Random mutagenesis can be conducted at a target codon and the expressed human IL-13 mutants can then be screened for the desired activity. Methods for making substitution mutations at predetermined sites in DNA having a known sequence are well known in the art, e.g., by M13 primer mutagenesis. See also Sambrook et al. (1989) and Ausubel et al. (1987 and periodic Supplements).

The mutations in the DNA normally should not place coding sequences out of reading frames and preferably will not create complementary regions that could hybridize to produce secondary mRNA structure such as loops or hairpins.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence. Polymerase chain reaction (PCR) techniques can often be applied in mutagenesis. Alternatively, mutagenesis primers are commonly used methods for generating defined mutations at predetermined sites.

IV. Proteins, Peptides

As described above, the present invention encompasses the human IL-13 whose sequence is disclosed in Table I and described above. Allelic and other variants are also contemplated.

The present invention also provides recombinant proteins, e.g., heterologous fusion proteins using segments from this human protein. A heterologous fusion protein is a fusion of proteins or segments which are naturally not normally fused in the same manner. Thus, the fusion product of a growth factor with an interleukin is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional or structural domains from other related proteins, e.g., growth factors or other cytokines. For example, receptor-binding or other segments may be "swapped" between different new fusion polypeptides or fragments. See, e.g., Cunningham et al. (1989) *Science* 243:1330–1336; and O'Dowd et al. (1988) *J. Biol. Chem.* 263:15985–15992, each of which is incorporated herein by reference. Thus, new chimeric polypeptides exhibiting new combinations of specificities will result from the functional linkage of receptor-binding specificities. For example, the receptor binding domains from other related ligand molecules may be added or substituted for other domains of this or related proteins. The resulting protein will often have hybrid function and properties. For example, a fusion protein may include a targeting domain which may serve to provide sequestering of the fusion protein to a particular organ, e.g., a ligand portions which is specifically bound by spleen cells and would serve to accumulate in the spleen.

Candidate fusion partners and sequences can be selected from various sequence data bases, e.g., GenBank, c/o IntelliGenetics, Mountain View, Calif.; and BCG, University of Wisconsin Biotechnology Computing Group, Madison, Wis., which are each incorporated herein by reference.

"Derivatives" of the human IL-13 include amino acid sequence mutants, glycosylation variants, metabolic derivatives and covalent or aggregative conjugates with other chemical moieties. Covalent derivatives can be prepared by linkage of functionalities to groups which are found in the IL-13 amino acid side chains or at the N- or C- termini, e.g., by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the interleukin or fragments thereof with other proteins of polypeptides. These derivatives can be synthesized in recombinant culture such as N- or C-terminal fusions or by the use of agents known in the art for their usefulness in cross-linking proteins through reactive side groups. Preferred derivatization sites with cross-linking agents are at free amino groups, carbohydrate moieties, and cysteine residues.

Fusion polypeptides between the interleukin and other homologous or heterologous proteins are also provided. Homologous polypeptides may be fusions between different growth factors, resulting in, for instance, a hybrid protein exhibiting ligand specificity for multiple different receptors, or a ligand which may have broadened or weakened specificity of binding to its receptor. Likewise, heterologous fusions may be constructed which would exhibit a combination of properties or activities of the derivative proteins. Typical examples are fusions of a reporter polypeptide, e.g., luciferase, with a segment or domain of a receptor, e.g., a ligand-binding segment, so that the presence or location of a desired ligand may be easily determined. See, e.g., Dull et al., U.S. Pat. No. 4,859,609, which is hereby incorporated herein by reference. Other gene fusion partners include glutathione-S-transferase (GST), bacterial β-galactosidase, trpE, Protein A, β-lactamase, alpha amylase, alcohol dehydrogenase, and yeast alpha mating factor. See, e.g., Godowski et al. (1988) *Science* 241:812–816.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, for example, in Sambrook et al. (1989) *Molecular Cloning: A Laboratory Manual* (2d ed.), Vols. 1–3, Cold Spring Harbor Laboratory, and Ausubel et al. (eds)(1987 and periodic supplements) *Current Protocols in Molecular Biology*, Greene/Wiley, New York, which are each incorporated herein by reference. Techniques for synthesis of polypeptides are described, for example, in Merrifield (1963) *J. Amer. Chem. Soc*, 85:2149–2156; Merrifield (1986) *Science* 232: 341–347; and Atherton et al. (1989) *Solid Phase Peptide Synthesis: A Practical Approach*, IRL Press, Oxford; each of which is incorporated herein by reference.

This invention also contemplates the use of derivatives of the human IL-13 other than variations in amino acid sequence or glycosylation. Such derivatives may involve covalent or aggregative association with chemical moieties. These derivatives generally fall into three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of a receptor or other binding molecule, e.g., an antibody. For example, the human IL-13 ligand can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of IL-13 receptor, antibodies, or other similar molecules. The IL-13 can also be labeled with a detectable group, for example radioiodinated by the chloramine T procedure, covalently bound to rare earth chelates, or conjugated to another fluorescent moiety for use in diagnostic assays.

The human IL-13 of this invention can be used as an immunogen for the production of antisera or antibodies specific for the interleukin or any fragments thereof. The purified interleukin can be used to screen monoclonal antibodies or antigen-binding fragments prepared by immunization with various forms of impure preparations containing the protein. In particular, the term "antibodies" also encompasses antigen binding fragments of natural antibodies. The purified interleukin can also be used as a reagent to detect any antibodies generated in response to the presence of elevated levels of expression, or immunological disorders which lead to antibody production to the endogenous cytokine. Additionally, IL-13 fragments may also serve as immunogens to produce the antibodies of the present invention, as described immediately below. For example, this invention contemplates antibodies having binding affinity to or being raised against the amino acid sequence shown in Table 1, fragments thereof, or homologous peptides. In particular, this invention contemplates antibodies having binding affinity to, or having been raised against, specific fragments which are predicted to be, or actually are, exposed at the exterior protein surface of the native cytokine.

The blocking of physiological response to these interleukins may result from the inhibition of binding of the ligand to the receptor, likely through competitive inhibition. Thus, in vitro assays of the present invention will often use antibodies or ligand binding segments of these antibodies, or fragments attached to solid phase substrates. These assays will also allow for the diagnostic determination of the effects of either binding region mutations and modifications, or ligand mutations and modifications, e.g., ligand analogs.

This invention also contemplates the use of competitive drug screening assays, e.g., where neutralizing antibodies to the interleukin or fragments compete with a test compound for binding to a receptor or antibody. In this manner, the neutralizing antibodies or fragments can be used to detect the presence of any polypeptide which shares one or more binding sites to a receptor and can also be used to occupy binding sites on a receptor that might otherwise bind an interleukin.

V. Making Nucleic Acids and Protein

DNA which encodes the protein or fragments thereof can be obtained by chemical synthesis, screening cDNA libraries, or by screening genomic libraries prepared from a wide variety of cell lines or tissue samples. Natural sequences can be isolated using standard methods and the sequences provided herein, e.g., in Table 1.

This DNA can be expressed in a wide variety of host cells for the synthesis of a full-length human interleukin or fragments which can in turn, for example, be used to generate polyclonal or monoclonal antibodies; for binding studies; for construction and expression of modified agonist/antagonist molecules; and for structure/function studies. Each variant or its fragments can be expressed in host cells that are transformed or transfected with appropriate expression vectors. These molecules can be substantially free of protein or cellular contaminants, other than those derived from the recombinant host, and therefore are particularly useful in pharmaceutical compositions when combined with a pharmaceutically acceptable carrier and/or diluent. The human protein, or portions thereof, may be expressed as fusions with other proteins.

Expression vectors are typically self-replicating DNA or RNA constructs containing the desired receptor gone or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention include those which contain DNA which encodes a protein, as described, or a fragment thereof encoding a biologically active equivalent polypeptide. The DNA can be under the control of a viral promoter and can encode a selection marker. This invention further contemplates use of such expression vectors which are capable of expressing eukaryotic cDNA coding for such a protein in a prokaryotic or eukaryotic host, where the vector is compatible with the host and where the eukaryotic cDNA coding for the receptor is inserted into the vector Such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the interleukin protein or its fragments in various hosts using vectors that do not contain a replication origin that is recognized by the host cell. It is also possible to use vectors that cause integration of the human protein or its fragments into the host DNA by recombination.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels et al. (1985 and Supplements) *Cloning Vectors: A Laboratory Manual,* Elsevier, N.Y., and Rodriquez et al. (eds) *Vectors: A Survey of Molecular Cloning Vectors and Their Uses,* Buttersworth, Boston, 1988, which are incorporated herein by reference.

Transformed cells are cells, preferably mammalian, that have been transformed or transfected with receptor vectors constructed using recombinant DNA techniques. Transformed host cells usually express the desired protein or its fragments, but for purposes of cloning, amplifying, and manipulating its DNA, do not need to express the subject protein. This invention further contemplates culturing transformed cells in a nutrient medium, thus permitting the interleukin to accumulate in the culture. The protein can be recovered, either from the culture or from the culture medium.

For purposes of this invention, nucleic sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the receptor or its fragments include, but are not limited to, such vectors as those containing the lac promoter (pUC-series); trp promoter (pBR322-trp); lpp promoter (the pIN-series); lambda-pP or pR promoters (pOTS); or hybrid promoters such as ptac (pDR540). See Brosius et al. (1988) "Expression Vectors Employing Lambda-, trp-, lac-, and lpp-derived Promoters", in *Vectors; A Survey of Molecular Cloning Vectors and Their Uses,* (eds. Rodriguez and Denhardt), Buttersworth, Boston, Chapter 10, pp. 205–236, which is incorporated herein by reference.

Lower eukaryotes, e.g., yeasts and Dictyostelium may be transformed with IL-13 sequence containing vectors. For purposes of this invention, the most common lower eukaryotic host is the baker's yeast, *Saccharomyces cerevisiae.* It will be used to generically represent lower eukaryotes although a number of other strains and species are also available. Yeast vectors typically consist of a replication origin (unless of the integrating type), a selection gene, a promoter, DNA encoding the receptor or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are normally the preferred host cells for expression of the functionally active interleukin protein. In principle, any higher eukaryotic tissue culture cell line is workable, e.g., insect baculovirus expression systems, whether from an invertebrate or vertebrate source. However, mammalian cells are preferred. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, Sv40, parvoviruses, vaccinia virus, or cytomegalovirus. Representative examples of suitable expression vectors include pCDNA1; pCD, see Okayama et al. (1985) *Mol. Cell Biol.* 5:1136–1142; pMClneo PolyA, see Thomas et al. (1987) *Cell* 51:503–512; and a baculovirus vector such as pAC 373 or pAC 610.

For secreted proteins, an open reading frame usually encodes a polypeptide that consists of a mature or secreted product covalently linked at its N-terminus to a signal peptide. The signal peptide is cleaved prior to secretion of the mature, or active, polypeptide. The cleavage site can be predicted with a high degree of accuracy from empirical rules, e.g., von-Heijne (1986) *Nucleic Acids Research* 14:4683–4690, and the precise amino acid composition of the signal peptide does not appear to be critical to its function, e.g., Randall et al. (1989) *Science* 243:1156–1159; Kaiser et al. (1987) *Science* 235:312–317.

It will often be desired to express these polypeptides in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the interleukin gene may be co-transformed with one or more genes encoding mammalian or other glycosylating enzymes. Using this approach, certain mammalian glycosylation patterns will be achievable in prokaryote or other cells.

The source of human IL-13 can be a eukaryotic or prokaryotic host expressing recombinant huIL-13 DNA, such as is described above. The source can also be a cell line such as mouse Swiss 3T3 fibroblasts, but other mammalian cell lines are also contemplated by this invention, with the preferred cell line being from the human species.

Now that the entire sequence is known, the human IL-13, fragments, or derivatives thereof can be prepared by conventional processes for synthesizing peptides. These include processes such as are described in Stewart and Young (1984) *Solid Phase Peptide Synthesis,* Pierce Chemical Co., Rockford, Ill.; Bodanszky and Bodanszky (1984) *The Practice of Peptide Synthesis,* Springer-Verlag, New York; and Bodanszky (1984) *The Principles of Peptide Synthesis,* Springer-Verlag, New York; all of each which are incorporated herein by reference. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The IL-13 protein, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction typically must be protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonylhydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield et al. (1963) in *J. Am. Chem. Soc.* 85:2149–2156, which is incorporated herein by reference.

The prepared protein and fragments thereof can be isolated and purified from the reaction mixture by means of peptide separation, for example, by extraction, precipitation, electrophoresis, various forms of chromatography, and the like. The interleukin of this invention can be obtained in varying degrees of purity depending upon its desired use. Purification can be accomplished by use of the protein purification techniques disclosed herein or by the use of the antibodies herein described in methods of immunoabsorbant affinity chromatography. This immunoabsorbant affinity chromatography is carried out by first linking the antibodies to a solid support and then contacting the linked antibodies with solubilized lysates of appropriate cells, lysates of other cells expressing the interleukin, or lysates or supernatants of cells producing the protein as a result of DNA techniques, see below. Generally, the purified protein will be at least about 40% pure, ordinarily at least about 50% pure, usually at least about 60% pure, typically at least about 70% pure, more typically at least about 80% pure, preferable at least about 90% pure and more preferably at least about 95% pure, and in particular embodiments, 97%–99% or more. Purity will usually be on a weight basis, but can also be on a molar basis. Different assays will be applied as appropriate.

VI. Antibodies

Antibodies can be raised to the various human IL-13 proteins and fragments thereof, both in naturally occurring native forms and in their recombinant forms, the difference being that antibodies to the active ligand are more likely to recognize epitopes which are only present in the native conformations. Anti-idiotypic antibodies are also contemplated, which would be useful as agonists or antagonists of a natural receptor or an antibody.

Antibodies, including binding fragments and single chain versions, against predetermined fragments of the protein can be raised by immunization of animals with conjugates of the fragments with immunogenic proteins. Monoclonal antibodies are prepared from cells secreting the desired antibody. These antibodies can be screened for binding to normal or defective protein, or screened for agonistic or antagonistic activity. These monoclonal antibodies will usually bind with at least a $K_D$ of about 1 mM, more usually at least about 300 µM, typically at least about 100 µM, more typically at least about 30 µM, preferably at least about 10 µM, and more preferably at least about 3 µM or better.

The antibodies, including antigen binding fragments, of this invention can have significant diagnostic or therapeutic value. They can be potent antagonists that bind to the interleukin and inhibit binding to the receptor or inhibit the ability of human IL-13 to elicit a biological response. They also can be useful as non-neutralizing antibodies and can be coupled to toxins or radionuclides to bind producing cells, or cells localized to the source of the interleukin. Further, these antibodies can be conjugated to drugs or other therapeutic agents, either directly or indirectly by means of a linker.

The antibodies of this invention can also be useful in diagnostic applications. As capture or non-neutralizing antibodies, they can bind to the interleukin without inhibiting receptor binding. As neutralizing antibodies, they can be useful in competitive binding assays. They will also be useful in detecting or quantifying IL-13.

Protein fragments may be joined to other materials, particularly polypeptides, as fused or covalently joined polypeptides to be used as immunogens. The human IL-13 and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York; and Williams et al. (1967) *Methods in Immunology and Immunochemistry*, Vol. 1, Academic Press, New York; each of which are incorporated herein by reference, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites et al. (eds) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed) Academic Press, New York; and particularly in Kohler and Milstein (1975) in *Nature* 256: 495–497, which discusses one method of generating monoclonal antibodies. Each of these references is incorporated herein by reference. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse et al. (1989) "Generation of a Large Combinatorial Library of the Immunoglobulin Repertoire in Phage Lambda," *Science* 246:1275–1281; and Ward et al. (1989) *Nature* 341:544–546, each of which is hereby incorporated herein by reference. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant or chimeric immunoglobulins may be produced, see Cabilly, U.S. Pat. No. 4,816,567. These patents are incorporated herein by reference.

The antibodies of this invention can also be used for affinity chromatography in isolating the IL-13. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified protein will be released.

The antibodies may also be used to screen expression libraries for particular expression products. Usually the antibodies used in such a procedure will be labeled with a moiety allowing easy detection of presence of antigen by antibody binding.

Antibodies raised against each human IL-13 will also be used to raise anti-idiotypic antibodies. These will be useful in detecting or diagnosing various immunological conditions related to expression of the protein or cells which express receptors for the protein. They also will be useful as agonists or antagonists of the interleukin, which may be competitive inhibitors or substitutes for naturally occurring ligands.

VII. Uses of IL-13 compositions, nucleic acids

Both naturally occurring and recombinant forms of the human Interleukin P molecules of this invention are particularly useful in kits and assay methods. For example, these methods would also be applied to screening for binding activity to these proteins. Several methods of automating assays have been developed in recent years so as to permit screening of tens of thousands of compounds per year. See, e.g., a BIOMEK automated workstation, Beckman Instruments, Palo Alto, Calif., and Fodor et al. (1991) *Science* 251:767–773, which is incorporated herein by reference. The latter describes means for testing binding by a plurality of defined polymers synthesized on a solid substrate. The development of suitable assays to screen for a receptor or agonist/antagonist homologous proteins can be greatly facilitated by the availability of large amounts of purified, soluble interleukin in an active state such as is provided by this invention.

Rational drug design may also be based upon structural studies of the molecular shapes of a receptor or antibody and other effectors or ligands. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form the molecular contact regions. For a detailed description of protein structural determination, see, e.g., Blundell and Johnson (1976) *Protein Crystallography*, Academic Press, New York, which is hereby incorporated herein by reference.

Purified interleukin can be coated directly onto plates for use in the aforementioned receptor screening techniques. However, non-neutralizing antibodies to these proteins can be used as capture antibodies to immobilize the respective interleukin on the solid phase, useful, e.g., in diagnostic uses.

This invention also contemplates use of interleukin-13, fragments thereof, peptides, and their fusion products in a variety of diagnostic kits and methods for detecting the presence of the protein or its receptor. Alternatively, or additionally, antibodies against the molecules may be incorporated into the kits and methods. Typically the kit will have a compartment containing either a defined IL-13 peptide or gene segment or a reagent which recognizes one or the other. Typically, recognition reagents, in the case of peptide, would be a receptor or antibody, or in the case of a gene segment, would be a probe.

A preferred kit for determining the concentration of, for example, IL-13, a sample would typically comprise a labeled compound, e.g., receptor or antibody, having known binding affinity for IL-13, a source of IL-13 (naturally occurring or recombinant) as a positive control, and a means for separating the bound from free labeled compound, for example a solid phase for immobilizing the IL-13 in the test sample. Compartments containing reagents, and instructions, will normally be provided.

Antibodies, including antigen binding fragments, specific for IL-13 or a peptide fragment, or receptor fragments are useful in diagnostic applications to detect the presence of elevated levels of IL-13 and/or its fragments. Diagnostic assays may be homogeneous (without a separation step between free reagent and antibody-antigen complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA) and the like. For example, unlabeled antibodies can be employed by using a second antibody which is labeled and which recognizes the antibody to IL-13 or to a particular fragment thereof. These assays have also been extensively discussed in the literature. See, e.g., Harlow and Lane (1988) *Antibodies: A Laboratory Manual*, CSH., and Coligan (Ed.) (1991) and periodic supplements, *Current Protocols In Immunology* Greene/Wiley, New York.

Anti-idiotypic antibodies may have similar use to serve as agonists or antagonists of IL-13. These should be useful as therapeutic reagents under appropriate circumstances.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled receptor is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium having appropriate concentrations for performing the assay.

Any of the aforementioned constituents of the diagnostic assays may be used without modification or may be modified in a variety of ways. For example, labeling may be achieved by covalently or non-covalently joining a moiety which directly or indirectly provides a detectable signal. In any of these assays, a test compound, IL-13, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both of the patents are incorporated herein by reference. Possibilities for indirect labeling include biotinylation of one constituent followed by binding to avidin coupled to one of the above label groups.

There are also numerous methods of separating the bound from the free ligand, or alternatively the bound from the free test compound. The IL-13 can be immobilized on various matrixes followed by washing. Suitable matrices include plastic such as an ELISA plate, filters, and beads. Methods of immobilizing the receptor to a matrix include, without limitation, direct adhesion to plastic, use of a capture antibody, chemical coupling, and biotin-avidin. The last step in this approach involves the precipitation of antibody/antigen complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle et al. (1984) *Clin. Chem*, 30(9):1457–1461, and the double antibody magnetic particle separation as described in U.S. Pat. No. 4,659,678, each of which is incorporated herein by reference.

The methods for linking protein or fragments to various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of an IL-13. These sequences can be used as probes for detecting levels of the IL-13 in patients suspected of having a proliferative cell conditions, e.g., cancer. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet et al. (1989) *Progress in Growth Factor Res.* 1:89–97.

VIII. Therapeutic Utility

This invention provides reagents with significant therapeutic value. The IL-13 (naturally occurring or recombinant), fragments thereof, and antibodies thereto, along with compounds identified as having binding affinity to the interleukin or its receptor or antibodies, should be useful in the treatment of conditions exhibiting abnormal expression of the interleukin. Such abnormality will typically be manifested by immunological disorders. Additionally, this invention should provide therapeutic value in any disease or disorder associated with abnormal expression or abnormal triggering of response to the interleukin.

Recombinant IL-13 or IL-13 antibodies can be purified and then administered to a patient. These reagents can be combined for therapeutic use with additional active ingredients, e.g., in conventional pharmaceutically acceptable carriers or diluents, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof which are not complement binding.

Receptor screening using IL-13 or fragments thereof can be performed to identify molecules having binding affinity to the interleukin. Subsequent biological assays can then be utilized to determine if a receptor can provide competitive binding, which can block intrinsic stimulating activity. Receptor fragments can be used as a blocker or antagonist in that it blocks the activity of IL-13. Likewise, a compound having intrinsic stimulating activity can activate the receptor and is thus an agonist in that it simulates the activity of IL-13. This invention further contemplates the therapeutic use of antibodies to IL-13 as antagonists.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman et al. (eds) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; each of which is hereby incorporated herein by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Because of the likely high affinity binding between an IL-13 and its receptors, low dosages of these reagents would be initially expected to be effective. Thus, dosage ranges would ordinarily be expected to be in amounts lower than 1 mM concentrations, typically less than about 10 µM concentrations, usually less than about 100 nM, preferably less than about 10 pM (picomolar), and most preferably less than about 1 fM (femtomolar), with an appropriate carrier. Slow release formulations, or slow release apparatus will often be utilized for continuous administration.

IL-13 fragments thereof, and antibodies or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations comprise at least one active ingredient, as defined above, together with one or more acceptable carriers thereof. Each carrier must be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman et al. (eds) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; each of which is hereby incorporated herein by reference. The therapy of this invention may be combined with or used in association with other immunotherapeutic or immunopreventive agents.

The broad scope of this invention is best understood with reference to the following examples, which are not intended to limit the inventions in any manner.

EXAMPLES

Outline

I. Isolation of cDNA clone encoding human IL-13
II. Expression and purification of mouse P600 and human IL-13 protein
III. Biological Effects on B cells
  A. cofactor/factor proliferation; cell viability
  B. sustained survival of B cells; selectivity
  C. modification of Ig surface markers
  D. effects on CD40
  E. IgE switching
IV. Biological Effects on PBMC and macrophages
  A. induction of morphological change
  B. modification of cell surface markers
  C. nitric oxide synthesis
  D. IL-6
V. Antigen Dependent Cell-mediated Cytoxicity
VI. IL-4 antagonist; interactions
VII. Antibodies to human IL-13

Many techniques applicable to IL-4 and IL-10 may be applied to IL-13, as described, e.g., in U.S. Pat. No. 5,017,691 (IL-4) and U.S. Pat. NO. 5,231,012 (IL-10), each of which is incorporated herein by reference for all purposes.

I. Isolation of cDNA clone encoding human IL-13

An approximately 400 bp DNA fragment derived from a Pst/PvuII restriction digest of the mouse P600 cDNA clone was isolated by polyacrylamide gel electrophoresis and subsequent elution and ethanol precipitation. This fragment, which encompasses most of the coding region of the mouse P600 cDNA, was radioactively labeled by random priming in the presence of [$^{32}$P]dCTP.

Filter lifts were prepared following standard procedures from ten agar plates each with approximately 5000 colonies of a B21 cDNA library. This library was made from cloned human T cells, designated B21, which had been stimulated with anti-CD3 for 7 hours prior to the isolation of the RNA. The construction of this library is described in U.S. Ser. No. 07/453,951.

The filters were hybridized overnight at 42° C. with the labeled mouse P600 fragment in 20% formamide, 6X SSPE, 0.1% SDS, 5X Denhardt's solution, and 100 µg/ml tRNA. The filters were washed 3 times with 2X SSPE, 0.1% SDS at room temperature for 20 minutes each, twice with 1X SSPE, 0.1% SDS at 55° C. for 1 hour, then exposed to film overnight. Eight positives were identified and picked for further purification. Seven of these were positive upon rescreening. Six clones had BamH1 inserts of 1.35 kb and one an insert of only 0.6 kb. The 1.35 kb insert of one clone, designated pB21.2Bf, was subcloned into M13 and sequenced by the dideoxy method. Sequence comparison demonstrated that this 1.16 kb cDNA encodes a human homolog of mouse P600.

The huIL-13 cDNA isolated from the B21 library was not full length as compared to the mouse P600 cDNA. Repeated attempts to isolate a full-length cDNA from the B21 library were unsuccessful. Thus, a different library was screened with the pB21.2Bf insert for a full length clone. A PCR probe was derived from the human cDNA beginning 50 bp from the 5' end and ending at the stop codon.

A cDNA library was made from a clone of an A10 T cell line. The same hybridization conditions as described above were used. The filters were washed once in 1X SSPE, 0.05% SDS at room temperature for 15 minutes and then twice at 55° C. for 30 min to one hour. They were exposed to film overnight. Several positives colonies were detected and rescreened. Double stranded sequence obtained from the 5' end of several of the cDNA inserts from these positives indicated that they were full-length. One of the 1.3 kb cDNA inserts, from a clone designated pA10.66, was subcloned into M13 and sequenced. Its sequence is shown in Table 1. The sequence of the full length clone differed from the sequence shorter clone by a single codon, which is present in the full length clone, see Table 3.

II. Expression and purification of mouse P600 and human IL-13 protein

The pB21.2Bf clone, containing a 1.16kb cDNA encoding human IL-13, lacked the first 23 N-terminal amino acids. The insert was prepared for ligation into an expression vector pGEX-2T by using PCR to provide unique restriction sites at the 5' BamH1 and 3' EcoR1 ends. The pGEX-2T vector is designed to produce a fusion protein, where the distinct protein segments are separated by a readily cleaveable protease site. The gel purified DNA was ligated into the expression vector pGEX-2T so that when the plasmid is expressed in *E. coli* the protein encoded by the DNA insert produces a fusion protein with glutathione-S-transferase with a thrombin cleavage site in between as described in detail by Smith et al. (1988) *Gene* 67:31–40. The resulting plasmid was transformed into *E. coli* and successful transformants were grown in the presence of IPTG. Expression products of this construct, when grown under inducing conditions, accumulated in inclusion bodies.

Mouse P6001 Refolding and Purification

Transformed *E. coli* cells were grown in media at 37° C. and induced with IPTG at 0.5 OD. The induced cells were grown until maximal OD was reached either by shake flask or fermentation. Cells were harvested by centrifugation at 4000×g at 4° C. for 30 min and were frozen at −10° C.

Cells were resuspended at room temperature in TE buffer (50 mM Tris-HCl, 10 mM EDTA pH 8 with 1 mM Peflobloc, a protease inhibitor). Cells were passed through a microfluidizer at 18000 psi, collected, and centrifuged at 10,000×g at 4° C. for 30 min. Cell pellets were repeatedly washed in TE buffer and centrifuged until supernatant was clear. The pellet was solubilized with 6M guanidine-HCl, 10 mM DTT, 50 mM Tris-HCl pH 9, and 1 mM Peflobloc and mixed at 4° C. for 2 hours. The protein concentration was measured by the Bradford Protein method and typically was approximately 2.5 mg/ml total protein concentration. The mixture was diluted over a period of hours to 100 fold of its unfolding volume into 50 mM Tris-HCl, 150 mM NaCl, 2 mM reduced glutathione, 1 mM oxidized glutathione, 0.5M guanidine-HCl, and 10 mM EDTA at pH 9.0. The solution was mixed at 4° C. for 24 hours, allowing refolding of disulfide linkages of the molecule.

Precipitates were removed by centrifugation at 4000×g for 30 min at 4° C. The supernatant was concentrated using a Pellicon and diafilter against 50 mM Trizma pH 7.5 buffer at 4° C. The glutathione-S-transferase fusion partner was cleaved off by adding $CaCl_2$ to 2.5 mM final concentration and human thrombin at 10 μg per 50 μg of fusion protein. The mixture was mixed at 4° C. for 18 hrs to allow the fusion protein to be cleaved by thrombin. SDS-PAGE gels and TF1 bioassay was used to characterize P600 conformation and activity.

Refolded material was adjusted to pH 4.5 with concentrated acetic acid (HoAc) and loaded onto an S-Sepharose fast flow column, equilibrated at pH 4.5 with 50 mM sodium acetate, 10 mM NaCl buffer. The column was washed with equilbration buffer until the A280 approached baseline. The column was eluted with a 0–1M NaCl gradient in equilibration buffer for 5 bed volumes. Fractions were collected and SDS-PAGE gels run to observe P600 presence. Fractions were pooled and concentrated in a 3000 molecular cutoff Filtron stir cell, to a volume less than 5% of the bed volume of the gel filtration column (Sephracryl 200).

The S-200 column was equilibrated with depyrogenated buffer 50 mM NaPi, 150 mM NaCl, and 0.01% Tween-20 pH 6.0. The concentrated S pool was loaded onto the gel filtration column and fractions were collected and verified for P600 protein content by SDS-PAGE gels. Fractions were pooled based on SDS-PAGE, concentrated, filtered through 0.22 μm filters and tested by the TF1 bioassay for biological activity. Protein concentration was determined by silver staining and scan using the Molecular Dynamic gel scanner. Endotoxin was measured using the Whittaker colorimetric Limulus assay and typically was <1 eu/ml typical preparations resulted in >95% purity by staining, with a bioactivity of about $8 \times 10^5$ units/ml. Protein concentration was typically around 300 μg/ml. Variations on the refolding procedure will be effective, e.g., protein concentrations may vary over some range, typically a 5-fold difference will also work. The glutathione concentrations may be varied, and the periods of time for slow dilution and overnight incubations may be titrated. Each of the refolding parameters described should be titrated where appropriate.

Similar procedures were used prepare and to purify human IL-13.

III. Activities on B cells

A. cofactor/factor proliferation; cell viability

Mouse P600 functions as a stimulator/costimulator of cell viability, e.g., mouse P600 made from *E. coli* can stimulate or costimulate proliferation of large in vivo activated mouse B cells. Decreasing amounts of P600 administered to the cells resulted in lessened cell growth as determined by $^3$H-thymidine incorporation.

To construct a cDNA encoding the extracellular domain of CD40 (designated "soluble CD40"), the following PCR primers containing an XhoI site were synthesized on an Applied Biosystems 380A DNA synthesizer: sense: 5'-ACAGCTCGAGCCATGGTGTCTTTGCCTCGGCTGT G-3' and antisense: 5'-GTAGCTCGAGCTCACCGG-GACTTTAAACCACAGATG-3' SEQ ID NO: 5 and 6. These primers were used to produce PCR fragments encoding 191 amino acids from the start codon of mouse CD40. PCR fragments were digested with XhoI and then ligated into XhoI cleaved mammalian/bacterial expression vector (pME18S). The inserted fragment was sequenced by the dideoxy sequencing method to confirm the sequence.

Plasmids carrying the soluble CD40 cDNA were transfected into COS7 cells by electroporation by standard procedures, See Ausubel et al. (1987 and periodic supplements). Briefly, 0.75 ml of COS7 cell suspension in serum free Dulbecco's Minimal Essential (DME) medium at $10^7$ cells per ml were incubated with 50 μl of 20 μg plasmid at room temperature for 10 min, and subjected to electroporation using a Bio-Rad gene pulser (960 F, 220 V). Ten minutes after electroporation, COS7 cells were cultured in four 10 cm dishes for 3 days. For the purification of soluble CD40, medium was changed to phenol red-free RPMI 1640 supplemented with HB101 (HANA Biologics, Alameda, Calif.) one day after electroporation.

Soluble CD40 was purified by ion exchange chromatography on anion exchange columns using standard procedures. The protein was eluted from the column using a linear NaCl gradients and analyzed by Western Blotting using a rabbit antiserum against a CD40 peptide made by standard methods.

Eight week old female Lewis rats were obtained from Harlan Sprague-Dawley (Indianapolis, Ind.). These rats were immunized intaperitoneally with 10 μg of soluble CD40 in complete Freund's adjuvant followed by boosts of 10, 10, 10, and 50 μg of soluble CD40 in incomplete Freund's adjuvant at 3, 4.5, 6, and 8.5 weeks, respectively. A final boost in saline was injected at 12 weeks. Test bleeds were evaluated for anti-CD40 antibody content by ELISA.

Small dense B cells from unstimulated mouse spleens were prepared as described in Hodgkin et al. (1991) *Cell, Immunol.* 134:14. Spleens were teased into complete RPMI (cRPMI) containing 5% fetal calf serum (FCS; J. R. Scientific, Woodland, Calif.), $5 \times 10^{-5}$M 2-mercaptoethanol (Polysciences, Inc., Warrington, Pa.), 2 mM glutamine (J. R. Scientific), and 25 mM HEPES buffer (Irvine Scientific, Santa Ana, Calif.), 100 U/ml penicillin, and 100 μg/ml streptomycin (Irvine). Red blood cells were lysed using 0.83% ammonium chloride, pH 7.4. T cells were removed using two successive treatments with anti-mouse Thy 1.2 mAb (New England Nuclear, Boston, Mass.) and anti-L3T4 antibody (RL172.4 hybridoma, a gift from Dr. H. R. MacDonald, Ludwig Institute, Epalinges, Switzerland) for 20 min on ice followed by complement (1:10 dilution of rabbit low-tox complement, Cedarlane Laboratory, Ontario, Canada) for 30 min at 37° C. Small dense B cells were then isolated by density gradient centrifugation using a discontinuous gradient composed of 75%, 65%, and 50% percoll (Pharmacia Fine Chemicals, Uppsala, Sweden) at 2500×g for 25 min at 4° C. Cells collected from the interface between 65% and 75% percoll were used in subsequent experiments. Large in vivo activated B cells were collected from the 65% and 50% interface. B cells were cultured in flat bottomed 96 well tissue culture plates (3072, Falcon Labware) at various cell densities in cRPMI, plus additional stimulants, as indicated. Proliferation was evaluated via a 4 hr pulse of $^3$H-thymidine (Amersham) added at 48 hr after culture initiation.

B. sustained survival of B cells; selectivity

Reagents

The anti-CD40 mAb89 and anti-CD23 mAb25 were produced by standard procedures against the respective antigens, see Vallé et al. (1989) *Eur. J. Immonol* 19:1463–1467; Bonnefoy et al. (1987) *J. Immunol.* 138:2970–2978. The CDw32/Fcg RII transfected Ltk-cell line (CDw32 L cells) was described by Peltz et al. (1988) *J. Immunol.* 141:1891–1896. Anti-IgM antibodies coupled to beads (anti-µ) were purchased from Biorad (Richmond, Calif.). Cell phenotype was determined using FITC conjugated mAb originating from Becton Dickinson (Mountain View, Calif.). The neutralizing anti-IL-4 monoclonal antibody was kindly provided by Dr. Grassi. The extracellular domain of the 130 kDa IL-4 receptor was derived from Cos-7 cells transfected with a plasmid containing a truncated IL-4 cDNA described by Garrone et al. (1991) *Eur. J. Immunol.* 21:1365–1369. The recombinant protein was purified from transfected cell culture supernatant by purification on an IL-4-Affi-gel 10 column. The anti-130 kDa IL-4 receptor antibody was generated after immunization of mice with the extracellular domain of the IL-4 receptor. Cultures were carried out in modified Iscove's medium.

B Cell Preparations and Cell Cultures.

B cells were isolated from tonsils as described by Defrance et al. (1987) *J. Immunol.* 139:1135–1144. Briefly, after a rosetting step with sheep red blood cells, non-rosetting cells were further incubated with anti-CD2, anti-CD3, and anti-CD14 mAbs prior to negative selection performed with magnetic beads coated with anti-mouse IgG (Dynabeads, Dynal, Oslo, Norway). The isolated population expressed >98% CD19 or CD20 (B cells) and <1% CD2 (T cells) or CD14 (monocytes).

Assays with antigen receptor activated B cells.

B lymphocytes, adjusted at $5 \times 10^5$ cells/ml. were stimulated for 72 h with insolubilized anti-IgM (5 µg/ml). A 16 h pulse with 1 µCi ($^3$H)TdR was usually performed at day 3 and 6. ($^3$H)TdR uptake was measured by standard liquid scintillation counting techniques.

CD40 system.

For proliferation assays, $2.5 \times 10^4$ purified B cells were cultured in the presence of $2.5 \times 10^3$ irradiated (7000 rad) CDw32 L cells and 0.5 µg/ml of anti-CD40 mAb89 in a final volume of 200 µl. For Ig production, B cells were tested at $2.5 \times 10^5$ cells/ml. Supernatants were harvested after 10 days and Ig levels were determined by ELISA.

Isolation of sIgD$^+$ and sIgD$^-$ B cell populations.

Purified B lymphocytes were separated using a preparative magnetic cell separation system (MACS, Becton-Dickinson), according to the experimental procedure described in detail by Miltenyi et al. (1990) *Cytometry* 11:231–238. The separation based on sIgD expression has been described earlier by Defrance et al. (1992) *J. Exptl. Med.* 175:671–682. Purity of the sorted cell populations were >99% for the sIgD$^+$ B cell subpopulation, while <1% of sIgD$^-$ B cell subpopulation expressed dIgD, as assessed by fluorescence analysis using a FACScan.

Cytokines.

Purified recombinant hIL-2 (Amgen, Thousand Oaks, Calif., $3 \times 10^6$ U/ml), recombinant hIL-4 (Schering-Plough Research Institute, Bloomfield, N.J., $1 \times 10^7$ U/mg), recombinant hIL-10 (Schering-Plough Research Institute, Bloomfield, N.J., $1 \times 10^7$ U/ml) were respectively used at 10U/ml, 50 U/ml, and 100 ng/ml. IL-13 was expressed as a fusion protein with glutathione-Stransferase using the pGEX-2T vector (Pharmacia, Uppsala, Swede). A DNA fragment encoding hIL-13 residues 24–109 was prepared by polymerase chain reaction (PCR) and cloned into the BamHI/EcoRI site of the vector. A DNA fragment encoding mIL-13 residues 19–109 was also prepared and cloned. The human and mouse IL-13 fusion proteins were expressed as insoluble aggregates in *Escherichia coli*, extracted by centrifugation, solubilized, and subjected to a renaturation step, see van Kimmenade et al. (1988) *Eur. J. Biochem.* 173:109–114. The refolded IL-13 was cleaved from the fusion partner by thrombin, purified by cation exchange (S-Sepharose FPLC, Pharmacia) and gel filtration (Sephacryl s-200 FPLC, Pharmacia) chromatography. The gel filtration column was calibrated with protein standards (Bio-Rad). Proteins were quantitated by SDS-PAGE, silver staining (ISS), and scanning densitometry (Molecular Dynamics) with normalization to chicken egg lysozyme (Sigma, St. Louis, Mo.). Endotoxin (determined by the Limulus ameobocyte lysate assay (Whittaker Bioproducts, Inc.) was typically <1 eu/ml.

IL-13 enhances the DNA synthesis of B cells activated through their antigen receptor.

Figure 2A:
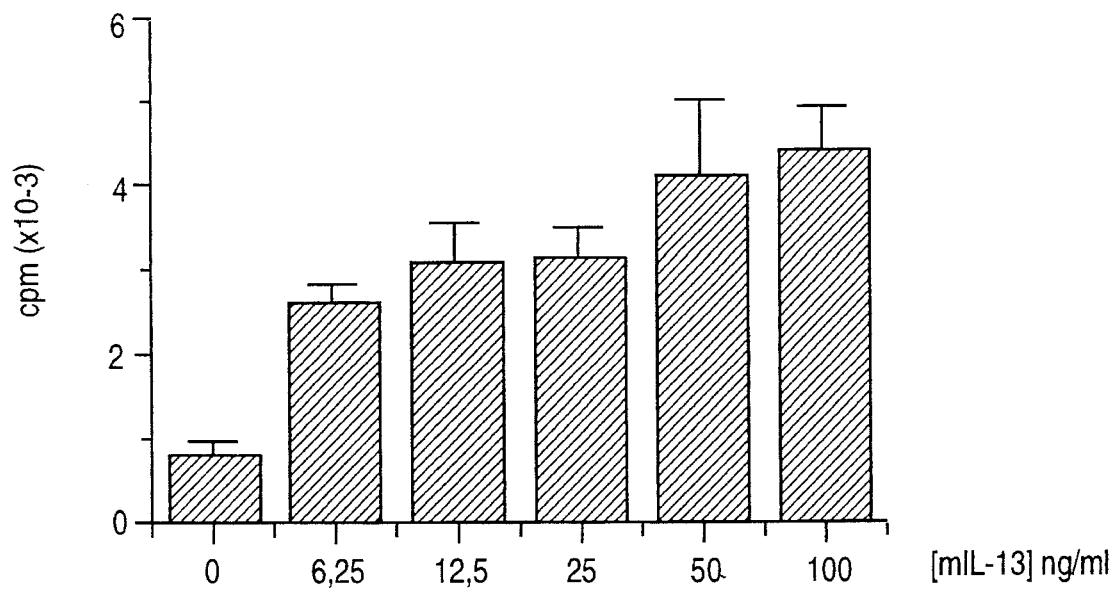
FIGS. 2A–2B show that IL-13 enhances the DNA synthesis of B lymphocytes activated through their antigen receptor. $5\times10^5$ purified B cells were cultured in microwells together with 5 µg/ml anti-IgM beads.
Figure 2B:
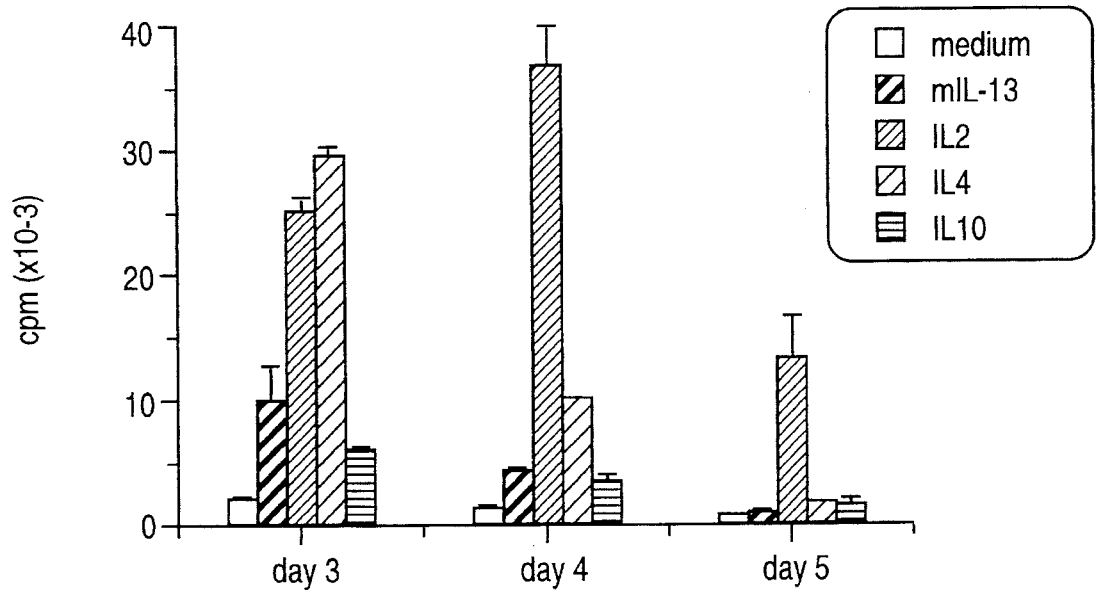

The DNA synthesis of highly purified human B lymphocytes activated through their antigen receptor with anti-IgM antibody is enhanced by recombinant cytokines, such as IL-2, IL-4, and IL-10. Results illustrated in FIG. 2A show that recombinant murine IL-13 also enhanced, in a dose dependent fashion, the day 3 DNA synthesis of human tonsillar B lymphocytes cultured in the presence of insolubilized anti-IgM antibody. The maximum stimulation was obtained for a concentration of 10–25 ng/ml of murine (or human) IL-13. As shown in FIG. 2B, the stimulatory effect was lower than that of either IL-2 or IL-4 but comparable to that of IL-10. As IL-4, but unlike IL-2, the co-stimulatory effect of IL-13 on anti-IgM activated B cells could be observed after 3 days of culture, but not after 6 days.

IL-13 acts as growth factor for B Cells stimulated through their CD40 antigen.

Figure 3A:
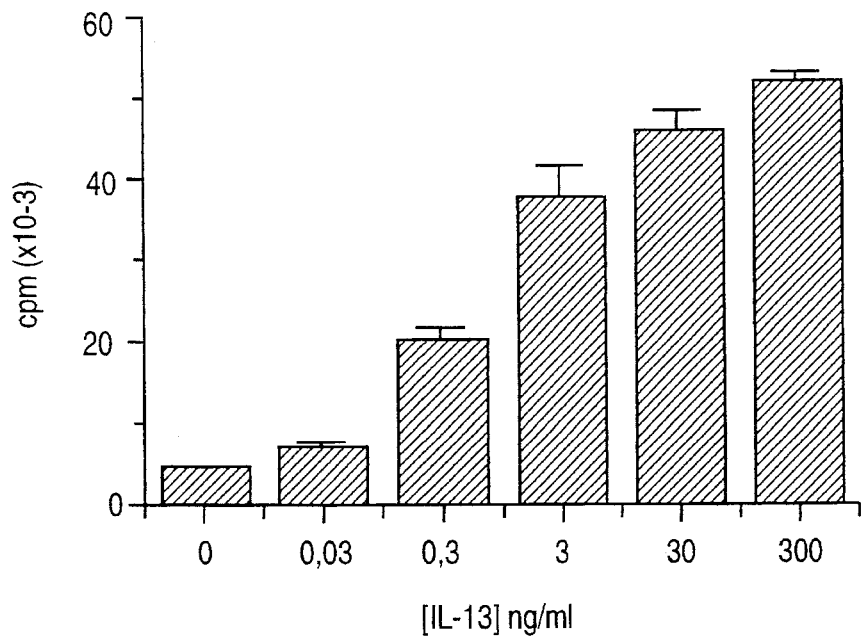
FIGS. 3A–3D show IL-13 induces profileration of anti-CD40 activated B lymphocytes. $2.5\times10^4$ purified B cells were cultured on $2.5\times10^3$ irradiated CDw32 L cells with 0.5 µg/ml mAb89.
Figure 3B:
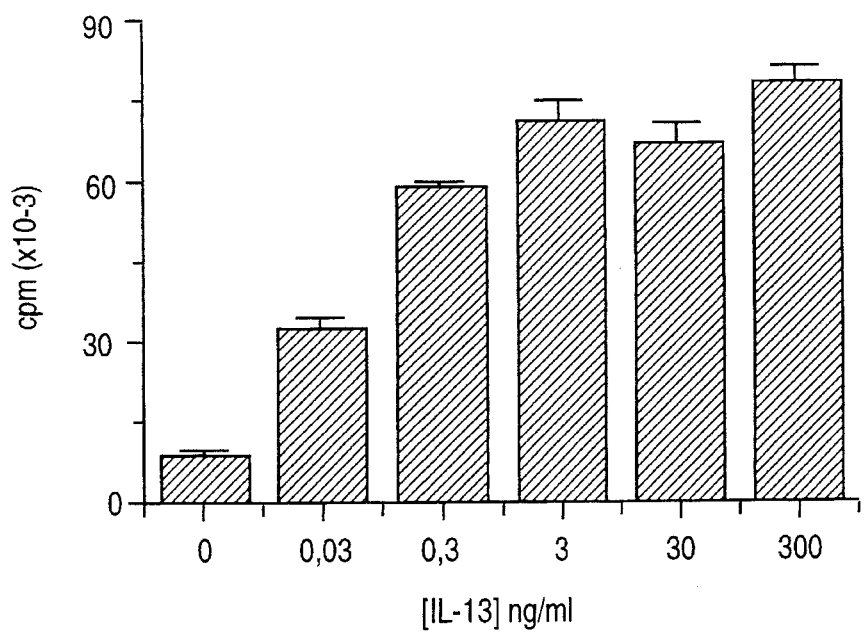
Figure 3C:
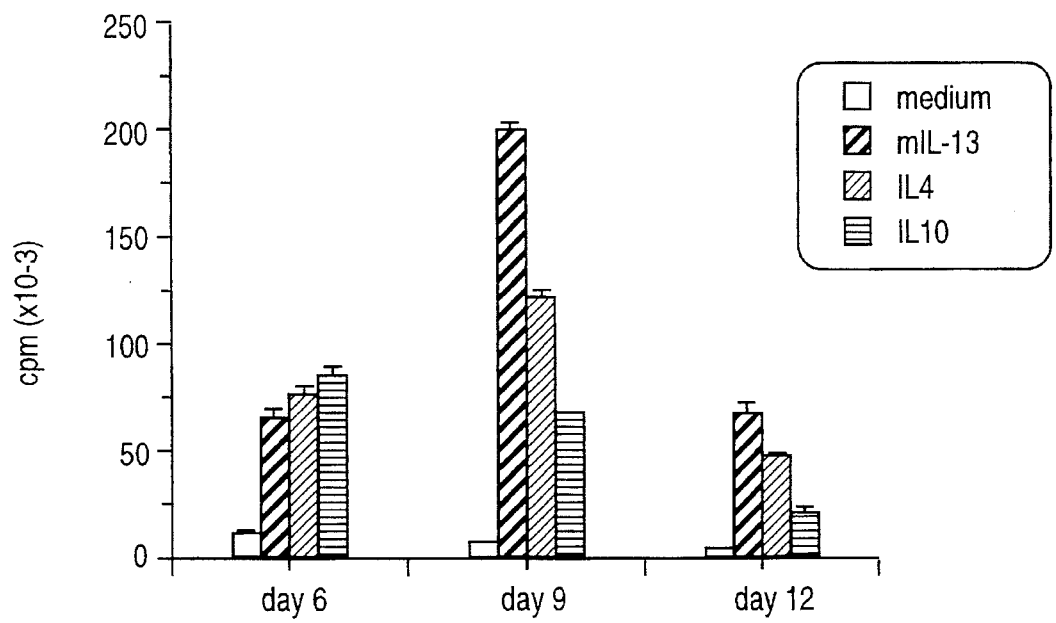
Figure 3D:
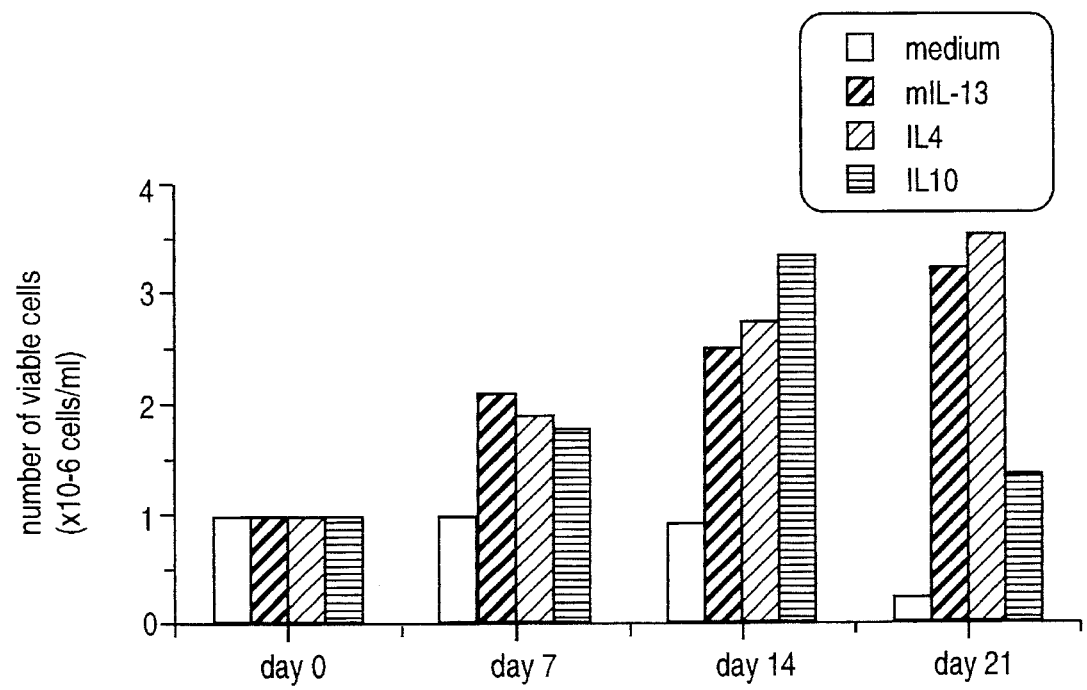
Figure 4A:
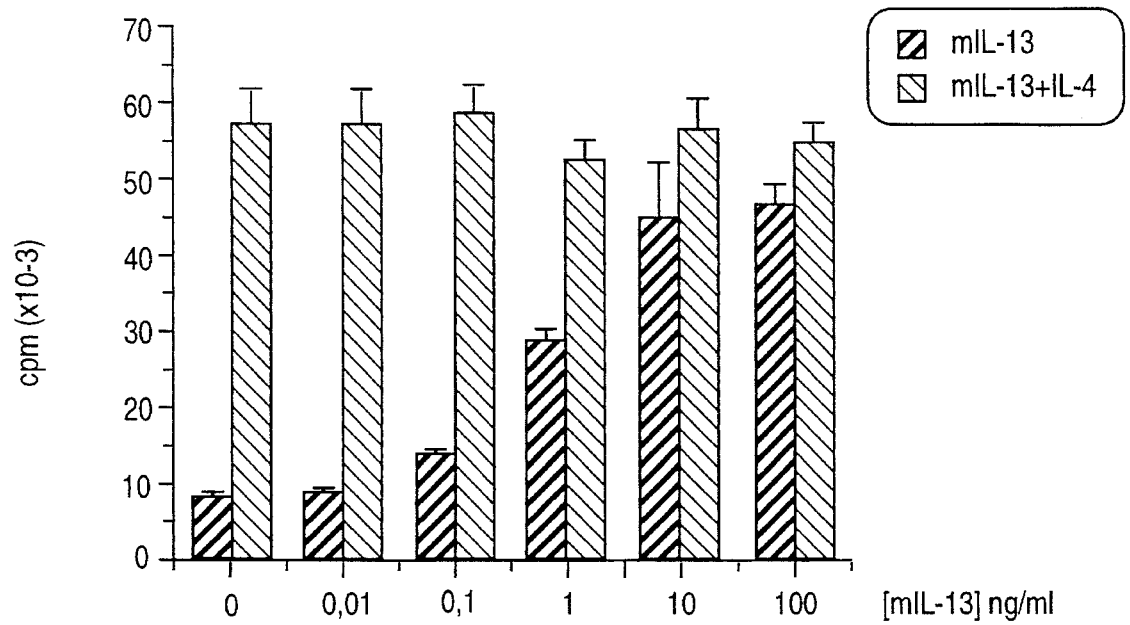
FIGS. 4A–4C show additive effectives of IL-13 and IL-10 but not IL-13 and IL-4 on the proliferation of CD40 activated B cells. $2.5\times10^4$ purified B cells were cultured on $2.5\times10^3$ irradiated CDw32 L cells with 0.5 µg/ml mAb89 and increasing concentrations of murine IL-13.
Figure 4B:
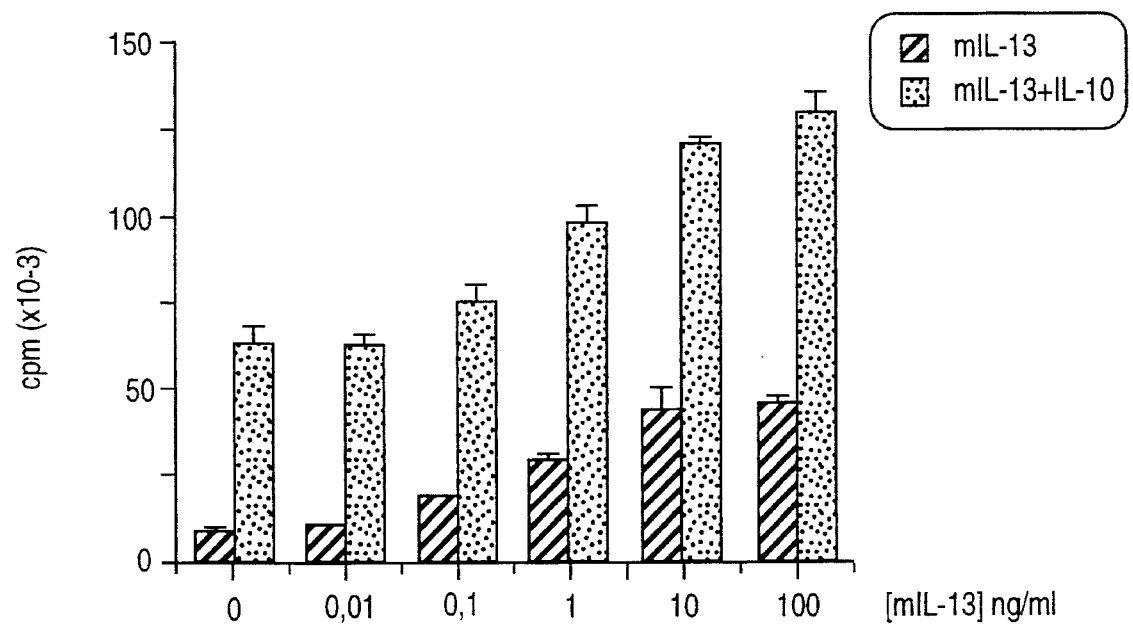
Figure 4C:
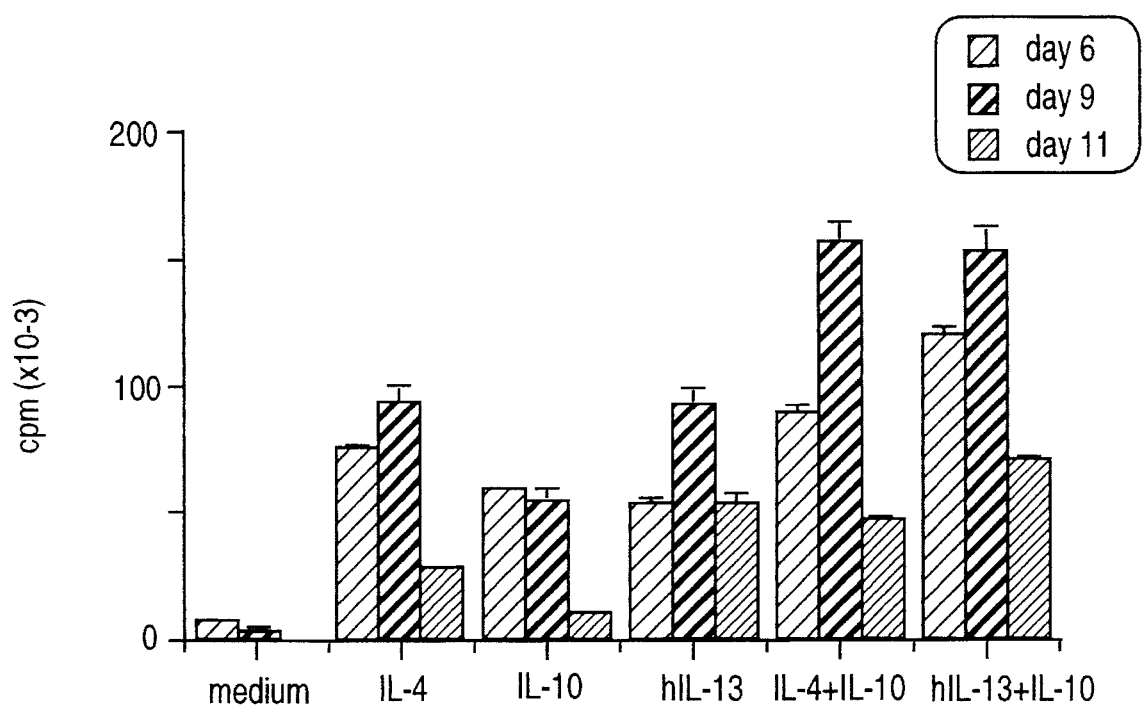

IL-13 was also assayed for its ability to enhance the proliferation of anti-CD40 activated B cells in comparison with IL-4 and IL-10. Thus, $2.5 \times 10^4$ purified tonsillar B lymphocytes were cultured over CDw32 expressing L cells together with 0.5 µg/ml of the anti-CD40 antibody Mab 89 with or without increasing concentrations of IL-13. ($^3$H)TdR incorporation was measured at day 6. As shown in FIGS. B2A and B2B, both murine and human IL-13 strongly enhanced anti-CD40 induced DNA synthesis. Maximum stimulation was reached between 3 and 30 ng/ml IL-13 and plateaued thereafter without demonstrating any inhibitory effect (even at 1000 ng/ml). Under these culture conditions, the half maximal stimulation was observed between 0.03 and 0.3 ng/ml in three independent experiments. The growth stimulatory effects of IL-13 were then compared to those of IL-4 and IL-10. As shown in FIGS. 3C and 4C, IL-13 activity was comparable to that of IL-4 and IL-10 when assayed early in the vulture at day 6. The IL-13 stimulatory activity was particularly striking at day 9 where it surpassed that of IL-10 and more notably that of IL-4. IL-13 also showed stimulatory effects at day 12 and again was more efficient than either IL-4 or IL-10. Cultures grown in the presence of IL-13 formed extremely tight clumps. Clumps were very difficult to dissociate and thus rendered extremely inaccurate the enumeration of viable lymphocytes during cell cultures. Nevertheless, cell cultures were split every fifth day for up to 25 days, at which time the number of viable B lymphocytes had increased about 12 fold (estimated conservatively).

Whether IL-13 could act in concert with IL-4 or IL-10 for maximal B cell proliferation was studied. As shown in FIG. 4A, combination of optimal concentration of IL-4 and with increasing concentration of IL-13 resulted in a DNA synthesis which was comparable to that obtained with IL-4, thus indicating the lack of synergy and even additivity between these two cytokines. In contrast, combination of IL-13 and IL-10 (FIG. 4B) resulted in an additivity of their stimulatory effects. The additive effects of IL-13 and IL-10 on B cell proliferation were observed at all time tested (FIG. 4C). Taken together, these results indicate that IL-13 is a growth factor for human B lymphocytes.

IL-13 induces anti-CD40 activated B cells to secrete IgE.

In view of the powerful effects of IL-13 on the proliferation of anti-CD40 activated B cells, culture supernatants were analyzed for their immunoglobulin content. As shown in Table 5, as IL-4 but unlike IL-10, IL-13 did not stimulate the production of IgM, I9G, and I9A in day 8 cultures of anti-CD40 activated B cells. However, IL-13 was able to induce B cells to secrete IgE in a dose dependent fashion (Table 5, FIGS. 5A through 5E). IL-13 was comparable to IL-4 in its capacity to induce IgE (FIGS. 5A through 5E). The combination of IL-4 and IL-13 resulted in a production of IgE which was either comparable or slightly enhanced when compared to that obtained with IL-4 alone. IL-13 unable to induce either resting B cells or anti-μ activated B cells to secrete IgE.

TABLE 5

| IL-13 induces anti-CD40 activated B cells to secrete IgE. | | | | |
|---|---|---|---|---|
| cytokine | IgG (μg/ml) | IgA (μg/ml) | IgM (μg/ml) | IgE (μg/ml) |
| none | 1.2 ± 0.09 | 0.4 ± 0.04 | 0.08 ± 0.005 | <bg |
| IL-4 | 1.4 ± 0.01 | 0.4 ± 0.005 | 0.2 ± 0.005 | 37 ± 1.1 |
| IL-10 | 15.0 ± 1.9 | 12.0 ± 2 | 18.0 ± 0.6 | <bg |
| IL-13 | 1.6 ± 0.4 | 0.4 ± 0.001 | 0.2 ± 0.04 | 25.2 ± 3.3 |

$5 \times 10^4$ purified B cells were cultured for 10 days with $2.5 \times 10^3$ irradiated CDw32 L cells with the anti-CD40 mAb89 without or with 50 U/ml IL-4, 100 ng/ml IL-10, 30 ng/ml hIL-13. If levels represent the mean ± SD values of quadruplicate determinations. Representative of three experiments. (<bg = lower than 150 pg/ml of IgE.)

The IL-13 target B cell subpopulation is more restricted than the IL-4 one.

In order to further compare the effects of IL-4 and IL-13, B cells cultured in the CD40 system with either cytokine were phenotyped after six days of culture. As shown in FIGS. 6A through 6D, IL-13 is able to induce CD23 expression on cultured B cells with an intensity comparable to that obtained with IL-4. However, whereas IL-4 induced >90% of the cultured B cells to express CD23, IL-13 induced CD23 only on 40% of the B cell population. In addition, whereas IL-4 was able to readily induce CD23 on both resting and anti-μ activated B cells, IL-13 was much less efficient under these conditions.

Figure 6D:
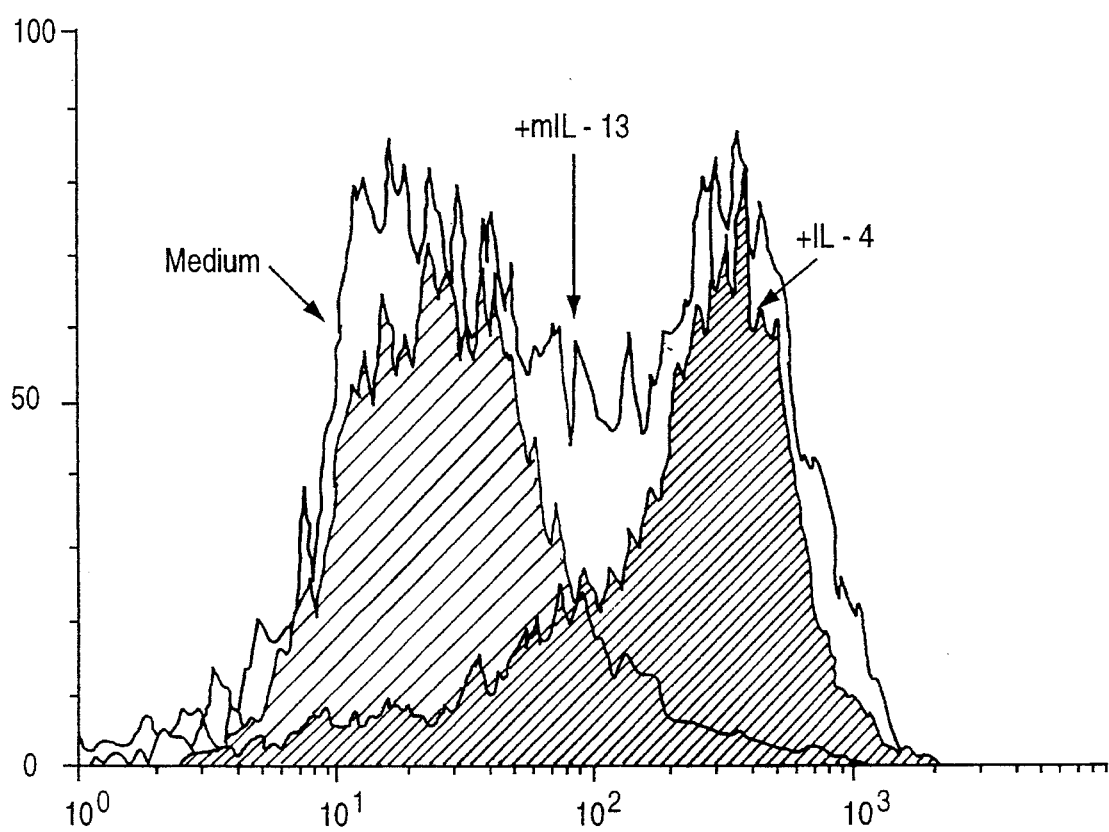

The transferrin receptor expression was also analyzed on B cells cultured for six days in the CD40 system with or without IL-4 or IL-13. As shown in FIG. 6D, all B cells expressed transferrin receptors (TfR), but two populations could be clearly distinguished according to levels of expression which were designated TfR low and TfR high. In the CD40 system alone, 80% of the B cells were TfR low, and 5% TfR high. In cultures performed with IL-13, 55% of the cells were TfR low and 40% were TfR high. In cultures performed with IL-4, 10% of the cells were TfR low and 85% were TfR high.

Figure 7:
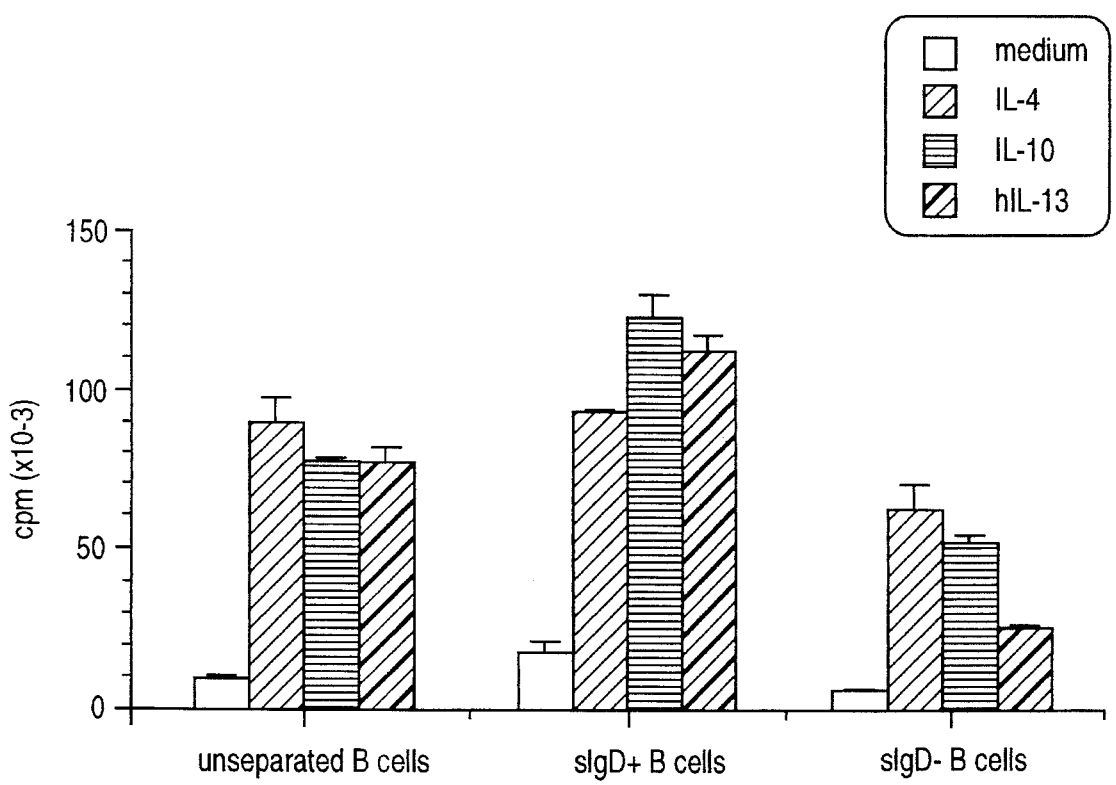
FIG. 7 shows IL-13 preferentially acts on sIgD+ B cells. $10^4$ unseparated, sIgD$^+$ or sIgD$^-$ B cells were cultured on $2.5\times10^3$ irradiated CDw32 L cells with 0.5 µg/ml mAb89 without cytokine or with 50 U/ml of IL-4 or 30 ng/ml of hIL-13. ($^3$H)TdR uptake was measured at day 6. Cultures were performed in triplicate, and means±SD are presented.

As sIgD$^+$B cells consist of naive B cells, whereas sIgD$^-$ B cells consist of a mixture of germinal center B cells and memory B cells, the reactivity to IL-4, IL-10, and IL-13 of sIgD$^+$ and sIgD$^-$ B cells was tested in the CD40 system. As shown in FIG. 7, both sIgD$^+$ and sIgD$^-$ B cells proliferated strongly in response to IL-4 and IL-40, as measured by ($^3$H)TdR incorporation after six days of culture. In contrast, IL-13 preferentially enhanced the anti-CD40 induced DNA synthesis of sIgD$^+$ cells. Furthermore, IL-13 and IL-4 were able to induce both sIgD$^+$ and sIgD$^-$ B cells to secrete IgE (FIG. 6D).

Taken together, these results indicate that IL-13 acts preferentially on sIgD$^+$ cells and thus acts on a B cell subpopulation more restricted in size than that stimulated by IL-4.

The IL-13 biological effects are independent of IL-4.

Figure 8A:
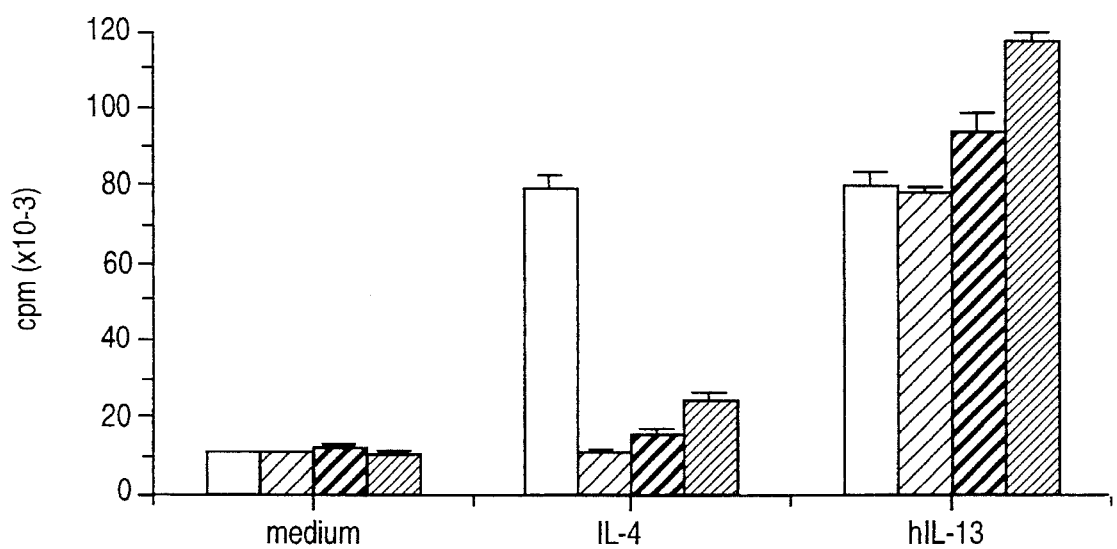
FIGS. 8A–8B show that IL-13 biological effects are independent of IL-4 and 130 kD IL-4 receptor. $2.5\times10^4$ for proliferation assay or $5\times10^4$ purified B cells were cultured on $2.5\times10^3$ irradiated CDw32 L cells with 0.5 µg/ml mAb89 without or with 50 U/ml of IL-4 or 30 ng/ml of hIL-13, without or with the following IL-4 antagonist: 10 µg/ml anti-130 kDa IL-4R mAbs 924, 10 µg/ml neutralizing anti-IL-4 mAb 5, 10 µg/ml of recombinant extracellular domain of the 130 kDa IL-4R.
Figure 8B:
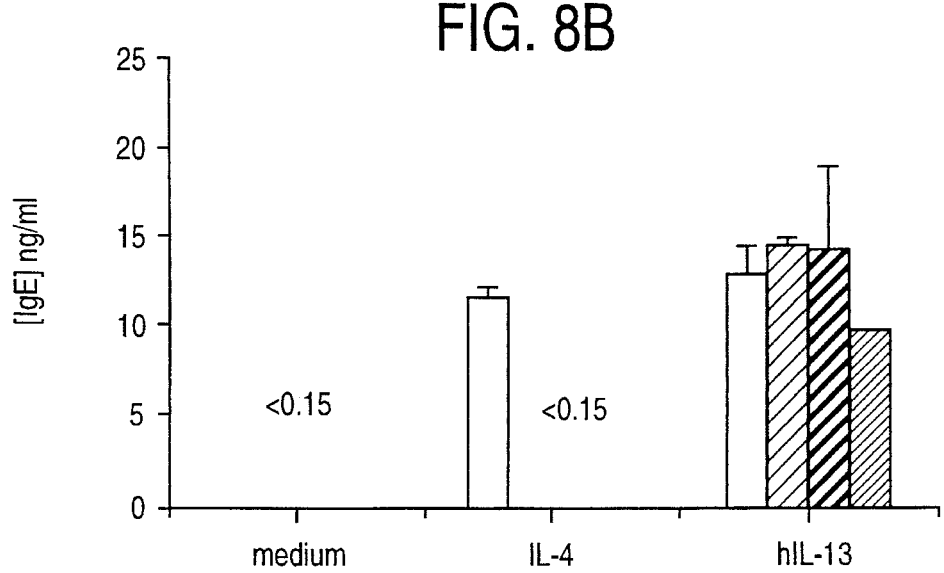

As IL-13 displays many of the biological effects of IL-4, it was suspected that it might act either through an induction of IL-4 secretion or through binding to the IL-4 receptor. To address this question, the IL-13 induced B cell proliferation was tested in the presence of three different IL-4 antagonists: 1) a neutralizing anti-IL-4 monoclonal antibody; 2) a soluble extracellular domain of the 130 kDa IL-4R (see Garrone et al. (1991) Eur. J. Immonol 21:1365–1369); 3) a blocking anti-130 kDa IL-4R monoclonal antibody. As shown in FIG. 8A, these three antagonists blocked by 80–90% the effects of IL-4 on the proliferation of anti-CD40 activated B lymphocytes without affecting the proliferation induced by IL-13. These IL-4 antagonists also failed to block IL-13 induced CD23 expression (FIG. 6A) and IgE production (FIG. 6B) while they did totally block that induced by IL-4.

Induction of B cell proliferation by IL-13 or IL-4 and COS cells expressing the human or mouse CD40-L.

Figure 9:
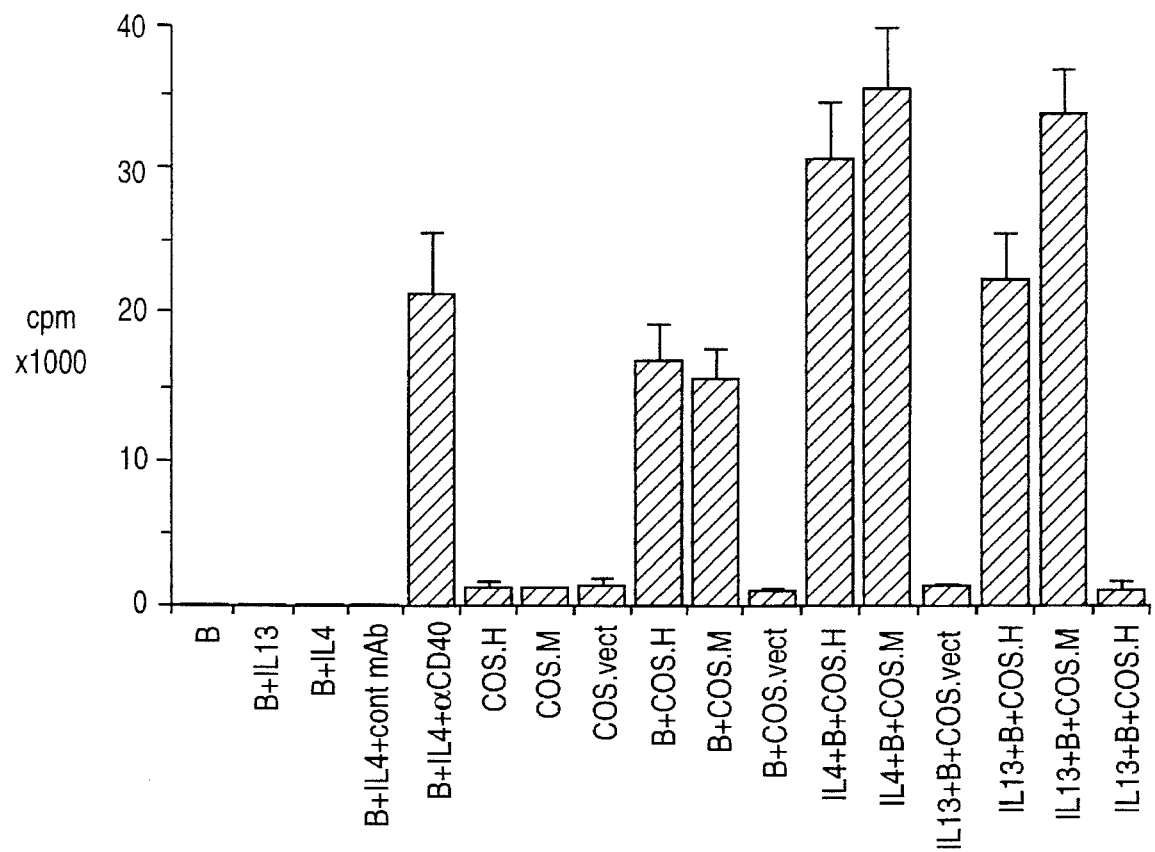
FIG. 9 illustrates the induction of B cell proliferation by IL-13 or IL-4 and COS cells expressing the human or mouse CD40L.

FIG. 9 illustrates this. Five ×10$^4$ highly purified (>98% CD20+) negatively sorted splenic B cells were co-cultured with 1.6×10$^4$ irradiated (7,000 rad) COS cells transfected with human or mouse CD40-L or the empty pJFE-14 vector as control. IL-13 or IL-4 were added at 400 U/ml. Soluble anti-CD40 mAB89 and the control mAbA4 were used at 50 μg/ml. The cultures were harvested 3 days later, after addition of $^3$H Thymidine in the last 16 h of culture. The values represent means and standard deviations of triplicate cultures. A representative experiment is shown.

Biological effects of IL-13 on human B cell growth and differentiation have been described. IL-13 costimulated with anti-IgM antibody to induce DNA synthesis but its effects were less conspicuous than those of IL-2 or IL-4. IL-13, as other cytokines, failed to induce the multiplication of B cells activated through their antigen receptor. However, IL-13 displayed striking growth promoting effects on B cells which were cultured in the CD40 system, which is composed of a fibroblastic cell line expressing the human Fc receptor CDw32 and monoclonal antibody to CD40. Under these conditions, IL-13 was at least as active as IL-4 and its effects on B cells were long lasting, thus allowing the multiplication of viable B cells. IL-13 altered the phenotype of activated B cells, as it induced B cells to express CD23.

The IL-13 dependent induction of CD23 on CD40 activated B cells is not mediated by an anti-CD40 activation, since resting and anti-IgM activated B cells can also be induced to express CD23 in response to IL-13. However, the proportion of cells expressing CD23 was lower with IL-13 than with IL-4. Likewise, IL-4 induced virtually all CD40 activated B cells to express high levels of transferrin receptors. IL-13 induced only half the cells to express transferrin receptors at high density. This indicated that IL-13 was acting on a subpopulation of B cells which was more restricted than that affected by IL-4. Accordingly, when cells were separated according to surface IgD (sIgD), which distinguishes naive B cells from germinal center and memory B cells, IL-13 was found to be more effective than IL-4 on sIgD+ cells. IL-4 was able to enhance better than IL-13 the proliferation of sIgD- B cells. The different population target for IL-13 and IL-4 could be explained by differential IL-13 and IL-4 receptors expression, the demonstration of which will await the availability of labeled IL-13 or of IL-13 receptor specific antibodies. The lower response of sIgD B cells is particularly interesting and warrants further analysis. IL-13, as IL-4, poorly enhanced the synthesis of IgG and IgM by B cells cultured in the CD40 system. Surprisingly, however, IL-13 induced anti-CD40 activated B cells to produce IgE. The levels of IgE produced in response to IL-13 were comparable to those produced in response to IL-4. IL-4, as well as IL-13, were able to induce IgE synthesis by anti-CD40 activated B cells. As a consequence of isotype switching, IL-13, like IL-4, was able to induce sIgD$^+$ to secrete IgE. As IL-4, IL-13 could not induce resting B cells to secrete IgE. At first, this IL-13 induced IgE production contrasts with other studies indicating IL-4 as being the sole induced of IgE synthesis. However, recent studies have described assays system resulting in the secretion of IgE, while IL-4 was totally blocked by neutralizing antibody. IL-2 has been reported to induce secretion by *Staphylococcus aureus* activated B cells, whereas IL-4 was ineffective. It may be possible that in these studies, IL-13 was responsible for these effects.

While IL-13 causes many functions similar to IL-4 on B cells, the present study demonstrates that these effects are independent of possible induction of IL-4 secretion or the use of the 130 kDA IL-4 receptor, e.g., neutralizing anti-IL-4 antibody, blocking soluble IL-4 receptor, and blocking anti-IL-4 receptor antibody were unable to affect the action of IL-13 on B cell proliferation and IgE secretion. However, it can not be excluded that IL-13 may share with IL-4 some common transducer. Crosslinking studies have shown the binding of IL-4 to 60–70 and 70–80 kDa component unrelated to the 130 kDa molecule. In this context, it is worth noting that both human and murine IL-13 act on human B cells with similar efficiency, while murine IL-4 is species specific. The respective roles of IL-13 and IL-4 in IgE production can be determined more particularly when mice which IL-4 gene has been knocked out (e.g., IL-4 knock-out mice) display no circulating IgE.

Finally, it will be important to establish whether human IL-13 is produced only by T cells or if other cell types also produce it. Furthermore, IL-13 may be involved in abnormal B cell proliferation, as occurs in leukemic and antoimmune diseases. Thus, agonists or antagonists of IL-13 may be useful in therapeutic treatment of such conditions.

C. modification of Ig surface markers on activated human B cells

Highly purified B cells were isolated from normal human spleens obtained from cadaver transplant donors. Splenocytes were obtained by aseptically squashing spleens though a sterile metal mesh and frozen in aliquots for subsequent use. Highly purified B cells (>98% CD20$^+$) were obtained by negative FAGStar Plus Becton Dickinson sorting after staining the splenocytes with the following PE-conjugated mAb: anti-CD3, anti-CD4, anti-CD8, anti-CD14, anti-CD16, and anti-CD56. (Becton Dickinson).

Human IL-13 was used at 30 ng/ml final concentration. Recombinant IL-4 (used at 400 U/ml) was provided by Schering Research (Bloomfield, N.J.).

Five thousand highly purified B cells were co-cultured with an equal number of T cells from clones B21 or spA3, harvested five days after stimulation with feeder cells and PHA, in a final volume of 0.2 ml of Yssel's medium supplemented with 10% FCS, 10 µg/ml ultra pure transferrin (Pierce), and 400 U/ml recombinant IL-4. Cultures were set up in eight replicates in U-bottom 96 well plates (Linbro) and incubated 14 days at 37° C. in 5% CO$_2$. At the end of the incubation period, the supernatants from each of the eight wells were harvested and pooled for isotype determination. In some cultures, the T cell clones were replaced by 5 µg of plasma membranes derived from the T cell clones, or by 50 µg/ml anti-CD40 mAb 89.

Ig content of the supernatants was determined by ELISA as described by Gascan et al. (1992) *Eur. J. Immunol.* 22:1133–1141. Plasma membranes were prepared from the CD4$^+$ T cell clone B21, also as described therein. The results are described above, and the data presented in FIGS. 10A through 10O.

FIG. 11A through 11B also shows induction of Ig synthesis by IL-13 or IL-4 and COS cells expressing CD40-L. Highly purified sIgD+ splenic B cells (5000 cells/well) were co-cultured with pJFE14 vector transfected or sorted Cos7 cells (250 cells/well) transfected with and expressing the human (h) or mouse (m) CD40-L. IL-13 (30 ng/ml) and IL-4 (400 U/ml) were added as indicated. The sensitivities of the ELISAs (0.2 ng/ml for IgE and IgM, 0.4 ng/ml for IgG4 and total IgG) were determined with calibrated Ig standards (Behring, Marburg, Germany). In FIGS. 11A through 11B some IgG determinations were not possible, as there was detection of the Ig portion of CD40-Ig fusion protein added.

D. effects of CD40 ligand

The human CD40 ligand (hCD40L) was cloned from a cDNA library constructed from an activated CD8$^+$T-cell clone and detected two cDNA's representing a 2.1 kb and a 1.2 kb clone. Both cDNA clones had identical open reading frames of 261 amino acids and differed only in the length of their 3' untranslated ends, and probably represent the 2.1 kb and 1.2 kb transiently expressed mRNA species detected by Northern analysis in an activated CD4$^+$ T-cell clone. hCD40L transcripts could also be detected in CD4$^+$ and CD8$^+$ T cell receptor (TCR) αβ T cells, TCR γδ T cells, natural killer cells, monocytes, small intestine, and fetal thymocytes, but not in purified B cells, fetal liver, fetal bone marrow, brain, kidney, or heart.

COS-7 cells transfected with hCD40L (COS-7/hCD40L) induced human B cell activation as judged by the induction of homotypic aggregates of Epstein-Barr Virus (EBV) transformed, and normal B cells. In addition, COS-7/hCD40L induced B cell proliferation, which was further enhanced by IL-4, or IL-13. IL-13, like IL-4, synergized with the mouse- and hCD40L to induce IgM, total IgG, IgG4, and IgE, but not IgA production by highly purified B cells. Anti-IL-4 antibodies inhibited IL-4 and COS-7/hCD40L induced Ig production by B cells, but had no effect on IL-13 and COS-7/hCD40L induced B cell differentiation, indicating that IL-13 and hCD40L induced Ig production, including isotype switching to IgE, independently of IL-4. hCD40L induced B cell differentiation was blocked by soluble CD40, confirming the requirement for specific engagement of CD40L. Collectively, these data indicate that CD40L and IL-13 expressed by human CD4+ T helper cells are important components of T and B cell interactions resulting in B cell proliferation, differentiation, and IgE switching. However, the distribution of the hCD40L suggests a broader function of this molecule.

Induction of B cell proliferation and differentiation into Ig producing cells requires T cell help. Antigen-specific T cell and B cell interactions involving binding of the TCR to peptide class II MHC complexes in the B cells result in T cell activation. Activated T cells deliver both contact and cytokine mediated signals, inducing B cell proliferation and differentiation. Once T cells are activated, they can interact with any B cell in an antigen independent class II MHC non-restricted fashion. Lymphokines produced by the activated T helper cells do not only determine the amounts of Ig produced, but they also direct isotype switching. IL-4 is a B cell growth factor and induces human B cells to switch to IgG4 and IgE production, whereas TGF-β directs IgA switching. The human cDNA homologue of P600, a protein produced by mouse Th2 clones following activation, has been recently cloned and expressed, as described herein. The human P600 protein induced human monocyte and B cell growth and differentiation. Therefore this novel cytokine was designated IL-13. Human IL-13 is a non-glycosylated protein of 132 amino acids with a molecular mass ($M_r$) of 10,000 and is produced by T cells. IL-13 has no significant homology with other cytokines except IL-4, which is ~30% homologous. IL-13, like IL-4, can specifically induce IgG4 and IgE switching in human B cells, independently of IL-4.

The contact mediated signals delivered by activated T helper cells can be replaced by anti-CD40 mAbs. One of the contact T helper signals is delivered by the CD40 ligand (CD40L), a 33 kDa molecule expressed on activated CD4+ T cells. CD40L transfectants induced proliferation of B cells and induced IgE production in the presence of IL-4. Here is described the isolation of human CD40L clones from a cDNA library constructed from an activated CD8+ T-cell clone. The distribution of the human CD40L, its ability to activate B cells, and its role as a co-activation molecule with IL-13 compared with IL-4 to differentiate B cells were assessed. Cells transfected with the human CD40L exhibited induced B cell aggregation, proliferation, and considerable Ig production, including IgE synthesis, in the presence of IL-13.

Reagents.

Human rIL-4 was provided by Schering-Plough Research (Bloomfield, N.J.) and human rIL-13 was provided by Dr. W. Dang (DNAX Research Institute, Palo Alto, Calif.). The CD40-Ig fusion protein was obtained by fusion of the cDNA segments encoding the extracellular domain of CD40 to cDNA fragments encoding the human IgG1. The mAb89 was kindly provided by Dr. J. Banchereau (Schering-Plough, Dardilly, France). Streptavidin-PE and all antibodies, unless stated otherwise, were from Becton-Dickinson (Mountain View, Calif.).

Cell purification and culture.

B lymphocytes (>98% CD20+) were purified from spleen using density gradient centrifugation over Ficoll-Hypaque (Pharmacia Fine Chemicals, Piscataway, N.J.), followed by negative cell sorting using a FACStar Plus (Becton Dickinson). Surface IgD+ positive cells were sorted directly from the negatively sorted B cell population. The CD4+ T-cell clone B21 and the CD8+ T-cell clone A10 have been described by Roncarolo et al. (1988) *J. Exp. Med.* 167:1523–1534. In co-culture experiments, various numbers of purified B cells were cultured with different concentrations of COS-7 cells in U-bottom 96-well trays in 0.2 ml as indicated in the text. After 10 days, 50% of the medium was replenished, and after 14 days the supernatants harvested and assayed for Ig's by ELISA. COS-7 cells were transiently transfected. For CD40L staining, COS-7 or B21 cells were incubated on ice with 1.4 μg/ml biotinylated CD40-Ig in PBS, 1% FCS for 20 min, washed twice in PBS with 1% FCS, and stained with ⅕ dilution of streptavidin-PE, and washed twice again. Cells specifically expressing CD40L were sorted using a FACStar Plus (Becton Dickinson) before use.

Human and mouse CD40L cDNA's.

Mouse CD40L DNA provided as a PCR product by Dr. N. Harada and Dr. R. Chang (DNAX Research Institute) was subcloned into the mammalian expression vector pJFE14. The human CD40L was cloned by using the mouse CD40L cDNA as a probe to screen colony blots of a cDNA library derived from the CD8+T-cell clone A10. To make the library, $10^8$ A10 Cells were activated for 8 h with 10 μg/ml con A, harvested, and extracted for RNA. mRNA was purified using a Pharmacia (Uppsala, Sweden) mRNA Purification Kit. cDNA was synthesized and cloned essentially according to the manufacturers instructions using the SuperScript Plasmid System (BRL, Grand Island, N.Y.) the only modification being the use of pJFE14 as the vector for cloning. The library contained $10^6$ independent clones with an average insert size of 1.4 kb.

Northern and PCR analysis.

RNA was isolated using RNAzol B (CNNA: Biotech, Friendswood, Tex.) according to manufacturers instructions. RNA from brain, heart, kidney and small intestine were from Clontech (Palo Alto, Calif.). cDNA was synthesized using SuperScript (BRL) and PCR reactions performed in a Gene-Amp PCR System (PerkinElmer Cetus, Emeryville, Calif.) with 30 cycles of 94° C., 55° C., and 72° C. for 0.5 min, 0.5 min, and 1 min respectively. Primers for detection of CD40L transcripts were 5'-ACA GCA TGA TCG AAA CAT ACA-3', 5'- TGG CTC ACT TGG CTT GGA TCA GTC-3' and for hypoxanthine phosphoribosyltransferase (HPRT) transcripts 5'-TAT GGA CAG GAC TGA ACG TCT TGC-3', 5'-GAG ACA AAC ATG ATT CAA ATC CCT GA-3'. SEQ ID NO: 7–10. Products of PCR reactions were electrophoresed through 1.2% agarose and transferred by capillary blotting to GeneScreen nylon membranes (NEN Research Products, Boston, Mass.) according to manufacturers instructions. For Northern analysis RNA was electrophoresed through 0.85% agarose and transferred to BA-S nitrocellulose (Schleicher and Schuell, Keone, N.H.). CD40L $^{32}$P cDNA probes for Northern and Southern blots were made using as a template a 1.3 kb EcoRI-XhoI fragment of pJFE14-CD40L containing the CD40L coding region.

Cloning and characterization of the human CD40L

To obtain clones of the human CD40L, a cDNA library derived from the CD8+T-cell clone A10 was screened using the mouse CD40L cDNA as a probe, see Armitage et al. (1992) *Nature* 57:80–82.

Positive clones were present in the library at 0.005% and were represented predominantly by a 2.1 kb length clone, but an additional clone of 1.2 kb was detected. Both cDNA's contained an identical open reading frame of 261 amino acids, which would give rise to a protein with an unmodified molecular mass of 29254. The 2.1 kb and 1.2 kb clones differed only in the length of their 3' untranslated ends, and presumably represent the two mRNA species of that size detected by Northern analysis (FIGS. 12A through 12D). The nucleotide and predicted amino acid sequences of the human CD40L cloned here were identical to those reported by Hollenbaugh et al. (1992) *EMBO J.* 11:4313–4321; and Spriggs et al. (1992) *J. Exp. Med.* 176:1543–1550.

Using a biotinylated human CD40-Fc fusion protein in combination with streptavidin-PE, specific expression could be easily detected of human CD40L on COS-7 cells transiently transfected with an expression plasmid pJFE14 containing the 2.1 kb human CD40L cDNA, but not on control cells transfected with empty pJFE14 vector DNA. The human CD40-Fc reagent reacted also with COS-7 cells transfected with the same expression vector containing the mouse CD40L cDNA, which is consistent with previous studies, indicating cross-species binding of human CD40 to mouse CD40L.

The CD40L induces homotypic aggregation of B cells and B cell proliferation

B cell activation with antibodies to CD40 results in homotypic aggregation. To determine whether the CD40L had similar effects, COS-7 cells expressing the CD40L were purified by FACS and co-cultured with purified B cells or JY cells, an EBV transformed B cell line. Indeed, aggregation of JY cells following incubation with the COS-7 cells expressing human or mouse CD40L was observed, whereas mock-transfected COS-7 cells were ineffective (see FIGS. 12A through 12D). Similarly, purified B cells co-cultured with cells expressing human or mouse CD40L displayed marked homotypic aggregations, whereas B cells cultured with untransfected COS-7 cells remained disperse (FIGS. 12A through 12D).

Consistent with the B cell activation observed microscopically, significant proliferation was obtained when purified B cells were co-cultured with COS-7/human CD40L or COS-7/mouse CD40L (see Table 6). This proliferation was further enhanced in the presence of IL-4 or IL-13 (Table 6). The growth promoting effects of IL-4 and IL-13 seem to be comparable under these culture conditions.

TABLE 6

Induction of B cell proliferation by IL-13 or IL-4 and COS cells expressing the human or mouse CD40-L

|  | $^3$H TdR incorporation (c.p.m. × 10$^{-3}$) |
| --- | --- |
| B | 0.1 ± 0 |
| B + IL-13 | 0.1 ± 0 |
| B + IL-4 | 0.2 ± 0 |
| B + IL-4 + control mAb | 0.2 ± 0 |
| B + IL-4 + anti-CD40 | 21.2 ± 4.1 |
| COS hCD40-L | 1.1 ± 0.2 |
| COS mCD40-L | 1.0 ± 0.1 |
| COS | 1.4 ± 0.2 |
| B + COS hCD40-L | 16.9 ± 2.4 |
| B + COS mCD40-L | 17.5 ± 2.1 |
| B + COS | 1.2 ± 0.2 |
| B + IL-4 COS hCD40-L | 30.7 ± 3.8 |

TABLE 6-continued

Induction of B cell proliferation by IL-13 or IL-4 and COS cells expressing the human or mouse CD40-L

|  | $^3$H TdR incorporation (c.p.m. × 10$^{-3}$) |
| --- | --- |
| B + IL-4 COS mCD40-L | 35.4 ± 4.5 |
| B + IL-4 COS | 1.3 ± 0.2 |
| B + IL-13 COS hCD40-L | 22.5 ± 3.0 |
| B + IL-13 COS mCD40-L | 33.8 ± 2.8 |
| B + IL-13 COS | 1.2 ± 0.4 |

Five × 10$^4$ highly purified (>98% CD20$^+$) negatively sorted splenic B cells were co-cultured with 1.6 × 10$^4$ irradiated (7,000 rads) COS cells transfected with human or mouse CD40-L or the empty pJFE-14 vector as control. IL-13 or IL-4 were added at 400 U/ml. Soluble anti-CD40 mAb 89 and the control mAb A4 were used at 50 μg/ml. The cultures were harvested 3 days later after addition of $^3$H Thymidine in the last 16 hours of culture. The values represent means and standard deviations of triplicate cultures.

IL-13 induces Ig production by COS7/hCD40L stimulated B cells.

COS-7 cells expressing human or mouse CD40L also induced Ig production by highly purified naive surface IgD+ human B cells in the presence of IL-4 or IL-13 (Table 7). Considerable levels of IgM, IgG4, total IgG and IgE, but no IgA were produced. There was no IgA production is compatible with previous observations which indicated that IL-4 specifically inhibits IgA synthesis under these culture conditions (9). Ig levels induced by IL-13 were in the same range as those induced by IL-4. No Ig production was obtained in the presence of mock-transfected COS-7 cells (Table 7). Induction of all Ig isotypes by COS-7 cells expressing CD40L was effectively blocked by CD40-Ig (10 μg/ml), confirming that specific engagement of the CD40L is necessary for induction of B cell differentiation and Ig production. Inhibition of total IgG production by CD40Ig could not be measured, since the Ig portion of the CD40-Ig fusion protein gave a strong signal in the IgG ELISA. Interestingly, Ig production, including IgG4 and IgE production, induced by IL-13 in the presence of COS-7/CD40L cells was not blocked by anti-IL-4 mAbs (10 μg/ml), whereas these mAbs strongly blocked IL-4-induced Ig production in the presence of COS-7/CD40L (Table 7). These results indicate that IL-13 induces Ig production independently from IL-4. These data furthermore indicate that IL-13 is another cytokine that directs naive surface IgD+ human B cells to switch to IgG4 and IgE producing cells in the presence of a contact-mediated costimulatory signal delivered by COS-7 cells expressing the mouse or human CD40L.

TABLE 7

Induction of Ig synthesis by Il-13 or Il-4 and COS cells expressing CD40-L

|  | IgM | IgG | IgG4 | IgE |
|  |  |  | ng/ml |  |
| --- | --- | --- | --- | --- |
| COS hCD40-L | 4 ± 2 | 38 ± 4 | 12 ± 1 | <0.2 |
| COS mCD40-L | <0.2 | 6 ± 0 | 3 ± 0 | <0.2 |
| IL-4 + COS hCD40-L | 87 ± 8 | 195 ± 21 | 148 ± 30 | 80 ± 4 |
| IL-4 + COS hCD40-L + CD40-Ig | 3 ± 0.5 | ND* | 1.8 ± 1.4 | 2.7 ± 1.2 |
| IL-4 + COS hCD40-L + anti-IL-4 | 8 ± 3 | 28 ± 7 | 5 ± 3 | 4 ± 2 |
| IL-4 + COS mCD40-L | 64 ± 6 | 208 ± 5 | 177 ± 42 | 68 ± 7 |
| IL-4 + COS mCD40-L + CD40-Ig | <0.2 | ND* | <0.4 | <0.2 |
| IL-4 + COS | 0 ± 0 | 4 ± 0 | 1 ± 0 | <0.2 |
| IL-13 + COS hCD40-L | 51 ± 1 | 151 ± 9 | 127 ± 9 | 54 ± 7 |
| IL-13 + COS mCD40-L | 31 ± 3 | 100 ± 2 | 55 ± 0 | 37 ± 6 |

TABLE 7-continued

Induction of Ig synthesis by Il-13 or Il-4 and COS cells expressing CD40-L

|  | IgM | IgG | IgG4 | IgE |
|---|---|---|---|---|
|  |  | ng/ml |  |  |
| IL-13 + COS | 3 ± 3 | 5 ± 0 | 1 ± 1 | <0.2 |
| IL-13 + COS hCD40-L + antiIL-4 | 48 ± 8 | 167 ± 12 | 111 ± 7 | 48 ± 4 |
| — | <0.2 | 8 ± 1 | 2 ± 0 | <0.2 |
| IL-13 | <0.2 | 7 ± 0 | 1 ± 1 | <0.2 |
| IL-4 | <0.2 | 4 ± 1 | 2 ± 0 | <0.2 |

Highly purified sIgD$^+$ splenic B cells (5,000 cells/well) were co-cultured with pJFE14 vector transfected or sorted COS-7 cells (250 Cells/well) transfected with and expressing the human (h) or mouse (m) CD40-L. IL-13 (30 ng/ml) and IL-4 (400 U/ml) were added as indicated. The sensitivities of the ELISAs (0.2 ng/ml for IgE and Igm, 0.4 ng/ml for IgG4 and total IgG) were determined with calibrated Ig standards (Behring, Marburg, Germany).
*No IgG determination was possible as there was detection of the Ig portion of CD40-Ig fusion protein added.

Expression and distribution of the hCD40L.

Figure 13A:
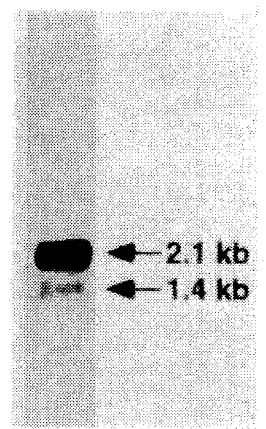
FIGS. 13A–13B show expression of CD40L transcripts.
Figure 13B:
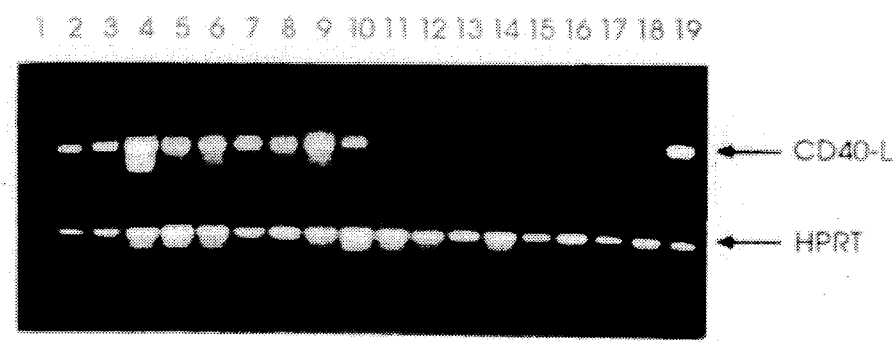
Figure 14A:
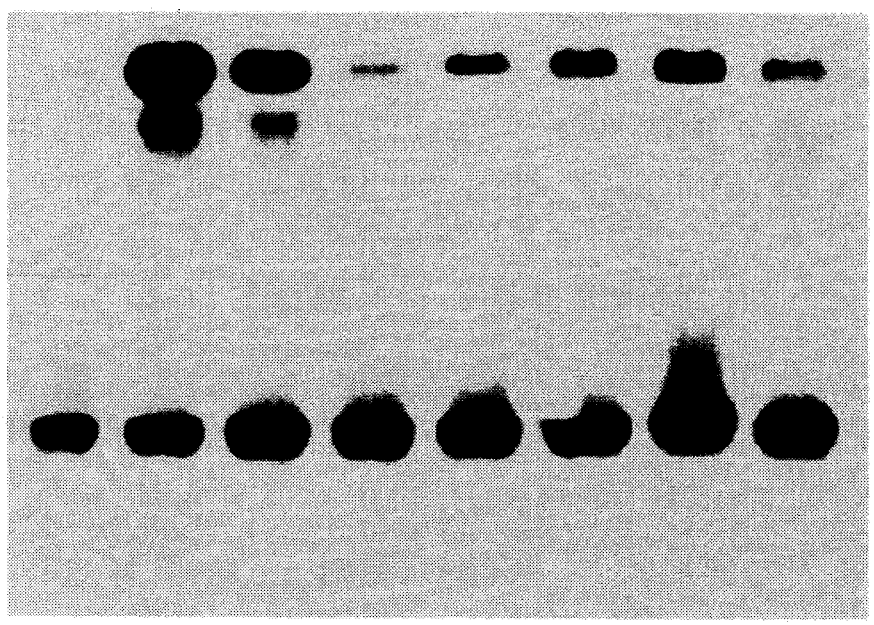
Figure 14B:
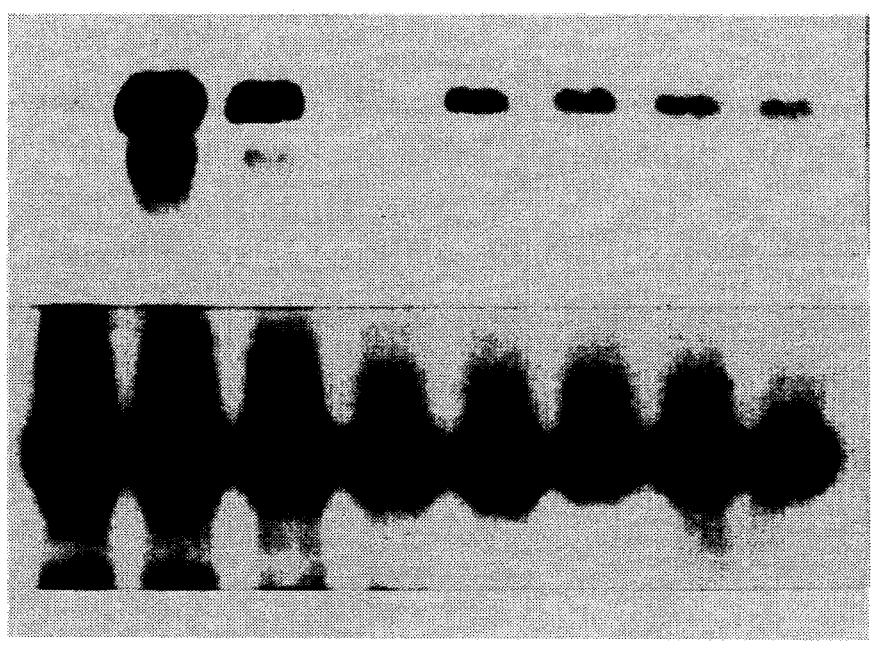
Figure 14C:
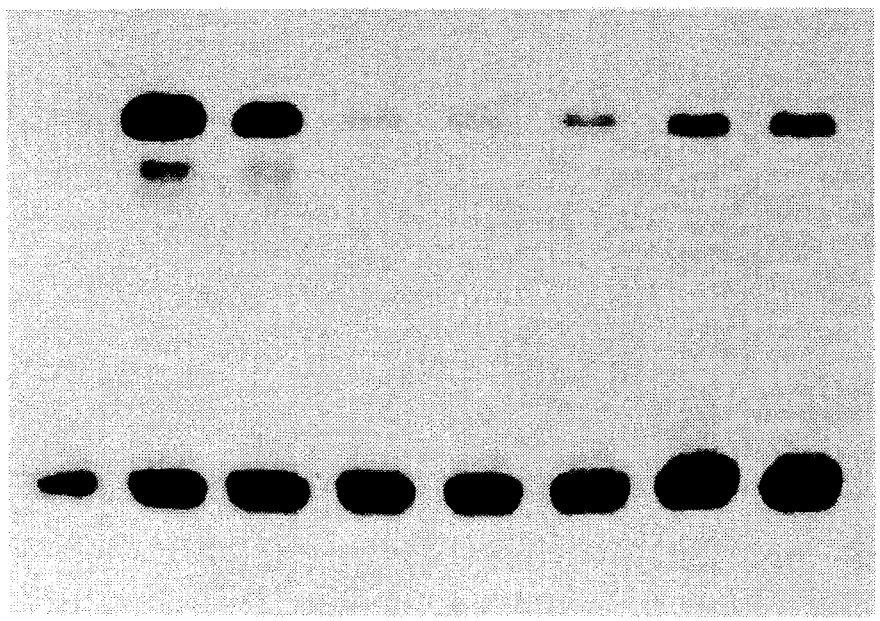
Figure 14D:
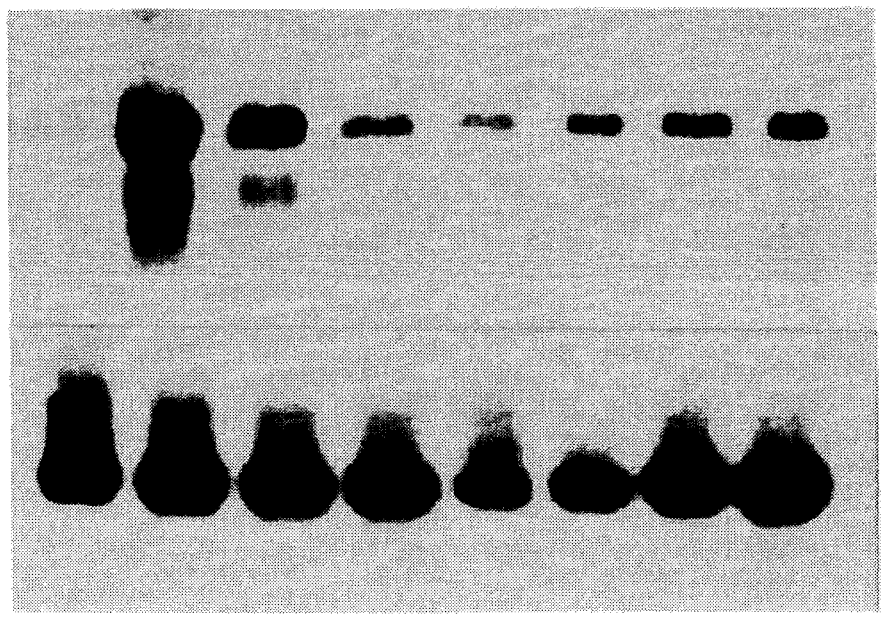
Figure 15A:
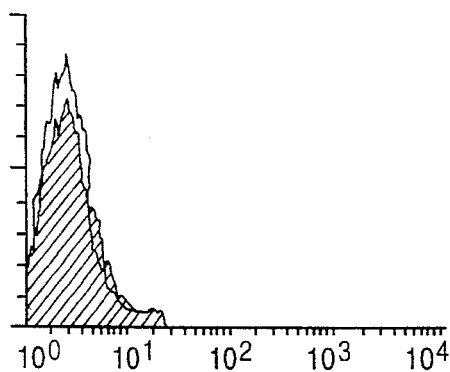
FIGS. 15A–15H show the effect of IL-13 on B cell phenotype. Purified B cells were cultured, with or without IL-13 (200 U/ml) for 72 h, and the cells were harvested and stained using the following mAbs: control Ab (FIG. 15A); CD19 (FIG. 15B); CD23 (FIG. 15C); CD72 (FIG. 15D); Class I MHC (FIG. 15E); Class II MHC (FIG. 15F); LFA-1 (FIG. 15G); sIgM (FIG. 15H). Stained cells were analyzed by FACScan flow cytometer. Open and gray histograms indicate analysis of cells cultured with and without IL-13, respectively.
Figure 15B:
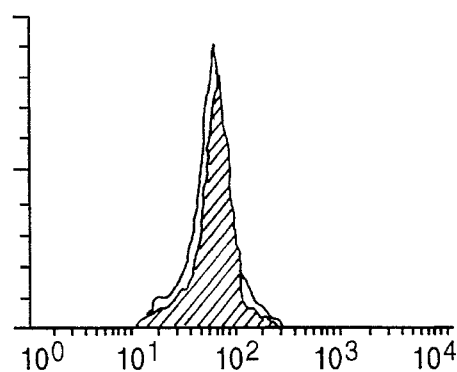
Figure 15C:
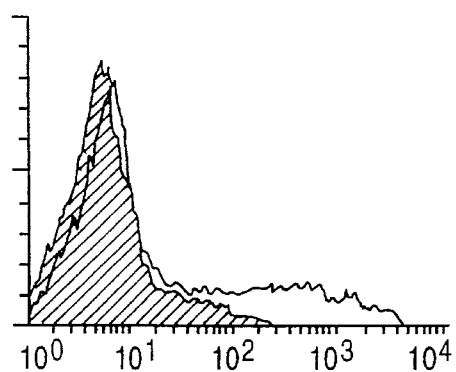
Figure 15D:
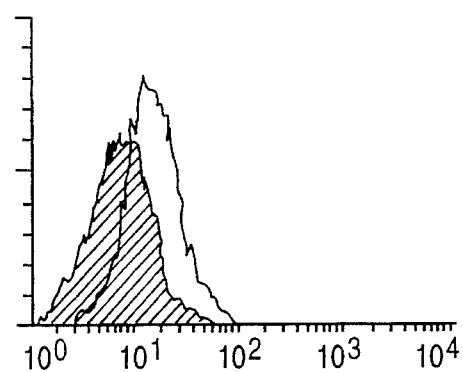
Figure 15E:
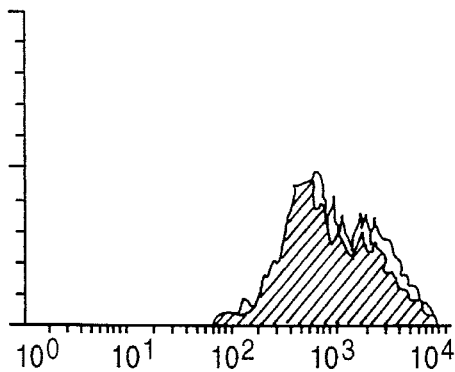
Figure 15F:
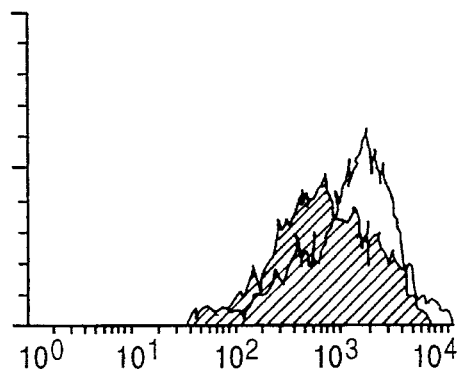
Figure 15G:
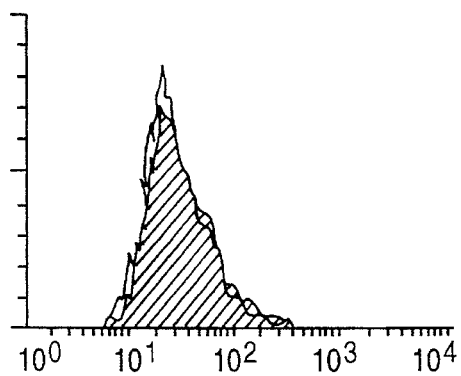
Figure 15H:
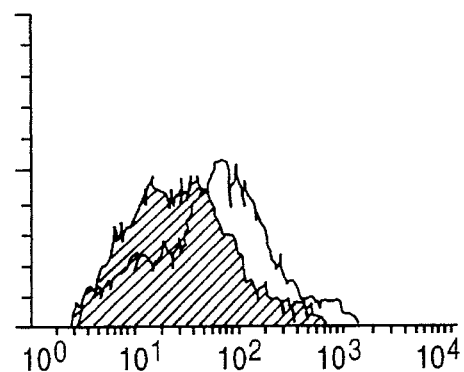

Resting CD4$^+$ T cell clones expressed no, or very low levels of CD40L, as judged by binding of PE-labeled streptavidin to biotinylated CD40-Ig bound to the T cells. However, significant expression of the CD40L was observed on the CD4$^+$ T cell clone B21 4 h after activation with PHA. Consistent with its presence on the surface of B21 cells, hCD40L mRNA was detected by Northern analysis and by PCR (FIGS. 13A through 13B and 14A through 14D). Low levels of hCD40L mRNA were expressed in resting B21 cells. Kinetic studies indicated that the 2.1 kb and 1.2 kb mRNA species were already maximally expressed within 2 hours following activation, irrespective of the mode of activation of the T cells (FIG. 14A through 14D). The expression was somewhat reduced after 4 h. Considerable reduction in the CD40L mRNA expression was observed 7 hours after activation, but appreciable levels of CD40L mRNA were still visible 48 h after activation. Activation of the B21 cells by Ca$^{2+}$ ionophore plus PMA, Con A, anti-CD3 mAbs plus PMA, or PHA plus PMA, did not result in major quantitative differences, or differences in the kinetics of the hCD40L mRNA expression, although it seems that activation with Ca$^{2+}$ ionophore plus PMA is slightly more effective (FIGS. 14A through 14D). Distribution of the hCD40L was analyzed by PCR, using primers complimentary to the coding region of the human CD40L gene. CD40L transcripts were not present in B cells, brain, kidney, heart, fetal liver, or fetal bone marrow, but could be readily detected in CD4$^+$T cell clones, CD8$^+$ T cell clones, a TCR γδ T-cell clone, purified NK cells, monocytes, fetal thymocytes, and small intestine (FIGS. 13A and 13B). It should be noted that expression of CD40L in the small intestine may reflect IL-13 production by infiltrating MNC.

In the present study it is demonstrated that the human CD40L cDNA, which was cloned and expressed in COS7 cells is very effective in inducing human B cell activation. COS7/hCD40L induced homotypic aggregation of EBV-transformed and normal B cells and B cell proliferation, similarly as observed with anti-CD40 mAbs. In addition, differentiation of B cells into Ig secreting plasma cells was observed in the presence of IL-4 or IL-13. The 2.1 kb hCD40L cDNA was isolated from a CD8$^+$ T cell cDNA library and appeared to be a full-length clone, which was by sequence comparison, identical to the 1.8 kb cDNA's described earlier. An additional 1.2 kb cDNA clone probably represents a second mRNA species of that size which was detected in activated T cells and which apparently encodes the same protein. The hCD40L has 80% homology with the corresponding mouse gene. Interestingly, the hCD40L has also some degree of homology with TNF-α and TNF-β. The positioning of the four cysteine residues and the potential extracellular N-linked glycosylation site in the mouse CD40L are conserved in the human CD40L, however the human protein has an additional cysteine substituted at position 194. The CD40L is reported to be a type II membrane anchored protein and there is a hydrophobic region of the human protein (amino acids 22–45) representing a potential signal/anchor domain near the amino terminus. B cell proliferation induced by COS7/CD40L was enhanced by IL-4 or IL-13. IL-4 and IL-13 seemed to be equally effective, indicating that IL-13, like IL-4, has B cell growth promoting activity. IL-13, like IL-4, also induced Ig production in cultures of naive surface IgD$^+$ B cells that have been co-stimulated by COS7/hCD40L. Considerable levels of IgM, IgG4, total IgG, and IgE were produced under these culture conditions. The profile of Ig production induced by IL-4 and IL-13 with hCD40L is similar to that obtained in the presence of IL-4 and anti-CD40 mAbs. Thus IL-13 and IL-4 appear equally potent in inducing both proliferation and Ig synthesis in B cells. Furthermore, these results indicate that the hCD40L provides a co-stimulatory signal for IL-4 or IL-13 induced B cell differentiation, confirming the important role for CD40 in B cell activation and differentiation. Since these experiments were carried out with naive sIgD$^+$, these results confirm previous observations that IL-13, in addition to IL-4, is another CD4$^+$ T cell derived lymphokine that can direct B cells to switch to IgG4 and IgE producing cells (see Table B1 and FIGS. 5A through 5E). Ig production, including IgG4 and IgE production, induced by IL-13 in the presence of hCD40L was not blocked by anti-IL-4 mAbs, indicating that the effects of IL-13 are mediated independently of IL-4.

Help provided by the CD40L transfectants, and the specific blocking of this help by CD40-Ig, indicates that expression of CD40L on CD4$^+$ T cells may be an important component of both antigenic and non-specific T-B cell interactions, leading to B cell activation and differentiation. These data are compatible with blocking studies carried out with mAbs against mouse CD40L, or CD40-Ig, which indicated that CD40L and CD40 interaction is critical for T cell help in the mouse system. It is of importance to note that there is a difference in the consequences of signaling by CD40 and activated CD4$^+$ T cells suggesting that additional T cell surface molecules may be involved in productive T-B cell interaction. In fact, the transmembrane form of TNF-α expressed on activated CD4$^+$ T cells is also associated with T cell induced B cell activation and differentiation.

Considering these similarities in functions, it is interesting that the CD40L and the cell surface form of TNF-α are homologous and share some structural similarities, as do CD40 and the TNF receptor. The substantial help given to human B cells by the cloned human and mouse CD40L's is consistent with previous studies, demonstrating that signaling through CD40 is of significant consequence for B cell survival, activation, and differentiation. The mouse CD40L appears as effective as the human CD40L in activating human B cells, which is consistent with the ability of murine CD40L to bind human CD40. The similarity of the protein sequences and the ability of both mouse and human CD40L to bind CD40 cross-species indicates this is an important interaction in vivo to be so well conserved.

Interestingly, human IL-13 cDNA was isolated form the same $CD8^+$ T-cell clone library as CD40L. However, although IL-13 is expressed in the $CD8^+$ T cells, far more IL-13 is expressed in $CD4^+$ T cells. The potency of the combination of these two novel molecules for induction of IgE synthesis, and their abundant co-expression by $CD4^+$ T cells, together with the prolonged expression of IL-13 mRNA following T cell activation may be a mechanism contributing to IgE production in vivo and IgE mediated allergic reactions.

These experiments have focused on the function of CD40L expressed on $CD4^+$ T cells as it relates to B cell activation. CD40L expression on cells other than $CD4^+$ T cells, including $CD8^+$ T cells from which the gene was cloned, suggests a broader function for the molecule than in T-B cell interaction. It is likely that CD40L is expressed on other cell types, and even $CD4^+$ T cells, which will have important consequences for their function, rather than just providing a one way stimulus to CD40 positive cells such as B cells. For example CD40L and CD40 expression, in thymocytes (FIGS. 13A and 13B) and thymic epithelium may be indicative of interactions involved in T cell development.

E. IgE Switching

The present series of experiments demonstrate that IL-13 induces IgG4 and IgE synthesis by human B cells. IL-13 induced IgG4 and IgE synthesis by unfractionated peripheral blood mononuclear cells (PBMNC) and highly purified B cells cultured in the presence of activated $CD4^+$ T cells or their membranes. IL-13-induced IgG4 and IgE synthesis is IL-4-independent, since it was not affected by neutralizing anti-IL-4 monoclonal antibody (mAb). Highly purified $sIgD^+$ B cells could also be induced to produce IgG4 and IgE by IL-13, indicating that the production of these isotypes reflected IgG4 and IgE switching and not a selective outgrowth of committed B cells. IL-4 and IL-13, added together at optimal concentrations, had no additive or synergistic effect, suggesting that common signaling pathways may be involved. This notion is supported by the observation that IL-13, like IL-4, induced CD23 expression on B cells and enhanced CD72, surface IgM (sIgM) and class II MHC antigen expression. In addition, like IL-4, IL-13 induced germline ε transcription in highly purified B cells. Collectively, these data indicate that IL-13 is another T cell-derived cytokine that, in addition to IL-4, efficiently directs naive human B cells to switch to IgG4 and IgE production.

B cells undergo Ig isotype switching and differentiation into Ig-secreting cells in response to sIgM mediated signals in the presence of costimulatory factors provided by $CD4^+$ T cells. Antigen-specific T-B cell interactions require binding of the T cell receptor to peptide-class II major histocompatibility complexes (MHC) on B cells, which results in T-cell activation and cytokine synthesis. Once the T cells are activated they can activate B cells in an antigen-independent fashion.

Cytokines are essential for B-cell proliferation and differentiation; they not only determine Ig secretion quantitatively, but they also direct Ig isotype switching. IL-4 induces IgG4 and IgE switching, whereas transforming growth factor-β (TGF-β) directs IgA switching. See, e.g., Van Vlasselaer et al. (1992) *J. Immunol.*, 148, 2062–2067; and Defrance et al. (1992) *J. Exp. Med.* 175:671–682. In addition to cytokines, contact-mediated signals delivered by $CD4^+$ T cells are required for B cell proliferation and Ig production. Recently the ligand for CD40, which is expressed on activated $CD4^+$ T cells, was shown to be one such membrane associated molecule that acts as a costimulatory signal for IL-4-dependent IgE production by both murine and human B cells. See, e.g., Armitage et al. (1992) *Nature* 357:80–82. Moreover, several cytokines, such as IL-2, IL-5, IL-6, IL-8, IL-10, IL-12, interferon-α (IFN-β), IFN-γ, tumor necrosis factor-α (TNF-α), and TGF-β modulate IL-4-induced IgG4 and IgE synthesis.

IL-4 has been thought to be the only cytokine capable of inducing IgE synthesis. Out of 16 cytokines tested, IL-4 was the only one inducing germline or productive ε transcripts or IgE synthesis. In addition, anti-IL-4 mAbs preferentially inhibit IgE synthesis induced by IL-4 producing T cell clones without significantly affecting IgM, IgG, or IgA synthesis. Also in murine models, anti-IL-4 antibodies strongly inhibit IgE synthesis in vivo without affecting the other Ig isotypes. Most importantly, IL-4 deficient mice lack IgE in their sera following nematode infection. However, a non-IL-4-producing T cell clone induces germline s transcription in purified B cells indicating that an IL-4-independent pathway of induction of germline ε transcription is operational.

As described above, the human cDNA sequence is 66% homologous to that of the mouse and encodes a protein that is 58% homologous to the mouse P600. P600 and IL-4 are related with a homology of −30%, but no great homology with other cytokines was detected. Human P600 protein was biologically active and was shown to induce monocyte and B cell growth and differentiation. This novel cytokine was designated IL-13. Human IL-13 is a non-glycosylated protein of 132 amino acids with a molecular mass (Mr) of 10000. IL-13 induces CD23 expression and germline ε mRNA synthesis and IgG4 and IgE switching in human B cells. The activity of IL-13 is shown to be independent of IL-4.

Reagents.

Human recombinant IL-13 was purified as described herein. Recombinant IL-4, IFN-α, and IFN-γ were provided by Schering-Plough Research (Bloomfield, N.J.). Fluorescein isothiocyanate (FITC)-conjugated anti-CD72 mAb and neutralizing anti-TGF-β mAb were purchased from R&D Systems, Inc. (Minneapolis, Minn.). FITC- and phycoerythrin (PE)-conjugated mAbs specific for CD3, CD4, CD8, CD14, CD16, CD19, CD20, CD23, CD25, CD56, HLA-DR, and control antibodies with irrelevant specificities were obtained from Becton-Dickinson (Mountain View, Calif.). FITC- or PE-conjugated mAbs specific for LFA-1 (L130), LFA-3, ICAM-1 (LB2), B7 (L307), and class I MHC antigen were kindly provided by Dr. J. Phillips (DNAX). FITC-conjugated anti-IgD and anti-IgM mAbs were obtained from Nordic Immunological Laboratories (Tilburg, The Netherlands). The purified anti-CD40 mAb 89 (IgG1) described by Banchereau et al. (1991) *Science* 251:70–72 was a gift of Dr. J. Banchereau (Schering-Plough France, Dardilly, France).

The neutralizing anti-IL-4 mAb 25D2.11 was kindly provided by Dr. J. Abrams (DNAX).

Cell Preparations

Blood samples and spleens were obtained from healthy volunteers or from patients undergoing splenectomy due to trauma, respectively. Mononuclear cells were isolated by centrifugation over Histopaque-1077 (Sigma, St. Louis, Mo.).

Purified B cells were obtained by negative sorting using a fluorescence-activated cell sorter FACStar Plus (Becton-Dickinson) or magnetic beads (Dakopatts, Norway). Briefly, splenic MNC were washed twice and PE-conjugated mAbs against CD3, CD4, CD8, CD14, CD16, and CD56 were added at saturating concentrations and incubated at 4° C. for 30 min. The cells were washed twice with PBS. Cells with the light scatter characteristics of lymphocytes were gated, and $PE^-$ cells were sorted. Alternatively, cells stained with mAbs against CD3, CD4, CD8, CD14, CD16, and CD56 were incubated for 30 min at 4° C. with magnetic beads coated with anti-mouse Ig mAbs. The cells bearing murine Ig were removed using a magnetic field. The remaining cells were washed, counted, and used in further experiments. For isolation of $sIgD^+$ B cells, positive sorting by FACStar Plus was used. Splenic MNC were stained with PE-conjugated mAbs against CD3, CD4, CD8, CD14, CD16, and CD56 and FITC-conjugated anti-IgD mAb, and $FITC^+$, $PE^-$ cells were sorted. On reanalysis, purities of the sorted cell populations were >98%, and that of cells isolated using magnetic beads >95%.

The $CD4^+$ T cell clone B21 and the $CD4^+$ non-IL-4 producing T cell clone SP-A3 were cultured according to Roncarolo et al. (1988) *J. Exp. Med.* 167:1523–1534. The cells were obtained 4–6 days after they had been activated by the feeder cell mixture and PHA. In addition, IL-2 (100 U/ml) was added to maintain the activation state of the T cell clones.

Preparation Of T Cell Membranes

The membranes of a $CD4^+$ T cell clone were prepared according to Gascan et al. (1992) *Eur. J. Immunol.* 22:1133–1141. Briefly, the $CD4^+$ T cell clone B21 was harvested 12 days after activation with feeder cell mixture and phytohemagglutinin (PHA), the cells were washed and restimulated with 10 µg/ml of Concanavalin A (Con A) for 7–8 h at 37° C. During the last 30 min of the Con A stimulation, 100 µg/ml of a-methyl-D-mannoside (Sigma, St. Louis, Mo.) was added. From these cells, membranes were prepared using the method described by Brian (1988) *Proc. Natl. Acad. Sci. USA* 85:564–567; and Maeda et al. (1983) *Biochem. Biophys. Acta* 731:115–120; and they were stored under liquid nitrogen ($1 \times 10^8$ T cell equivalents/ml= 0.2 mg protein/ml membrane preparation) until used.

Culture conditions

Purified B cells were cultured at 5000 cells/well in quadruplicate, in round-bottomed 96-well plates (Linbro, McLean, Va.) at 37° C. in a humidified atmosphere containing 5% $CO_2$ in 0.2 ml Yssel's medium supplemented with 10% fetal calf serum (FCS). Unfractionated PBMNC were cultured at $10^5$ cells/well in 12 replicates. In coculture experiments, the $CD4^+$ T cell clone SP-A3 was cultured at 5000 cells/well (T:B cell ratio 1:1). After a culture period of 12 days, Ig levels in the culture supernatants were measured by ELISA.

Measurement of Ig Production

IgM, total IgG, IgA, and IgE secretion was determined by ELISA as described in Pène et al. (1988) *Proc. Natl. Acad. Sci. USA* 85:6880–6884. IgG4 secretion was determined by ELISA as described in Punnonen, et al. (1992) *J. Immunol.* 148:3398–3404. The sensitivities of IgM, total IgG, and IgA ELISAs were 0.5–1 ng/ml, and the sensitivities of IgG4 and IgE ELISAs were 0.2 ng/ml.

Phenotypic Analysis of Cultured Cells

Purified B cells were cultured as described and they were harvested and washed twice. FITC- and PE-conjugated mAbs were added at saturating concentrations and incubated at 4° C. for 30 min. FITC- and PE-conjugated mAbs with irrelevant specificities were used as negative controls. The cells were washed twice with PBS and cells with the light scatter characteristics of lymphocytes were analyzed using a FACScan flow cytometer (Becton-Dickinson).

RNA Isolation and Northern Analysis

Total RNA was isolated using RNAzol B (CNNA: Biotech, Friendswood, Tex.) according to manufacturers instructions. RNA was electrophoresed through 0.85% agarose and transferred to BA-S nitrocellulose (Schleicher and Schuell, Keone, N.H.). $^{32}p$ cDNA probes were made by random priming using as templates, an EcoR I/Hind III fragment of pBSIgE1-4 for germline ε, and DNA complementary to the Bgl I/Sma I fragment of pHFgA-1 for actin. See Gauchat et al. (1990) *J. Exp. Med.* 172:463–473; and Erba et al. (1986) *Nucleic Acids Res.* 14:5275–5280.

IL-13 Induces CD23 Expression On Purified B Cells

The effect of IL-13 on the expression of a variety of B cell surface antigens was investigated by FACS-analysis. Incubation of purified B cells with IL-13 (200 U/ml) resulted in strong induction of CD23 expression on a proportion of the B cells (FIGS. 15A–H). IL-13 also upregulated class II MHC antigen, sIgM, and CD72 expression on B cells. These effects of IL-13 were similar to those observed by IL-4. CD23 expression was already detectable after a culture period of 24 h, but maximal responses were observed after 72 h of culture. The expression of CD19, CD20, CD25, CD40, class I MHC antigen, B7, ICAM-1, LFA-71, and LFA-3 were not significantly modified by IL-13 (FIGS. 15A through 15H).

IL-13 Induces IgE Synthesis by PBMNC

Because CD23 expression on B cells has been associated with IgE synthesis, IL-13 was tested for induction of IgE synthesis by human PBMNC. As shown in FIGS. 16A–16D, IL-13 induced IgE synthesis by unfractionated PBMNC in a dose-dependent manner in the absence of exogenous IL-4. In addition, strong IgG4 production in response to IL-13 was observed. Interestingly, neutralizing anti-IL-4 mAbs failed to inhibit IL-13-induced IgE synthesis (FIG. 16C), whereas IL-4-induced IgE production was virtually completely blocked (FIG. 16D), indicating that IL-13-induced IgE synthesis was not mediated through induction of IL-4 production by PBMNC. Similarly to IL-4, maximal induction of IgE synthesis by IL-13 was usually obtained at concentrations of 50 U/ml. The mean level of IgE produced in response to IL-13 was somewhat lower (63 ng/ml, n=6) than that induced by IL-4 (169 ng/ml, n=6). No additive or synergistic effects were observed when both IL-4 and IL-13 were used at saturating concentrations.

IL-13 Induces IgG4 and IgE Switching in B Cells

Figure 16A:
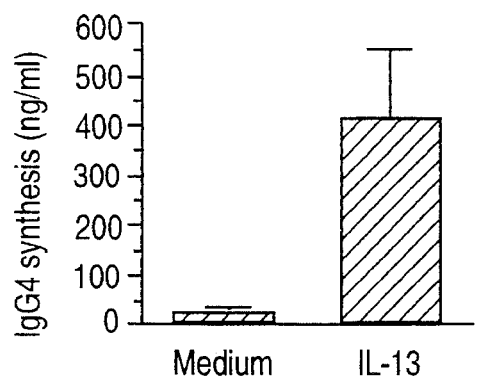
FIGS. 16A–16D show IL-13 inducts IgG4 and IgE synthesis by PBMNC. Unfractionated PBMNC were cultured in IL-13 (500 U/ml), and IgG4 (FIG. 16A) and IgE (FIG. 16B) levels in the culture supernatants were measured after a culture period of 12 days.
Figure 16B:
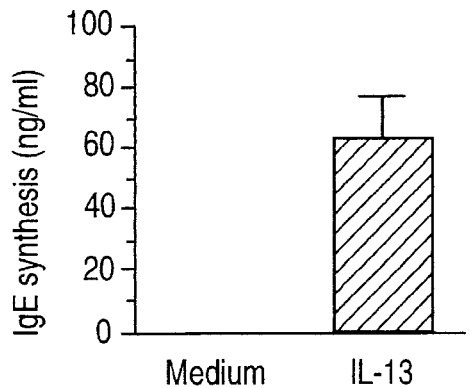
Figure 16C:
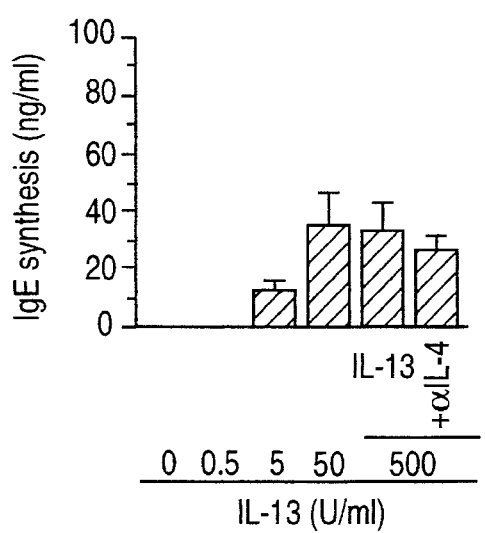
Figure 16D:
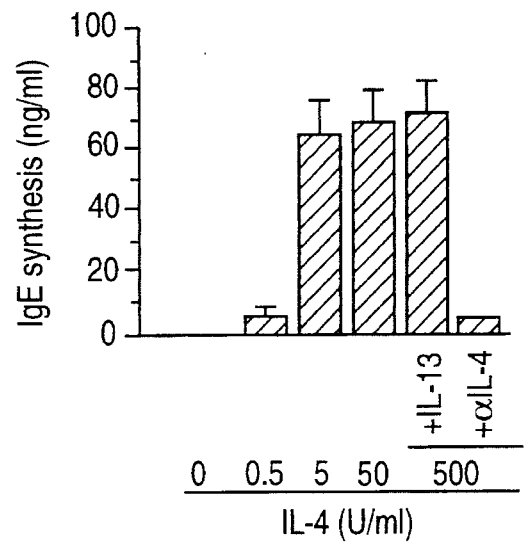
Figure 17A:
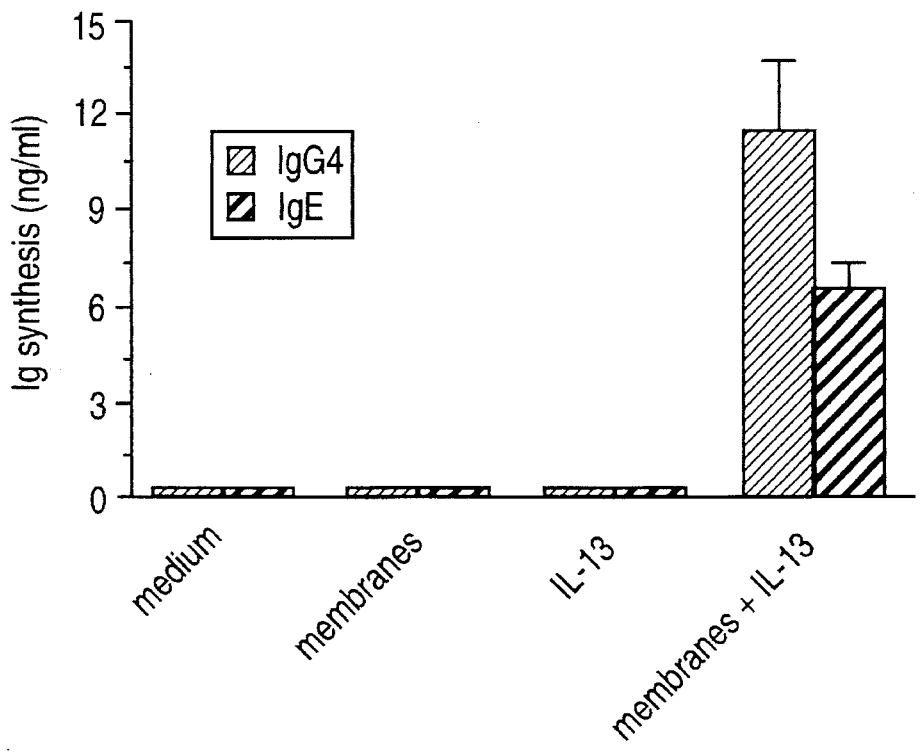
FIGS. 17A–17B show IL-13-induced IgG4 and IgE synthesis reflect Ig isotype switching. Highly purified, sorted B cells (FIG. 17A) or sorted sIgD+ B cells (FIG. 17B) were cultured in the presence of IL-13 (400 U/ml) and membranes of $CD4^+$ T cells (FIG. 17A) or with the activated, non-IL-4 producing T cell clone SP-A3 (5000 cells/well) in the presence or absence of neutralizing anti-IL-4 mAb ($\alpha$IL-4, 10 μg/ml) (FIG. 17B). IgG4 and IgE levels in the culture supernatants were measured by ELISA after a culture period of 12 days. The data represent mean±SEM of quadruplicate cultures.

The ability of IL-13 to induce IgG4 and IgE synthesis by purified B cells was also tested. As shown in FIG. 17A, IL-13 induced IgG4 and IgE synthesis by highly purified B cells cultured in the presence of membranes of an activated $CD4^+$ T cell clone. Also in this culture system the levels of IL-13-induced IgG4 and IgE production were generally lower than those induced by IL-4. The difference was in the same range as observed in the cultures of unfractionated PBMNC (FIG. 16C and 16D). IL-13 also induced significant levels of IgM and total IgG production (FIG. 17A), but no IgA synthesis was observed. See also FIGS. 5A through 5E and Table B1. In this aspect IL-13 has similar properties as IL-4, which generally inhibits IgA synthesis, see Van Vlasselaer et al. (1992) *J. Immunol.* 148:1674–1684. These results show that IL-13 induces IgG4 and IgE synthesis by human B cells in the absence of IL-4, and indicate that IL-13 acts directly on B cells to induce IgG4 and IgE synthesis. Furthermore, these results strongly suggest that IL-13 induces Ig isotype switching to IgG4 and IgE in an IL-4-independent manner.

Figure 17B:
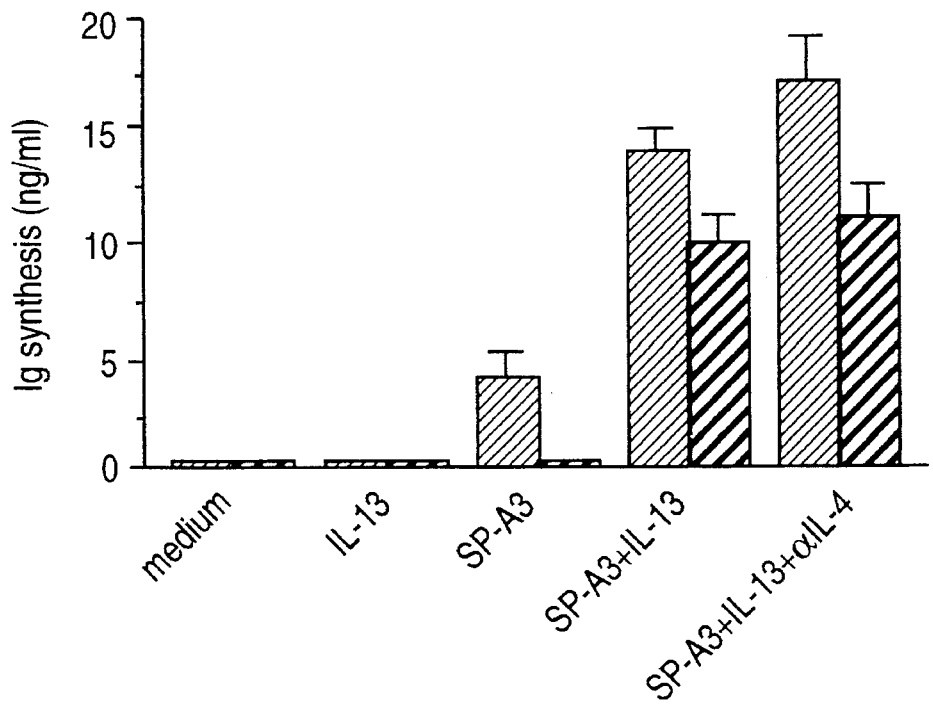
Figure 18A:
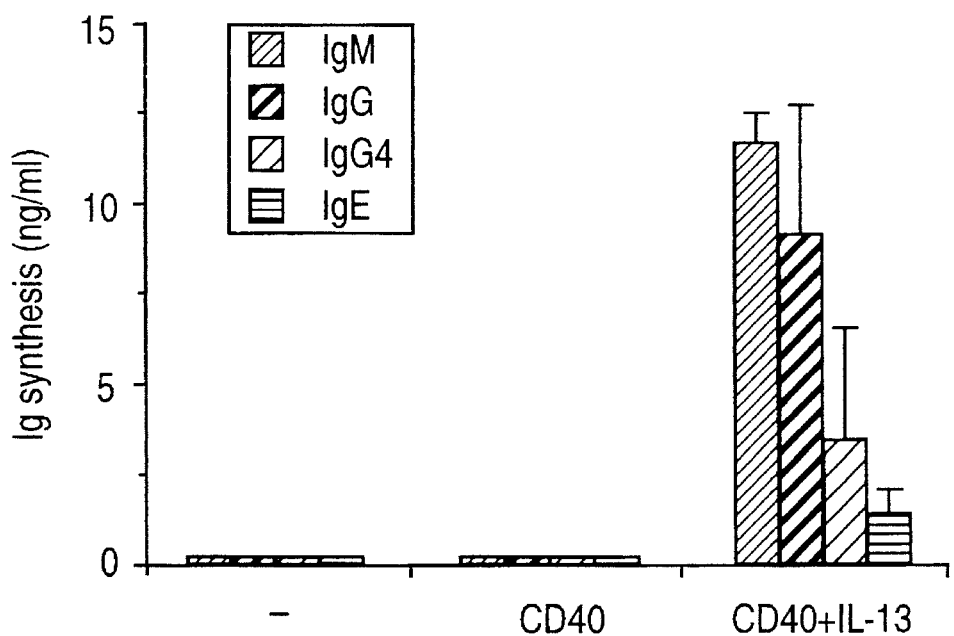
FIGS. 18A–18B show IL-13 or IL-4 induced synthesis of IgM, IgG, IgG4, or IgE with anti-CD40 mAb 89. The effects of IL-13 are comparable, but less potent, than those of IL-4.
Figure 18B:
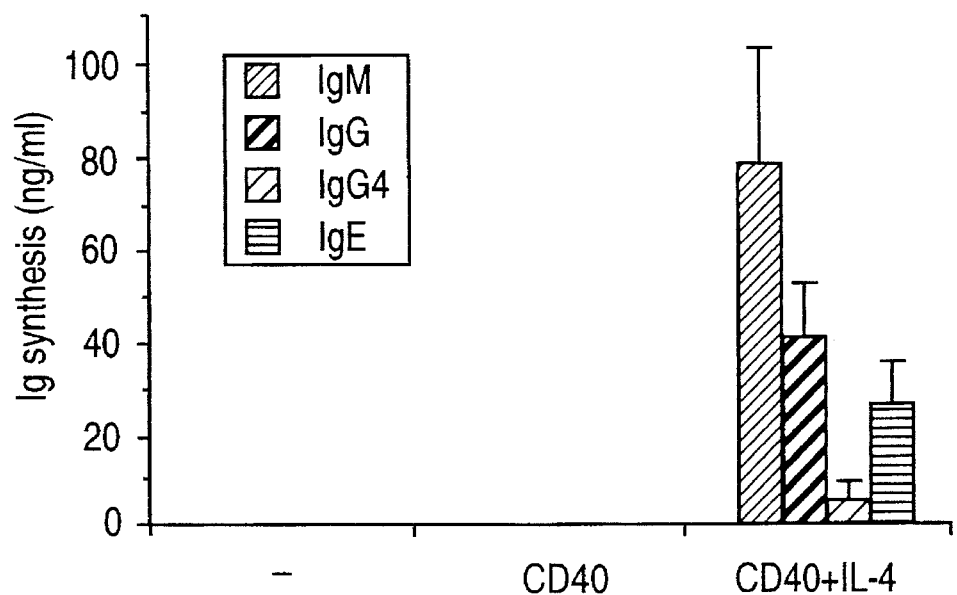
Figure 19A:
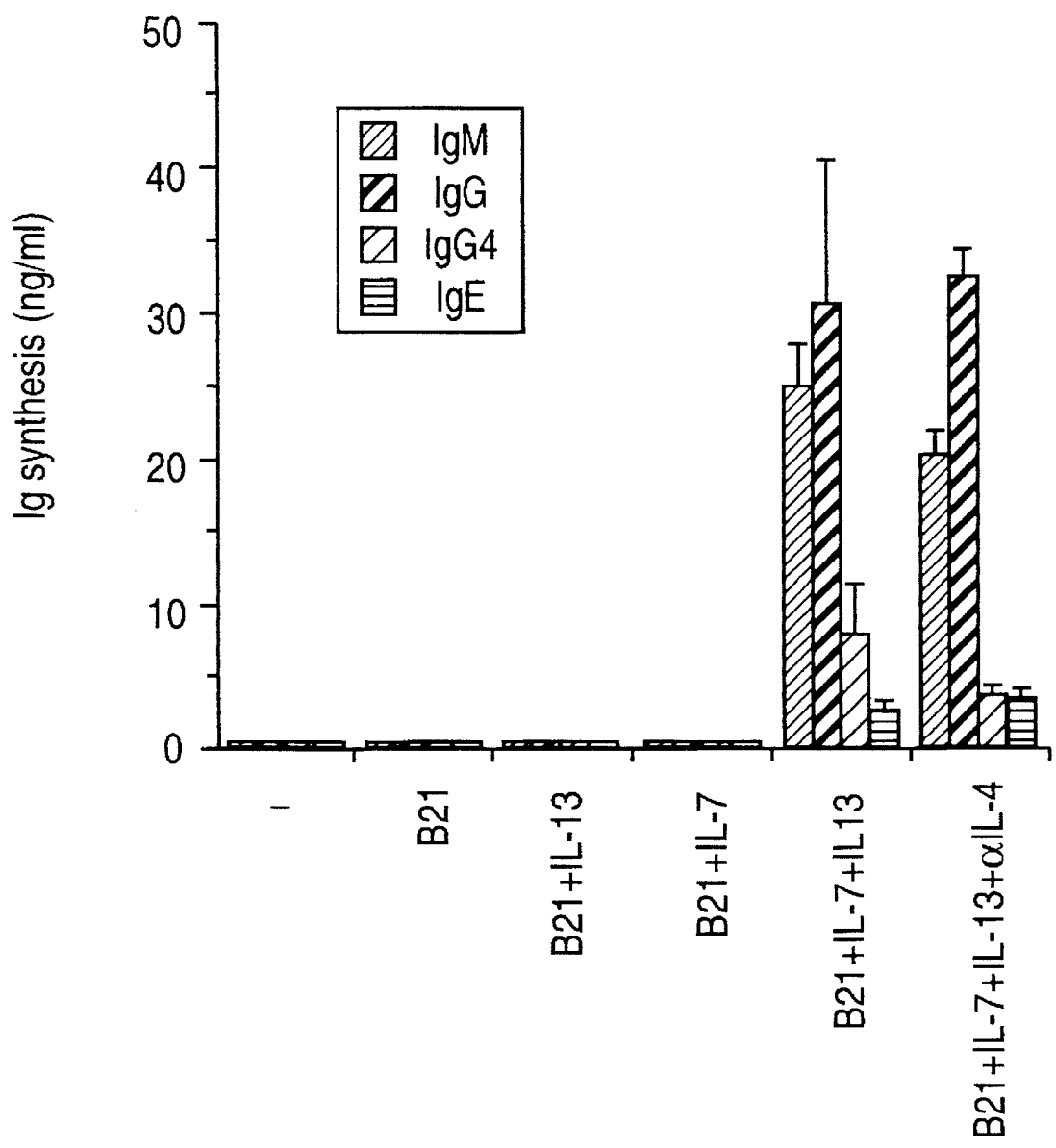
FIGS. 19A–19B show the effects of IL-13, alone or in combination, with other cytokines, on expression of various surface markers. Each of FIGS. 19A–19B are with different cells.
Figure 19B:
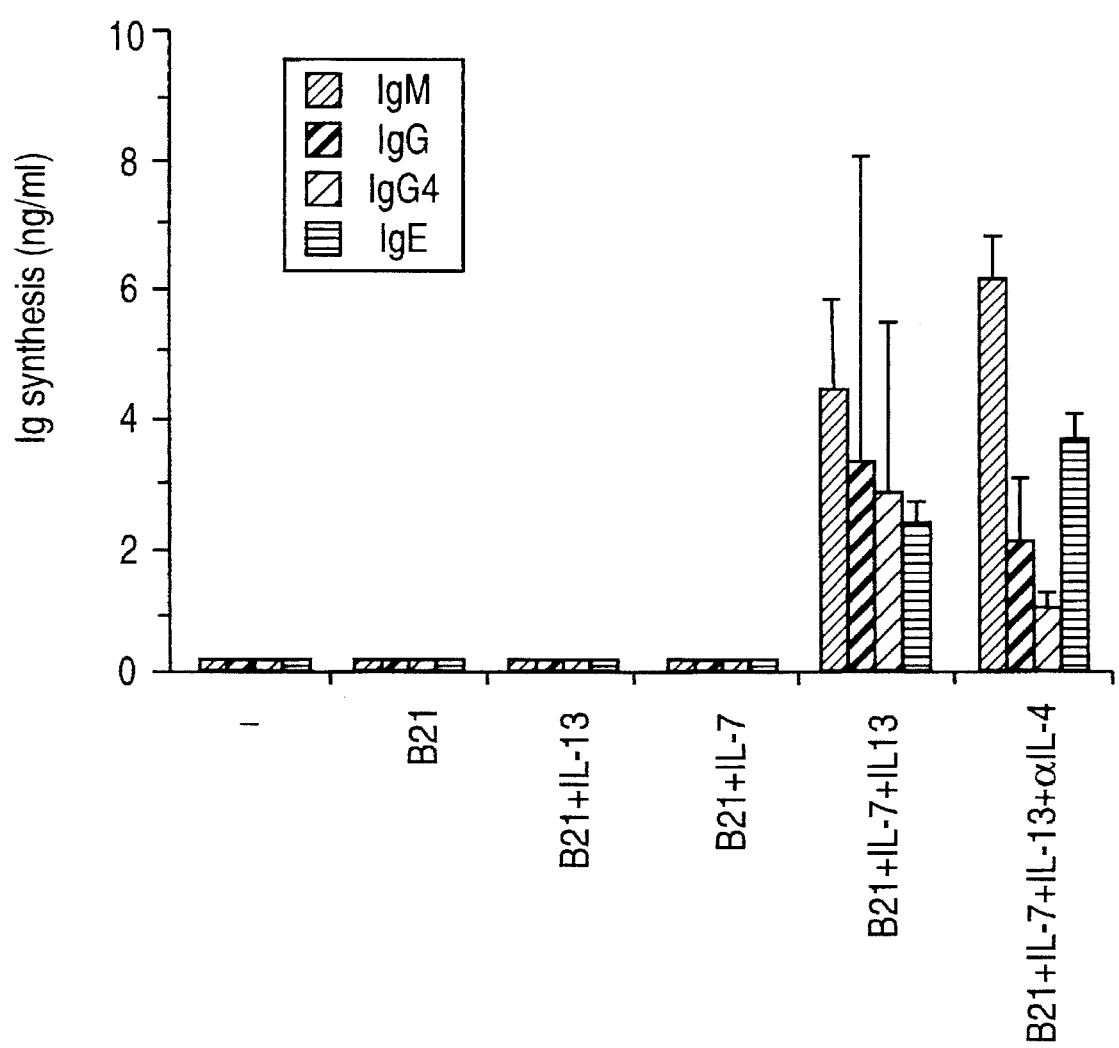

To confirm that IgE synthesis observed in above experiments was due to Ig isotype switching and not to an outgrowth of a few IgE-committed B cells, the effects of IL-13 on naive sIgD$^+$ B cells was studied. Culturing of highly purified sIgD$^+$ B cells with the activated, non-IL-4 producing T cell clone SP-A3 in the presence of IL-13 resulted in induction of IgE synthesis (FIG. 17B). In addition, IL-13 enhanced IgG4 synthesis induced by this non-IL-4 producing T cell clone alone. As was demonstrated for PBMNC, IL-13-induced IgG4 and IgE synthesis could not be inhibited by anti-IL-4 mAbs.

Induction of Germline ε transcription by IL-13

So far, IL-4 has been the only cytokine known to induce germline ε transcription in B cells. Since switching to ε by IL-4 is preceded by the induction of germline ε RNA synthesis, it was hypothesized that IL-13 may induce germline ε transcription as well. Indeed, when highly purified B cells were cultured in the presence of IL-13 and anti-CD40 mAbs, germline ε mRNA synthesis, at levels comparable to that in the presence of IL-4 and anti-CD40 mAbs, was detected after a culture period of five days (see FIGS. 19A through 19B). Since anti-CD40 mAbs alone do not induce germline ε transcription in B cells, these results indicate that IL-13 is another T cell-derived cytokine that, like IL-4, can induce germline ε transcripts in B cells. In addition, these results confirm the correlation between germline ε transcription and subsequent switching to IgE synthesis.

Effect of IL-12 on IL-13 Plus Anti-CD40-induced IgE Synthesis

Figure 20A:
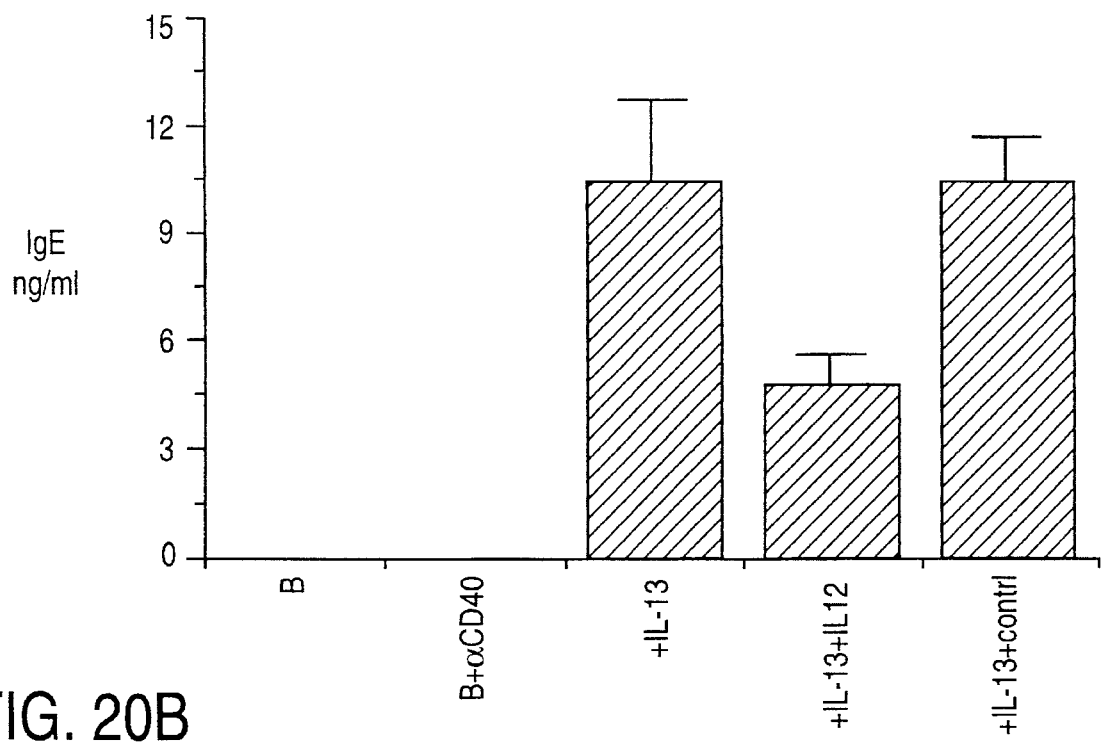
FIGS. 20A–20B show the effect of IL-12 on IL-13 plus anti CD40-induced IgE synthesis.
Figure 20B:
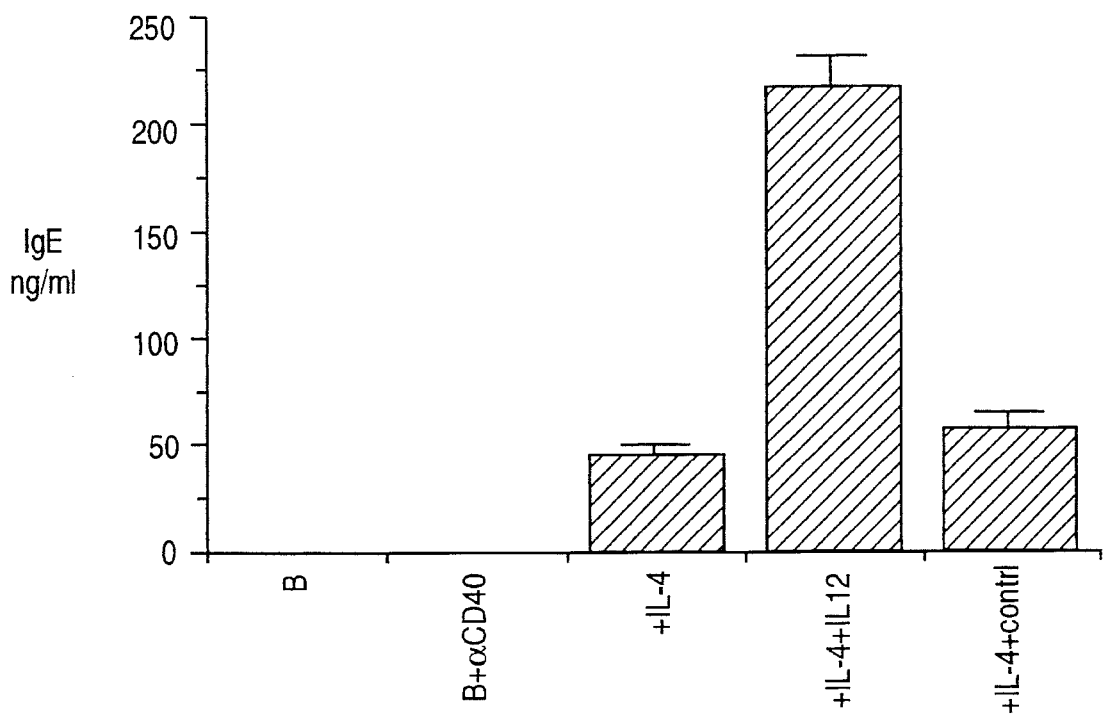

Ten thousand highly purified B cells were cultured in the presence of anti-CD40 monoclonal antibodies (20 μg/ml) and IL-13 (400 U/ml) (FIGS. 20A through 20B, upper panel) or IL-4 (400 U/ml) (FIGS. 20A through 20B, lower panel). Cos supernatant containing IL-12 or mock Cos supernatant was added as indicated in the was measured by. ELISA after 14 days of culture. Note that IL-12 decreases the IL-13 effect, while it increases the IL-4 effect.

IL-13 is a non-glycosylated protein with a relative molecular mass of 10,000. Early biological characterizations have indicated that IL-13 has monocyte and B cell differentiation inducing activities. These experiments show that IL-13 induces CD23 expression and IgG4 and IgE production by naive human B cells.

IL-4 has been considered as the only cytokine to induce IgE switching in human or murine B cells. This was based on studies showing that anti-IL-4 mAbs preferentially block IgE synthesis both in vitro and in vivo, and on the observation that no circulatory IgE could be detected in mice, in which the IL-4 gene had been disrupted. However, these data show that IL-13-induced IgE synthesis is independent of IL-4, since IL-13 induced IgG4 and IgE synthesis in cultures of highly purified B cells in the absence of exogenous IL-4. In addition, anti-IL-4 mAbs, which efficiently blocked IL-4-induced IgE synthesis, failed to affect IL-13-induced IgE production. Moreover, IL-13-induced IgG4 and IgE synthesis, like that induced by IL-4, reflects Ig isotype switching and is not due to a selective outgrowth of a few B cells committed to IgG4 or IgE synthesis, since IL-13 also induced IgG4 and IgE synthesis by naive, sorted sIgD$^+$ B cells.

Switching to IgE by IL-13 was preceded by induction of germline ε mRNA synthesis, but costimulatory signals provided by activated T cells were required for induction of IgE production. This is consistent with studies showing that IL-4-induced switching to ε in both murine and human B cells is preceded by the induction of germline ε RNA synthesis, and that co-stimulatory signals provided by activated CD4$^+$ T-cell clones or anti-CD40 mAbs are required for the induction of productive ε mRNA transcripts and IgE synthesis by IL-4. Although their exact role remains to de determined, it has been suggested that germline ε transcripts play an important role in the s-switch process. Despite the fact that IL-4 has been considered to be the only cytokine to induce germline ε transcription in B cells, an IL-4-independent pathway of induction of germline ε transcription is operational, since a non-IL-4 producing T cell clone was also capable of inducing strong germline ε RNA synthesis. It is likely that IL-13 produced by the non-IL-4 producing T cell clones is responsible for the IL-4-independent induction of germline ε mRNA in B cells. The present findings may also explain why induction of IgE synthesis by IL-4 producing T-cell clones was never completely inhibited by anti-IL-4 mAbs. A combination of IL-4 and IL-13 antagonists may be quite effective in blocking the switching process, each present at a lower level below threshold levels for adverse side effects.

No additive or synergistic effects on IgE synthesis was observed when IL-4 and IL-13 were added together at optimal concentrations, suggesting that IL-4 and IL-13 may use common signaling pathways for induction of IgG4 and IgE switching. Indeed, recent studies have shown that receptors for IL-13 and IL-4 share a common subunit that functions in signal transduction. However, IL-13 does not bind to cells bearing the 130 kDa IL-4 receptor indicating that IL-13 does not act through this IL-4 binding protein. The commonality between IL-13 and IL-4 was further supported by the observation that IL-13, like IL-4, induced CD23 expression on purified B cells. Similarly to IL-4, IL-13 also upregulated expression of class II MHC antigen, sIgM, and CD72, which is the ligand for CD5. Although the exact role of CD23 in the regulation of IgE synthesis remains to be determined, a strong correlation between CD23 expression and induction of IgE synthesis has been observed and soluble forms of CD23 have been found to enhance IgE synthesis. Since IL-13 induced significant expression of CD23 within 24 h, these data also indicate that CD23 expression precedes IL-13-induced ε switching, thereby confirming the correlation between induction CD23 expression and subsequent IgE synthesis.

Despite the similarities between IL-4 and IL-13 in their effects on B cells, the functions of IL-4 and IL-13 are not identical. The levels of IgG4 and IgE produced in response to IL-13 were generally lower than those induced by IL-4. Moreover, preliminary results have indicated that IL-13, in contrast to IL-4, does not act on T cells or T-cell clones. IL-13 has no T cell growth promoting activity and does not induce CD8a expression on CD4$^+$T-cell clones, which may be due to lack of functional IL-13 receptors on T cells. The activation state of T cells is essential for their ability to deliver co-stimulatory signals required for B cell proliferation and differentiation. Therefore, the lack of T cell activation inducing effect of IL-13 may partially explain why maximal IgG4 and IgE synthesis by PBMNC in response to IL-13 was lower than that induced by IL-4.

These data seem to be incompatible with the finding that IL-4 deficient mice have no detectable circulatory IgE following nematode infections. However, it is not clear whether IL-13 also induces IgE synthesis by murine B cells. Preliminary data show that IL-13 is produced for much longer periods than IL-4 following T cell activation, suggesting an important role for IL-13 in the regulation of enhanced IgE synthesis in allergic individuals.

IV. Activities on PBMC and Macrophages

A. Induction of Morphological Change in Non-adherent Human PBMC

Peripheral blood mononuclear cells (PBMNC) were isolated from normal health human donors by centrifugation over FicollHypaque. Total PBMNC ($1\times10^8$ cells) were incubated for 30 min at 37° C. in 10 mm tissue culture dishes. Nonadherent cells were removed by extensive washing of the dish with phosphate buffered saline (PBS). Adherent cells were incubated in Yssels's medium Yssel et al., *J. Immunol. Methods*, 72:219 (1974) with 1% human AB serum alone, or with mouse P600 derived from *E. coli* (lot 560-137-1; used at a concentration of 30 ng/ml), as described above. Alternatively, COS7 derived mouse P600 or human IL-13 was used at a final dilution of 1/20. Cells were observed at regular intervals.

B. Modification of Cell Surface Markers on Non-adherent cells

Five or ten days after nonadherence selection, as described above, the resulting cells were analyzed for expression of cell surface markers by fluorescence activated cell sorting (FACS) e.g., as described in Shapiro (1988) *Practical Flow Cytometry* (2nd Ed.), Alan Liss, New York, which is incorporated herein by reference. Exemplary antibodies for recognizing each marker are: CD11a (LFA-1; SFN-L7, from DNAX, Palo Alto, Calif.), CD11b (Bearl, see Spits et al. (1984) *Eur. J. Immunol.* 14:229–304), CD11c (p150; NGH 93, see Visser et al. (1989) *Blood* 74:320–325); CD54 (ICAM; LB2, see Azuma et al. (1992) *J. Expt'l Med*, 175:353–360), Class I MHC (W6/32, from Sera Labs, see also Barnstable et al. (1978) *Cell* 14:9–16; Class II MHC (Q5/13, see Quaranta et al (1980) *J. Immunol* 125:1421–1428, Class II MHC (Pc15.2, see Koning et al. (1984) *Human Immunol*, 9:221–226, Class II MHC (DQ; SFN-L3), CD58 (LFA-3; TS2/9, see Krensky et al. (1984) *J. Immunol.* 132:2180–2182), CD32 (IV.3, see Looney et al. (1986) *J. Immunol.* 136:1641–1647), CD16 (granulocyte-1, see Huizinga et al. (1988) *Nature* 333:667–669; or Leu 11a, Becton Dickinson, Mountain View, Calif.); CD23 (gp25, from DNAX, Palo Alto, Calif.), IL-2Rα (7G7; or BB10, see Herve et al. (1990) Blood 75:1017–1023), CD44 (NkI-Pa; see Vennegoor et al. (1992) *J. Immunol.* 148:1093–1101, CD14 (LeuM3, Becton Dickinson), and CD18 and B7 (L130 and L307; both described in Azuma et al. (1992) J. Immunol, 149:1115–1123.

Mouse P600 material from either COS7 supernatants or *E. coli* inclusion bodies were compared to COS7 supernatants of human IL-13. See FIGS. 23A through 23G C. Nitric Oxide Synthesis IL-13 (P600) has been assayed by its inhibitory effect on the production of nitric oxide (NO) by GM-CSF-derived bone marrow macrophages. The macrophages are derived by 9–12 days culture in RPMI containing GM-CSF and purified by retention of adherent, GM-CSF-responsive fraction. Cells are 99+% pure, as determined by FACS analysis using two color staining.

Macrophages are activated to produce NO by stimulation with LPS at 3 µg/ml in the appropriate figures, either with or without prior stimulation with cytokines, as indicated. The macrophages were incubated for 16 h with the cytokines (if used) 16 h prior to treatment with LPS. Supernatants were taken at the indicated times relative to LPS addition, i.e., 0 h is the time of addition of LPS.

Supernatants were assayed for NO production by the standard Griess assay for nitrites. See, e.g., Coligan (1991 and periodic supplements) *Current Protocols in Immunology* Greene/Wiley, New York. Addition of cytokines after addition of LPS to the macrophage cultures or at the time of LPS addition has been tested; under these conditions, none of the cytokines tested (including IL-13) had significant effects. Other macrophages have also been tested, but since they generally produce lower levels of NO, they have not been used as extensively for bioassay.

FIG. 24A shows NO production from GM-CSF-treated bone marrow derived macrophages after treatment for 16 h with designated cytokines. Note that IFN-γ induces NO production, while IL-4 or IL-13 inhibit NO production. L-NMMA is a specific inhibitor of NO production. Panels B and C are similar experiments titrated over different ranges of P600 amounts. In each case, the IL-13 decreased the production of NO.

D. Modulation of IL-1α; IL-6 IL-13 inhibits the production of IL-1α, IL-6, IL-10, and TNFα by LPS activated human monocytes Peripheral blood mononuclear cells were isolated from normal healthy donors by centrifugation over Ficoll-Hypague. Total PBMNC ($100\times10^6$ cells/100 mm tissue culture dish) were incubated for 30 min at 37° C. and subsequently nonadherent cells were removed by extensive washing of the tissue culture dish with PBS. Adherent cells were incubated in Yssels medium with 1% human AB serum in the absence or presence LPS (*E. coli* 0127:B8, Difco, Detroit, Mich.) in combination with IL-4 (50 ng/ml), In-13 (50 ng/ml), or IL-10 (100 U/ml). In addition, cells were activated by LPS in combination with IL-4 or IL-13 in the presence of neutralizing anti-IL-10 mAb 19F1 (10 Bg/ml). Supernatants were collected after 12 hrs and production of IL-1α, IL-6, IL-10, and TNF-α was measured by cytokine-specific ELISA. Table 4 shows the data of these studies.

These results indicate that IL-4 and IL-13 inhibit the production of IL-1α, IL-6, IL-10, and TNF-α by LPS activated human monocytes. IL-10 also inhibits the production of IL-1α, IL-6, and TNF-α by LPS activated human monocytes. IL-10 is produced by human monocytes and inhibits IL-1α, IL-6, and TNF-α in an autoregulatory fashion. Addition of IL-10 neutralizing mAb 19F1 shows that endogenously produced IL-10 also inhibits the production of IL-1α, IL-6, and TNF-α. The inhibitory effects of IL-4 and IL-13 on cytokine production by LPS activated human monocytes are independent of IL-10 since IL-4 and IL-13 inhibit the production of IL-1α, IL-6, and TNF-α in the presence of neutralizing anti-IL-10 mAb 19F1.

VE. Antigen Dependent Cell-mediated Cytotoxicity (ADCC)

The present experiments investigate the effects of IL-13 alone or in combination with IL-4, IFN-γ, or IL-10 on human monocytes. IL-13 induced significant changes in the phenotype of monocytes. Like IL-4, it enhanced the expression of CD11b, CD11c, CD18, CD29, CD49e (VLA-5), class II MHC, CD13, and CD23 whereas it decreased the expression of B7, CD64, CD32, CD16, and CD14 in a dose dependent manner. See FIGS. 22A through 22Y-1 and 23A through 23G-3. IL-13 induced upregulation of class II MHC antigens and its downregulatory effects on CD64, CD32, and CD16 expression were prevented by IL-10. IFN-γ could also partially prevent the IL-13 induced downregulation of CD64, but not that of CD32 and CD16. However, IL-13 strongly inhibited spontaneous and IL-10 or IFN-γ induced antigen dependent cell-mediated cytotoxicity (ADCC) activity of human monocytes toward anti-IgD coated $Rh^+$ erythrocytes, indicating that the cytotoxic activity of monocytes was inhibited.

Furthermore, IL-13 inhibited production of IL-1α, IL-1β, IL-6, IL-8, IL-10, IL-12 P35, IL-12 P40, GM-CSF, G-CSF, IFN-α and TNF-α by monocytes activated with LPS. In contrast, IL-13 enhanced the production of IL-1RA by these cells. Similar results on cytokine production were observed or have been obtained for IL-4. Thus IL-13 shares most of its activities on human monocytes with IL-4, but no additive or synergistic effects of IL-4 and IL-13 on human monocytes were observed suggesting that these cytokines may share common receptor components. Taken together, these results indicate that IL-13 has anti-inflammatory and immunoregulatory activities.

Activated T cells secrete a number of biologically active polypeptides, which regulate the proliferation, differentiation and function of cells participating in immune responses against antigens. T cells producing IL-2, IL-3, IL-4, IL-5, IL-6, IL-10, IFN-γ, GM-CSF, and TNF/LT simultaneously following antigenic or polyclonal stimulation have been described in both mouse and man. These T helper cells were designated Th0 cells in order to distinguish them from the more specialized Th1 and Th2 subsets. Murine Th1 cells produce IL-2, IFN-γ, TNF/LT, IL-3, and GM-CSF which supports their function as regulatory and effector cells in cellular immune responses such as delayed type hypersensitivity (DTH) whereas Th2 cells produce IL-4, IL-5, IL-6, IL-10, IL-3, and GM-CSF which makes them suitable for providing help to B cells in the production of immunoglobulins of different isotypes. In man, T cell clones with restricted cytokine production profiles have also been isolated from patients with inflammatory or allergic diseases. Although these types of clones resembled murine Th1 and Th2 clones, there were some differences. Depending on their mode of activation, Th1 clones generally could still produce low quantities of IL-4 whereas Th2 clones were able to produce low to normal quantities of IFN-γ. However, a clear imbalance in the production ratios of IL-4 and IFN-γ by Th2 clones was observed following antigenic stimulation. Therefore human T cell clones were defined which produce high levels of IFN-γ and no, or low levels of IL-4 Th1 "like" cells and T cell clones which produce no, or low levels of IFN-γ and high levels of IL-4 Th2 "like" cells. Furthermore, IL-10 which is exclusively produced by Th0 and Th2 T cell subsets in the mouse, is produced by Th0, Th1 "like", and Th2 "like" subsets in man.

The present invention makes available a new cytokine, human IL-13, which is related to the mouse P600 protein. Both human IL-13 and mouse P600 proteins were biologically active and affected human monocyte and B cell functions. Human IL-13 is a unglycosylated protein of 132 amino acids with a molecular mass (Mr) of 10.000 D. Both human and mouse IL-13 induced proliferation of the human TF1 pre-myeloid cell line. In addition, IL-13 was shown to induce changes in the morphology of the adherent fraction of human PBL which contained predominantly monocytes. These cells formed long cellular processes and adhered strongly to the substrate. See FIGS. 21A–21B. IL-13 also induced changes in the phenotype of human monocytes and human B cells by upregulating class II MHC expression and inducing the expression of the low affinity receptor for IgE (CD23, FcεRII). Furthermore, IL-13 acted on human B cells by inducing proliferation and immunoglobulin production. In particular, IL-13 induced human B cells to switch to ε and produce IgG4 and IgE in the presence of T cell clones, T cell membranes, or CD40 ligand. See above. These results indicated that many of the presently known biological activities of IL-13 are shared with IL-4.

In this study the biological activities of mouse and human IL-13 on human monocytes were further characterized and compared to those of IL-4, IL-10, and IFN-γ, other cytokines with stimulatory of inhibitory actions on human monocytes. IL-13 induced dramatic changes in the phenotype of human monocytes and inhibited the production of IL-1α, IL-1β, IL-6, IL-8, IL-10, GM-CSF, G-CSF, and TNF-α following activation by LPS, whereas it induced the production of IL-1RA. These results indicate that IL-13 has anti-inflammatory activities and may play an important regulatory role in immune responses.

Isolation and Culture of Human Monocytes

Human monocytes were isolated from peripheral blood of healthy donors by centrifugation over Ficall-Hypaque and adherence to plastic. Briefly, 100×10⁶ PBMNC were plated on a 100 mm tissue culture dish in Yssel's medium supplemented with human serum albumin (HSA) and 1% pooled human AB⁺ serum and incubated at 37° C. for 30 min. This culture medium was endotoxin free as determined by the Limulus amoebocyte lysate assay (<0.2 ng/ml of endotoxin). Subsequently, nonadherent cells were removed by extensive washing and cultured in Yssel's medium with HSA and 1% pooled human AB serum as indicated. Alternatively, highly purified human peripheral blood monocytes were obtained from 500 ml blood of normal donors by centrifugal elutriation. Mononuclear cells were isolated by density centrifugation in a blood component separator, followed by fractionation into lymphocytes and monocytes. The monocyte preparation was >95% pure, as judged by nonspecific esterase staining and contained more than 98% viable cells. These monocytes were cultured in Yssel's medium with HSA and 1% pooled human AB⁺ serum at a concentration of 4×10⁶ cells/ml in teflon bags (Jansen MNL, St Niklaas, Belgium), which prevented adhesion of these cells. After culture for the times indicated, monocytes were collected and analyzed for cell surface expression by indirect immunofluorescence or analyzed for lymphokine gene expression by Northern and PCR analysis. In addition, monocyte culture supernatants were collected for determination of IL-1α, IL-1β, IL-6, IL-8, IL-10, TNF-α, GM-CSF, G-CSF, and IL-1RA production following activation of these cells by LPS (*E. coli* 0127:B8) (Difco, Detroit, Mich.) at 1 μg/ml. The viability of the cells after culture always exceeded 95% as determined by trypan blue exclusion.

Reagents

Recombinant human and mouse IL-13 were expressed in *E. coli* as insoluble aggregates of glutathione-S-transferase fusion proteins, extracted by centrifugation, solubilized, and subjected to renaturation prior to digestion with thrombin to remove the N-terminal fusion part. Subsequently, proteins were purified by cation exchange and gel filtration chromatography, which resulted in active human and mouse IL-13. Purified human r-IL-10, r-IL-4, and r-IFN-γ were provided by Schering-Plough Research Institute (Bloomfield, N.J.). The neutralizing anti-IL-4 mAb 25D2 (Chretien et al. (1989) *J. Immunol. Methods*, 117.67–81), and anti-IL-10 mAb 19F1 (Abrams, et al. (1992) *Immunol. Rev.* 125:5–24), were described previously. The following mAbs were used for immunofluorescence studies on the expression of cell surface markers: SPV-L7 (CD11a; Spits et al. (1983) *Hybridoma* 2:423–437), Bear-1 (CD11b; Keizer et al. (1985) *Eur. J. Immunol.* 15:1142–1148), CLB FcR gran-1 (CD16; Klaassen et al. (1990) *J. Immunol.* 144:599–606), gp25 (CD23; Bonnefoy et al. (1987) *J. Immunol.* 138:2970–2978), IV.3 (CD32; Looney et al. (1986) *J. Immunol.* 136:1641–1647), 32.2 (CD64; Anderson et al. ELISA as described in Pène et al. (1988) *Proc. Natl. Acad. Sci*, (1986)

J. Biol. Chem. 261:12856–12864), Q5/13 (HLA-DR/DP; Quaranta et al. (1980) J. Immunol. 125:1421–1428), PdV5.2 (HLA-DR/DP/DQ; Koning et al. (1984) Hum. Immunol. 9:221–226), SAM-1 (VLA-5, CD49e; Keizer et al. (1987) Eur. J. Immunol. 17:1317–1322), CD-29 (Ts2/16; a kind gift of C. Figdor, Amsterdam), L307 (B7; Azuma et al. (1992) J. Immunol. 149:1115–1123), IOM13 (CD13; purchased from AMAC, Inc., Westbrook, Me.); Leu-M3 (CD14), Leu15 (CD11c), and L130 (CD18) were obtained from Becton-Dickinson (San Jose, Calif.).

Probes

Oligonucleotides used for Southern analysis of IL-1a, IL-1β, IL-6, IL-8, IL-10, TNF-α, GM-CSF, G-CSF, and β-actin PCR products have been described by de Waal Malefyt et al. (1991) J. Exp. Med. 174:1209–1213. The following oligonucleotides were used to detect IFN-α: 5'-TTCTGGCTGTGAGGAAATACT-3' (nt 360–378), IL-1RA: 5'-GTCAATTTAGAAGAAAAGATAGATGTGG-3' (nt 207–234), IL-12 P35: 5'-AATGGGAGTTGCCTGGC-CTC-3' (nt 488–507), IL-12 P40: 5'-TAAGACCTTTCTAA-GATGCGAGGCC-3' (nt 417–441), and TGF-β1: 5'-CGAGCCTGAGGCCGACTACTACGCCAAG-GAGGTCACCCGC-3' (nt 1131–1170). SEQ ID NO:11–15.

mRNA Isolation and Northern Analysis

Total RNA was isolated from 20×10⁶ monocytes by a guanidinium thiocyanate-CsCl procedure. For northern analysis, 10 μg total RNA per sample was separated according to size on 1% agarose gels containing 6.6% formaldehyde, transferred to Nytran nylon membranes (Schleicher a Schuell, Keene, N.H.), and hybridized with probes, labeled to high specific activity (>10⁸ cpm/μg) by a hexamer labeling technique. Filters were hybridized, washed under stringent conditions, and developed.

PCR Analysis

One microgram of total RNA was reverse transcribed using oligo (dT)12–18 as primer (Boehringer Mannheim, Indianapolis, Ind.) and AMV reverse transcriptase (Boehringer Mannheim) in a 20 μl reaction. Two microliters of reverse transcript (equivalent to 100 ng of total RNA) was used directly for each amplification reaction. Conditions for PCR were as follows: in a 50 μl reaction, 25 nmol of each primer, 125 μM each of dGTP, dATP, dCTP, and dTTP (Pharmacia, Uppsala, Sweden.), 50 mM KCl, 10 mM Tris-HCl, pH 8.3, 1.5 mMMgCl₂, 1 mg/ml gelatin, 100 μg/ml non-acetylated BSA and 1 unit Vent DNA polymerase (New England Biolabs, Beverly, Mass.). Primers used to amplify IL-1α, IL-1β, IL-6, IL-8, IL-10, TNF-α, GM-CSF, G-CSF, and β-actin have been described previously de waal Malefyt, et al. (1991) J. Exp. Med., 174:1209–1220. The following primers were also used: IFN-α sense primer: 5'-GCT-GAAACCATCCCTGTC-3' (nt 161–178), IFN-α antisense primer: 5'-CTGCTCTGACAACCTCCCAG-3' (nt 450–430), IL-1RA sense primer: 5'-GCAAGCCTTCA-GAATCTGGGATG-3' (nt 118–141), IL-1RA antisense primer: 5'-GATGTTAACTGCCTCCAGCTGGAGTC-3' (nt 344–319), IL-12 P35 sense primer: 5'-CTTCACCACTC-CCAAAACCTG-3' (nt 281–302), IL-12 P35 antisense primer: 5'-AGCTCGTCACTCTGTCAATAG-3' (nt 813–792), IL-12 P40 sense primer: 5'-CATTCGCTCCT-GCTGCTTCAC-3' (nt 337–358), IL-12 P40 antisense primer: 5'-TACTCCTTGTTGTCCCCTCTG-3' (nt 603–582), TGF-β1 sense primer: 5'-ACCGGGTGGC-CGGGGAGAGTGC-3' (nt 1097–1118), TGF-β1 antisense primer: 5'-GCCGGTTGCTGAGGTATCGCCAGG-3' (nt 1399–1376). SEQ ID NO: 16–25. Reactions were incubated in a Perkin-Elmer/Cetus D Thermal cycler 9600 for 25 cycles (denaturation 30 s at 94° C., annealing 30 s at 55° C., extension 60 s at 72° C.). Forty microliter of each reaction was loaded on 1% agarose gels in TAE buffer and PCR products were visualized by ethidium bromide staining. Subsequently, gels were denatured in 0.5M NaOH, 1.5M NaCl, neutralized in 1M ammonium acetate, and transferred to Nytran nylon membranes. Membranes were pre-hybridized in 6 x SSC, 1% SDS, 10 x Denhardt's solution (0.2% Ficoll, 0.2% polyvinylpyrrolidone, 0.2% BSA, pentax fraction V), and 200 μg/ml E. coli tRNA (Boehringer, Mannheim, FRG) for 4 h at 55° C. Oligonucleotide probes (200 ng), specific for a sequence internal to the primers used in the amplification, were labeled at the 5' end by T4 polynucleotide kinase (New England Biolabs) and γ-³²P-ATP (Amersham, Arlington Heights, Ill.). Probes were separated from non-incorporated nucleotides by passage over a Nick column (Pharmacia, Uppsala, Sweden) and added to the hybridization mix. Following hybridization for 12 hrs at 55° C., filters were washed in 0.1 x SSC (1 x SSC: 150 mM NaCl, 15 mM Na-citrate pH=7.0), 1% SDS at room temperature, and exposed to Kodak XAR-5 films for 1–2 hrs. In addition, signals were quantified on a Molecular Dynamics phosphor-imager (Molecular Dynamics, Sunnyvale, Calif.)

Lymphokine Determinations

The production of cytokines by monocytes was determined in culture supernatants by cytokine specific ELISA's. The cytokine specific ELISA's and their sensitivities were the following: IL-1α Endogen (Boston, Mass.) (50 pg/ml), TNF-α Endogen (Boston, Mass.) (10 pg/ml), IL-1β Cistron (Pine Brook, N.J.) (20 pg/ml)., IL-6 Genzyme (Boston, Mass.) (0.313 ng/ml), IL-8 R&D Systems (Minneapolis, Min.) (4.7 pg/ml), G-CSF R&D Systems (Minneapolis, Min.) (7.2 pg/ml), IL-1RA R&D Systems (Minneapolis, Min.) (12.5 pg/ml), GM-CSF Bacchetta, et al. (1990) J. Immunol. 144:902–908 (50 pg/ml) and IL-10 Abrams, et al., (1992) 75 pg/ml).

Immunofluorescence Analysis

Cells (10⁵) were incubated in V bottom microtiter plates (Flow Laboratories, McLean, Va.) with 10 μl of purified mAb (1 mg/ml) for 30 min at 4° C. After two washes with PBS containing 0.02 mM sodium azide and 1% BSA (Sigma, St Louis, Mo.), the cells were incubated with 1/40 dilution of FITC labeled F(ab')2 fragments of goat anti-mouse antibody (TAGO, Inc. Burlingame, Calif.) for 30 min at 4° C. After three additional washes, the labeled cell samples were analyzed by flow microfluometry on a FAC-Scan (Becton Dickinson, Sunnyvale, Calif.).

Antigen Dependent Cell-mediated Cytotoxicity (ADCC)

ADCC activity of cultured human monocytes against antibody coated rhesus positive human erythrocytes was performed as previously described te Velde, et al. (1992) Immunol. 149:4048–4052.

IL-13 and IL-4 Induce Identical Changes in the Expression of Cell Surface Antigens by Human Monocytes Both mouse and human IL-13 induced expression of CD23 (FceRII) and upregulated the expression of class II MHC antigens on human monocytes. The effects of IL-13 on the expression of a larger panel of cell surface antigens was examined here. In FIG. 25A through 25D-2 it is shown that IL-13 affected the expression of multiple cell surface molecules belonging to different supergene families. IL-13 enhanced the expression of several members of the integrin superfamily of adhesion molecules. The expression of a subunits CD11b (C3bi receptor, Mac-1), CD11c (gp150,95), and VLA-5 (FNR), as well as their respective β subunits CD18 (b2) and CD29 (b1, VLA-b) were upregulated by IL-13. The expression of other members of this family, including CD11a (LFA-1), VLA-2 (CD49b), VLA-3, VLA-4

(CD49d), VLA-6 (CD49f), b3 (CD61), and b4 was not significantly affected by IL-13. See FIGS. 22A through 22Y-1 and 23A through 23G-3.

IL-13 enhanced the expression of class II MHC antigens and slightly decreased the expression of B7, the counter-structure of CD28 (FIG. 25A through 25D-2). The expression of HLA-DR, HLA-DP and HLA-DQ was upregulated by IL-13. Expression of other members of the Immunoglobulin superfamily including class I MHC, CD11a (LFA-1), CD54 (ICAM-1), ICAM-2, and CD58 (LFA-3) was not affected by IL-13.

IL-13 modulated the expression of the various Fc receptors on monocytes. The expression of CD64 (FCγRI), CD32 (FCγRII), and CD16 (FcγRIII) on human monocytes was strongly downregulated by IL-13 (FIG. 25A through 25D-2). In contrast, IL-13 induced the expression of CD23 (FceRII). In addition, IL-13 upregulated the expression of CD13 (Aminopeptidase N) and downregulated the expression of CD14 (FIG. 25A through 25D-2). No effect of IL-13 was detected on the expression of CD25, CD33, and CD44.

IL-4 induced upregulation of CD11b, CD11c, CD18, VLA-5, CD29, class II MHC, CD13, and CD23, and inhibited the expression of CD16, CD32, CD64, CD14, and B7 on human monocytes to the same extend as did IL-13 (FIG. 25A through 25D-2). Taken together, these data indicate that the IL-13 induced changes in the expression of cell surface molecules are identical to those induced by IL-4 (FIG. 25A through 25D-2). Interestingly, incubation of monocytes with saturating concentrations of both IL-4 and IL-13 did not result in changes in the phenotype as compared to those induced by either cytokine alone (FIG. 25A through 25D-2). No additive or synergistic activities of IL-13 and IL-4 on the expression of the various cell surface molecules were detected under these conditions. To date, no evidence has been presented that monocytes are able to produce IL-4. However, to exclude the possibility that IL-13 acted through the induction of IL-4 by monocytes or by a few contaminating T cells, monocytes were incubated in the presence of IL-13 and a neutralizing anti-IL-4 mAb. As shown in Table 8, the induction of CD23, downregulation of CD14, and upregulation of class II MHC by IL-13 was not affected by the anti-IL-4 mAb. The anti-IL-4 mAb, however, was effective since it completely inhibited the effects of IL-4 in control experiments (Table 8). Thus, IL-13 acts independently of IL-4.

TABLE 8

| | IL-13 acts independently of IL-4. | | | | |
|---|---|---|---|---|---|
| mAb | medium | IL-13 | IL-13 + αIL-4 | IL-4 | IL-4 + αIL-4 |
| control | 3* | 5 | 6 | 5 | 3 |
| MHC class II | 443 | 1904 | 1845 | 2084 | 220 |
| CD23 | 3 | 99 | 79 | 89 | 8 |
| CD14 | 222 | 97 | 83 | 80 | 444 |

Monocytes were incubated with medium, IL-13 (50 ng/ml) or IL-4 (400 U/ml) in the absence or presence of neutralizing anti-IL-4 mAb 25D5 (10 μg/ml) at 37° C. for 120 h and expression of HLA-DR/DP (Q5/13), CD23 (gp25), and CD14 (Leu-M3) was determined by indirect immunofluorescence.
*Mean Fluorescence Intensity (channel number)

IL-13 induced changes in expression of cell surface markers were dose-dependent as shown for the modulation of CD11b, CD18, CD16, CD32, CD64, CD23, class II MHC, CD13, and CD14 expression in Table 9. Generally, incubation of human monocytes with 5 pg/ml IL-13 was insufficient to induce changes in the expression of these cell surface markers, whereas 0.5 ng/ml IL-13 resulted in significant changes in phenotype, comparable to those induced by 0.5 ng/ml IL-4. Maximal responses were induced by 50 ng/ml IL-13, which were again in the same range as those induced by 50 ng/ml of IL-4, indicating that IL-4 and IL-13 are equally effective.

TABLE 9

| | Il-13 induces changes in cell surface phenotype of monocytes in a dose dependent manner. | | | | | |
|---|---|---|---|---|---|---|
| | IL-13 (pg/ml) | | | | IL-4 (U/ml) | |
| mAB | 0 | 5 | 500 | 50000 | 4 | 400 |
| control | 3* | 3 | 3 | 4 | 3 | 3 |
| CD11b | 59 | 54 | 102 | 139 | 102 | 168 |
| CD18 | 71 | 54 | 79 | 108 | 99 | 127 |
| CD16 | 25 | 20 | 20 | 15 | 20 | 13 |
| CD32 | 50 | 48 | 44 | 40 | 43 | 39 |
| CD64 | 57 | 50 | 36 | 26 | 31 | 17 |
| CD23 | 4 | 4 | 12 | 56 | 7 | 67 |
| MHC class II | 355 | 386 | 586 | 607 | 609 | 908 |
| CD13 | 26 | 26 | 113 | 121 | 57 | 102 |
| CD14 | 110 | 110 | 75 | 37 | 86 | 16 |

Monocytes were incubated with medium, IL-13 (5 pg/ml, 500 pg/ml, or 50,000 pg/ml) or IL-4 (4 U/ml, or 400 U/ml) at 37° C. for 120 h and the expression of cell surface antigens was determined by indirect immunofluorescence.
*Mean Fluorescence Intensity (channel number)

IL-10 Downregulates IL-13 Induced Class II MHC Expression on Human Monocytes

To compare the effects of IL-13 with those of other cytokines which modulate the cell surface phenotype, monocytes were incubated with IL-10 or IFN-γ in the absence or presence of IL-13 and the expression of cell surface antigens was analyzed. As shown in FIG. 25A through 25D-2, IL-10 or IFN-γ alone did not significantly affect the expression of CD11b, CD11c, CD18, CD13, CD23, CD29, and VLA-5. In addition, IL-10 or IFN-γ did not affect the IL-13 induced increase in expression of these markers. IL-10 or IFN-γ had also no effect on the expression of CD14 and the IL-13 induced inhibition of CD14 expression. However, IL-10 downregulated not only the constitutive class II expression on monocytes, but also inhibited strongly the IL-13 induced class II MHC expression. Similar data were obtained when highly purified monocytes isolated by elutriation and cultured in teflon bags were used (Table 10) An increased expression of class II MHC antigens was observed following incubation of monocytes in medium alone, which was completely prevented by IL-10. m-IL-13, h-IL-13, IL-4, and IFN-γ all induced high levels of class II MHC expression which were blocked by IL-10 (Table H3). Class II MHC expression induced by IFN-γ was further enhanced by IL-13 (FIG. 25A through 25D-3). IFN-γ slightly upregulated expression of B7 which was not significantly affected by IL-13 (FIG. 25A through 25D-2). Taken together, these results indicate that IL-13, IL-10, and IFN-γ independently modulate the expression of cell monocyte surface antigens.

TABLE 10

| Il-10 inhibits constitutive, IL-13-, IL-4-, and IFN-γ- induced MHC class II expression on human monocytes. | | |
|---|---|---|
| | IL-10 (200 U/ml) | |
| incubation | + | − |
| control 4° C. | 69* | nd** |
| medium 37° C. | 150 | 46 |
| mIL-13 | 212 | 73 |

TABLE 10-continued

Il-10 inhibits constitutive, IL-13-, IL-4-, and IFN-γ- induced MHC class II expression on human monocytes.

| incubation | IL-10 (200 U/ml) | |
| --- | --- | --- |
| | + | − |
| hIL-13 | 197 | 81 |
| IL-4 | 407 | 94 |
| IFN-γ | 347 | 36 |

Elutriated monocytes were incubated in medium at 4° C or 37° C. mIL-13 (50 ng/ml), hIL-13 (50 ng/ml), IL-4 (400 U/ml) or IFN-γ (100 U/ml) in the absence or presence of IL-10 (200 U/ml) in teflon bags for 48 h and expression of HLA-DR/DP was determined by indirect immunoflourescence.
*Mean Fluorescence Intensity (channel number)
**Not done IL-13 Inhibits Monocyte FcγR Cell Surface Expression and Cytotoxicity IFN-γ, IL-4, and IL-10 are able to modulate the expression of FcγRI (CD64), FCγRII (CD32), and FcγRIII (CD16) on human monocytes. IFN-γ and IL-10 enhance the expression of CD64 whereas IL-4 downregulates the expression of CD64, CD32, and CD16 (FIG 25A through 25D-2). Adding combinations of these cytokines to monocytes showed that IL-10 was able to prevent the IL-4 induced downregulation in cell surface expression of all three FcγR and that IFN-γ partially restored the downregulatory effects of IL-4 on CD64 expression. The effects of IL-10 and IFN-γ on IL-13 induced downregulation of the expression of the various FcγR are shown in FIG. 25A through 25D-2. IL-10 prevented IL-13 induced downregulation of CD64, CD32, and CD16. In addition, IFN-γ could partially rescue IL-13 induced downregulation of CD64, but did not affect the IL-13 induced downregulation of CD32 and CD16. See FIG. 25A through 25D-2.

Figure 26:
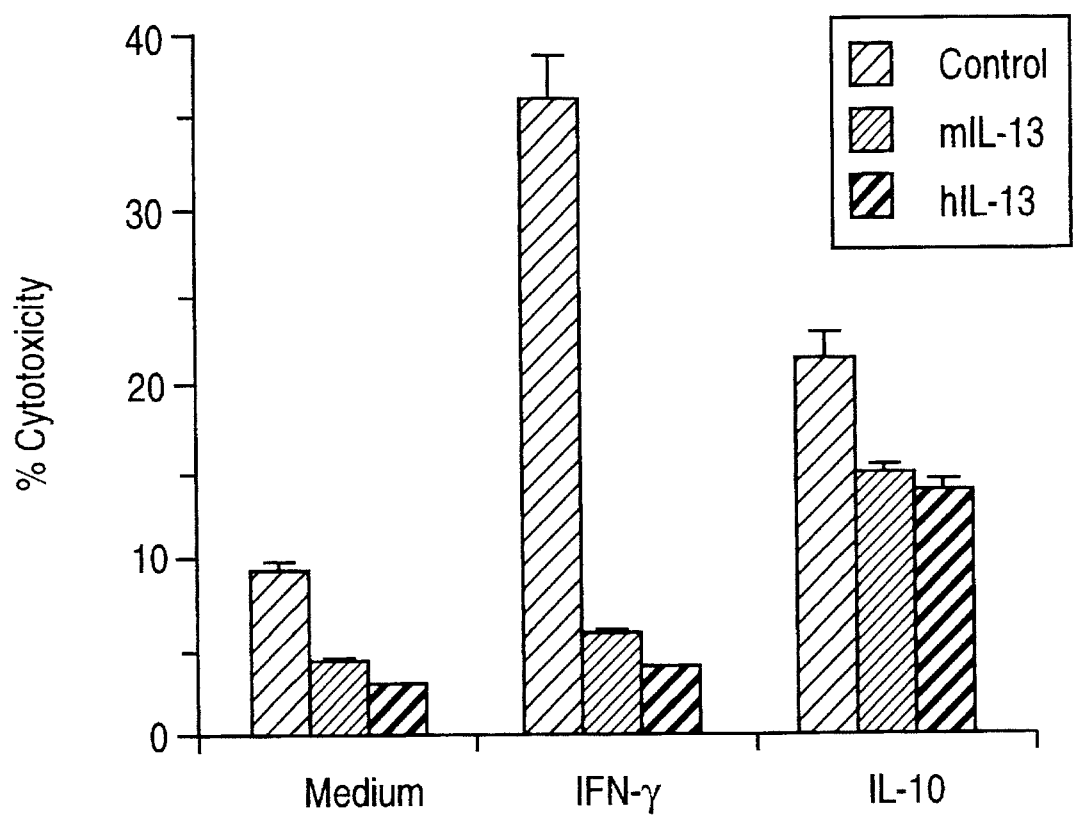
FIG. 26 shows that IL-13 inhibits spontaneous, IFN-$\gamma$, and IL-10 induced ADCC activity by monocyte. Elutriated monocytes ($4 \times 10^6$) cells/ml) were cultured in medium, IL-10 (200 U/ml), or IFN-$\gamma$ (100 U/ml) in the absence or presence of IL-13 (50 ng/ml) for 40 h and ADCC activity against anti-IgD coated Rhesus$^+$ human erythrocytes was determined at an ET ratio of 0.4.

The level of ADCC activity of human monocytes has been shown to correlate with the expression of FcγRI. The effects of IL-13 on the functional activity of FcγRI on monocytes was determined by their ability to lyse anti-D opsonized human Rh⁺ erythrocytes. As shown in FIG. 26, both human and mouse IL-13 were able to inhibit ADCC activity of monocytes cultured in medium alone. On the other hand, ADCC activity was enhanced when monocytes were cultured in the presence of IFN-γ or IL-10. Interestingly, IL-13 significantly inhibited these effects of IFN-γ and IL-10 despite the fact that IFN-γ and IL-10 partially or completely reversed the inhibition of FcγRI expression (FIG. 25A through 25D-2), indicating that IL-13 affected the FcγR mediated cytotoxicity also by other mechanisms.

IL-13 Inhibits Production of Proinflammatory Cytokines Hemopoietic Growth Factors But Induces IL-RA The effects of IL-13 on the production of cytokines by human monocytes was investigated. Monocytes were activated by LPS and cytokine production was determined in the culture supernatants after 6 and 24 hours by cytokine specific ELISA's. Activation of monocytes by LPS resulted in the production of IL-1α, IL-1β, IL-6, IL-8, IL-10, GM-CSF, G-CSF, TNF-α, and IL-1RA. Significant levels of IL-1α, IL-1β, IL-6, IL-8, TNF-α, and IL-1RA were present at 6 h after activation, whereas the production of IL-10, G-CSF, and GM-CSF was detected at 24 h. At 6 and 24 h after activation, IL-13, IL-4, and IL-10 inhibited the production of IL-1α, IL-1β, IL-6, IL-8, IL-10, TNF-α, G-CSF, and GM-CSF, but enhanced the production of IL-1RA.

The present experiments determined the biological activities of IL-13 on human monocytes. IL-13 affected the morphology, phenotype, function, and cytokine production of monocytes. Incubation of monocytes with IL-13 induced strong adherence of these cells to plastic substrates and their morphology changed to a dendritic appearance, see FIGS. 21A–21B. In addition, homotypic aggregates of cells were observed. The finding that IL-13 upregulated the expression of CD11b, CD11c, CD18, VLA-5, and CD29, which are members of the integrin superfamily, is compatible with the observed aggregation and changes in morphology, since CD11b/CD18 and CD11c/CD18 heterodimers are involved in cell-cell interactions, homotypic aggregation, adhesion to artificial substrates, and bind fibrinogen. In addition, the α5β1 integrin VLA-5/CD29 is the receptor for fibronectin, which is an abundant extracellular matrix protein involved in adhesion processes. IL-13 did not induce changes in the expression of other molecules involved in adhesion or cell-cell interaction, e.g., CD11a, VLA-2, VLA3, VLA-4, VLA-6, β3, β4, ICAM-1, ICAM-2, LFA-3, MEL-14, and CD44 but it remains possible that other cell surface structures are involved in the IL-13 induced changes in morphology and adherence.

IL-13 upregulated the expression of class II MHC antigens on human monocytes. The expression of HLA-DR, HLA-DP, and HLA-DQ was significantly increased by IL-13. IL-10 inhibits constitutive, IL-4-, and IFN-γ induced class II MHC expression on human monocytes. These experiments show that IL-10 inhibits IL-13 induced class II MHC expression, which further supports the general immunosuppressive activities of IL-10.

The expression of the various Fc receptors for IgG and IgE on monocytes is influenced by several cytokines. CD64 (FcγRI) expression is upregulated by IFN-γ and IL-10 and inhibited by IL-4. Furthermore, IFN-γ and IL-10 are able to prevent the downregulation of CD64 induced by IL-4. Here it is shown that IL-13 inhibited the constitutive expression of CD64 and that this inhibition could also be prevented by IL-10 and IFN-γ. The expression of CD64 has been shown to correlate with ADCC activity of monocytes. The FcγRI mediated spontaneous-, IL-10-, or IFN-γ-induced cytotoxicity of monocytes towards IgD coated rhesus positive erythrocytes was strongly inhibited by IL-13 indicating that IL-13 not only affected the phenotype but also the function of human monocytes. Although IL-10 could prevent the IL-13 induced downregulation of CD64 expression, ADCC activity was still inhibited. This supports the notion that ADCC activity is determined by factors other than just the levels of CD64 expression.

IL-13 also affected the expression of FcγRII and FcγRIII. IL-13 downregulated the expression of CD32 and CD16 in a dose dependent manner. However, IL-10, but not IFN-γ, could block the IL-13 induced downregulation of CD32 and CD16 on monocytes. These results indicate that the level of Fc receptor expression is highly regulated by cytokines.

The only cytokine known to induce the low affinity Fc receptor for IgE (CD23) on monocytes was IL-4. However, IL-13 also induces the expression of CD23 on monocytes. Here it is demonstrated that the IL-13 induced expression of CD23 could be partially suppressed by IFN-γ. It is also shown that IL-13 could induce production of IgE by PBMC, see FIGS. 15 through 19. In addition, IL-13 could initiate germline ε transcription in purified sIgM⁺ B cells and switching to IgE production when a second signal provided by T cell clones, T cell membranes, or CD40 ligand was present. The production of IgE is regulated by number of cytokines, including soluble CD23, which have either enhancing or inhibitory effects. The effects of IL-13 and IFN-δ on the expression of CD23 by human monocytes fit well within this concept.

VI. Activities of IL-4 Antagonist; Interactions

Interleukin-4 (IL-4) and interleukin-13 (IL-13) are two cytokines that are secreted by activated T cells and have similar effects on monocytes and B cells. The present experiments show a mutant form of human interleukin-4 (hIL-4) that competitively antagonizes both hIL-4 and human interleukin-13 (hIL-13). The amino acid sequences of IL-4 and IL-13 are about 30% homologous and circular dichroism spectroscopy (CD) shows that both proteins have a highly Q-helical structure. IL-13 competitively inhibits hIL-4-binding to functional human IL-4 receptors (called hIL-4R) expressed on a hIL-4-responsive cell line, but not to the cloned IL-4R ligand-binding protein expressed on heterologous cells. hIL-4 has about a 50-fold lower affinity for the IL-4R ligand-binding protein than for the functional IL-4R, while the mutant hIL-4 antagonist protein binds to both receptor types with the lower affinity. The above results demonstrate that IL-4 and IL-13 share a receptor component that is important for signal transduction. In addition, these data establish that IL-4R is a complex of at least two components one of which is a novel affinity-converting subunit that is critical for cellular signal transduction.

IL-13 is one of a number of protein hormones called cytokines that are secreted by activated T cells. Human IL-13 elicits morphological and cell-surface phenotype changes on human monocytes and also facilitates growth and immunoglobulin (Ig) production by human B cells. All these biological effects are also elicited by hIL-4, another protein hormone secreted by activated T cells.

The biological actions of IL-4 are mediated by a cell surface receptor that binds IL-4 with high specificity and affinity (Dissociation constant or $K_d$~$10^{-10}$M. See Harada et a1.(1992) in Spits et al. (eds) IL-4: structure and function CRC Press, Boca Raton, 33–54. Human and mouse IL-4R have been characterized by cDNA cloning which defined a 130 kDa glycoprotein (herein referred to as IL-4R ligand-binding protein) with a single transmembrane span. The extracellular domain sequence of IL-4R ligand-binding protein is structurally homologous to the extracellular domains of other cytokine receptor proteins. Several of these other proteins participate in heteromeric interactions where one subunit by itself binds the ligand at a relatively low affinity and the other subunit(s) contribute additional binding affinity and often are important for signaling. However, the extracellular domain of the IL-4R ligand-binding protein alone appears to bind IL-4 at the high affinity that characterizes IL-4R on various IL-4-responsive cells. Although the intracellular domain is unimportant for binding, it is important for signal transduction.

The structural homologies between many of the cytokine receptors is mirrored by structural homologies between their ligands. For example, IL-4, interleukin-2 (IL-2), Growth Hormone, Macrophage Colony-Simulating Factor (M-CSF), and Granulocyte Macrophage Colony-Stimulating Factor (GM-CSF) are not related at the sequence level, yet all have a similar compact-core-bundle structure of four antiparallel α-helices. See, e.g., Diederichs et al. (1991) *Science* 254:1779–1782; Bazan (1992) *Science* 57:410–413; McKay (1992) *Science* 257:412–413; and Powers et al. (1992) *Science* 256:1673–1677. In mouse IL-2, exhaustive mutational analyses led to the discovery that substitution of a residue (Gln141 to Asp) at the C-terminus of the fourth a-helix results in loss of receptor-activation, but retention of most receptor-binding. This mutant protein is a potent and specific competitive antagonist of IL-2 biological action.

Based on the structural homology between IL-2 and IL-4, the importance of residues of hIL-4 that might be analogous to mIL-2 Gln141 was investigated. In these experiments, substitution of a residue (Tyr124 with Asp) at the C-terminus of the fourth α-helix of human IL-4 (hIL-4) specifically abrogates IL-4R-activation and renders the protein a competitive antagonist of IL-4 biological action. This property of hIL-4.Tyr124 to Asp (called hIL-4.Y124D) has been described independently. See Kruse et al. (1992) *EMBO J.* 11:3237–3244. In these experiments, this mutant hIL-4 antagonist is specifically shown to be defective in interaction with a previously unknown second subunit of the functional IL-4R. In addition, the hIL-4 antagonist blocks IL-13 biological action.

Materials and methods

Mutagenesis of hIL-4

Based on mutagenesis studies of mIL-2 (Zurawski et al. (1990) *EMBO J.* 9:3899–3905; Zurawski et al. (1992) *EMBO J.* 11:3905–3910), the shared structural frameworks of hIL-2 and hIL-4 (Bazan (1992) *Science* 257:410–413; McKay (1992) *Science* 257:412–413; Powers et al. (1992) *Science* 256:1673–1677), and assuming evolutionary conservation of functionally important residues, hIL-4 residues E114, K117, and Y124 were selected as those most likely to be specifically involved in receptor activation. Substitution mutagenesis at these positions used a synthetically reconstructed hIL-4 coding region inserted in the pTacRBS *Escherichia coli* expression plasmid (Zurawski et al. (1986) *J. Immunol.* 137:3354–60. Double stranded synthetic oligonucleotides (synthesizer and reagents, Applied Biosystems) corresponding to the sequence between SalI and HindIII recognition sites in the C-terminal coding region and containing equimolar amounts of each deoxynucleotide at the codon selected for randomized substitution were ligated to SalI and HindIII digested pTac-hIL-4 plasmid. Recombinant plasmids were recovered by transformation and the DNA sequence (Sequenase 2.0 kit, US Biochemical Corp.) of their SalI-HindIII intervals were determined. Partially pure mutant hIL-4 proteins were prepared as described for mIL-2 proteins (Zurawski et al. (1989) *EMBO J.* 8:2583–2590), except that the refolding buffer contained reduced and oxidized glutathione, and assayed using TF-1 cells (see below). We found that substitutions at Y124 resulted in proteins that were partial agonists and that the Y124D substitution had the most drastic defect in cellular activation. During the course of this work similar observations were made by others (Kruse et al. (1992) *EMBO J.* 11:3237–3244) who also showed that hIL-4.Y124D and hIL-4 have similar affinities for hIL-4R. For production of pure hIL-4.Y124D, the pTrpC11-hIL-4 *E. coli* expression plasmid was subjected to PCR (GeneAmp kit, Perkin Elmer Cetus) using the oligonucleotides: CTCCAAGAACACAACTGAGAAGGAAACCTT (proximal to the single PstI restriction site in the coding region) and TTGATTAAGCTTTCAGCTCGAACACTTTGAATCTTTCTC (a HindIII recognition site precedes the underlined part which corresponds to the C-terminal coding region containing a GAT codon for residue 124). SEQ ID NO 26–27. The PCR product and pTrpC11-hIL-4 plasmid were cleaved with PstI and HindIII, ligated, and pTrpC11-hIL-4Y124D plasmid was recovered and validated by transformation and sequence analysis using previously described methods (Zurawski et al. (1989) *EMBO J.* 8:2583–2590). Corresponding changes in hIL-13 at those positions should also have IL-13 antagonistic effects.

Purification of Proteins E. coli-derived hIL-4 (van Kimmenade et al. (1988) Eur. J. BioChem. 173:109–114), human interleukin-1α (hIL-1α; Kronheim et al. (1986) Bio/Technology 4:1078–1082), and mIL-13 (see above) were purified as described. hIL-4Y124D was prepared from E. coli K12 cells (strain CQ21) harboring the DTrpC11-hIL-4.Y142D plasmid grown overnight at 37° C. in 12 liters of L-Broth containing 50 µg/ml ampicillin in a G 53 rotatory shaker (New Brunswick Scientific) at 200 rpm. The cells were harvested by centrifugation in a RC-3 centrifuge (all rotors Sorvall) at 4,500 rpm, 10 min, 4° C. The pellets were resuspended in 450 ml of TE buffer (50 mM Tris-HCl pH 8, 1 mM EDTA) by shaking at 200 rpm for 15 min. Cells were ruptured by 4 passes through an ice-cooled Microfluidizer model 110 cell disrupter (Microfluidics). Inclusion bodies were collected by centrifugation in a GS-3 rotor at 9,000 rpm, 40 min, 4° C. The pellet was then washed by resuspension in 450 ml of TE and Triton X-100 was added to a final concentration of 0.5%. Samples were kept at room temperature for 30 min and were then pelleted in a GSA rotor at 8,500 rpm, 10 min, 4° C. The inclusion bodies were resuspended in 60 ml 5M guanidine-HCl in PBS (120 mM NaCl, 2.7 mM KCl, 10 mM NaPi pH 7.4), 2 mM reduced glutathione, 0.2 mM oxidized glutathione and any remaining insoluble material was removed by centrifugation in a SS-34 rotor at 20,000 rpm, 30 min, 4° C. The supernatant was diluted 10-fold into the same buffer without guanidine hydrochloride and stirred gently overnight at 4° C. to permit refolding and oxidization. Concentration and exchange into 100 ml 50 mMNa Acetate pH 5.0 was then performed using a Millipore Pellicon apparatus (Millipore) equipped with a tangential flow ultrafiltration cassette with a size exclusion of 10 kDa. The sample was subjected to anion exchange chromatography (CM sepharose 16/100 column, Pharmacia) in the same buffer with elution via a 0–0.7M NaCl gradient. Fractions containing hIL-4 protein were pooled and subjected to reverse phase chromatography (Poros R 10/100 column, Perspective Biosystems) with elution via a gradient of 0–50% acetonitrile in 0.1% trifluoroacetic acid/water. Fractions containing hIL-4 were lyophilized, dissolved in 50 mMNa Acetate pH 5.0, and quantified by densitometry (Molecular Dynamics) of stained SDS-PAGE with chicken egg lysozyme (Sigma) as a standard.

Cell Proliferation Assays

Colorimetric cell proliferation assays used the human TF-1 cell line at 30,000 cells per well for 3 days and were performed as described Mosmann (1983) J. Immunol. Methods 65:55–63. Cells were assayed in RPMI medium with L-glutamine and 10% fetal bovine serum (JRH Biosciences), 0.5 mM β-mercaptoethanol (Sigma). Cells were maintained in the above medium containing 1 nM hGM-CSF (Schering-Plough).

PHA blasts were prepared by incubation of $10^6$ peripheral blood mononuclear cells per ml with 0.1 mg/ml phytohaemagglutinin (Wellcome Diagnostics) in Yssel's medium (see Yssel et al. (1984) J. Immunol. Methods 72:219–227), supplemented with 1% human AB+ serum in 24 well Linbro plates (Flow Laboratories) and were used in the proliferative assay after six days of incubation. SP-B21 is a CD4+ cloned T cell line with unknown antigen specificity and was cultured as previously described (Spits et al. (1982) J. Immunol. 128:95–105. Proliferative responses of both PHA blasts and SP-B21 cells were determined at $5 \times 10^4$ cells per well and were performed and developed colorimetrically after three days as described for TF-1 cells.

Ligand-Binding

Procedures for preparation of cells, separation of bound from free ligand, computer analysis, and quantitation have been described in Zurawski et al. (1992) EMBO J. 11:3905–3910. Ba/F3 cells expressing surface hIL-4R-S protein (hIL-4R ligand-binding protein deleted for most of the intracellular domain) were grown as for TF-1 cells except that mouse interleukin-3 (IL-3, 100 U/ml) replaced hGM-CSF and 50 µg/ml gentamycin sulphate (Sigma) and 800 µg/ml Neomycin G418 (Schering-Plough) were added. $I^{125}$-radiolabeling of E. coli-derived hIL-4 and binding conditions were as described in Harada et al. (1992) J. Biol. Chem. 67:22752–22758.

Circular Dichroism Spectroscopy

Secondary structural features of hIL-4, hIL-1α, and mIL-13 proteins were examined on a J720 spectrophotometer with the 450 W xenon lamp and J700 data analysis software (Jasco). The samples were dialyzed against 20 mM NaPi, pH 7. Protein concentrations of the samples were re-determined by UV absorption scanning on a Lambda 6 spectrophotometer (Perkin-Elmer). The absorption maximum at 280 nm was used to calculate the amount of protein using theoretical extinction coefficients based on known molecular weights and expected residue absorption contributions. Samples were diluted to 0.2 mg/ml in a 0.2 mm path length cell. Typical scan parameters for the near UV range were a continuous wavelength scan at 10 mdeg sensitivity, 0.1 nm step resolution at a scan speed of 50 nm/min with a time constant of 2 s. Four accumulations/scan were averaged for an increased signal to noise ratio. Phosphate buffer blanks were run and subtracted out from subsequent protein scans and the spectra were noise-reduced using J700 data analysis software.

Mutant hIL-4 antagonist blocks IL-13 action on TF-1 cells

Figure 27A:
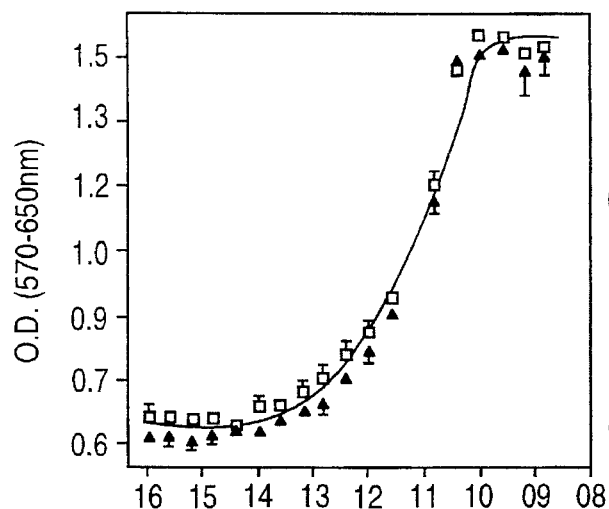
FIGS. 27A–27D show that mutant hIL-4.Y124D protein antagonizes the action of hIL-4, hIL-13, and mIL-13, but not hGM-CSF on TF-1 cells. Dose responses of TF-1 cells to (FIG. 27A) hGM-CSF, (FIG. 27B) hIL-4, (FIG. 27C) mIL-13, and (FIG. 27D) hIL-13 were determined in the absence (open square) and presence of $2.4 \times 10^{-8}$M (.) or $8.0 \times 10^{-9}$M (solid triangle) hIL-4.Y124D. Abscissa in −log [M] protein. Error bars are standard deviations (n=3).
Figure 27B:
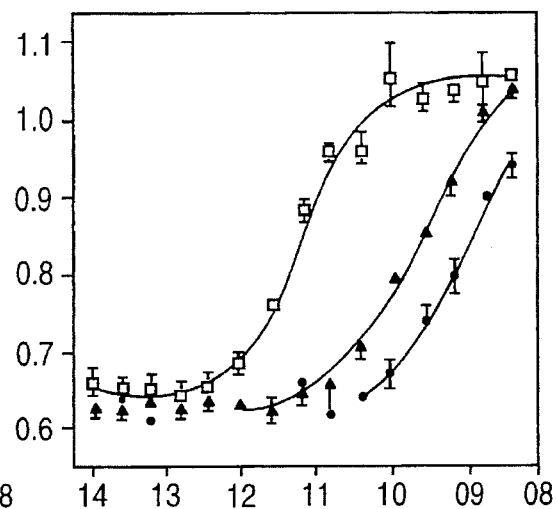
Figure 27C:
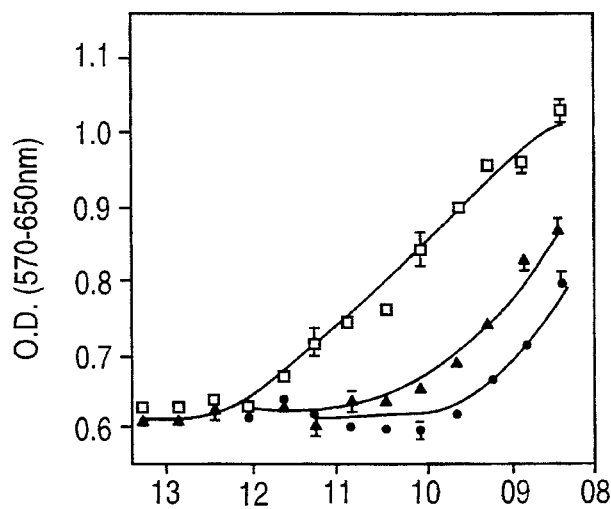
Figure 27D:
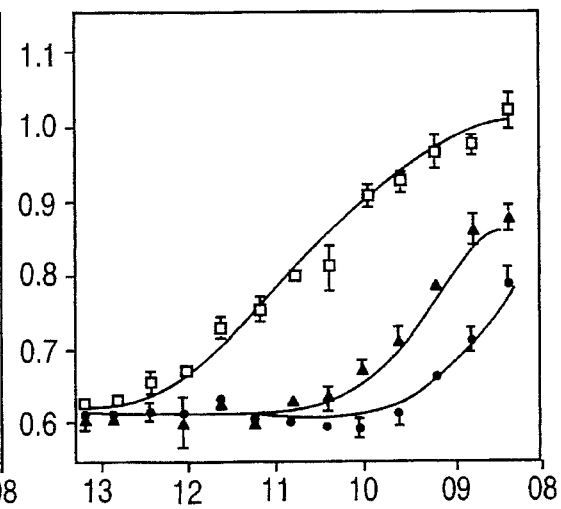

In a search for mutant hIL-4 antagonists, it was noted that an Asp substitution at residue Tyr124 of hIL-4 resulted in loss of receptor-activation without significant loss of receptor-binding. As expected from these properties, hIL-4.Y124D was a competitive antagonist of the action of native hIL-4 on TF-1 cells (FIG. 27B). TF-1 is a human pre-myeloid erythroleukemic cell line that shows a growth response to various human protein hormones, such as GM-CSF, interleukin-3 (IL-3), interleukin-6 (IL-6), IL-4, and both human and mouse IL-13. The maximal responses of TF-1 cells to these factors varies widely, but the maximal biological responses of IL-4 and IL-13 are similar. hIL-4.Y124D had no effect on the TF-1 responses to GM-CSF (FIG. 27A), IL-3, or IL-6. In contrast, hIL-4.Y124D was a potent antagonist of both mIL-13 and hIL-13 action on TF-1 cells (FIG. 27C, 27D). hIL-4.Y124D was equipotent against hIL-4, mIL-13, and hIL-13 activities on TF-1 cells and inhibited in a dose-dependent manner (FIG. 27B, 27C, 27D).

IL-13 Competitively Inhibits hIL-4 Binding to TF-1 Cells

Figure 28A:
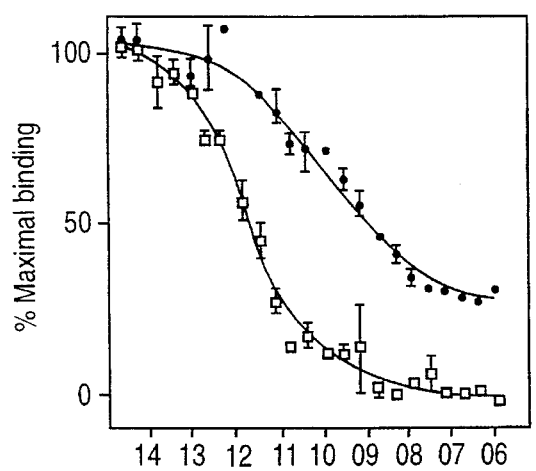
FIGS. 28A–28B show that hIL-4 and mIL-13 competitively displace $I^{125}$-hIL-4 binding to TF-1 cells. Various amounts of non-labeled hIL-4 (open square) and mIL-13 (.) were incubated for 2 h at 4° C. with 7.0×10$^{-12}$M I$^{125}$-hIL-4 and cells. I$^{125}$-hIL-4 bound to cells was then determined. Error bars are standard deviations (n=2). Other experiments gave analogous results.

Since hIL-4.Y124D antagonizes hIL-4 via competitive inhibition of hIL-4 binding to IL-4R, a similar mechanism was hypothesized for its action against IL-13. Such a mode of hIL-4.Y124D action against IL-13 would imply commonalty between IL-4R and IL-13R. This was tested by comparing the abilities of hIL-4 and mIL-13 to competitively displace $I^{125}$-hIL-4 binding to TF-1 cells. hIL-4 fully competed $I^{125}$-hIL-4 binding to TF-1 cells with the concentration required for 50% inhibition (or $IC_{50}$)~$2 \times 10^{-12}$M (FIG. 28A). mIL-13 also competed $I^{125}$-hIL-4 binding (FIG. 28A). However, compared to hIL-4, it could not completely displace $I^{125}$-hIL-4 binding (~70% of the binding was displaced) and its $IC_{50}$ value ($2 \times 10^{-10}$M) was higher.

IL-13 Does Not Bind to the IL-4R Ligand-binding Protein

Figure 28B:
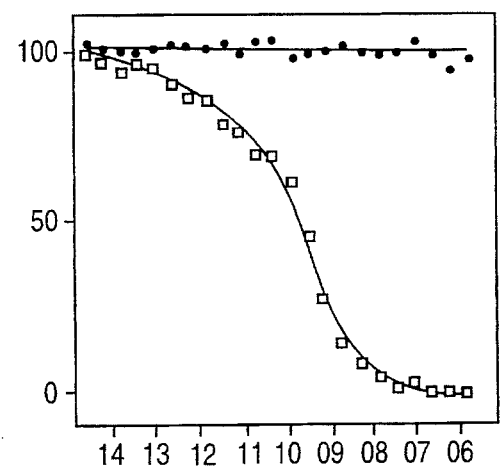

A possible basis for the commonalty between IL-4R and IL-13R is that they are the same. This was tested by comparing the abilities of hIL-4 and mIL-13 to competitively displace $I^{125}$-hIL-4 binding to a derivative of the cloned hIL-4R ligand-binding protein expressed on mouse pro-B Ba/F3 cells. Ba/F3 hIL-4R-S cells were used, which have a large number of binding sites/cell (~2000) in the form of a hIL-4R ligand-binding protein deleted for most of the cytoplasmic domain. See Harada et al. (1992) *J. Biol. Chem.* 267:22752–22758. Although hIL-4 fully competed $I^{125}$-hIL-4 binding to Ba/F3 hIL-4R-S cells with $IC_{50} \sim 2 \times 10^{-10}M$, even high levels of mIL-13 ($10^{-6}M$) did not compete (FIG. 28B).

Some hIL-4-responsive Cell Types Do Not Respond to IL-13

Figure 29A:
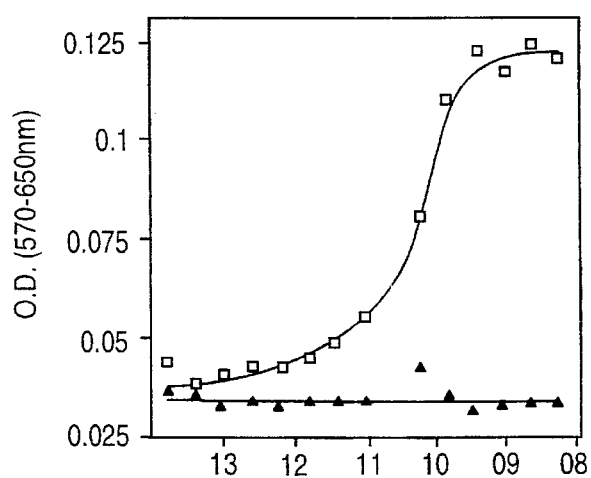
FIGS. 29A–29B show that some human cell types respond to hIL-4 but not to hIL-13. Dose responses to hIL-4 (open square) and hIL-13 (solid triangle) of two cell types were determined.
Figure 29B:
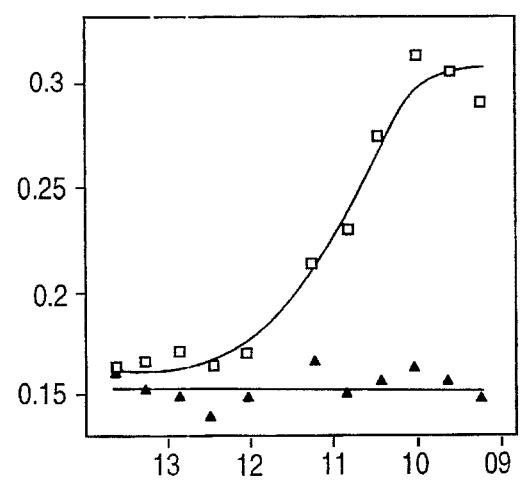

The earliest characterizations of the biological activities of IL-13 have shown concordance between cellular responses to IL-4 and IL-13, as described herein. Human peripheral blood mononuclear cells (PBMNC) activated with phytohaemagglutinin (PHA) and certain human T cell cloned cell lines such as SP-B21 proliferate in response to hIL-4. FIG. 29 shows that both these hIL-4-responsive cell types did not proliferate in response to hIL-13.

The Binding Properties of hIL-4 Y124D and hIL-4

The binding of hIL-4 to Ba/F3 hIL-4R-S cells ($K_d=1.6 \times 10^{-10}M$; FIGS 28B and 30B) corresponded closely to that previously characterized for the high affinity IL-4R ($K_d \sim 10^{-10}M$). Human lymphoma Raji cells have high affinity binding sites for hIL-4 ($K_d \sim 10^{-10}M$; see Kruse et al. (1992) *EMBO J.* 11:3237–3244) and hIL-4.Y124D protein binds to these cells with only a 3-fold reduced affinity compared to hIL-4. hIL-4.Y124D bound 3.5-fold less avidly to the hIL-4 binding sites expressed on Ba/F3 hIL-4R-S cells (FIG. 30B).

TF-1 cells bound hIL-4 with an apparent affinity that was ~50-fold higher than the "high affinity" binding of hIL-4 to Ba/F3 hIL-4R-S cells (compare FIGS. 30A and 28B). This is surprising because although comparisons were done in parallel and used identical conditions and reagents, these two cell types have been reported to have similar numbers of binding sites and affinities for hIL-4 as defined by equilibrium binding studies. In contrast to the different binding affinities of hIL-4 seen by competitive displacement binding studies, hIL-4.Y124D bound equally to both TF-1 and Ba/F3 hIL-4R-S cells (FIG. 4A versus 4B). In other experiments, hIL-4.Y124D was used as the labeled ligand and the results were analogous to those shown in FIGS. 30A and 30B.

IL-4 and IL-13 Are Structural Homologues

Figure 31:
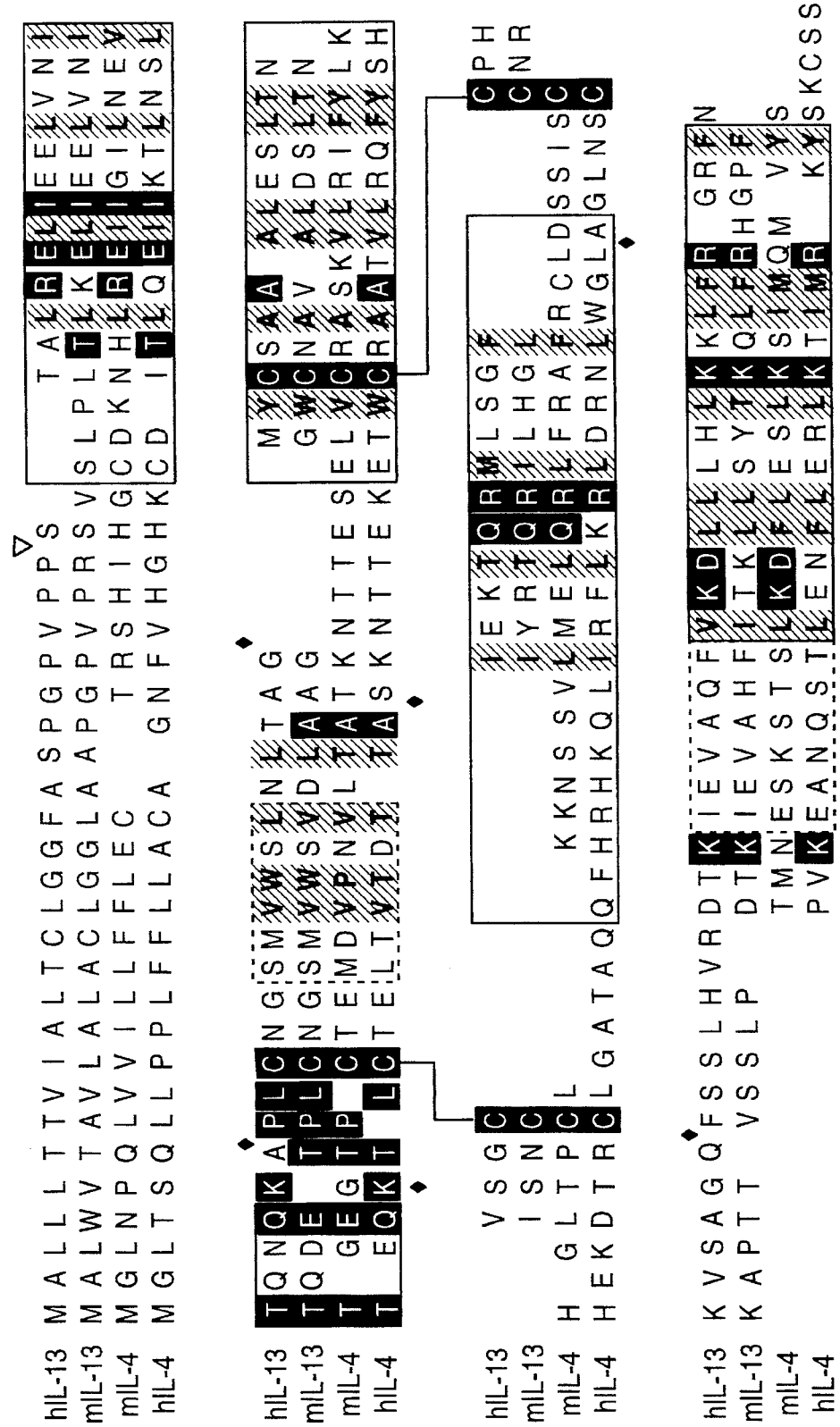
FIG. 31 shows sequence relatedness of IL-4 and IL-13. Alignment of the mature protein sequences of human and mouse IL-4 (see, e.g., Lee, et al. (1986) *Proc. Natl Acad Sci USA* 83:2061–2065; Noma, et al. (1986) *Nature* 319:640–646; and Yokota, et al. (1986) *Proc. Natl Acad. Sci. USA* 83:5894–5898) and IL-13 (Brown, et al. (1989) *J. Immunol.* 142:679–687; and herein). Residues in black backgrounds are common to at least one IL-4 and IL-13 sequence. Residues in shaded backgrounds have hydrophobic side chains in hIL-4 that are buried in the structural core (Powers, et al. (1992) *Science* 256:1673–2677). Black boxes delineate the four α-helical regions of hIL-4 and gray boxes delineate the two β-strands of hIL-4. ∇ indicates the leader peptide processing site (Lee, et al. (1988) *J. Biol. Chem.* 263:10817–10832) and solid diamonds indicate the gene exon/intron junctions (Otsuka, et al. (1987) *Nuc. Acids Res.* 15:333–344; Arai, et al. (1989) *J. Immunol.* 142:274–282). Right angle symbols indicate the disulfide linkages that are known for hIL-4 (Trotta (1992) in Spits (ed). IL-4; *Structure and Function* CRC Press, Boca Raton, 15–32).

The commonalty between IL-4R and IL-13R prompted a close examination of the sequence relatedness of IL-4 and IL-13. Only the sequences of the mature human and mouse IL-4 and IL-13 proteins were examined, while assuming that known disulfide linkages for IL-4 are preserved for IL-13. The alignment shown in FIG. 31 shows that there was significant, although low (~30%) sequence homology between IL-4 and IL-13. The significance of this observation was increased when the known structural features of hIL-4 were considered. All of the 25 residues that contribute to the hIL-4 hydrophobic structural core were conserved or had conservative hydrophobic replacements in IL-13. Extensive insertion/deletion differences between IL-4 and IL-13 were, with one exception, confined to loops that connect the four α-helices or two short β-strands. The exception was a shortened α-helix C, although all the α-helix C residues that contribute to the structural core were retained in IL-13 (FIG. 31).

Figure 32:
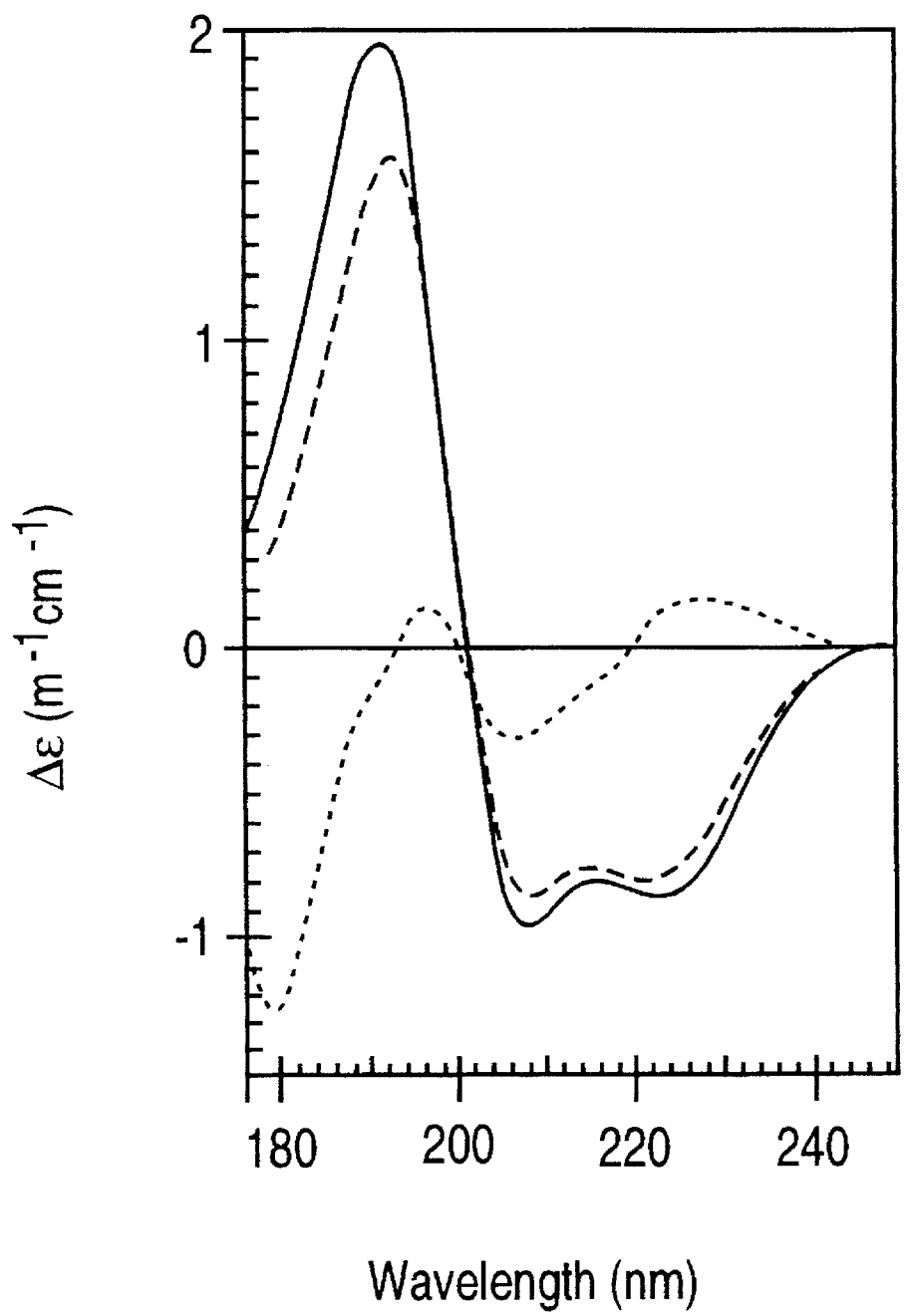
FIG. 32 shows mIL-13 has a high α-helical content. Far UV CD spectra of mIL-13) (—), hIL-4 (- - -), and hIL-1α (dotted).
Figure 33A:
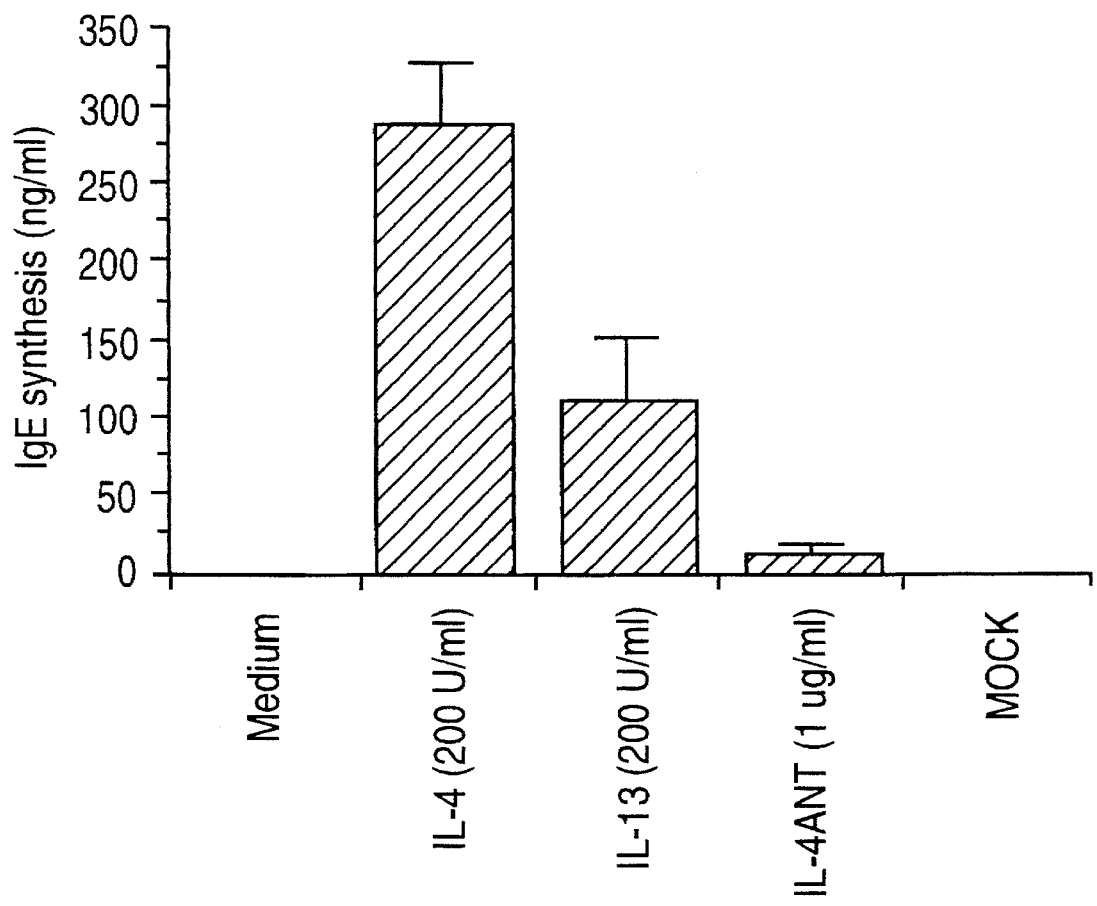
FIGS. 33A–33B show the effect of IL-4 antagonist on IgE synthesis. These experiments (FIGS. 33A–33B) were performed as described with other IgE experiments.
Figure 33B:
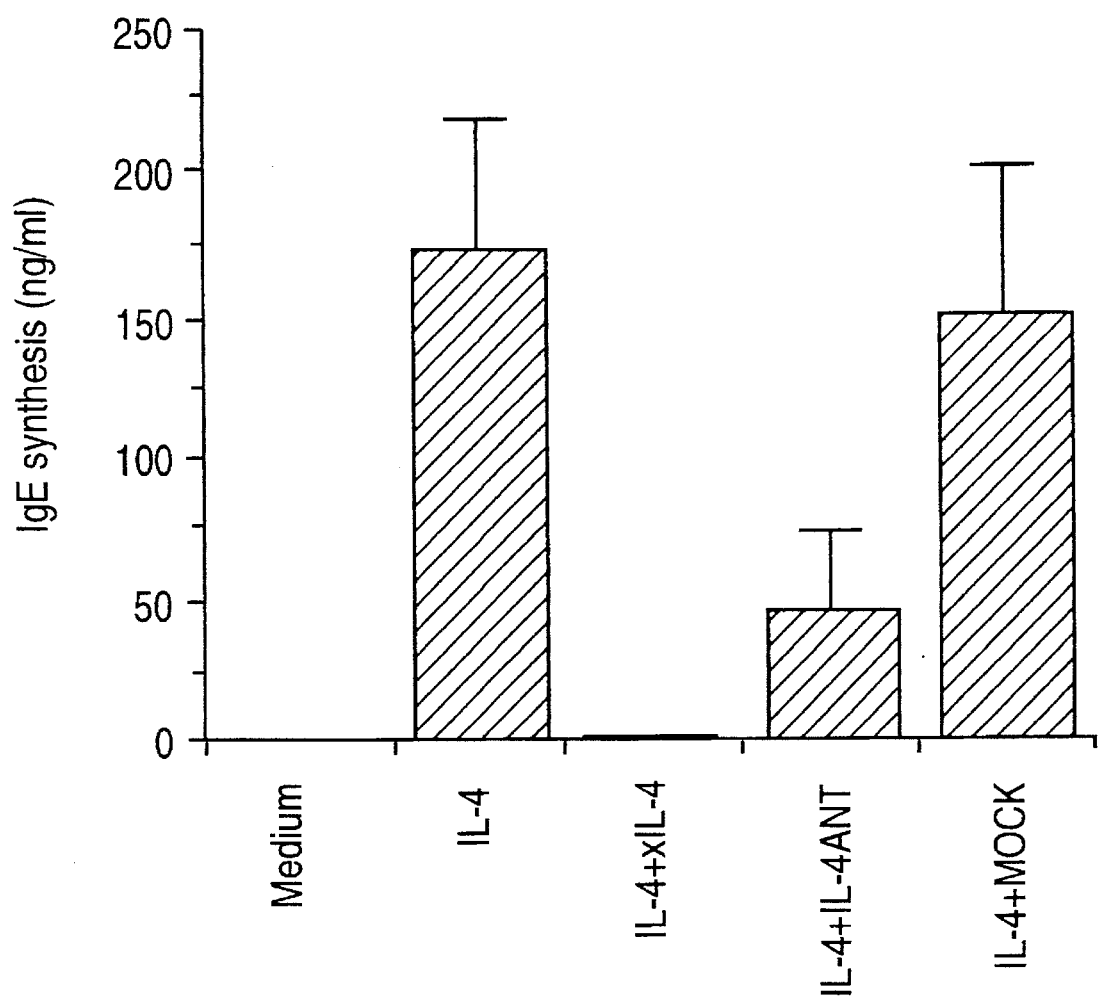
Figure 34:
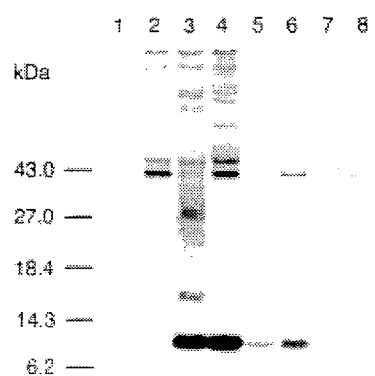
FIG. 34 illustrates immunoprecipitation of $^{35}$S-methonine labeled COS supernatants expressing soluble human IL-13 using rat polyclonal antibodies (lanes 1–6) or normal rat serum (lanes 7–8). Supernatants prepared from cells grown in tunicamycin (lanes 2, 4, 6, and 8) exhibit a single band compared to control supernatants, which exhibit higher molecular weight forms. Different parallel loadings were run.

The circular dichroism (CD) absorption spectrum in the far UV range of mIL-13, hIL-4, and hIL-1α is shown in FIG. 32. mIL-13, unlike the β-stranded hIL-1α, had a CD absorption spectrum characteristic of a highly a-helical protein such as hIL-4 (see Johnson (1988) *Ann. Rev. Biophys. Chem.* 17:146–166).

The similarity in the two cytokines allow for modifications to either cytokine to effect similar properties on the other. Thus, insight into the mechanism of IL-4 antagonist with its receptor will likely be useful in modulating IL-13 with its receptor. In particular, the present study provides locations in the IL-13 molecule which would be expected to lead to IL-13 antagonists. Moreover, the described IL-4 receptor would be expected to be modifiable while retaining its IL-13 antagonist activity. This would suggest that shortening of the IL-4 antagonist would be useful while retaining its antagonist function. In particular, specific regions of the cytokine are suggested as useful to modify to achieve the desired biological activity.

IL-13 and IL-4 Receptors Are Functionally Related

These observations that the hIL-4.Y124D antagonist competitively inhibits the biological action on TF-1 cells of both hIL-4 and IL-13 demonstrates a relationship between IL-4R and IL-13R. The ability of mIL-13 to compete for $I^{125}$-hIL-4 binding to TF-1 cells confirmed the commonalty of IL-4R and IL-13R. This relatedness may also have been expected from the similar biological responses known to be elicited by hIL-4 and IL-13 and perhaps from the close linkage of the IL-4 and IL-13 genes in both humans and mice. See, e.g., Morgan et al. (1992) *Nucleic Acids Res.* 20:5173–5179, and other experiments herein. A straightforward explanation of the above observations would be that IL-4 and IL-13 act through the same receptor.

However, some cell types respond to IL-4 and not to IL-13. This is prima facie evidence that IL-4R and IL-13R are different entities. The above result does not exclude the possibility that IL-13 is a weak partial agonist of IL-4 and that only a subset of IL-4R-bearing cells can efficiently amplify signals generated by IL-13 binding to IL-4R. Three lines of evidence helped in resolving the conundrum involving IL-4R and IL-13R. Firstly, IL-13 failed to compete for $I^{125}$-hIL-4-binding to cells bearing only the hIL-4R ligand-binding protein. This result demonstrated that the hIL-4R ligand-binding protein is, itself, not the IL-13R. Secondly, two T cell types responded to hIL-4, but not to hIL-13. If hIL-13 is a partial agonist acting via hIL-4R, then hIL-13 should competitively antagonize the action of hIL-4 on these cells. This is not the case in one hIL-4-responsive T-cell system that has been tested. Thirdly, if hIL-13 is a partial agonist acting via hIL-4R, then hIL-13 should be capable of fully competing hIL-4 binding to all cell types bearing hIL-4R. However, IL-13 only partially competed for binding of $I^{125}$-hIL-4 to TF-1 cells.

The conclusion from the above three lines of evidence is that IL-13 is not a partial agonist of IL-4 and that IL-4R and IL-13R are different. On TF-1 cells, mIL-13 competed hIL-4 binding and hIL-4.Y124D antagonized the action of IL-13. These data compel a further conclusion that IL-4R and IL-13R have a functionally important receptor component in common. This conclusion is contrary to a consensus that the IL-4R ligand-binding protein itself has all of the functional properties of IL-4R. IL-4R complexity is suggested by studies that find proteins associated with the IL-4R ligand-binding protein. Also, kinetic studies of soluble natural mouse IL-4R ligand-binding proteins indicate that membrane-bound functional IL-4R/IL-4 complexes are more stable than soluble IL-4R/IL-4.

Functional IL-4R Contains an Additional Subunit(s) That Enhances Affinity, Helms Transduce the Signal, and is Shared With IL-13R Two results from receptor-binding analyses show that IL-4R on TF-1 cells are complex and can exist in a higher affinity state than thought previously. Firstly, the apparent affinity of hIL-4 for hIL-4R on TF-1 cells was ~50-fold greater than for the cloned hIL-4R ligand-binding protein on Ba/F3 IL-4R-S cells. The hIL-4 binding sites on Ba/F3 IL-4R-S cells were the typical 'high affinity' IL-4R that are present on many cell types. Dissociation constant estimates for binding of hIL-4 to hIL-4R commonly vary somewhat, but fall within a 5-fold range of $K_d \sim 10^{-10}$M. Because the experiments were parallel, replicated independently, used the same reagents and cells with similar IL-4R numbers, and gave analogous results using a different labeled ligand, the "higher affinity" hIL-4 binding detected on TF-1 cells should be significant. Secondly, while it bound with only a slightly reduced affinity to IL-4R ligand-binding protein expressed on Ba/F3 cells, hIL-4.Y124D bound to IL-4R on TF-1 cells with an affinity ~50-fold less than did hIL-4. In essence, this result provided an internal control to confirm the "higher affinity" hIL-4 binding detected on TF-1 cells. Since the hIL-4R ligand-binding protein cDNA was cloned from TF-1 cells, it is unlikely that an unusual IL-4R ligand-binding protein accounts for the above results.

A model that does account for the above observations is that functional IL-4R on TF-1 cells are a complex between the IL-4R ligand-binding protein and an additional component (or components) that enhances the affinity of the IL-4R ligand-binding protein for IL-4. This additional component (s) also associates with an IL-13 ligand-binding protein present only on a subset of IL-4-responsive cells to form IL-13R. Furthermore, interaction of hIL-4 Tyr124 residue with this component is essential for productive signal transduction. Nevertheless, hIL-4.Y124D, which fails to elicit this productive signal transduction, maintains an association between the IL-4 ligand-binding protein and this additional component(s). In this model, hIL-4.Y124D antagonizes hIL-4 action by competing for IL-4 binding sites, but antagonizes IL-13 action by sequestering the additional component(s) from the IL-13R complex by forming a non-productive hIL-4R/hIL-4.Y124D complex.

Past Failures to Correctly Define IL-4R and Proposed Tests of the New Model

Two factors may have contributed to past failures to recognize the 'higher affinity' state of IL-4R that were detected on TF-1 cells. Firstly, the integrity of the hIL-4 Tyr124 residue is now known to be vital for this 'higher affinity' binding (this is also the case for the analogous Tyr119 residue of mIL-4 where substitution with Asp results in a potent competitive antagonist of mIL-4 biological action). The standard procedure for radio-labeling IL-4 is via iodination of Tyr residues. There are only two Tyr residues in hIL-4, thus it is probable that labeling hIL-4 converts Tyr124 to iodotyrosine. Indeed, hIL-4.Y124D labeled with the Bolton-Hunter reagent about 3-fold less efficiently than hIL-4. It is possible that hIL-4.Y124iodoTyr has a reduced affinity for functional IL-4R and that affinity constants derived using this reagent in direct-binding experiments have underestimated the actual affinity of IL-4R for IL-4. This was not an issue in the experiments which used hIL-4.Y124iodoTyr as the labeled-ligand and native hIL-4 as a 'cold' competitor. A second factor that may have hindered the discovery of two affinity states for IL-4R is that the difference between the two affinities is only ~50-fold. Thus, if cells have a mixture of IL-4R in both states, or if the 'lower affinity' state predominates, then two affinities may be impossible to recognize separately using conventional methods. As shown here, the hIL-4R subunit-specific defect of hIL-4.Y124D is a powerful new reagent for dissection of hIL-4R complexity.

The notion that IL-4-responsive cell types vary in IL-4R composition is being tested. Other direct tests of this model will require molecular characterization of the IL-13R ligand-binding protein by binding analyses, cross-linking studies, and cloning. However, the reagents to permit direct characterization of IL-13R have not yet been developed. Also, it is tempting to speculate that the very low affinity ($K_d \sim 3 \times 10^{-8}$M) IL-4-binding sites that have been detected on human lymphocytes may be a property of an additional IL-4R component.

Common Subunits in Other Cytokine Receptors

The molecular nature of the functionally important receptor component in common between IL-4R and IL-13R is unclear. The above model to account for our data is based on the existence of other affinity-modulating proteins that are obligatory components shared between several functional cytokine receptors. Such shared components have been discovered in receptors for IL-6, oncostatin-M, leukemia inhibitory factor, and ciliary neurotrophic factor, which all share gp130 (see Kishimoto et al. (1992) *Science* 258:593–597), as well as for human IL-3, interleukin-5 (IL-5), and GM-CSF receptors, which all share the $\beta_c$ protein (Miyajima et al. (1992) *Trends In Biochemical Sciences* 17:378–382). This shared $\beta_c$ receptor subunit accounts for the observed cross-competition of IL-3, IL-5, and GM-CSF binding to certain cell types. When assayed on TF-1 cells, hIL-4.Y124D did not antagonize the biological activities of hIL-6, mouse leukemia inhibitory factor, hIL-3, or hGM-CSF, and neither hIL-6 or hGM-CSF competed for hIL-4 binding. Therefore, gp130 or the $\beta_c$ protein are not likely candidates for the additional IL-4R component, nor the component shared between IL-4R and IL-13R.

On the basis of their common genetic locations/structures and relation in protein structure, it has been proposed that IL-4, IL-3, IL-5, and GM-CSF form a protein family. See Boulay et al. (1992) *J. Biol. Chem.* 267:20525–20528. The biological data regarding commonality between IL-4 and IL-13 show that IL-13 also belongs to this family. However, the available data support a clear functional separation between the receptors for IL-4/IL-13 and IL-3/IL-5/GM-CSF. For example, no effects of hIL-4.Y124D on IL-3 or GM-CSF responses on TF-1 were noted. Also, in TF-1 cells the pattern of intracellular tyrosine-phosphorylation that is elicited by IL-3/GM-CSF is different from that elicited by IL-4.

Implications Of Jointly Antagonizing IL-4 and IL-13Responses in Vivo

The ability of the hIL-4.Y124D antagonist to act against both hIL-4 and hIL-13 biological responses should provoke a reappraisal of the therapeutic potential of hIL-4.Y124D. These results show that, unlike soluble IL-4R ligand-binding protein or anti-IL-4 antibodies, hIL-4.Y124D is not a specific antagonist of hIL-4 action. Inhibitory IL-4 variants have been suggested as potentially useful drugs in the treatment of IgE-mediated diseases. The possibility exists for antagonizing both hIL-4 and hIL-13 responses by hIL-4.Y124D treatment for various disease states. The structural homology between IL-4 and IL-13 and sharing of receptor subunit(s) between IL-4R and IL-13R suggest that particular IL-13 residues within α-helix D are specifically important for receptor signaling and that substitutions in these residues may result in IL-13 variants that are antagonists. These results also predict that such IL-13 antagonists will be effective antagonists against IL-4-responses on cell types that also respond to IL-13.

Antagonistic Effect on Other IL-13 Activities

Results with cocultures of highly purified B cells and activated T cell clones with 400 U/ml IL-4 showed inhibition of IgE synthesis by the IL-4 antagonist used at 10 µg/ml. See FIGS. 33A–33B. Assay was as described above for IgE synthesis.

VII. Antibodies to Human IL-13

Rat polyclonal antiserum was raised against coli-derived human IL-13 by standard procedures. See, e.g., Harlow & Lane (1989) or Coligan (1991 and supplements). Serum from these rats was useful in immunoprecipitating $^{35}$S-methionine labeled supernatants of COS7 cells expressing IL-13.

More specifically, monoclonal antibodies against hIL-13 were produced using the protocol described in (1989) *J. Immunology* 117:67–81. Rats were immunized with *E. coli* produced hIL-13. The neutralizing capability of four different monoclonal antibodies were tested on TF-1 cells stimulated with COS produced hIL-13 (FIG. 35, upper panel) compared to *E. coli* produced hIL-13 (FIG. 35, lower panel).

5000 TF-1 cells/well were incubated for 72 h with 1:100 dilution of Cos produced hIL-13 (upper panel) or 5 ng/ml *E. coli* produced hIL-13 (lower panel), with dilutions for supernatants containing rat anti-hIL-13 Monoclonal antibody. After 72 h, cell viability was determined by alamar blue staining.

Figure 36:
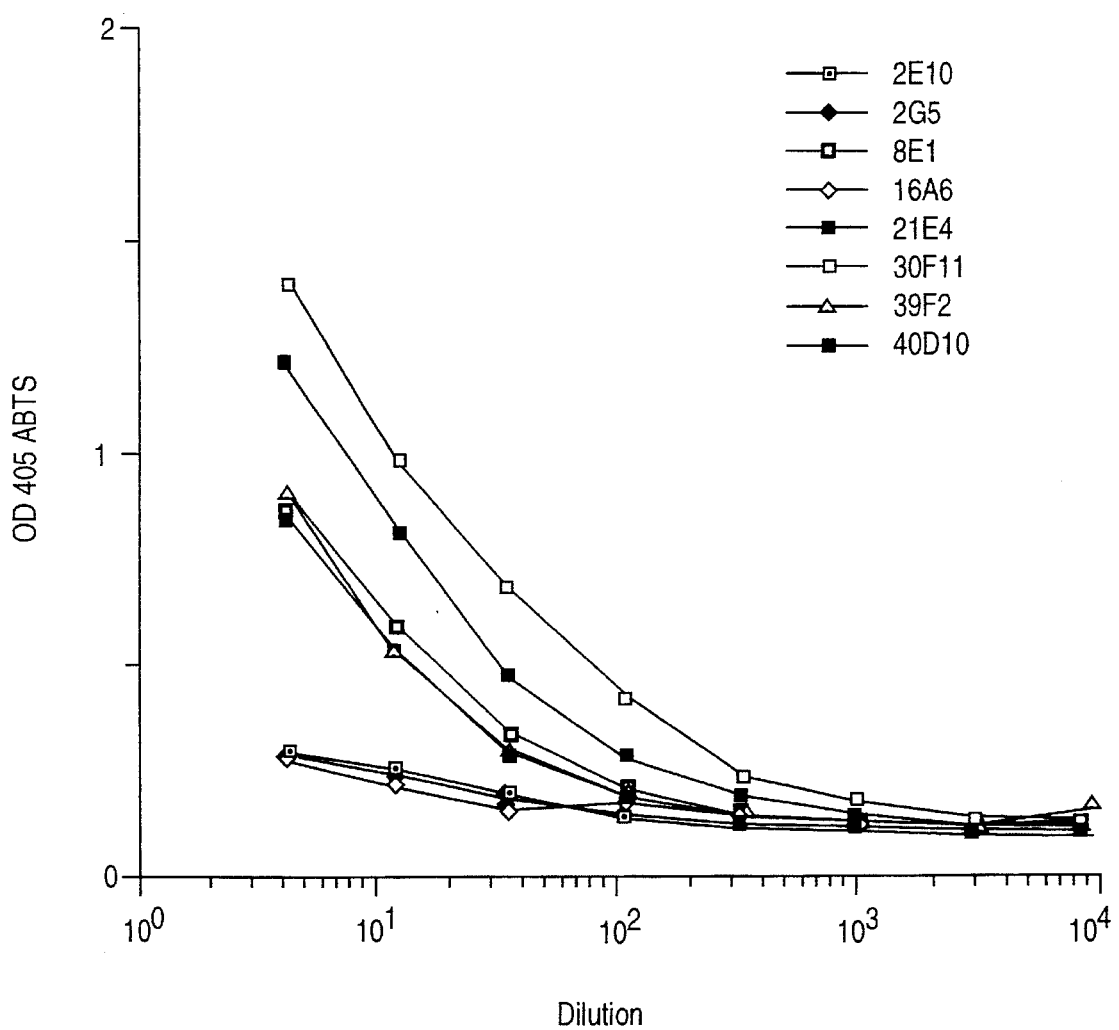
FIGS. 36 and 37A–37B show ELISA sensitivity for IL-13 at various dilutions of antibody.
Figure 37A:
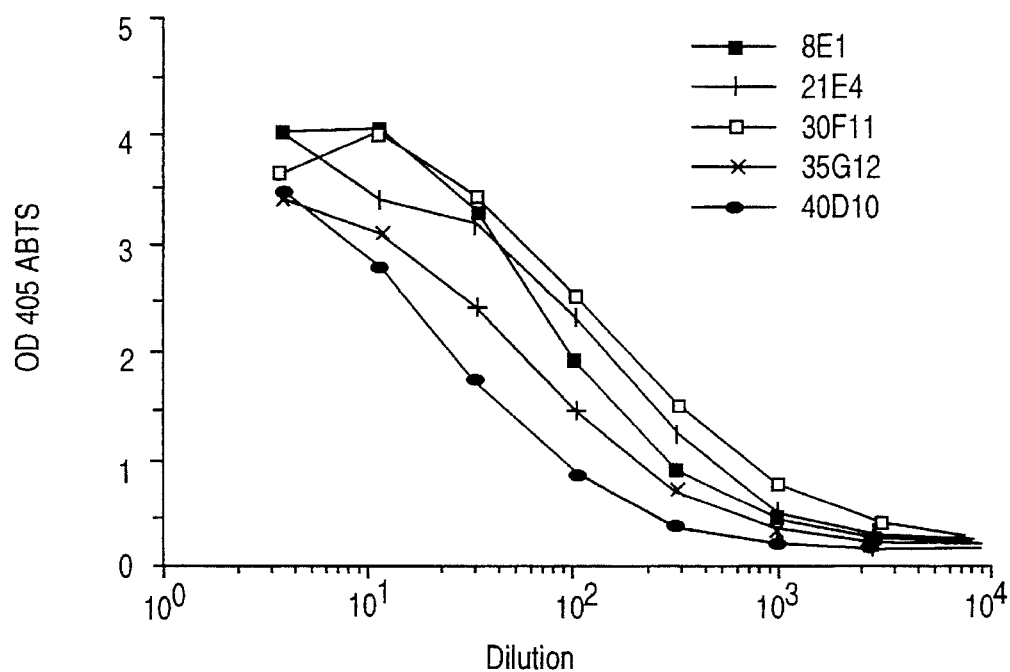
Figure 37B:
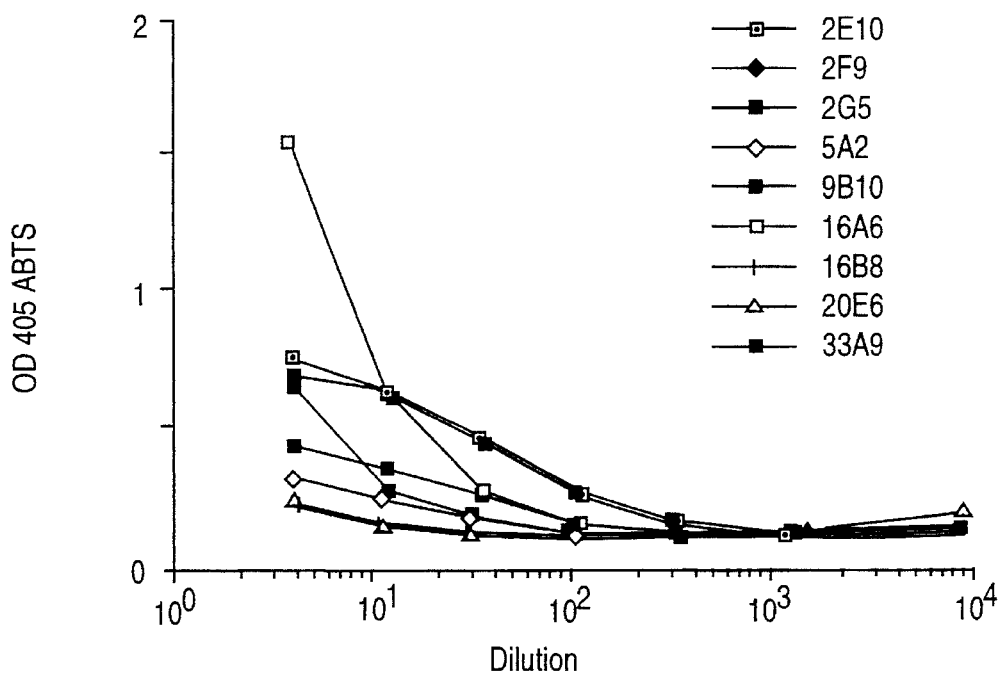

To determine which monoclonal antibodies from the above spleen-hybridoma fusions bind to hIL-13 produced from Cos or *E. coli*, an indirect ELISA was performed. See FIG. 36. PVC microtiter plates were coated for 2 h with either 0.5 µg/ml *E. coli* produced hIL-13 or a 1:15 dilution of COS produced hIL-13 in PBS at 37° C., A standard ELISA protocol was used.

All publications and patent applications herein are incorporated by reference to the same extent as if each individual publication or patent application was specifically and individually indicated to be incorporated by reference.

While a number of embodiments of this invention are described herein, it is apparent that the embodiments can be altered to provide other embodiments that utilize the compositions and processes of this invention. Therefore, it will be appreciated that the scope of this invention includes all alternative embodiments and variations which are defined in the foregoing specification and by the claims appended hereto; and the invention is not to be limited by the specification and by the claims appended hereto; and the invention is not to be limited by the specific embodiments that have been presented herein by way of example.

---

What is claimed is:

1. A method of refolding a denatured human IL-13 protein comprising the steps of:
   a) solubilizing said protein in 6M guanidine at a concentration of about 2.5 mg/ml;
   b) diluting said guanidine to about 60 mM over a period of hours in the presence of both reduced and oxidized glutathione; and
   c) incubating said diluted guanidine solution for at least about 12 hrs.

2. The method of claim 1 wherein said protein, upon refolding, exhibits an activity-selected from the group consisting of:
   a) supporting monocyte proliferation;
   b) sustaining monocyte viability;
   c) supporting B cell proliferation; and d) sustaining B cell viability.

3. The method of claim 1, wherein said protein is produced in *E. coli*.

4. The method of claim 1, wherein said reduced and oxidized glutathione are present in a ratio of about 2:1.

5. The method of claim 1, wherein said reduced glutathione is present in a concentration of about 2 mM, and/or said oxidized glutathione is present in a concentration of about 1 mM.

6. The method of claim 1, wherein said incubating is about 24 hours.

7. The method of claim 1, wherein a protease inhibitor is present in the solubilizing step or diluting step.

8. The method of claim 1, wherein at least one step is performed in Tris-EDTA buffer.

9. The method of claim 1, wherein said method further includes purification of said protein.

10. The method of claim 9, wherein said purification uses a step of size selection chromatography.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 1290 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 45..443

( x i ) SEQUENCE DESCRIPTION: SEQ ID NO:1:

```
TTCGGCATCC  GCTCCTCAAT  CCTCTCCTGT  TGGCACTGGG  CCTC ATG GCG CTT TTG      56
                                                     Met Ala Leu Leu
                                                      1

TTG ACC ACG GTC ATT GCT CTC ACT TGC CTT GGC GGC TTT GCC TCC CCA         104
Leu Thr Thr Val Ile Ala Leu Thr Cys Leu Gly Gly Phe Ala Ser Pro
 5               10                  15                  20

GGC CCT GTG CCT CCC TCT ACA GCC CTC AGG GAG CTC ATT GAG GAG CTG         152
Gly Pro Val Pro Pro Ser Thr Ala Leu Arg Glu Leu Ile Glu Glu Leu
             25                  30                  35

GTC AAC ATC ACC CAG AAC CAG AAG GCT CCG CTC TGC AAT GGC AGC ATG         200
Val Asn Ile Thr Gln Asn Gln Lys Ala Pro Leu Cys Asn Gly Ser Met
                 40                  45                  50

GTA TGG AGC ATC AAC CTG ACA GCT GGC ATG TAC TGT GCA GCC CTG GAA         248
Val Trp Ser Ile Asn Leu Thr Ala Gly Met Tyr Cys Ala Ala Leu Glu
         55                  60                  65
```

| TCC | CTG | ATC | AAC | GTG | TCA | GGC | TGC | AGT | GCC | ATC | GAG | AAG | ACC | CAG | AGG | 296 |
|-----|-----|-----|-----|-----|-----|-----|-----|-----|-----|-----|-----|-----|-----|-----|-----|-----|
| Ser | Leu | Ile | Asn | Val | Ser | Gly | Cys | Ser | Ala | Ile | Glu | Lys | Thr | Gln | Arg | |
| | | 70 | | | | 75 | | | | | 80 | | | | | |

| ATG | CTG | AGC | GGA | TTC | TGC | CCG | CAC | AAG | GTC | TCA | GCT | GGG | CAG | TTT | TCC | 344 |
|-----|-----|-----|-----|-----|-----|-----|-----|-----|-----|-----|-----|-----|-----|-----|-----|-----|
| Met | Leu | Ser | Gly | Phe | Cys | Pro | His | Lys | Val | Ser | Ala | Gly | Gln | Phe | Ser | |
| 85 | | | | | 90 | | | | | 95 | | | | | 100 | |

| AGC | TTG | CAT | GTC | CGA | GAC | ACC | AAA | ATC | GAG | GTG | GCC | CAG | TTT | GTA | AAG | 392 |
|-----|-----|-----|-----|-----|-----|-----|-----|-----|-----|-----|-----|-----|-----|-----|-----|-----|
| Ser | Leu | His | Val | Arg | Asp | Thr | Lys | Ile | Glu | Val | Ala | Gln | Phe | Val | Lys | |
| | | | | 105 | | | | | 110 | | | | | 115 | | |

| GAC | CTG | CTC | TTA | CAT | TTA | AAG | AAA | CTT | TTT | CGC | GAG | GGA | CGG | TTC | AAC | 440 |
|-----|-----|-----|-----|-----|-----|-----|-----|-----|-----|-----|-----|-----|-----|-----|-----|-----|
| Asp | Leu | Leu | Leu | His | Leu | Lys | Lys | Leu | Phe | Arg | Glu | Gly | Arg | Phe | Asn | |
| | | | 120 | | | | | 125 | | | | | 130 | | | |

| TGAAACTTCG | AAAGCATCAT | TATTTGCAGA | GACAGGACCT | GACTATTGAA | GTTGCAGATT | 500 |
|---|---|---|---|---|---|---|
| CATTTTTCTT | TCTGATGTCA | AAAATGTCTT | GGGTAGGCGG | GAAGGAGGGT | TAGGGAGGGG | 560 |
| TAAAATTCCT | TAGCTTAGAC | CTCAGCCTGT | GCTGCCCGTC | TTCAGCCTAG | CCGACCTCAG | 620 |
| CCTTCCCCTT | GCCCAGGGCT | CAGCCTGGTG | GGCCTCCTCT | GTCCAGGGCC | CTGAGCTCGG | 680 |
| TGGACCCAGG | GATGACATGT | CCCTACACCC | CTCCCTGCC | CTAGAGCACA | CTGTAGCATT | 740 |
| ACAGTGGGTG | CCCCCCTTGC | CAGACATGTG | GTGGGACAGG | GACCCACTTC | ACACACAGGC | 800 |
| AACTGAGGCA | GACAGCAGCT | CAGGCACACT | TCTTCTTGGT | CTTATTTATT | ATTGTGTGTT | 860 |
| ATTTAAATGA | GTGTGTTTGT | CACCGTTGGG | GATTGGGGAA | GACTGTGGCT | GCTGGCACTT | 920 |
| GGAGCCAAGG | GTTCAGAGAC | TCAGGGCCCC | AGCACTAAAG | CAGTGGACCC | CAGGAGTCCC | 980 |
| TGGTAATAAG | TACTGTGTAC | AGAATTCTGC | TACCTCACTG | GGGTCCTGGG | GCCTCGGAGC | 1040 |
| CTCATCCGAG | GCAGGGTCAG | GAGAGGGGCA | GAACAGCCGC | TCCTGTCTGC | CAGCCAGCAG | 1100 |
| CCAGCTCTCA | GCCAACGAGT | AATTTATTGT | TTTTCCTCGT | ATTTAAATAT | TAAATATGTT | 1160 |
| AGCAAAGAGT | TAATATATAG | AAGGGTACCT | TGAACACTGG | GGGAGGGGAC | ATTGAACAAG | 1220 |
| TTGTTTCATT | GACTATCAAA | CTGAAGCCAG | AAATAAAGTT | GGTGACAGAT | AAAAAAAAAA | 1280 |
| AAAAAAAAA | | | | | | 1290 |

( 2 ) INFORMATION FOR SEQ ID NO:2:

( i ) SEQUENCE CHARACTERISTICS:
        ( A ) LENGTH: 132 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ala | Leu | Leu | Leu | Thr | Thr | Val | Ile | Ala | Leu | Thr | Cys | Leu | Gly | Gly |
|-----|-----|-----|-----|-----|-----|-----|-----|-----|-----|-----|-----|-----|-----|-----|-----|
| 1 | | | | 5 | | | | | 10 | | | | | 15 | |

| Phe | Ala | Ser | Pro | Gly | Pro | Val | Pro | Pro | Ser | Thr | Ala | Leu | Arg | Glu | Leu |
|-----|-----|-----|-----|-----|-----|-----|-----|-----|-----|-----|-----|-----|-----|-----|-----|
| | | | 20 | | | | | 25 | | | | | 30 | | |

| Ile | Glu | Glu | Leu | Val | Asn | Ile | Thr | Gln | Asn | Gln | Lys | Ala | Pro | Leu | Cys |
|-----|-----|-----|-----|-----|-----|-----|-----|-----|-----|-----|-----|-----|-----|-----|-----|
| | | 35 | | | | | 40 | | | | | 45 | | | |

| Asn | Gly | Ser | Met | Val | Trp | Ser | Ile | Asn | Leu | Thr | Ala | Gly | Met | Tyr | Cys |
|-----|-----|-----|-----|-----|-----|-----|-----|-----|-----|-----|-----|-----|-----|-----|-----|
| | 50 | | | | | 55 | | | | | 60 | | | | |

| Ala | Ala | Leu | Glu | Ser | Leu | Ile | Asn | Val | Ser | Gly | Cys | Ser | Ala | Ile | Glu |
|-----|-----|-----|-----|-----|-----|-----|-----|-----|-----|-----|-----|-----|-----|-----|-----|
| 65 | | | | | 70 | | | | | 75 | | | | | 80 |

| Lys | Thr | Gln | Arg | Met | Leu | Ser | Gly | Phe | Cys | Pro | His | Lys | Val | Ser | Ala |
|-----|-----|-----|-----|-----|-----|-----|-----|-----|-----|-----|-----|-----|-----|-----|-----|
| | | | | 85 | | | | | 90 | | | | | 95 | |

| Gly | Gln | Phe | Ser | Ser | Leu | His | Val | Arg | Asp | Thr | Lys | Ile | Glu | Val | Ala |
|-----|-----|-----|-----|-----|-----|-----|-----|-----|-----|-----|-----|-----|-----|-----|-----|
| | | | 100 | | | | | 105 | | | | | 110 | | |

```
Gln Phe Val Lys Asp Leu Leu Leu His Leu Lys Lys Leu Phe Arg Glu
        115                 120                 125
Gly Arg Phe Asn
        130
```

( 2 ) INFORMATION FOR SEQ ID NO:3:

( i ) SEQUENCE CHARACTERISTICS:
    ( A ) LENGTH: 1212 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: 70..465

( x i ) SEQUENCE DESCRIPTION: SEQ ID NO:3:

```
GACAAGCCAG CAGCCTAGGC CAGCCCACAG TTCTACAGCT CCCTGGTTCT CTCACTGGCT         60

CTGGGCTTC ATG GCG CTC TGG GTG ACT GCA GTC CTG GCT CTT GCT TGC           108
          Met Ala Leu Trp Val Thr Ala Val Leu Ala Leu Ala Cys
              1               5                      10

CTT GGT GGT CTC GCC GCC CCA GGG CCG GTG CCA AGA TCT GTG TCT CTC         156
Leu Gly Gly Leu Ala Ala Pro Gly Pro Val Pro Arg Ser Val Ser Leu
     15              20                  25

CCT CTG ACC CTT AAG GAG CTT ATT GAG GAG CTG AGC AAC ATC ACA CAA         204
Pro Leu Thr Leu Lys Glu Leu Ile Glu Glu Leu Ser Asn Ile Thr Gln
 30              35                  40                  45

GAC CAG ACT CCC CTG TGC AAC GGC AGC ATG GTA TGG AGT GTG GAC CTG         252
Asp Gln Thr Pro Leu Cys Asn Gly Ser Met Val Trp Ser Val Asp Leu
                 50                  55                  60

GCC GCT GGC GGG TTC TGT GTA GCC CTG GAT TCC CTG ACC AAC ATC TCC         300
Ala Ala Gly Gly Phe Cys Val Ala Leu Asp Ser Leu Thr Asn Ile Ser
             65                  70                  75

AAT TGC AAT GCC ATC TAC AGG ACC CAG AGG ATA TTG CAT GGC CTC TGT         348
Asn Cys Asn Ala Ile Tyr Arg Thr Gln Arg Ile Leu His Gly Leu Cys
         80                  85                  90

AAC CGC AAG GCC CCC ACT ACG GTC TCC AGC CTC CCC GAT ACC AAA ATC         396
Asn Arg Lys Ala Pro Thr Thr Val Ser Ser Leu Pro Asp Thr Lys Ile
     95                  100                 105

GAA GTA GCC CAC TTT ATA ACA AAA CTG CTC AGC TAC ACA AAG CAA CTG         444
Glu Val Ala His Phe Ile Thr Lys Leu Leu Ser Tyr Thr Lys Gln Leu
110                 115                 120                 125

TTT CGC CAC GGC CCC TTC TAATGAGGAG AGACCATCCC TGGGCATCTC                492
Phe Arg His Gly Pro Phe
                 130

AGCTGTGGAC TCATTTTCCT TTCTCACATC AGACTTTGCT GGGGAGAGGC AGGGAGGAGG       552

GTTGAGGAGG AAGGGAGATG CCTCAGCTTT GGCCTCAGCC TGCACTGCCT GCCTAGTGCT       612

CAGGGTCTCA GCCTGGCAAC ACCCCCACCC CACCCCCACC CCGCCGCCC CATCCCATCC        672

CTACAGAAAA CTGCAGCAAG ACCGTGAGTC CAGCCTGTGG CCTGGTCCAC ACAGGGCAAC       732

TGAGGCAGGC AGCAGCTTGA GCACATTTCT TCTTGATCTT ATTTATTATG GTTGTGTGTT      792

ATTTAAATGA GTCTGTCAGT ATCCCGGTGG GGACATGGTT TGCTGCCTAT GCCCTGGGGG      852

CTCCAGCATT GAAGCAGTGG GCTCTGGGGT CCCTGGCAAT ATTACTGTAT ACATAACTCT     912

GCTACCTCAC TGTAGCCTCC AGGTCTCACC CCAGGCAGGA GATGGGAGGG GAGGCCAGAG    972

CAACACTCCT GTCTGCCACG GCAGCAACCA GCCCTCAGCC ATGAAATAAC TTATTGTTTT    1032

GTTCTTATAT TTAAAGTATT AAATAGCTTA GCAAAGAGTT AATAATATAT GGAAGAATGG    1092
```

```
CCTGTTACAC  TCAAGGTGAT  GTGTAGTGAA  TGGGGGGAGG  GTGGTGGGTT  TGTCACTGAA    1152

CAAACTTTTC  ATTGACTGTC  AAACTAGAAA  CCGGAAATAA  AGATGGTGAC  AGATAAAAAA    1212
```

( 2 ) INFORMATION FOR SEQ ID NO:4:

( i ) SEQUENCE CHARACTERISTICS:
        ( A ) LENGTH: 131 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ala  Leu  Trp  Val  Thr  Ala  Val  Leu  Ala  Leu  Ala  Cys  Leu  Gly  Gly
 1              5                    10                   15

Leu  Ala  Ala  Pro  Gly  Pro  Val  Pro  Arg  Ser  Val  Ser  Leu  Pro  Leu  Thr
               20                   25                        30

Leu  Lys  Glu  Leu  Ile  Glu  Glu  Leu  Ser  Asn  Ile  Thr  Gln  Asp  Gln  Thr
          35                   40                        45

Pro  Leu  Cys  Asn  Gly  Ser  Met  Val  Trp  Ser  Val  Asp  Leu  Ala  Ala  Gly
     50                   55                        60

Gly  Phe  Cys  Val  Ala  Leu  Asp  Ser  Leu  Thr  Asn  Ile  Ser  Asn  Cys  Asn
65                        70                   75                        80

Ala  Ile  Tyr  Arg  Thr  Gln  Arg  Ile  Leu  His  Gly  Leu  Cys  Asn  Arg  Lys
                    85                        90                        95

Ala  Pro  Thr  Thr  Val  Ser  Ser  Leu  Pro  Asp  Thr  Lys  Ile  Glu  Val  Ala
               100                      105                      110

His  Phe  Ile  Thr  Lys  Leu  Leu  Ser  Tyr  Thr  Lys  Gln  Leu  Phe  Arg  His
          115                      120                      125

Gly  Pro  Phe
          130
```

( 2 ) INFORMATION FOR SEQ ID NO:5:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
ACAGCTCGAG  CCATGGTGTC  TTTGCCTCGG  CTGTG                                   35
```

( 2 ) INFORMATION FOR SEQ ID NO:6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

```
GTAGCTCGAG  CTCACCGGGA  CTTTAAACCA  CAGATG                                  36
```

( 2 ) INFORMATION FOR SEQ ID NO:7:

( i ) SEQUENCE CHARACTERISTICS:
        ( A ) LENGTH: 21 base pairs
        ( B ) TYPE: nucleic acid (C) STRANDEDNESS: single
(D) TOPOLOGY: linear (ii) MOLECULE TYPE: cDNA (xi) SEQUENCE DESCRIPTION: SEQ ID NO:7:

ACAGCATGAT CGAAACATAC A    21

(2) INFORMATION FOR SEQ ID NO:8:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:8:

TGGCTCACTT GGCTTGGATC AGTC    24

(2) INFORMATION FOR SEQ ID NO:9:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:9:

TATGGACAGG ACTGAACGTC TTGC    24

(2) INFORMATION FOR SEQ ID NO:10:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:10:

GAGACAAACA TGATTCAAAT CCCTGA    26

(2) INFORMATION FOR SEQ ID NO:11:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:11:

TTCTGGCTGT GAGGAAATAC T    21

(2) INFORMATION FOR SEQ ID NO:12:

(i) SEQUENCE CHARACTERISTICS:
(A) LENGTH: 28 base pairs
(B) TYPE: nucleic acid
(C) STRANDEDNESS: single
(D) TOPOLOGY: linear (ii) MOLECULE TYPE: cDNA ( x i ) SEQUENCE DESCRIPTION: SEQ ID NO:12:

GTCAATTTAG AAGAAAAGAT AGATGTGG  28

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

AATGGGAGTT GCCTGGCCTC  20

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

TAAGACCTTT CTAAGATGCG AGGCC  25

( 2 ) INFORMATION FOR SEQ ID NO:15:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

CGAGCCTGAG GCCGACTACT ACGCCAAGGA GGTCACCCGC  40

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

GCTGAAACCA TCCCTGTC  18

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

CTGCTCTGAC AACCTCCCAG  20

( 2 ) INFORMATION FOR SEQ ID NO:18:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:18:

GCAAGCCTTC AGAATCTGGG ATG    23

( 2 ) INFORMATION FOR SEQ ID NO:19:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:19:

GATGTTAACT GCCTCCAGCT GGAGTC    26

( 2 ) INFORMATION FOR SEQ ID NO:20:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:20:

CTTCACCACT CCCAAAACCT G    21

( 2 ) INFORMATION FOR SEQ ID NO:21:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:21:

AGCTCGTCAC TCTGTCAATA G    21

( 2 ) INFORMATION FOR SEQ ID NO:22:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:22:

CATTCGCTCC TGCTGCTTCA C    21

( 2 ) INFORMATION FOR SEQ ID NO:23:

( i ) SEQUENCE CHARACTERISTICS:
  ( A ) LENGTH: 21 base pairs
  ( B ) TYPE: nucleic acid ( C ) STRANDEDNESS: single
        ( D ) TOPOLOGY: linear ( i i ) MOLECULE TYPE: cDNA ( x i ) SEQUENCE DESCRIPTION: SEQ ID NO:23:

TACTCCTTGT TGTCCCCTCT G                        21

( 2 ) INFORMATION FOR SEQ ID NO:24:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

ACCGGGTGGC CGGGGAGAGT GC                       22

( 2 ) INFORMATION FOR SEQ ID NO:25:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

GCCGGTTGCT GAGGTATCGC CAGG                     24

( 2 ) INFORMATION FOR SEQ ID NO:26:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

CTCCAAGAAC ACAACTGAGA AGGAAACCTT               30

( 2 ) INFORMATION FOR SEQ ID NO:27:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

TTGATTAAGC TTTCAGCTCG AACACTTTGA ATCTTTCTC     39